United States Patent
Berger et al.

(10) Patent No.: US 10,654,818 B2
(45) Date of Patent: May 19, 2020

(54) FURANE DERIVATIVES AS INHIBITORS OF ATAD2

(71) Applicant: BAYER PHARMA AKTIENGESELLSCHAFT, Berlin (DE)

(72) Inventors: Markus Berger, Berlin (DE); Jan Hübner, Berlin (DE); Antonius Ter Laak, Berlin (DE); Matyas Gorjanacz, Berlin (DE); Amaury Ernesto Fernandez-Montalvan, Berlin (DE); Vincent Rodeschini, Mions (FR); Didier Roche, Ecully (FR)

(73) Assignee: BAYER PHARMA AKTIENGESELLSCHAFT, Berlin (DE)

(*) Notice: Subject to any disclaimer, the term of this patent is extended or adjusted under 35 U.S.C. 154(b) by 0 days.

(21) Appl. No.: 15/779,691

(22) PCT Filed: Nov. 30, 2016

(86) PCT No.: PCT/EP2016/079173
§ 371 (c)(1),
(2) Date: May 29, 2018

(87) PCT Pub. No.: WO2017/093272
PCT Pub. Date: Jun. 8, 2017

(65) Prior Publication Data
US 2019/0218196 A1    Jul. 18, 2019

(30) Foreign Application Priority Data
Dec. 3, 2015 (EP) .................... 15197794

(51) Int. Cl.
| | |
|---|---|
| C07D 307/52 | (2006.01) |
| A61K 31/341 | (2006.01) |
| C07D 405/12 | (2006.01) |
| C07D 487/10 | (2006.01) |
| A61K 31/397 | (2006.01) |
| A61K 31/4025 | (2006.01) |
| A61K 31/403 | (2006.01) |
| A61K 31/4178 | (2006.01) |
| A61K 31/4196 | (2006.01) |
| A61K 31/4525 | (2006.01) |
| A61K 31/496 | (2006.01) |
| A61K 31/5377 | (2006.01) |
| A61K 45/06 | (2006.01) |

(52) U.S. Cl.
CPC .......... *C07D 307/52* (2013.01); *A61K 31/341* (2013.01); *A61K 31/397* (2013.01); *A61K 31/403* (2013.01); *A61K 31/4025* (2013.01); *A61K 31/4178* (2013.01); *A61K 31/4196* (2013.01); *A61K 31/4525* (2013.01); *A61K 31/496* (2013.01); *A61K 31/5377* (2013.01); *A61K 45/06* (2013.01); *C07D 405/12* (2013.01); *C07D 487/10* (2013.01)

(58) Field of Classification Search
CPC .. C07D 307/52; C07D 405/12; A61K 31/341; A61K 31/4525
USPC .......... 549/493, 492; 546/214; 514/471, 326
See application file for complete search history.

(56) References Cited

FOREIGN PATENT DOCUMENTS

| | | |
|---|---|---|
| WO | 2012/055880 | 5/2012 |
| WO | 2012055880 A1 | 5/2012 |
| WO | 2012/112363 A1 | 8/2012 |
| WO | 2014/140076 | 9/2014 |
| WO | 2014/140076 A1 | 9/2014 |

OTHER PUBLICATIONS

Fernandez-Montalvan, A. et al.: Isoform-selective ATAD2 chemical probe with novel chemical structure and unusual mode of action. ACS Chem. Biol., vol. 12, pp. 2730-2736, 2017.*
International Search Report and Written Opinion of the ISA for PCT/EP2016/079173, dated Jan. 25, 2017, 11 pages.
P. Bamborough et al., "Structure-Based Optimization of Naphthyridones into Potent ATAD2 Bromodomain Inhibitors", Journal of Medicinal Chemistry, vol. 58, No. 15, Aug. 2015, pp. 6151-6178.
M. Ciró et al., "ATAD2 is a Novel Cofactor for MYC, Overexpressed and Amplified in Aggressive Tumors", Molecular Biology, Pathobiology, and Genetics, The Journal of Cancer Research, 69, Oct. 20, 2009, pp. 8491-8498.
A. Katritzky et al., "Design, Synthesis, and Structure-Activity Relationship of a Novel Series of 2-Aryl 5-(4-Oxo-3-phenethyl-2-thioxothiazolidinylidenemethyl)furans as HIV-1 Entry Inhibitors", Journal of Medicinal Chemistry, 52, 2009, pp. 7631-7639.
Abdel-Magid, et al., "A Review on the Use of Sodium Triacetoxyborohydride in the Reductive Amination of Ketones and Aldehydes," Organic Process Research & Development, (2006), vol. 10: 971-1031.

(Continued)

*Primary Examiner* — Charanjit Aulakh
(74) *Attorney, Agent, or Firm* — McBee Moore & Vanik IP, LLC

(57) ABSTRACT

The invention relates to furane derivatives of formula (I) as inhibitors of ATAD2, a process for their preparation and use thereof.

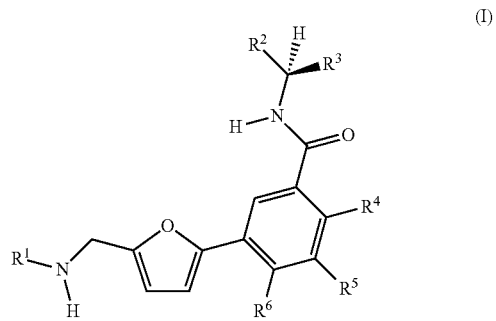

(I)

14 Claims, No Drawings
Specification includes a Sequence Listing.

(56) References Cited

OTHER PUBLICATIONS

American Cancer Society, Cancer Facts and Figures, (2015).
Filippakopoulos, et al, "The bromodomain interaction module," FEBS Letters, (2012), vol. 586, No. 17: 2692-2704.
Muller, et al., "Bromodomains as therapeutic targets," Expert Reviews in Molecular Medicine, (2011), vol. 13: e29.
Tanaka, et al., "Inhibitors of emerging epigenetic targets for cancer therapy: a patent review (2010-2014)," Pharm. Pat. Anal., (2015), vol. 4, No. 4: 261-284.
Ciro, et al., "ATAD2 is a Novel Cofactor for MYC, Overexpressed and Amplified in Aggressive Tumors," Cancer Res, (2009), vol. 69, No. 21: 8491-8498.
Revenko, et al., "Chromatin Loading of E2F-MLL Complex by Cancer-Associated Coregulator ANCCA via Reading a Specific Histone Mark," Mol. Cell. Biol., (2010), vol. 30, No. 22: 5260-5272.
Caron, et al., "Functional characterization of ATAD2 as a new cancer/testis factor and a predictor of poor prognosis in breast and lung cancers," Oncogene, (2010), vol. 29, No. 37: 5171-5181.
Kalashnikova, et al., "ANCCA/ATAD2 Overexpression Identifies Breast Cancer Patients with Poor Prognosis, Acting to Drive Proliferation and Survival of Triple-Negative Cells through Control of B-Myb and EZH2," Cancer Res., (2010), vol. 70, No. 22: 9402-9412.
Raeder, et al., "Integrated Genomic Analysis of the 8q24 Amplification in Endometrial Cancers Identifies ATAD2 as Essential to MYC-Dependent Cancers," PlosOne, (2013), vol. 8, No. 2: e54873.
Perrin, et al., "Secondary Deuterium Isotope Effects on the Acidity of Carboxylic Acids and Phenols," J. Am. Chem. Soc., (2007), vol. 129: 4490-4497.
Sharma, et al., "Nevirapine Bioactivation and Covalent Binding in the Skin," Chem. Res. Toxicol., (2013), vol. 26: 410-421.
Wenthur, et al., "Discovery of (R)-(2-Fluoro-4-((-4-methoxyphenyl)ethynyl)phenyl) (3-Hydroxypiperidin-1-yl)methanone (ML337), An mGlu3 Selective and CNS Penetrant Negative Allosteric Modulator (NAM)," J. Med. Chem., (2013), vol. 56: 5208-5212.
Schneider, et al., "Enhanced Plasma Concentration by Selective Deuteration of Rofecoxib in Rats," ArzneimForschDrugRes., (2006), vol. 56: 295.
Maltais, et al, "In Vitro and In Vivo Isotope Effects with Hepatitis C Protease Inhibitors: Enhanced Plasma Exposure of Deuterated Telaprevir versus Telaprevir in Rats," J. Med. Chem., (2009), vol. 52, 7993-8001.
Katritzky, et al., "Design, Synthesis, and Structure—Activity Relationship of a Novel Series of 2-Aryl 5-(4-Oxo-3-phenethyl-2-thioxothiazolidinylidenemethyl)furans as HIV-1 Entry Inhibitors," J. Med. Chem., (2009), vol. 52: 7631-7639.
He, et al., "Discovering Potent Inhibitors Against the β-Hydroxyacyl-Acyl Carrier Protein Dehydratase (FabZ) of Helicobacter pylori: Structure-Based Design, Synthesis, Bioassay, and Crystal Structure Determination," J. Med. Chem., (2009), vol. 52, 2465-2481.

Abdelmoty, et al., "Structural studies of reagents for peptide bond formation: Crystal and molecular structures of HBTU and HATU," Lett. Pept. Sci., (1994), vol. 1: 57-67.
Albericio, et al., "Use of Onium Salt-Based Coupling Reagents in Peptide Synthesis," J. Org. Chem., (1998), vol. 63: 9678-9683.
Aiello, et al., "Vascular Endothelial Growth Factor in Ocular Fluid of Patients with Diabetic Reitnopathy and other Retinal Disorders," New Engl. J. Med., (1994), vol. 331: 1480-1487.
Pe'er, et al., "Hypoxia-induced expression of vascular endothelial growth factor by retinal cells is a common factor in neovascularizing ocular diseases," Lab. Invest., (1995), vol. 72, No. 6: 638-645.
Lopez, et al., "Transdifferentiated Retinal Pigment Epithelial Cells are Immunoreactive for Vascular Endothelial Growth Factor in Surgically Excised Age-Related Macular Degeneration-Related Choroidal Neovascular Membranes," Invest. Opththalmol. Vis. Sci., (1996), vol. 37, No. 5: 855-868.
Bamborough, et al: "Structure-Based Optimization of Naphthyridones into Potent ATAD2 Bromodomain Inhibitors," Journal of Medicinal Chemistry, (2015), vol. 58, No. 15: 6151-6178.
Shi, et al., "Discovery of cancer drug targets by CRISPR-Cas9 screening of protein domains," Nat. Biotechnol., (2015), vol. 33, No. 6: 661-667.
Wan, et al., "ATAD2 is Highly Expressed in Ovarian Carcinomas and Indicates Poor Prognosis," Asian Pac. J. Cancer Prev., (2014), vol. 15, No. 6: 2777-2783.
Wu, et al., "miR-372 down-regulates the oncogene ATAD2 to influence hepatocellular carcinoma proliferation and metastasis," BMC Cancer, (2014), vol. 14, (107), 1-11.
Zheng, et al., "Oncogene ATAD2 promotes cell proliferation, invasion and migration in cervical cancer," Oncology Reports, (2015), vol. 33, No. 5: 2337-2344.
Fouret, et al., "A Comparative and Integrative Approach Identifies ATPase Family, AAA Domain Containing 2 as a Likely Driver of Cell Proliferation in Lung Adenocarcinoma," Clin. Cancer Res., (2012), vol. 18, No. 20: 5606-5616.
Duan, et al., "Developmental and Androgenic Regulation of Chromatin Regulators EZH2 and ANCAA/ATAD2 in the Prostate Via MLL Histone Methylase Complex," Prostate, (2013), vol. 73, No. 5: 455-466. (2013).
Wang, et al., "Gene-expression profiles to predict distant metastasis of lymph-node-negative primary breast cancer," Lancet, (2005), vol. 365: 671-679.
Zou, et al., "Androgen-Induced Coactivator ANCCA Mediates Specific Androgen Receptor Signaling in Prostate Cancer," Cancer Res., (2009), vol. 69, No. 8: 3339-3346.
Perrin, et al., "Secondary Deuterium Isotope Effects on the Acidity of Carboxylic Acids and Phenols," J. Am. Them. Soc., (2007), vol. 129: 4490-4497.
Perrin, et al., "Stereochemistry of β-Deuterium Isotope Effects on Amine Basicity," J. Am. Chem. Soc., (2005), vol. 127: 9641-9647.
El Tayar, et al., "The lipophilicity of deuterium atoms. A comparison of shake-flask and HPLC methods," Int. J. Pharm., (1984), vol. 19, No. 3: 271-281.
Mutlib, et al., "The Species-Dependent Metabolism of Efavirenz Produces a Nephrotoxic Glutathione Conjugate in Rats," Toxicol. Appl. Pharmacol., (2000), vol. 169: 102-103.

* cited by examiner

FURANE DERIVATIVES AS INHIBITORS OF ATAD2

This application is the U.S. national phase of International Application No. PCT/EP2016/079173 filed 30 Nov. 2016, which designated the U.S. and claims priority to EP Patent Application No. 15197794.9 filed 3 Dec. 2015, the entire contents of each of which are hereby incorporated by reference.

The invention relates to furane derivatives as inhibitors of ATAD2 and processes for their preparation, their use for the treatment and/or prophylaxis of diseases, and their use for the preparation of pharmaceuticals for the treatment and/or prophylaxis of diseases, in particular for the treatment and/or prophylaxis of cancer.

BACKGROUND

ATAD2 as a Cancer Target

Cancer is a group of different diseases which are commonly characterized by evolution of uncontrolled and abnormally proliferating cells which ultimately lead to death. Cancer is the second most common cause of death in the US and it is estimated that in 2015 more than 1.5 million new cases will be diagnosed and 589,430 Americans will die of cancer. With growing and ageing of the population these numbers are constantly growing and worldwide in 2030 about 21.7 million new cancer cases and 13 million cancer deaths are expected to occur (American Cancer Society, Cancer Facts and Figures, 2015).

On the current therapies the 5-years survival rate of all cancer patients is at about 68%, however, for particular cancer types it might be significantly lower, e.g. the 5-years survival rates of liver and lung cancer are 17%, of pancreatic cancer 7% and of glioblastoma less than 5% (American Cancer Society, Cancer Facts and Figures, 2015). These data strongly indicate that there is a need for new cancer therapeutics.

Gene expression controls the normal function, proliferation and differentiation of a cell. In normal cells gene expression is tightly regulated at multiple levels and steps, however, in cancer cells these mechanisms are often altered. Histone tails are well known protein-protein interaction domains which play a central role in gene expression regulation. They are subject to wide range of post-translational modification including methylation and acetylation. These modifications are reversible, i.e. specific "writer" and "eraser" enzymes exist which add or remove these marks. Ultimately, these marks are interpreted by "reader" proteins, which are known to translate these marks into gene expression changes.

Acetylation of histone tails is associated with active gene expression. Bromodomain, a small helical interacting module, is the best known protein domain which can specifically recognize and bind to the acetylated histone tails. Human genome encodes for 46 proteins contain altogether 61 diverse bromodomains (Filippakopoulos and Knapp, 2012, FEBS Let, 586: (17), 2692-2704). Bromodomain proteins recruit transcriptional machinery to acetylated chromatin sites and facilitate transcriptional activation. Bromodomain proteins are frequently implicated in cancer and the survival of different cancer types depend on their function (Muller et al., 2011, Epert Rev Mol Med, 13: e29; Shi J. et al., 2015, Nat Biotechnol, 33: (6), 661-667). Therefore recently several bromodomain inhibitors were developed to inhibit their binding to acetylated histone tails and to regulated gene expression. Some of these inhibitors have also entered clinical trials (Tanaka et al., 2015, Pharm Pat Anal, 4: (4), 261-284).

ATAD2, also known as ANCCA or PRO2000, is a bromodomain and AAA ATPase domain containing nuclear protein. ATAD2 was shown to function as a co-factor of oncogenic transcriptional factors such as MYC (Ciro et al., 2009, Cancer Res, 69: (21), 8491-8498), oestrogen receptor (ERα) (Zou et al., 2007, PNAS, 104: (46), 18067-18072), androgen receptor (AR) (Zou et al., 2009, Cancer Res, 69: (8) 3339-3346) and E2F (Revenko et al., 2010, Mol Cell Biol, 30: (22), 5260-5272) to activate the expression of their target genes involved in cell proliferation and survival. Such genes are different cyclins, cyclin-dependent kinases and kinesins. In normal tissues ATAD2 is expressed only in male germ cells, while in other normal tissues it is very low expressed and it could be detected only in dividing cells (Caron et al., 2010, Oncogene, 29: (37), 5171-5181). However, in large number of tumour types ATAD2 is frequently amplified and highly overexpressed, and its expression correlates with the advanced progression, metastasis and poor prognosis of breast cancer (Kalashnikova et al., 2010, Cancer Res, 70: (22), 9402-9412), endometrial cancer (Raeder et al., 2013, PlosOne, 8: (2), e54873), ovarian cancer (Wan et al., 2014, Asian Pac J Cancer Prev, 15: (6) 2777-2783), liver cancer (Wu et al., 2014, BMC Cancer, 14: (107), 1-11), cervical cancer (Zheng et al., 2015, Oncology Reports, 33: (5), 2337-2344) and lung cancer (Caron et al., 2010, Oncogene, 29: (37), 5171-5181). Until now ATAD2 was published to be overexpressed in breast cancer (Kalashnikova et al., 2010, Cancer Res, 70: (22), 9402-9412), endometrial cancer (Raeder et al., 2013, PlosOne, 8: (2), e54873), ovarian cancer (Wan et al., 2014, Asian Pac J Cancer Prev, 15: (6) 2777-2783), liver cancer (Wu et al., 2014, BMC Cancer, 14: (107), 1-11), colon cancer (Ciro et al., 2009, Cancer Res, 69: (21), 8491-8498), lung cancer (Fouer et al., 2012, Clin Cancer Res, 18: (20), 5606-5616), stomach cancer (Ciro et al., 2009, Cancer Res, 69: (21), 8491-8498), uterus cancer (Ciro et al., 2009, Cancer Res, 69: (21), 8491-8498), lymphoma (Ciro et al., 2009, Cancer Res, 69: (21), 8491-8498), cervical cancer (Zheng et al., 2015, Oncology Reports, 33: (5), 2337-2344), bladder cancer (Caron et al., 2010, Oncogene, 29: (37), 5171-5181), prostate cancer (Duan et al., 2013, Prostate, 73: (5), 455-466) and glioblastoma (Raeder et al., 2013, PlosOne, 8: (2), e54873). In normal breast tissues ATAD2 is barely detectable, while in tumour breast tissues ATAD2 expression was shown to increase with the grade and the proliferation state of the tumour (Kalashnikova et al., 2010, Cancer Res, 70: (22), 9402-9412). Moreover ATAD2 is one of the 70-genes signature predicting the disease outcome and one of the 76-gene signature that predict the disease outcome and the distant metastasis in breast cancer (Wang et al., 2005, Lancet, 365: (9460), 671-679). Down-regulation of ATAD2 by RNAi in cancer cells was shown to inhibit the proliferation and invasiveness of breast cancer cells (Kalashnikova et al., 2010, Cancer Res, 70: (22), 9402-9412; Revenko et al., 2010, Mol Cell Biol, 30: (22), 5260-5272), endometrial cancer cells (Raeder et al., 2013, PlosOne, 8: (2), e54873), ovarian cancer cells (Wan et al., 2014, Asian Pac J Cancer Prev, 15: (6) 2777-2783), liver cancer cells (Wu et al., 2014, BMC Cancer, 14: (107), 1-11), prostate cancer cells (Zou et al., 2009, Cancer Res, 69: (8) 3339-3346), cervical cancer cells (Zheng et al., 2015, Oncology Reports, 33: (5), 2337-2344), osteosarcoma (Ciro et al., 2009, Cancer Res, 69: (21), 8491-8498) and to promote apoptotic cancer cell death (Caron et al., 2010, Oncogene, 29: (37), 5171-5181).

Bromodomain of ATAD2 was found to bind different acetylation marks including H3K14ac (Revenko et al., 2010, Mol Cell Biol, 30: (22), 5260-5272) and H4K5Ac (Caron et al., 2010, Oncogene, 29: (37), 5171-5181) A rescue experiment by Revenko and colleagues demonstrated that mutagenesis of ATAD2 bromodomain inactivated ATAD2 function, which could not substitute for the wild-type ATAD2 in gene expression and survival of cancer cells. This suggest an essential function of the bromodomain of ATAD2 in cancer cells (Revenko et al., 2010, Mol Cell Biol, 30: (22), 5260-5272). Therefore potent and selective small molecular weight inhibitory compounds targeting the bromodomain function of ATAD2 might be useful for treatment of cancer types where ATAD2 is implicated in.

From WO2012/055880 the use of ATAD2 inhibitors for the treatment of autoimmune and inflammatory diseases is known.

The treatment of cancer is still a remaining problem. Thus there is the need for further provision of effective anti-cancer agents. The present invention identifies compounds which surprisingly are ATAD2 bromodomain inhibitors for which data are provided in the experimental section and which may thus be suitable for the treatment or prophylaxis of cancer.

In a first aspect, the present invention relates to compounds of general formula (I)

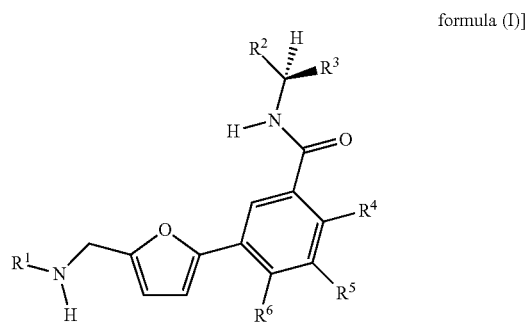

formula (I)]

in which
$R^1$ represents a benzyl group wherein the α-position is substituted by one methyl group of R configuration or two methyl groups, and the 4-position may be substituted by a methyl group, a halogen atom, a 4-trifluoromethyl group,
$R^2$ represents a $C_{1-6}$-alkyl group,
a $C_{1-6}$-hydroxyalkyl group,
a —$C_{1-3}$-alkylen-O—($C_{1-6}$-alkyl) group,
a —$C_{1-6}$-aminoalkyl group,
a —$C_{1-3}$-alkylen-N—($C_{1-6}$-alkyl)$_2$ group,
a —$C_{1-3}$-alkylen-NH—($C_{1-6}$-alkyl) group,
a —$C_{1-3}$-alkylen-NH—($C_{1-4}$-alkyl)-OH group,
a —$C_{1-3}$-alkylen-NH—($C_{3-7}$-cycloalkyl)-NH$_2$ group,
a —$C_{1-3}$-alkylen-NH—$C_{1-4}$-alkylen-heterocycloalkyl group which is optionally substituted with $C_{1-3}$-alkyl,
a —$C_{1-3}$-alkylen-NH-heterocycloalkyl group which is optionally substituted independently from each occurrence one or more times with $C_{1-4}$-alkyl, halogen, benzyl, C(O)$R^7$,
a —$C_{1-3}$-alkylen-NH—($C_{1-3}$-alkylen)-phenyl group
a —$C_{1-3}$-alkylen-NH—C(O)($C_{1-4}$-alkyl) group,
a —$C_{1-3}$-alkylen-NH—C(O)—$C_{1-4}$-alkylen-heterocycloalkyl group,
a —$C_{1-3}$-alkylen-NH—$C_{1-3}$-alkylen-C(O)-heterocycloalkyl group,
a —$C_{1-3}$-alkylen-NH—C(O)-heterocycloalkyl group,
a —$C_{1-3}$-alkylen-NH—S(O)$_2$—($C_{1-4}$-alkyl) group,
a —$C_{1-3}$-alkylen-(4-cyano-phenyl) group,
a —$C_{1-3}$-alkylen-C(O)—NH—($C_{1-6}$-alkyl) group,
a —$C_{1-3}$-alkylen-C(O)—NH—($C_{1-4}$-alkyl)-OH group
a —$C_{1-3}$-alkylen-C(O)—NR$^8$R$^9$ group,
a —$C_{1-3}$-alkylen-C(O)—R$^7$ group,
a —$C_{1-3}$-alkylen-C(O)-heterocycloalkyl group which is optionally substituted with $C_{1-3}$-alkyl,
a —$C_{1-3}$-alkylen-heterocycloalkyl group which is optionally one or more times substituted with $C_{1-3}$-alkyl,
a C(O)R$^7$ group,
a —C(O)—NR$^8$R$^9$ group,
a —C(O)—NH—($C_{3-7}$-cycloalkyl)-NH$_2$ group,
a —C(O)—NH-heterocycloalkyl group which is optionally substituted with $C_{1-3}$-alkyl,
a heteroaryl group,
$R^3$ a —$C_{1-3}$-alkylen-phenyl group which is independently from each occurrence optionally substituted 1 to 3 times with a substituent selected from the group cyano, halogen, $C_{1-3}$-alkyl, $C_{1-3}$-alkoxy, amino, C(O)R$^7$, C(O)NR$^8$R$^9$,
a —$C_{1-4}$-alkylen-heteroaryl group, or
$R^2$ and $R^3$ together with the carbon atom to which they are attached form the following 6-membered ring whereby the star * indicates the carbon atoms which are attached to said carbon atom of absolute configuration R

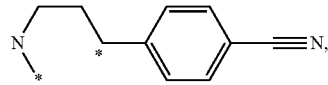

$R^4$ represents a hydrogen atom, a methyl group, a chlorine atom,
$R^5$ represents a hydrogen atom or a halogen atom
$R^6$ represents a hydrogen atom, a halogen atom, a hydroxy group, a $C_{1-3}$ alkoxy group, or a cyano group,
$R^7$ represents a —O—$C_{1-4}$-alkyl group,
$R^8$, $R^9$, represents, independently for each occurrence, a hydrogen atom or a $C_{1-4}$-alkyl group,
or the salts thereof, the solvates thereof or the solvates of the salts thereof,
with the proviso that the following compounds
2-Chlor-N-[(2R)-1-(4-cyanphenyl)-4-(methylamino)-4-oxobutan-2-yl]-5-[5-({[(1R)-1-(4-methylphenyl)ethyl]amino}methyl)-2-furyl]benzamide
N-[(2R)-1-(4-cyanophenyl)-4-(methylamino)-4-oxobutan-2-yl]-2-fluoro-5-[5-({[(1R)-1-(4-methylphenyl)ethyl]amino}methyl)-2-furyl]benzamide
2-chloro-N-[(2R)-1-(4-fluorophenyl)-4-(methylamino)-4-oxobutan-2-yl]-5-[5-({[(1R)-1-(4-methylphenyl)ethyl]amino}methyl)-2-furyl]benzamide
N-[(2R)-1-(4-cyanophenyl)-4-(methylamino)-4-oxobutan-2-yl]-2-methyl-5-[5-({[(1R)-1-(4-methylphenyl)ethyl]amino}methyl)-2-furyl]benzamide
2-chloro-N-[(2R)-1-(4-cyanophenyl)-4-(methylamino)-4-oxobutan-2-yl]-5-[5-({[(1R)-1-(4-fluorophenyl)ethyl]amino}methyl)-2-furyl]benzamide
are excluded.

In a second aspect, the present invention relates to compounds of general formula (I) in which
$R^1$ represents a benzyl group wherein the α-position is substituted by one methyl group of R configuration or two methyl groups, and the 4-position may be substituted by a methyl group, $R^2$ represents a $C_{1-6}$-alkyl group,
a $C_{1-6}$-hydroxyalkyl group,
a —$C_{1-3}$-alkylen-O—($C_{1-6}$-alkyl) group,
a —$C_{1-6}$-aminoalkyl group,
a —$C_{1-3}$-alkylen-N—($C_{1-6}$-alkyl)$_2$ group,
a —$C_{1-3}$-alkylen-NH—($C_{1-6}$-alkyl) group,
a —$C_{1-3}$-alkylen-NH—($C_{1-4}$-alkyl)-OH group,
a —$C_{1-3}$-alkylen-NH—($C_{3-7}$-cycloalkyl)-NH$_2$ group,
a —$C_{1-3}$-alkylen-NH—$C_{1-4}$-alkylen-heterocycloalkyl group which is optionally substituted with $C_{1-3}$-alkyl,
a —$C_{1-3}$-alkylen-NH-heterocycloalkyl group which is optionally substituted independently from each occurrence one or more times with $C_{1-4}$-alkyl, halogen, benzyl, C(O)R$^7$,
a —$C_{1-3}$-alkylen-NH—($C_{1-3}$-alkylen)-phenyl group,
a —$C_{1-3}$-alkylen-NH—C(O)($C_{1-4}$-alkyl) group,
a —$C_{1-3}$-alkylen-NH—C(O)—$C_{1-4}$-alkylen-heterocycloalkyl group,
a —$C_{1-3}$-alkylen-NH—$C_{1-3}$-alkylen-C(O)-heterocycloalkyl group,
a —$C_{1-3}$-alkylen-NH—C(O)-heterocycloalkyl group,
a —$C_{1-3}$-alkylen-NH—S(O)$_2$—($C_{1-4}$-alkyl) group,
a —$C_{1-3}$-alkylen-(4-cyano-phenyl) group,
a —$C_{1-3}$-alkylen-C(O)—NH—($C_{1-6}$-alkyl) group,
a —$C_{1-3}$-alkylen-C(O)—NH—($C_{1-4}$-alkyl)-OH group,
a —$C_{1-3}$-alkylen-C(O)—NR$^8$R$^9$ group,
a —$C_{1-3}$-alkylen-C(O)—R$^7$ group,
a —$C_{1-3}$-alkylen-C(O)-heterocycloalkyl group which is optionally substituted with $C_{1-3}$-alkyl,
a —$C_{1-3}$-alkylen-heterocycloalkyl group which is optionally one or more times substituted with $C_{1-3}$-alkyl,
a C(O)R$^7$ group,
a —C(O)—NR$^8$R$^9$ group,
a —C(O)—NH—($C_{3-7}$-cycloalkyl)-NH$_2$ group
a —C(O)—NH-heterocycloalkyl group which is optionally substituted with $C_{1-3}$-alkyl,
a heteroaryl group,
$R^3$ a —$C_{1-3}$-alkylen-phenyl group which is independently from each occurrence optionally substituted 1 to 3 times with a substituent selected from the group cyano, halogen, $C_{1-3}$-alkyl, $C_{1-3}$-alkoxy, amino, C(O)R$^7$, C(O)NR$^8$R$^9$,
a —$C_{1-4}$-alkylen-heteroaryl group or
$R^2$ and $R^3$ together with the carbon atom to which they are attached form the following 6-membered ring whereby the star * indicates the carbon atoms which are attached to said carbon atom of absolute configuration R

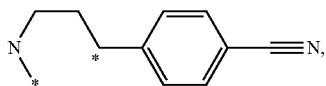

$R^4$ represents a chlorine atom,
$R^5$ represents a hydrogen atom
$R^6$ represents a hydrogen atom,
$R^7$ represents a —O—$C_{1-4}$-alkyl group
$R^8$, $R^9$, represents, independently for each occurrence, a hydrogen atom or a $C_{1-4}$-alkyl group,
or the salts thereof, the solvates thereof or the solvates of the salts thereof,
with the proviso that the following compounds
2-Chlor-N-[(2R)-1-(4-cyanphenyl)-4-(methylamino)-4-oxobutan-2-yl]-5-[5-({[(1R)-1-(4-methylphenyl)ethyl]amino}methyl)-2-furyl]benzamide N-[(2R)-1-(4-cyanophenyl)-4-(methylamino)-4-oxobutan-2-yl]-2-fluoro-5-[5-({[(1R)-1-(4-methylphenyl)ethyl]amino}methyl)-2-furyl]benzamide
2-chloro-N-[(2R)-1-(4-fluorophenyl)-4-(methylamino)-4-oxobutan-2-yl]-5-[5-({[(1R)-1-(4-methylphenyl)ethyl]amino}methyl)-2-furyl]benzamide
N-[(2R)-1-(4-cyanophenyl)-4-(methylamino)-4-oxobutan-2-yl]-2-methyl-5-[5-({[(1R)-1-(4-methylphenyl)ethyl]amino}methyl)-2-furyl]benzamide
2-chloro-N-[(2R)-1-(4-cyanophenyl)-4-(methylamino)-4-oxobutan-2-yl]-5-[5-({[(1R)-1-(4-fluorophenyl)ethyl]amino}methyl)-2-furyl]benzamide
are excluded.

In a further embodiment the present invention relates to compounds of general formula (I)
in which
$R^1$ represents a benzyl group wherein the α-position is substituted by one methyl group of R configuration or two methyl groups, and the 4-position may be substituted by a methyl group, a halogen atom, a 4-trifluoromethyl group,
$R^2$ represents a $C_{1-3}$-alkyl group,
a $C_{1-3}$-hydroxyalkyl group,
a —$C_{1-3}$-alkylen-O—($C_{1-3}$-alkyl) group,
a —$C_{1-3}$-aminoalkyl group,
a —$C_{1-3}$-alkylen-N—($C_{1-3}$-alkyl)$_2$ group,
a —$C_{1-3}$-alkylen-NH—($C_{1-3}$-alkyl) group,
a —$C_{1-3}$-alkylen-NH—($C_{1-3}$-alkyl)-OH group,
a —$C_{1-3}$-alkylen-NH—($C_{5-6}$-cycloalkyl)-NH$_2$ group,
a —$C_{1-3}$-alkylen-NH—$C_{1-3}$-alkylen-heterocycloalkyl group which is optionally substituted with $C_{1-3}$-alkyl,
a —$C_{1-3}$-alkylen-NH-heterocycloalkyl group which is optionally substituted independently from each occurrence one or more times with $C_{1-4}$-alkyl, halogen, benzyl, C(O)R$^7$,
a —$C_{1-3}$-alkylen-NH—($C_{1-3}$-alkylen)-phenyl group,
a —$C_{1-3}$-alkylen-NH—C(O)($C_{1-3}$-alkyl) group,
a —$C_{1-3}$-alkylen-NH—C(O)—$C_{1-3}$-alkylen-heterocycloalkyl group,
a —$C_{1-3}$-alkylen-NH—$C_{1-3}$-alkylen-C(O)-heterocycloalkyl group,
a —$C_{1-3}$-alkylen-NH—C(O)-heterocycloalkyl group,
a —$C_{1-3}$-alkylen-NH—S(O)$_2$—($C_{1-3}$-alkyl) group,
a —$C_{1-3}$-alkylen-(4-cyano-phenyl) group,
a —$C_{1-3}$-alkylen-C(O)—NH—($C_{1-3}$-alkyl) group,
a —$C_{1-3}$-alkylen-C(O)—NH—($C_{1-3}$-alkyl)-OH group
a —$C_{1-3}$-alkylen-C(O)—NR$^8$R$^9$ group,
a —$C_{1-3}$-alkylen-C(O)—R$^7$ group,
a —$C_{1-3}$-alkylen-C(O)-heterocycloalkyl group which is optionally substituted with $C_{1-3}$-alkyl,
a —$C_{1-3}$-alkylen-heterocycloalkyl group which is optionally one or more times substituted with $C_{1-3}$-alkyl,
a C(O)R$^7$ group,
a —C(O)—NR$^8$R$^9$ group,
a —C(O)—NH—($C_{5-6}$-cycloalkylen)-NH$_2$ group,
a —C(O)—NH-heterocycloalkyl group which is optionally substituted with $C_{1-3}$-alkyl,
a heteroaryl group,
$R^3$ a —$C_{1-3}$-alkylen-phenyl group which is independently from each occurrence optionally substituted 1 to 3 times with a substituent selected from the group cyano, halogen, $C_{1-3}$-alkyl, $C_{1-3}$-alkoxy, amino, C(O)R$^7$, C(O)NR$^8$R$^9$,
a —$C_{1-4}$-alkylen-heteroaryl group, or
$R^2$ and $R^3$ together with the carbon atom to which they are attached form the following 6-membered ring whereby the star * indicates the carbon atoms which are attached to said carbon atom

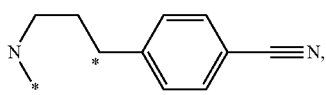

R⁴ represents a hydrogen atom, a methyl group, a chlorine atom,
R⁵ represents a hydrogen atom or a halogen atom
R⁶ represents a hydrogen atom, a halogen atom, a hydroxy group, a $C_{1-3}$ alkoxy group, or a cyano group,
R⁷ represents a —O—$C_{1-4}$-alkyl group
R⁸, R⁹, represents, independently for each occurrence, a hydrogen atom or a $C_{1-4}$-alkyl group,
or the salts thereof, the solvates thereof or the solvates of the salts thereof,
with the proviso that the following compounds
2-Chlor-N-[(2R)-1-(4-cyanphenyl)-4-(methylamino)-4-oxobutan-2-yl]-5-[5-({[(1R)-1-(4-methylphenyl)ethyl]amino}methyl)-2-furyl]benzamide
N-[(2R)-1-(4-cyanophenyl)-4-(methylamino)-4-oxobutan-2-yl]-2-fluoro-5-[5-({[(1R)-1-(4-methylphenyl)ethyl]amino}methyl)-2-furyl]benzamide
2-chloro-N-[(2R)-1-(4-fluorophenyl)-4-(methylamino)-4-oxobutan-2-yl]-5-[5-({[(1R)-1-(4-methylphenyl)ethyl]amino}methyl)-2-furyl]benzamide
N-[(2R)-1-(4-cyanophenyl)-4-(methylamino)-4-oxobutan-2-yl]-2-methyl-5-[5-({[(1R)-1-(4-methylphenyl)ethyl]amino}methyl)-2-furyl]benzamide
2-chloro-N-[(2R)-1-(4-cyanophenyl)-4-(methylamino)-4-oxobutan-2-yl]-5-[5-({[(1R)-1-(4-fluorophenyl)ethyl]amino}methyl)-2-furyl]benzamide
are excluded.

In another embodiment, the present invention relates to compounds of general formula (I
in which
R¹ represents a benzyl group wherein the α-position is substituted by one methyl group of R configuration or two methyl groups, and the 4-position may be substituted by a methyl group, a halogen atom, a 4-trifluoromethyl group,
R² represents a methyl group,
a hydroxymethyl group,
—(CH₂)₂OH,
—C(OH)(CH₃)₂,
—CH(OH)CH₃,
—C(OH)(CH₃)₂,
—CH(OH)—CH₂—CH(CH₃)₂,
—CH₂—O—CH₃,
—CH₂—NH₂,
—CH₂—N(CH₃)₂,
—(CH₂)₂—NH—CH(CH₃)₂,
—CH₂—NH—CH₂—CH(CH₃)₂,
—CH₂—NH—(CH₂)₂—OH,
—CH₂—NH-(1,4-cyclohexylen)-NH₂,
—CH₂—NH—(CH₂)₂-piperidine-4-yl,
—(CH₂)₂—NH—CH₂-(1-methyl-piperidine-4-yl),
—CH₂—NH—CH₂-(3-azabicyclo[3.1.0]hex-6-yl),
—CH₂—NH-(1-ethyl-piperidine-4-yl),
—CH₂—NH-(1-isobutyl-piperidine-4-yl),
—CH₂—NH-(1-phenylmethyl-piperidine-4-yl),
—CH₂—NH-(1-tert.butoxycarbonyl-piperidine-4-yl),
—CH₂—NH-2,2-dimethyl-piperidine-4yl),
—(CH₂)₂—NH-(1-methyl-pyrrolidin-3-yl),
—CH₂—NH-(piperidin-4-yl),
—CH₂—NH-(1-methyl-piperidin-4-yl),
—CH₂—NH-(2-methyl-propyl-piperidin-3-yl),
—CH₂—NH-(3-fluoropiperidin-4-yl),
—CH₂—NH—CH₂-phenyl,
—CH₂—NH—C(O)—CH₃,
—CH₂—NH—C(O)—CH₂-piperidine-4-yl,
—CH₂—NH—CH₂—C(O)-piperazine-1-yl,
—CH₂—NH—C(O)-piperidine-4-yl, —CH₂—NH—S(O)₂—CH₃,
—CH₂-(4-cyano-phenyl),
—CH₂—C(O)—NH—CH₃,
—CH₂—C(O)—NH—(CH₃)₂,
—CH₂—C(O)—NH—CH(CH₃)₂,
—CH₂—C(O)—NH—(CH₂)₂—OH,
—CH₂—C(O)—NH—(CH₂)₃—OH,
—CH₂—C(O)—NH₂,
—CH₂—C(O)—N(CH₃)₂,
—CH₂—C(O)—NH—CH₃,
—CH₂—C(O)—OCH₃,
—CH₂—C(O)-(morpholine-4-yl),
—CH₂—C(O)-(4-methyl-piperazine-1-yl),
—CH₂—C(O)—(N-pyrrolidine),
—(CH₂)₂-(3-methylpiperazine-1-yl),
—CH₂-(4-methyl-piperazine-1-yl),
—(CH₂)₂-(4-methyl-piperazine-1-yl),
—CH₂-(morpholine-4-yl),
—(CH₂)₂-(morpholine-4-yl),
—(CH₂)₂-(2,4-dimethylpiperazine-1-yl),
—(CH₂)₂-(6-methyl-2,6-diazaspiro[3.3]hept-2-yl),
—CH₂—(N-pyrrolidine),
—C(O)OCH₃,
—C(O)—NH₂,
—C(O)NH-(4-amino-cyclohexylen),
—C(O)—NH-(1-methyl-piperidine-4-yl),
1H-1,2,4-triazol-5-yl,
1H-imidazol-2-yl,
R³ a —CH₂-phenyl group which is independently from each occurrence optionally substituted 1 to 3 times with a substituent selected from the group cyano, halogen, $C_{1-3}$-alkyl, $C_{1-3}$-alkoxy, amino, C(O)R⁷, C(O)NR⁸R⁹,
—CH₂-pyridine-4-yl, or R² and R³ together with the carbon atom to which they are attached form the following 6-membered ring whereby the star * indicates the carbon atoms which are attached to said carbon atom

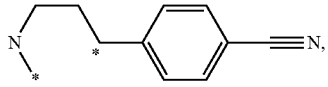

R⁴ represents a hydrogen atom, a methyl group, a chlorine atom,
R⁵ represents a hydrogen atom or a fluorine atom
R⁶ represents a hydrogen atom, a chlorine atom, a hydroxy group, a $C_{1-3}$ alkoxy group, or a cyano group,
R⁷ represents a methoxy group
R⁸, R⁹, represents, independently for each occurrence, a hydrogen atom or a methyl group,
or the salts thereof, the solvates thereof or the solvates of the salts thereof,
with the proviso that the following compounds
2-Chlor-N-[(2R)-1-(4-cyanphenyl)-4-(methylamino)-4-oxobutan-2-yl]-5-[5-({[(1R)-1-(4-methylphenyl)ethyl]amino}methyl)-2-furyl]benzamide
N-[(2R)-1-(4-cyanophenyl)-4-(methylamino)-4-oxobutan-2-yl]-2-fluoro-5-[5-({[(1R)-1-(4-methylphenyl)ethyl]amino}methyl)-2-furyl]benzamide 2-chloro-N-[(2R)-1-(4-fluorophenyl)-4-(methylamino)-4-oxobutan-2-yl]-5-[5-({[(1R)-1-(4-methylphenyl)ethyl]amino}methyl)-2-furyl]benzamide N-[(2R)-1-(4-cyanophenyl)-4-(methylamino)-4-oxobutan-2-yl]-2-methyl-5-[5-({[(1R)-1-(4-methylphenyl)ethyl]amino}methyl)-2-furyl]benzamide 2-chloro-N-[(2R)-1-(4-cyanophenyl)-4-(methylamino)-4-oxobutan-2-yl]-5-[5-({[(1R)-1-(4-fluorophenyl)ethyl]amino}methyl)-2-furyl]benzamide are excluded.

In one aspect of the invention compounds of formula (I) as described above are selected from the group consisting of:

2-chloro-N-[(2R)-1-(4-cyanophenyl)-4-(dimethylamino)-4-oxobutan-2-yl]-5-[5-({[(1R)-1-(4-methylphenyl)ethyl]amino}methyl) furan-2-yl]benzamide, Nα-{2-chloro-5-[5-({[(1R)-1-(4-methylphenyl)ethyl]amino}methyl)-2-furyl]benzoyl}-4-cyano-D-phenylalaninamide, N-[(2R)-4-amino-1-(4-cyanophenyl)-4-oxobutan-2-yl]-2-chloro-5-[5-({[(1R)-1-(4-methylphenyl)ethyl]amino}methyl)furan-2-yl]benzamide, 2-chloro-N-[(2R)-1-(4-cyanophenyl)-3-hydroxypropan-2-yl]-5-[5-({[(1R)-1-(4-methyl-phenyl)ethyl]amino}methyl)-2-furyl]benzamide, Nα-{2-chloro-5-[5-({[(1R)-1-(4-methylphenyl)ethyl]amino}methyl)furan-2-yl]-benzoyl}-4-cyano-N-methyl-D-phenylalaninamide, 2-chloro-N-[(2R)-1-(4-cyanophenyl)-4-(isopropylamino)-4-oxobutan-2-yl]-5-[5-({[(1R)-1-(4-methylphenyl)ethyl]amino}methyl)-2-furyl]benzamide, 2-chloro-N-{(2R)-1-(4-cyanophenyl)-4-[(2-hydroxyethyl)amino]-4-oxobutan-2-yl}-5-[5-({[(1R)-1-(4-methylphenyl)ethyl]amino}methyl)-2-furyl]benzamide, 2-chloro-N-{(2R)-1-(4-cyanophenyl)-4-[(3-hydroxypropyl)amino]-4-oxobutan-2-yl}-5-[5-({[(1R)-1-(4-methylphenyl)ethyl]amino}methyl)-2-furyl]benzamide, 2-chloro-N-[(2R)-1-(4-cyanophenyl)-4-oxo-4-(pyrrolidin-1-yl)butan-2-yl]-5-[5-({[(1R)-1-(4-methylphenyl)ethyl]amino}methyl)-2-furyl]benzamide, 2-chloro-N-[(2R)-1-(4-cyanophenyl)-4-(morpholin-4-yl)-4-oxobutan-2-yl]-5-[5-({[(1R)-1-(4-methylphenyl)ethyl]amino}methyl)-2-furyl]benzamide, 2-chloro-N-[(2R)-1-(4-cyanophenyl)-4-(4-methylpiperazin-1-yl)-4-oxobutan-2-yl]-5-[5-({[(1R)-1-(4-methylphenyl)ethyl]amino}methyl)-2-furyl]benzamide, 2-chloro-N-[(2R)-1-(4-cyanophenyl)-3-hydroxy-3-methylbutan-2-yl]-5-[5-({[(1R)-1-(4-methylphenyl)ethyl]amino}methyl)furan-2-yl]benzamide, 2-chloro-N-[(2R)-1-(4-cyanophenyl)-4-hydroxybutan-2-yl]-5-[5-({[(1R)-1-(4-methyl-phenyl)ethyl]amino}methyl)furan-2-yl]benzamide, 2-chloro-N-[(2R)-1-(4-cyanophenyl)-3-methoxypropan-2-yl]-5-[5-({[(1R)-1-(4-methyl-phenyl)ethyl]amino}methyl) furan-2-yl]benzamide, methyl N-{2-chloro-5-[5-({[(1R)-1-(4-methylphenyl)ethyl]amino}methyl)furan-2-yl]-benzoyl}-4-cyano-D-phenylalaninate, 2-chloro-N-[(2R,3R)-1-(4-cyanophenyl)-3-hydroxybutan-2-yl]-5-[5-({[(1R)-1-(4-methylphenyl)ethyl]amino}methyl)furan-2-yl]benzamide, 2-chloro-N-[(2R,3R)-1-(4-cyanophenyl)-3-hydroxybutan-2-yl]-5-[5-({[(1R)-1-(4-methylphenyl)ethyl]amino}methyl)furan-2-yl]benzamide, 2-chloro-N-[(2R)-1-hydroxy-3-(4-iodophenyl)propan-2-yl]-5-[5-({[(1R)-1-(4-methyl-phenyl)ethyl]amino}methyl) furan-2-yl]benzamide, 2-chloro-N-[(1S)-2-(4-cyanophenyl)-1-(1H-imidazol-2-yl)ethyl]-5-[5-({[(1R)-1-(4-methylphenyl)ethyl]amino}methyl)furan-2-yl]benzamide, 2-chloro-N-[(1R)-2-(4-cyanophenyl)-1-(1H-1,2,4-triazol-5-yl)ethyl]-5-[5-({[(1R)-1-(4-methylphenyl)ethyl]amino}methyl)furan-2-yl]benzamide, 2-chloro-N-[(2R)-1-(4-cyanophenyl)-3-(4-methylpiperazin-1-yl)propan-2-yl]-5-[5-({[(1R)-1-(4-methylphenyl)ethyl]amino}methyl)furan-2-yl]benzamide, 2-chloro-N-[(2R)-1-(4-cyanophenyl)-3-(morpholin-4-yl)propan-2-yl]-5-[5-({[(1R)-1-(4-methylphenyl)ethyl]amino}methyl)furan-2-yl]benzamide, 2-chloro-N-{(2R)-1-(4-cyanophenyl)-3-[(2-hydroxyethyl)amino]propan-2-yl}-5-[5-({[(1R)-1-(4-methylphenyl)ethyl]amino}methyl)furan-2-yl]benzamide, 2-chloro-N-[(2R)-1-(4-cyanophenyl)-3-(dimethylamino)propan-2-yl]-5-[5-({[(1R)-1-(4-methylphenyl)ethyl]amino}methyl)furan-2-yl]benzamide, 2-chloro-N-[(2R)-1-(4-cyanophenyl)-4-(4-methylpiperazin-1-yl)butan-2-yl]-5-[5-({[(1R)-1-(4-methylphenyl)ethyl]amino}methyl)furan-2-yl]benzamide, 2-chloro-N-[(2R)-1-(4-cyanophenyl)-4-(propan-2-ylamino)butan-2-yl]-5-[5-({[(1R)-1-(4-methylphenyl)ethyl]amino}methyl) furan-2-yl]benzamide, 2-chloro-N-{(2R)-1-(4-cyanophenyl)-4-[(3R)-3-methylpiperazin-1-yl]butan-2-yl}-5-[5-({[(1R)-1-(4-methylphenyl)ethyl]amino}methyl)furan-2-yl]benzamide, 2-chloro-N-{(2R)-1-(4-cyanophenyl)-4-[(3S)-3-methylpiperazin-1-yl]butan-2-yl}-5-[5-({[(1R)-1-(4-methylphenyl)ethyl]amino}methyl)furan-2-yl]benzamide, 2-chloro-N-[(2R)-1-(4-cyanophenyl)-4-(morpholin-4-yl)butan-2-yl]-5-[5-({[(1R)-1-(4-methylphenyl)ethyl]amino}methyl)furan-2-yl]benzamide, Nα-{2-chloro-5-[5-({[(1R)-1-(4-methylphenyl)ethyl]amino}methyl)furan-2-yl]-benzoyl}-4-cyano-N-(1-methylpiperidin-4-yl)-D-phenylalaninamide, 2-chloro-N-{(2R)-1-(4-cyanophenyl)-4-[(2S)-2,4-dimethylpiperazin-1-yl]butan-2-yl}-5-[5-({[(1R)-1-(4-methylphenyl)ethyl]amino}methyl) furan-2-yl]benzamide, 2-chloro-N-{(2R)-1-(4-cyanophenyl)-4-[(2R)-2,4-dimethylpiperazin-1-yl]butan-2-yl}-5-[5-({[(1R)-1-(4-methylphenyl)ethyl]amino}methyl) furan-2-yl]benzamide, 2-chloro-N-[(2R)-1-(4-cyanophenyl)-4-{[(1-methylpiperidin-4-yl)methyl]amino}butan-2-yl]-5-[5-({[(1R)-1-(4-methylphenyl)ethyl]amino}methyl)furan-2-yl]benzamide, 2-chloro-N-[(2R)-1-(4-cyanophenyl)-4-{[(3R)-1-methylpyrrolidin-3-yl]amino}butan-2-yl]-5-[5-({[(1R)-1-(4-methylphenyl)ethyl]amino}methyl)furan-2-yl]benzamide, 2-chloro-N-[(2R)-1-(4-cyanophenyl)-4-{[(3S)-1-methylpyrrolidin-3-yl]amino}butan-2-yl]-5-[5-({[(1R)-1-(4-methylphenyl)ethyl]amino}methyl)furan-2-yl]benzamide, 2-chloro-N-[(2R)-1-(4-cyanophenyl)-4-(6-methyl-2,6-diazaspiro[3.3]hept-2-yl)butan-2-yl]-5-[5-({[(1R)-1-(4-methylphenyl)ethyl]amino}methyl)furan-2-yl]benzamide, 2-chloro-N-[(2R)-1-(4-cyano-3-methylphenyl)-3-hydroxypropan-2-yl]-5-[5-({[(1R)-1-(4-methylphenyl)ethyl]amino}methyl) furan-2-yl]benzamide, 2-chloro-N-[(2R)-1-(4-cyano-5-fluoro-2-methylphenyl)-3-hydroxypropan-2-yl]-5-[5-({[(1R)-1-(4-methylphenyl)ethyl]amino}methyl)furan-2-yl]benzamide, 2-chloro-N-[(2R)-1-(4-cyano-2-methoxyphenyl)-3-hydroxypropan-2-yl]-5-[5-({[(1R)-1-(4-methylphenyl)ethyl]amino}methyl) furan-2-yl]benzamide, N-[(2R)-1-(3-amino-4-cyanophenyl)-3-hydroxypropan-2-yl]-2-chloro-5-[5-({[(1R)-1-(4-methylphenyl)ethyl]amino}methyl)furan-2-yl]benzamide,
N-[(2R)-1-(2-amino-4-cyanophenyl)-3-hydroxypropan-2-yl]-2-chloro-5-[5-({[(1R)-1-(4-methylphenyl)ethyl]amino}methyl)furan-2-yl]benzamide,
2-chloro-N-[(2S)-1-(4-cyanophenyl)propan-2-yl]-5-[5-({[(1R)-1-(4-methylphenyl)-ethyl]amino}methyl)-2-furyl]benzamide,
N-[(2R)-1-(acetylamino)-3-(4-cyanophenyl)propan-2-yl]-2-chloro-5-[5-({[(1R)-1-(4-methylphenyl)ethyl]amino}methyl)furan-2-yl]benzamide,
2-chloro-N-[(2R)-1-(3-cyanophenyl)-3-hydroxypropan-2-yl]-5-[5-({[(1R)-1-(4-methyl-phenyl)ethyl]amino}methyl)furan-2-yl]benzamide,
2-chloro-N-[(2R,3R)-1-(4-cyanophenyl)-3-hydroxy-5-methylhexan-2-yl]-5-[5-({[(1R)-1-(4-methylphenyl)ethyl]amino}methyl) furan-2-yl]benzamide,
2-chloro-N-[(2R,3S)-1-(4-cyanophenyl)-3-hydroxy-5-methylhexan-2-yl]-5-[5-({[(1R)-1-(4-methylphenyl)ethyl]amino}methyl) furan-2-yl]benzamide,
2-chloro-N-[(2R)-1-hydroxy-3-(pyridin-4-yl)propan-2-yl]-5-[5-({[(1R)-1-(4-methyl-phenyl)ethyl]amino}methyl)furan-2-yl]benzamide,
N-[(2R)-1-(4-carbamoylphenyl)-3-hydroxypropan-2-yl]-2-chloro-5-[5-({[(1R)-1-(4-methylphenyl)ethyl]amino}methyl)furan-2-yl]benzamide,
2-chloro-N-[(2R)-1-(4-cyanophenyl)-3-(pyrrolidin-1-yl)propan-2-yl]-5-[5-({[(1R)-1-(4-methylphenyl)ethyl]amino}methyl) furan-2-yl]benzamide,
methyl (3R)-3-({2-chloro-5-[5-({[(1R)-1-(4-methylphenyl)ethyl]amino}methyl)-2-furyl]benzoyl}amino)-4-(4-cyanophenyl)butanoate,
methyl 4-[(2R)-2-({2-chloro-5-[5-({[(1R)-1-(4-methylphenyl)ethyl]amino}methyl)-furan-2-yl]benzoyl}amino)-3-hydroxypropyl]benzoate,
N-[(2R)-1-amino-3-(4-cyanophenyl)propan-2-yl]-2-chloro-5-[5-({[(1R)-1-(4-methyl-phenyl)ethyl]amino}methyl)furan-2-yl]benzamide,
2-chloro-N-{(2R)-1-(4-cyanophenyl)-3-[(methylsulfonyl)amino]propan-2-yl}-5-[5-({[(1R)-1-(4-methylphenyl)ethyl]amino}methyl)furan-2-yl]benzamide,
2-chloro-N-[(2R)-1-(4-cyanophenyl)-3-{[2-oxo-2-(piperazin-1-yl)ethyl]amino}propan-2-yl]-5-[5-({[(1R)-1-(4-methylphenyl)ethyl]amino}methyl)furan-2-yl]benzamide,
N-[(2R)-2-({2-chloro-5-[5-({[(1R)-1-(4-methylphenyl)ethyl]amino}methyl)furan-2-yl]-benzoyl}amino)-3-(4-cyanophenyl)propyl]piperidine-4-carboxamide,
2-chloro-N-{(2R)-1-(4-cyanophenyl)-3-[(piperidin-4-ylacetyl)amino]propan-2-yl}-5-[5-({[(1R)-1-(4-methyl-phenyl)ethyl]amino}methyl)furan-2-yl]benzamide,
2-chloro-N-{(2R)-1-(4-cyanophenyl)-3-[(1-methylpiperidin-4-yl)amino]propan-2-yl}-5-[5-({[(1R)-1-(4-methyl-phenyl)ethyl]amino}methyl) furan-2-yl]benzamide,
N-[(2R)-1-[(1-benzylpiperidin-4-yl)amino]-3-(4-cyanophenyl)propan-2-yl]-2-chloro-5-[5-({[(1R)-1-(4-methylphenyl)ethyl]amino}methyl)furan-2-yl]benzamide,
N-[(2R)-1-(benzylamino)-3-(4-cyanophenyl)propan-2-yl]-2-chloro-5-[5-({[(1R)-1-(4-methylphenyl)ethyl]amino}methyl)furan-2-yl]benzamide,
2-chloro-N-{(2R)-1-(4-cyanophenyl)-3-[(2-methylpropyl)amino]propan-2-yl}-5-[5-({[(1R)-1-(4-methylphenyl)ethyl]amino}methyl)furan-2-yl]benzamide,
2-chloro-N-{(2R)-1-(4-cyanophenyl)-3-[(1-ethylpiperidin-4-yl)amino]propan-2-yl}-5-[5-({[(1R)-1-(4-methylphenyl)ethyl]amino}methyl) furan-2-yl]benzamide,
2-chloro-N-[(2R)-1-(4-cyanophenyl)-3-{[1-(2-methylpropyl)piperidin-4-yl]amino}-propan-2-yl]-5-[5-({[(1R)-1-(4-methylphenyl)ethyl]amino}methyl)furan-2-yl]benzamide,
tert-butyl 4-{[(2R)-2-({2-chloro-5-[5-({[(1R)-1-(4-methyl-phenyl)ethyl]amino}methyl)-furan-2-yl]benzoyl}amino)-3-(4-cyanophenyl)propyl]amino}piperidine-1-carboxylate,
2-chloro-N-[(2R)-1-(4-cyanophenyl)-3-{[(3S)-1-methylpiperidin-3-yl]amino}propan-2-yl]-5-[5-({[(1R)-1-(4-methylphenyl)ethyl]amino}methyl)furan-2-yl]benzamide,
N-[(2R)-1-{[(1R,5S,6r)-3-azabicyclo[3.1.0]hex-6-ylmethyl]amino}-3-(4-cyanophenyl)-propan-2-yl]-2-chloro-5-[5-({[(1R)-1-(4-methylphenyl)ethyl]amino}methyl) furan-2-yl]-benzamide,
2-chloro-N-[(2R)-1-(4-cyanophenyl)-3-(piperidin-4-ylamino)propan-2-yl]-5-[5-({[(1R)-1-(4-methylphenyl)ethyl]amino}methyl)furan-2-yl]benzamide,
2-chloro-N-[(2R)-1-(4-cyanophenyl)-3-{[(4R)-2,2-dimethylpiperidin-4-yl]amino}-propan-2-yl]-5-[5-({[(1R)-1-(4-methylphenyl)ethyl]amino}methyl)furan-2-yl]benzamide,
2-chloro-N-{(2R)-1-(4-cyanophenyl)-3-[(piperidin-4-ylmethyl)amino]propan-2-yl}-5-[5-({[(1R)-1-(4-methylphenyl)ethyl]amino}methyl) furan-2-yl]benzamide,
2-chloro-N-[(2R)-1-(4-cyanophenyl)-3-{[2-(piperidin-4-yl)ethyl]amino}propan-2-yl]-5-[5-({[(1R)-1-(4-methylphenyl)ethyl]amino}methyl) furan-2-yl]benzamide,
N-[(2R)-1-[(cis-4-aminocyclohexyl)amino]-3-(4-cyanophenyl)propan-2-yl]-2-chloro-5-[5-({[(1R)-1-(4-methylphenyl)ethyl]amino}methyl) furan-2-yl]benzamide,
N-[(2R)-1-[(cis-4-aminocyclohexyl)amino]-3-(4-cyanophenyl)propan-2-yl]-2-chloro-5-[5-({[(1R)-1-(4-methylphenyl)ethyl]amino}methyl)furan-2-yl]benzamide,
2-chloro-N-[(2R)-1-(4-cyanophenyl)-3-{[(3S,4R)-3-fluoropiperidin-4-yl]amino}propan-2-yl]-5-[5-({[(1R)-1-(4-methylphenyl)ethyl]amino}methyl)furan-2-yl]benzamide,
N-[(2R)-1-amino-3-(4-cyanophenyl)propan-2-yl]-2-chloro-5-{5-[({2-[4-(trifluoro-methyl)phenyl]propan-2-yl}amino)methyl]furan-2-yl}benzamide,
N-[(2R)-1-amino-3-(4-cyanophenyl)propan-2-yl]-2-chloro-5-{5-[({(1R)-1-[4-(trifluoro-methyl)phenyl]ethyl}amino)methyl]furan-2-yl}benzamide,
2-chloro-N-[(3R,4R)-4-(4-cyanophenyl)piperidin-3-yl]-5-[5-({[(1R)-1-(4-methyl-phenyl)ethyl]amino}methyl)furan-2-yl]benzamide,
2-chloro-N-[(2R)-1-(4-cyanophenyl)-3-hydroxypropan-2-yl]-3-fluoro-5-[5-({[(1R)-1-(4-methylphenyl)ethyl]amino}methyl) furan-2-yl]benzamide,
2,4-dichloro-N-[(2R)-1-(4-cyanophenyl)-3-hydroxypropan-2-yl]-5-[5-({[(1R)-1-(4-methylphenyl)ethyl]amino}methyl) furan-2-yl]benzamide,
4-cyano-N-[(2R)-1-(4-cyanophenyl)-3-hydroxypropan-2-yl]-3-[5-({[(1R)-1-(4-methyl-phenyl)ethyl]amino}methyl)furan-2-yl]benzamide,
N-[(2R)-1-(4-cyanophenyl)-3-hydroxypropan-2-yl]-4-methoxy-2-methyl-5-[5-({[(1R)-1-(4-methylphenyl)ethyl]amino}methyl) furan-2-yl]benzamide,
2-chloro-N-[(2R)-1-(4-cyanophenyl)-3-hydroxypropan-2-yl]-4-methoxy-5-[5-({[(1R)-1-(4-methylphenyl)ethyl]amino}methyl) furan-2-yl]benzamide,
2-chloro-N-[(2R)-1-(4-cyano-3-methylphenyl)-3-hydroxy-propan-2-yl]-4-methoxy-5-[5-({[(1R)-1-(4-methylphenyl)ethyl]amino}methyl)furan-2-yl]benzamide, N-[(2R)-1-amino-3-(4-cyanophenyl)propan-2-yl]-2-chloro-4-methoxy-5-[5-({[(1R)-1-(4-methylphenyl)ethyl]amino}methyl)furan-2-yl]benzamide, N-[(2R)-1-amino-3-(4-cyano-3-methylphenyl)propan-2-yl]-2-chloro-4-methoxy-5-[5-({[(1R)-1-(4-methylphenyl)ethyl]amino}methyl)furan-2-yl]benzamide, N-(trans-4-aminocyclohexyl)-Nα-{2-chloro-4-methoxy-5-[5-({[(1R)-1-(4-methyl-phenyl)ethyl]amino}methyl)furan-2-yl]benzoyl}-4-cyano-D-phenylalaninamide, N-[(2R)-1-[(cis-4-aminocyclohexyl)amino]-3-(4-cyanophenyl)propan-2-yl]-2-chloro-4-methoxy-5-[5-({[(1R)-1-(4-methylphenyl)ethyl]amino}methyl)furan-2-yl]benzamide, N-[(2R)-1-[(cis-4-aminocyclohexyl)amino]-3-(4-cyanophenyl)propan-2-yl]-2-chloro-4-methoxy-5-[5-({[(1R)-1-(4-methylphenyl)ethyl]amino}methyl)furan-2-yl]benzamide, N-[(2R)-1-[(cis-4-aminocyclohexyl)amino]-3-(4-cyano-3-methylphenyl)propan-2-yl]-2-chloro-4-methoxy-5-[5-({[(1R)-1-(4-methylphenyl)ethyl]amino}methyl)furan-2-yl]-benzamide, 2-chloro-5-[5-({[(1R)-1-(4-chlorophenyl)ethyl]amino}methyl)furan-2-yl]-N-[(2R)-1-(4-cyanophenyl)-4-(methylamino)-4-oxobutan-2-yl]benzamide, and 2-chloro-N-[(2R)-1-(4-cyanophenyl)-3-hydroxypropan-2-yl]-4-hydroxy-5-[5-({[(1R)-1-(4-methylphenyl)ethyl]amino}methyl) furan-2-yl]benzamide.

4-cyano-N-[(2R)-1-(4-cyanophenyl)-4-(methylamino)-4-oxobutan-2-yl]-3-[5-({[(1R)-1-(4-methylphenyl)ethyl]amino}methyl)-2-furyl]benzamide 2-chloro-N-[(2R)-4-(methylamino)-4-oxo-1-phenylbutan-2-yl]-5-[5-({[(1R)-1-(4-methylphenyl)ethyl]amino}methyl)furan-2-yl]benzamide 2-chloro-N-[(2R)-1-(4-cyanophenyl)-4-(methylamino)-4-oxobutan-2-yl]-5-(5-{[(2-phenylpropan-2-yl)amino]methyl}furan-2-yl)benzamide 2-chloro-N-[(2R)-1-(4-cyanophenyl)-4-(methylamino)-4-oxobutan-2-yl]-5-[5-({[2-(4-methylphenyl)propan-2-yl]amino}methyl)-2-furyl]benzamide Nα-{2-chloro-5-[5-({[2-(4-chlorophenyl)propan-2-yl]amino}methyl)-2-furyl]benzoyl}-4-cyano-D-phenylalaninamide 2-chloro-N-[(2R)-1-hydroxy-3-phenylpropan-2-yl]-5-[5-({[(1R)-1-(4-methylphenyl)ethyl]amino}methyl)-2-furyl]benzamide In accordance with a further aspect, the present invention provides compounds of general formula (I), as described supra, or stereoisomers, tautomers, hydrates, solvates, and salts thereof, particularly pharmaceutically acceptable salts thereof, or mixtures of same, for use in the treatment or prophylaxis of diseases, in particular hyperproliferative disorders, more particularly cancer disorders.

The compounds of the present invention can exist as a hydrate, or as a solvate, wherein the compounds of the present invention contain polar solvents, in particular water, methanol or ethanol for example, as structural element of the crystal lattice of the compounds. It is possible for the amount of polar solvents, in particular water, to exist in a stoichiometric or non-stoichiometric ratio. In the case of stoichiometric solvates, e.g. a hydrate, hemi-, (semi-), mono-, sesqui-, di-, tri-, tetra-, penta-etc. solvates or hydrates, respectively, are possible. The present invention includes all such hydrates or solvates.

Further, it is possible for the compounds of the present invention to exist in free form, e.g. as a free base, or as a free acid, or as a zwitterion, or to exist in the form of a salt. Said salt may be any salt, either an organic or inorganic addition salt, particularly any pharmaceutically acceptable organic or inorganic addition salt, which is customarily used in pharmacy, or which is used, for example, for isolating or purifying the compounds of the present invention.

The term "pharmaceutically acceptable salt" refers to an inorganic or organic acid addition salt of a compound of the present invention. For example, see S. M. Berge, et al. "Pharmaceutical Salts," J. Pharm. Sci. 1977, 66, 1-19.

Salts which are preferred for the purposes of the present invention are physiologically acceptable salts of the compounds of the invention. However, salts which are also encompassed are salts which are not themselves suitable for pharmaceutical applications, but may be used for example for isolating or purifying the compounds according to the invention.

A suitable pharmaceutically acceptable salt of the compounds of the present invention may be, for example, an acid-addition salt of a compound of the present invention bearing a nitrogen atom, in a chain or in a ring, for example, which is sufficiently basic, such as an acid-addition salt with an inorganic acid, or "mineral acid", such as hydrochloric, hydrobromic, hydroiodic, sulfuric, sulfamic, bisulfuric, phosphoric, or nitric acid, for example, or with an organic acid, such as formic, acetic, acetoacetic, pyruvic, trifluoroacetic, propionic, butyric, hexanoic, heptanoic, undecanoic, lauric, benzoic, salicylic, 2-(4-hydroxybenzoyl)-benzoic, camphoric, cinnamic, cyclopentanepropionic, digluconic, 3-hydroxy-2-naphthoic, nicotinic, pamoic, pectinic, 3-phenylpropionic, pivalic, 2-hydroxyethanesulfonic, itaconic, trifluoromethanesulfonic, dodecylsulfuric, ethanesulfonic, benzenesulfonic, para-toluenesulfonic, methanesulfonic, 2-naphthalenesulfonic, naphthalinedisulfonic, camphorsulfonic acid, citric, tartaric, stearic, lactic, oxalic, malonic, succinic, malic, adipic, alginic, maleic, fumaric, D-gluconic, mandelic, ascorbic, glucoheptanoic, glycerophosphoric, aspartic, sulfosalicylic, or thiocyanic acid, for example.

Further, another suitably pharmaceutically acceptable salt of a compound of the present invention which is sufficiently acidic, is an alkali metal salt, for example a sodium or potassium salt, an alkaline earth metal salt, for example a calcium, magnesium or strontium salt, or an aluminium or a zinc salt, or an ammonium salt derived from ammonia or from an organic primary, secondary or tertiary amine having 1 to 20 carbon atoms, such as ethylamine, diethylamine, triethylamine, ethyldiisopropylamine, monoethanolamine, diethanolamine, triethanolamine, dicyclohexylamine, dimethylaminoethanol, diethylaminoethanol, tris(hydroxymethyl)aminomethane, procaine, dibenzylamine, N-methylmorpholine, arginine, lysine, 1,2-ethylenediamine, N-methylpiperidine, N-methyl-glucamine, N,N-dimethylglucamine, N-ethyl-glucamine, 1,6-hexanediamine, glucosamine, sarcosine, serinol, 2-amino-1,3-propanediol, 3-amino-1,2-propanediol, 4-amino-1,2,3-butanetriol, or a salt with a quarternary ammonium ion having 1 to 20 carbon atoms, such as tetramethylammonium, tetraethylammonium, tetra(n-propyl) ammonium, tetra(n-butyl)ammonium, N-benzyl-N,N,N-trimethylammonium, choline or benzalkonium.

Those skilled in the art will further recognise that it is possible for acid addition salts of the claimed compounds to be prepared by reaction of the compounds with the appropriate inorganic or organic acid via any of a number of known methods. Alternatively, alkali and alkaline earth metal salts of acidic compounds of the present invention are prepared by reacting the compounds of the present invention with the appropriate base via a variety of known methods.

The present invention includes all possible salts of the compounds of the present invention as single salts, or as any mixture of said salts, in any ratio.

In the present text, in particular in the Experimental Section, for the synthesis of intermediates and of examples of the present invention, when a compound is mentioned as a salt form with the corresponding base or acid, the exact stoichiometric composition of said salt form, as obtained by the respective preparation and/or purification process, is, in most cases, unknown.

Unless specified otherwise, suffixes to chemical names or structural formulae relating to salts, such as "hydrochloride", "trifluoroacetate", "sodium salt", or "x HCl", "x $CF_3COOH$", "x Na+", for example, mean a salt form, the stoichiometry of which salt form not being specified.

This applies analogously to cases in which synthesis intermediates or example compounds or salts thereof have been obtained, by the preparation and/or purification processes described, as solvates, such as hydrates, with (if defined) unknown stoichiometric composition.

Furthermore, the present invention includes all possible crystalline forms, or polymorphs, of the compounds of the present invention, either as single polymorph, or as a mixture of more than one polymorph, in any ratio.

Moreover, the present invention also includes prodrugs of the compounds according to the invention. The term "prodrugs" here designates compounds which themselves can be biologically active or inactive, but are converted (for example metabolically or hydrolytically) into compounds according to the invention during their residence time in the body.

The compounds of the present invention optionally contain one or more asymmetric centres, depending upon the location and nature of the various substituents desired. It is possible that one or more asymmetric carbon atoms are present in the (R) or (S) configuration, which can result in racemic mixtures in the case of a single asymmetric centre, and in diastereomeric mixtures in the case of multiple asymmetric centres. In certain instances, it is possible that asymmetry also be present due to restricted rotation about a given bond, for example, the central bond adjoining two substituted aromatic rings of the specified compounds.

Preferred compounds are those which produce the more desirable biological activity. Separated, pure or partially purified isomers and stereoisomers or racemic or diastereomeric mixtures of the compounds of the present invention are also included within the scope of the present invention. The purification and the separation of such materials can be accomplished by standard techniques known in the art.

The optical isomers can be obtained by resolution of the racemic mixtures according to conventional processes, for example, by the formation of diastereoisomeric salts using an optically active acid or base or formation of covalent diastereomers. Examples of appropriate acids are tartaric, diacetyltartaric, ditoluoyltartaric and camphorsulfonic acid. Mixtures of diastereoisomers can be separated into their individual diastereomers on the basis of their physical and/or chemical differences by methods known in the art, for example, by chromatography or fractional crystallisation. The optically active bases or acids are then liberated from the separated diastereomeric salts. A different process for separation of optical isomers involves the use of chiral chromatography (e.g., HPLC columns using a chiral phase), with or without conventional derivatisation, optimally chosen to maximise the separation of the enantiomers. Suitable HPLC columns using a chiral phase are commercially available, such as those manufactured by Daicel, e.g., Chiracel OD and Chiracel OJ, for example, among many others, which are all routinely selectable. Enzymatic separations, with or without derivatisation, are also useful. The optically active compounds of the present invention can likewise be obtained by chiral syntheses utilizing optically active starting materials.

In order to distinguish different types of isomers from each other reference is made to IUPAC Rules Section E (Pure Appl Chem 45, 11-30, 1976).

The present invention includes all possible stereoisomers of the compounds of the present invention as single stereoisomers, or as any mixture of said stereoisomers, e.g. (R)- or (S)-isomers, in any ratio. Isolation of a single stereoisomer, e.g. a single enantiomer or a single diastereomer, of a compound of the present invention is achieved by any suitable state of the art method, such as chromatography, especially chiral chromatography, for example.

The present invention includes all possible tautomers of the compounds of the present invention as single tautomers, or as any mixture of said tautomers, in any ratio.

Where the compounds according to the invention can occur in tautomeric forms, the present invention includes all the tautomeric forms.

It is possible for the compounds of general formula (I) to exist as isotopic variants. The invention therefore includes one or more isotopic variant(s) of the compounds of general formula (I), particularly deuterium-containing compounds of general formula (I).

The term "Isotopic variant" of a compound or a reagent is defined as a compound exhibiting an unnatural proportion of one or more of the isotopes that constitute such a compound.

The term "Isotopic variant of the compound of general formula (I)" is defined as a compound of general formula (I) exhibiting an unnatural proportion of one or more of the isotopes that constitute such a compound.

The expression "unnatural proportion" means a proportion of such isotope which is higher than its natural abundance. The natural abundances of isotopes to be applied in this context are described in "Isotopic Compositions of the Elements 1997", Pure Appl. Chem., 70(1), 217-235, 1998.

Examples of such isotopes include stable and radioactive isotopes of hydrogen, carbon, nitrogen, oxygen, phosphorus, sulfur, fluorine, chlorine, bromine and iodine, such as $^2H$ (deuterium), $^3H$ (tritium), $^{11}C$, $^{13}C$, $^{14}C$, $^{15}N$, $^{17}O$, $^{18}O$, $^{32}P$, $^{33}P$, $^{33}S$, $^{34}S$, $^{35}S$, $^{36}S$, $^{18}F$, $^{36}Cl$, $^{82}Br$, $^{123}I$, $^{124}I$, $^{125}I$, $^{129}I$ and $^{131}I$, respectively.

With respect to the treatment and/or prophylaxis of the disorders specified herein the isotopic variant(s) of the compounds of general formula (I) preferably contain deuterium ("deuterium-containing compounds of general formula (I)"). Isotopic variants of the compounds of general formula (I) in which one or more radioactive isotopes, such as $^3H$ or $^{14}C$, are incorporated are useful e.g. in drug and/or substrate tissue distribution studies. These isotopes are particularly preferred for the ease of their incorporation and detectability. Positron emitting isotopes such as $^{18}F$ or $^{11}C$ may be incorporated into a compound of general formula (I). These isotopic variants of the compounds of general formula (I) are useful for in vivo imaging applications. Deuterium-containing and $^{13}C$-containing compounds of general formula (I) can be used in mass spectrometry analyses in the context of preclinical or clinical studies.

Isotopic variants of the compounds of general formula (I) can generally be prepared by methods known to a person skilled in the art, such as those described in the schemes and/or examples herein, by substituting a reagent for an isotopic variant of said reagent, preferably for a deuterium-containing reagent. Depending on the desired sites of deuteration, in some cases deuterium from $D_2O$ can be incorporated either directly into the compounds or into reagents that are useful for synthesizing such compounds. Deuterium gas is also a useful reagent for incorporating deuterium into molecules. Catalytic deuteration of olefinic bonds and acetylenic bonds is a rapid route for incorporation of deuterium. Metal catalysts (i.e. Pd, Pt, and Rh) in the presence of deuterium gas can be used to directly exchange deuterium for hydrogen in functional groups containing hydrocarbons. A variety of deuterated reagents and synthetic building blocks are commercially available from companies such as for example C/D/N Isotopes, Quebec, Canada; Cambridge Isotope Laboratories Inc., Andover, Mass., USA; and CombiPhos Catalysts, Inc., Princeton, N.J., USA.

The term "deuterium-containing compound of general formula (I)" is defined as a compound of general formula (I), in which one or more hydrogen atom(s) is/are replaced by one or more deuterium atom(s) and in which the abundance of deuterium at each deuterated position of the compound of general formula (I) is higher than the natural abundance of deuterium, which is about 0.015%. Particularly, in a deuterium-containing compound of general formula (I) the abundance of deuterium at each deuterated position of the compound of general formula (I) is higher than 10%, 20%, 30%, 40%, 50%, 60%, 70% or 80%, preferably higher than 90%, 95%, 96% or 97%, even more preferably higher than 98% or 99% at said position(s). It is understood that the abundance of deuterium at each deuterated position is independent of the abundance of deuterium at other deuterated position(s).

The selective incorporation of one or more deuterium atom(s) into a compound of general formula (I) may alter the physicochemical properties (such as for example acidity [C. L. Perrin, et al., J. Am. Chem. Soc., 2007, 129, 4490], basicity [C. L. Perrin et al., J. Am. Chem. Soc., 2005, 127, 9641], lipophilicity [B. Testa et al., Int. J. Pharm., 1984, 19(3), 271]) and/or the metabolic profile of the molecule and may result in changes in the ratio of parent compound to metabolites or in the amounts of metabolites formed. Such changes may result in certain therapeutic advantages and hence may be preferred in some circumstances. Reduced rates of metabolism and metabolic switching, where the ratio of metabolites is changed, have been reported (A. E. Mutlib et al., Toxicol. Appl. Pharmacol., 2000, 169, 102). These changes in the exposure to parent drug and metabolites can have important consequences with respect to the pharmacodynamics, tolerability and efficacy of a deuterium-containing compound of general formula (I). In some cases deuterium substitution reduces or eliminates the formation of an undesired or toxic metabolite and enhances the formation of a desired metabolite (e.g. Nevirapine: A. M. Sharma et al., Chem. Res. Toxicol., 2013, 26, 410; Efavirenz: A. E. Mutlib et al., Toxicol. Appl. Pharmacol., 2000, 169, 102). In other cases the major effect of deuteration is to reduce the rate of systemic clearance. As a result, the biological half-life of the compound is increased.

The potential clinical benefits would include the ability to maintain similar systemic exposure with decreased peak levels and increased trough levels. This could result in lower side effects and enhanced efficacy, depending on the particular compound's pharmacokinetic/pharmacodynamic relationship. ML-337 (C. J. Wenthur et al., J. Med. Chem., 2013, 56, 5208) and Odanacatib (K. Kassahun et al., WO2012/112363) are examples for this deuterium effect. Still other cases have been reported in which reduced rates of metabolism result in an increase in exposure of the drug without changing the rate of systemic clearance (e.g. Rofecoxib: F. Schneider et al., Arzneim. Forsch./Drug. Res., 2006, 56, 295; Telaprevir: F. Maltais et al., J. Med. Chem., 2009, 52, 7993). Deuterated drugs showing this effect may have reduced dosing requirements (e.g. lower number of doses or lower dosage to achieve the desired effect) and/or may produce lower metabolite loads.

A compound of general formula (I) may have multiple potential sites of attack for metabolism. To optimize the above-described effects on physicochemical properties and metabolic profile, deuterium-containing compounds of general formula (I) having a certain pattern of one or more deuterium-hydrogen exchange(s) can be selected. Particularly, the deuterium atom(s) of deuterium-containing compound(s) of general formula (I) is/are attached to a carbon atom and/or is/are located at those positions of the compound of general formula (I), which are sites of attack for metabolizing enzymes such as e.g. cytochrome $P_{450}$.

In another embodiment the present invention concerns a deuterium-containing compound of general formula (I) having 1, 2, 3 or 4 deuterium atoms, particularly with 1, 2 or 3 deuterium atoms.

DEFINITIONS

Where the plural form of the word "compounds", "salts", "polymorphs", "hydrates", "solvates" and the like, is used herein, this is taken to mean also a single compound, salt, polymorph, isomer, hydrate, solvate or the like.

If a constituent be it a chain or a ring system such as e.g. an alkyl group or a cycloalkyl group is found within a chain becoming an alkylen group or a cycloalkylen group the definition for pairs of groups, such as e.g. alkyl group/alkylen group or cycloalkyl group/cycloalkylen group is the same independently of binding two groups or just one.

The term "substituted" means that one or more hydrogens on the designated atom or group are replaced with a selected residue from the indicated group, provided that the designated atom's normal valency under the existing circumstances is not exceeded. Combinations of substituents and/or variables are permissible.

Constituents which are optionally substituted as stated herein, may be substituted, unless otherwise noted, one or more times, independently from one another at any possible position. When any variable occurs more than one time in any constituent, each definition is independent. For example, when $R^1$, $R^2$, $R^3$, $R^4$, $R^5$, $R^6$, $R^7$, $R^8$, $R^9$, occur more than one time in any compound of formula (I), each definition of $R^1$, $R^2$, $R^3$, $R^4$, $R^5$, $R^6$, $R^7$, $R^8$, $R^9$ is independent.

As used herein, the term "one or more", e.g. in the definition of the substituents of the compounds of general formula (I) of the present invention, means "1, 2, 3, 4 or 5, particularly 1, 2, 3 or 4, more particularly 1, 2 or 3, even more particularly 1 or 2".

The term "optionally substituted" means that the number of substituents can be equal to or different from zero. Unless otherwise indicated, optionally substituted groups may be substituted with as many optional substituents as can be accommodated by replacing a hydrogen atom with a non-hydrogen substituent on any available carbon or nitrogen atom as long as chemically stable groups can be achieved. Commonly, it is possible for the number of optional substituents, when present, to be 1, 2, 3, 4 or 5, in particular 1, 2 or 3.

As used herein, an oxo substituent represents an oxygen atom, which is bound to a carbon atom or to a sulfur atom via a double bond.

The term "ring system substituent" means a substituent attached to an aromatic or nonaromatic ring system replacing an available hydrogen atom on the ring system.

Should a constituent be composed of more than one part, e.g. ($C_1$-$C_4$-alkoxy)-($C_1$-$C_4$-alkyl)-, the position of a possible substituent can be at any of these parts at any suitable position. A hyphen at the beginning or at the end of the constituent marks the point of attachment to the rest of the molecule. Should a ring be substituted the substituent could be at any suitable position of the ring, also on a ring nitrogen atom if suitable.

The term "comprising" when used in the specification includes "consisting of".

If it is referred to "as mentioned herein" within the description it is referred to any of the disclosures made within the whole specification.

The term "halogen atom" means a fluorine, chlorine, bromine or iodine atom, under certain circumstances it may be mentioned otherwise e.g. if used in the context of leaving groups.

The term "$C_1$-$C_6$-alkyl" means a linear or branched, saturated, monovalent hydrocarbon group having 1, 2, 3, 4, 5 or 6 carbon atoms, e.g. a methyl, ethyl, propyl, isopropyl, butyl, sec-butyl, isobutyl, tert-butyl, pentyl, isopentyl, 2-methylbutyl, 1-methylbutyl, 1-ethylpropyl, 1,2-dimethylpropyl, neo-pentyl, 1,1-dimethylpropyl, hexyl, 1-methylpentyl, 2-methylpentyl, 3-methylpentyl, 4-methylpentyl, 1-ethylbutyl, 2-ethylbutyl, 1,1-dimethylbutyl, 2,2-dimethylbutyl, 3,3-dimethylbutyl, 2,3-dimethylbutyl, 1,2-dimethylbutyl or 1,3-dimethylbutyl group, or an isomer thereof. Particularly, said group has 1, 2, 3 or 4 carbon atoms ("$C_1$-$C_4$-alkyl"), e.g. a methyl, ethyl, propyl, isopropyl, butyl, sec-butyl isobutyl, or tert-butyl group, more particularly 1, 2 or 3 carbon atoms ("$C_1$-$C_3$-alkyl"), e.g. a methyl, ethyl, n-propyl or isopropyl group.

The term "$C_1$-$C_6$-hydroxyalkyl" means a linear or branched, saturated, monovalent hydrocarbon group in which the term "$C_1$-$C_6$-alkyl" is defined supra, and in which one, two or three hydrogen atom(s) are replaced with a hydroxy group, e.g. a hydroxymethyl, 1-hydroxyethyl, 2-hydroxyethyl, 1,2-dihydroxyethyl, 3-hydroxypropyl, 2-hydroxypropyl, 3-hydroxy-2-methyl-propyl, 2-hydroxy-2-methyl-propyl, 1-hydroxy-2-methyl-propyl group.

The term "$C_1$-$C_6$-alkoxy" means a linear or branched, saturated, monovalent group of formula ($C_1$-$C_6$-alkyl)-O—, in which the term "$C_1$-$C_6$-alkyl" is as defined supra, e.g. a methoxy, ethoxy, n-propoxy, isopropoxy, n-butoxy, sec-butoxy, isobutoxy, tert-butoxy, pentyloxy, isopentyloxy or n-hexyloxy group, or an isomer thereof. If the alkoxy group is used as a substituent of another constituent $C_1$-$C_3$-alkoxy is preferred.

The term "$C_3$-$C_7$-cycloalkyl" means a saturated, monovalent, mono- or bicyclic hydrocarbon ring which contains 3, 4, 5, 6, or 7 carbon atoms ("$C_3$-$C_7$-cycloalkyl"). Said $C_3$-$C_7$-cycloalkyl group is for example, a monocyclic hydrocarbon ring, e.g. a cyclopropyl, cyclobutyl, cyclopentyl, cyclohexyl, or cycloheptyl group, or a bicyclic hydrocarbon ring, e.g. a bicyclo[4.2.0]octyl or octahydropentalenyl The term "4- to 7-membered heterocycloalkyl" and "4- to 6-membered heterocycloalkyl" means a monocyclic, saturated heterocycle with 4 to 7 or, respectively, 4 to 6 ring atoms in total, which contains one or two identical or different ring heteroatoms from the series N, O and S; it being possible for said heterocycloalkyl group to be attached to the rest of the molecule via any one of the carbon atoms or, if present, a nitrogen atom.

Said heterocycloalkyl group, without being limited thereto, can be a 4-membered ring, such as azetidinyl, oxetanyl or thietanyl; or a 5-membered ring, such as tetrahydrofuranyl, 1,3-dioxolanyl, thiolanyl, pyrrolidinyl, imidazolidinyl, pyrazolidinyl, 1,1-dioxidothiolanyl, 1,2-oxazolidinyl, 1,3-oxazolidinyl or 1,3-thiazolidinyl; or a 6-membered ring, such as tetrahydropyranyl, tetrahydrothiopyranyl, piperidinyl, morpholinyl, dithianyl, thiomorpholinyl, piperazinyl, 1,3-dioxanyl, 1,4-dioxanyl or 1,2-oxazinanyl, or a 7-membered ring, such as azepanyl, 1,4-diazepanyl or 1,4-oxazepanyl for example. The term heterocycloalkyl in addition includes also fused and bridged heterocycloalkyl ring systems. Preferred are pyrrolidinyl, piperidinyl, piperazinyl and morpholinyl.

5- or 6-Membered heterocycloalkyl containing one ring nitrogen atom and optionally one further ring heteroatom from the series N or O is particularly preferred.

When the number of ring atoms permits the term "heterocycloalkyl" includes 4- to 7-membered heterocycloalkyl, fused heterocycloalkyl, bridged heterocycloalkyl and heterospirocycloalkyl.

The term "fused heterocycloalkyl" means a bicyclic, saturated heterocycle with 6 to 10 ring atoms in total, in which the two rings share two adjacent ring atoms, which "fused heterocycloalkyl" contains one or two identical or different ring heteroatoms from the series N, O and S; it being possible for said fused heterocycloalkyl group to be attached to the rest of the molecule via any one of the carbon atoms or, if present, a nitrogen atom.

Said fused heterocycloalkyl group is, for example, azabicyclo[3.1.0]hexyl, azabicyclo[3.3.0]octyl, azabicyclo[4.3.0]nonyl, diazabicyclo[4.3.0]nonyl, oxazabicyclo[4.3.0]nonyl, thiazabicyclo[4.4.0]decyl.

The term "bridged heterocycloalkyl" means a bicyclic, saturated heterocycle with 7 to 10 ring atoms in total, in which the two rings share two common ring atoms which are not adjacent, which "bridged heterocycloalkyl" contains one or two identical or different ring heteroatoms from the series N, O and S; it being possible for said bridged heterocycloalkyl group to be attached to the rest of the molecule via any one of the carbon atoms, except the spiro carbon atom, or, if present, a nitrogen atom.

Said bridged heterocycloalkyl group is, for example, azabicyclo[2.2.1]heptyl, oxazabicyclo[2.2.1]heptyl, thiazabicyclo[2.2.1]heptyl, diazabicyclo[2.2.1]heptyl, azabicyclo[2.2.2]octyl, diazabicyclo[2.2.2]octyl, oxazabicyclo[2.2.2]octyl, thiazabicyclo[2.2.2]octyl, azabicyclo[3.2.1]octyl, diazabicyclo[3.2.1]octyl, oxazabicyclo[3.2.1]octyl, thiazabicyclo[3.2.1]octyl, azabicyclo[3.3.1]nonyl, diazabicyclo[3.3.1]nonyl, oxazabicyclo[3.3.1]nonyl, thiazabicyclo[3.3.1]nonyl, azabicyclo[4.2.1]nonyl, diazabicyclo[4.2.1]nonyl, oxazabicyclo[4.2.1]nonyl, thiazabicyclo[4.2.1]nonyl azabicyclo[3.3.2]decyl, diazabicyclo[3.3.2]decyl, oxazabicyclo[3.3.2]decyl, thiazabicyclo[3.3.2]decyl or azabicyclo[4.2.2]decyl.

The term "heterospirocycloalkyl" means a bicyclic, saturated heterocycle with 6, 7, 8, 9, 10 or 11 ring atoms in total, in which the two rings share one common ring carbon atom, which "heterospirocycloalkyl" contains one or two identical or different ring heteroatoms from the series: N, O, S; it being possible for said heterospirocycloalkyl group to be attached to the rest of the molecule via any one of the carbon atoms, except the spiro carbon atom, or, if present, a nitrogen atom.

Said heterospirocycloalkyl group is, for example, azaspiro[2.3]hexyl, aza-spiro[3.3]heptyl, oxaazaspiro[3.3]heptyl, thiaazaspiro[3.3]heptyl, oxaspiro[3.3]heptyl, oxazaspiro[5.3]nonyl, oxazaspiro[4.3]octyl, azaspiro[4,5]decyl, oxazaspiro [5.5]undecyl, diazaspiro[3.3]heptyl, thiazaspiro[3.3]heptyl, thiazaspiro[4.3]octyl, azaspiro[5.5]undecyl, or one of the further homologous scaffolds such as spiro[3.4]-, spiro[4.4]-, spiro[2.4]-, spiro[2.5]-, spiro[2.6]-, spiro[3.5]-, spiro[3.6]-, spiro[4.5]- and spiro[4.6]-.

The term "heteroaryl" is understood as meaning a monovalent, monocyclic, bicyclic or tricyclic aromatic ring system having 5, 6, 8, 9, 10, 11, 12, 13 or 14 ring atoms (a "5- to 14-membered heteroaryl" group), particularly 5, 6, 9 or 10 ring atoms, which contains at least one ring heteroatom and optionally one, two or three further ring heteroatoms from the series N, O and/or S, and which is bound via a ring carbon atom or optionally via a ring nitrogen atom (when allowed by valency).

Said heteroaryl group can be a 5-membered heteroaryl group, such as, for example, thienyl, furanyl, pyrrolyl, oxazolyl, thiazolyl, imidazolyl, pyrazolyl, isoxazolyl, isothiazolyl, oxadiazolyl, triazolyl, thiadiazolyl or tetrazolyl; or a 6-membered heteroaryl group, such as, for example, pyridinyl, pyridazinyl, pyrimidinyl, pyrazinyl or triazinyl; or a bicyclic 9-membered heteroaryl group, such as, for example, benzofuranyl, benzothienyl, benzoxazolyl, benzisoxazolyl, benzimidazolyl, benzothiazolyl, benzotriazolyl, indazolyl, indolyl, isoindolyl, indolizinyl or purinyl; or a 10-membered heteroaryl group, such as, for example, quinolinyl, quinazolinyl, isoquinolinyl, cinnolinyl, phthalazinyl, quinoxalinyl or pteridinyl or a tricyclic heteroaryl group, such as, for example, carbazolyl, acridinyl or phenazinyl. Monocyclic heteroaryl groups are preferred.

In general, and unless otherwise mentioned, the heteroarylic or heteroarylenic radicals include all possible isomeric forms thereof, e.g.: tautomers and positional isomers with respect to the point of linkage to the rest of the molecule. Thus, for some illustrative non restricting example, the term pyridinyl includes pyridin-2-yl, pyridin-3-yl and pyridin-4-yl; or the term thienyl includes thien-2-yl and thien-3-yl.

The term indicating a number of carbon atoms such as e.g. "$C_1$-$C_6$", as used throughout this text, e.g. in the context of any definition such as e.g. "$C_1$-$C_6$-alkyl", "$C_1$-$C_6$-hydroxyalkyl", or "$C_1$-$C_6$-alkoxy" means an alkyl group having a finite number of carbon atoms of 1 to 6, i.e. 1, 2, 3, 4, 5 or 6 carbon atoms.

Further, as used herein, the term "$C_3$-$C_7$", as used throughout this text, e.g. in the context of the definition of "$C_3$-$C_7$-cycloalkyl", means a cycloalkyl group having a finite number of carbon atoms of 3 to 8, i.e. 3, 4, 5, 6, 7 or 8 carbon atoms.

When a range of values is listed, it is intended to encompass each value and sub-range within the range.

For example, "$C_1$-$C_6$" is intended to encompass $C_1$, $C_2$, $C_3$, $C_4$, $C_5$, $C_6$, $C_1$-$C_6$, $C_1$-$C_5$, $C_1$-$C_4$, $C_1$-$C_3$, $C_1$-$C_2$, $C_2$-$C_6$, $C_2$-$C_5$, $C_2$-$C_4$, $C_2$-$C_3$, $C_3$-$C_6$, $C_3$-$C_5$, $C_3$-$C_4$, $C_4$-$C_6$, $C_4$-$C_5$, and $C_5$-$C_6$.

For example, "$C_2$-$C_6$" is intended to encompass $C_2$, $C_3$, $C_4$, $C_5$, $C_6$, $C_2$-$C_6$, $C_2$-$C_5$, $C_2$-$C_4$, $C_2$-$C_3$, $C_3$-$C_6$, $C_3$-$C_5$, $C_3$-$C_4$, $C_4$-$C_6$, $C_4$-$C_5$, and $C_5$-$C_6$.

For example, "$C_3$-$C_{10}$" is intended to encompass $C_3$, $C_4$, $C_5$, $C_6$, $C_7$, $C_8$, $C_9$, $C_{10}$, $C_3$-$C_{10}$, $C_3$-$C_9$, $C_3$-$C_8$, $C_3$-$C_7$, $C_3$-$C_6$, $C_3$-$C_5$, $C_3$-$C_4$, $C_4$-$C_{10}$, $C_4$-$C_9$, $C_4$-$C_8$, $C_4$-$C_7$, $C_4$-$C_6$, $C_4$-$C_5$, $C_5$-$C_{10}$, $C_5$-$C_9$, $C_5$-$C_8$, $C_5$-$C_7$, $C_5$-$C_6$, $C_6$-$C_{10}$, $C_6$-$C_9$, $C_6$-$C_8$, $C_6$-$C_7$, $C_7$-$C_{10}$, $C_7$-$C_9$, $C_7$-$C_8$, $C_8$-$C_{10}$, $C_8$-$C_9$ and $C_9$-$C_{10}$.

For example, "$C_3$-$C_8$" is intended to encompass $C_3$, $C_4$, $C_5$, $C_6$, $C_7$, $C_8$, $C_3$-$C_8$, $C_3$-$C_7$, $C_3$-$C_6$, $C_3$-$C_5$, $C_3$-$C_4$, $C_4$-$C_8$, $C_4$-$C_7$, $C_4$-$C_6$, $C_4$-$C_5$, $C_5$-$C_8$, $C_5$-$C_7$, $C_5$-$C_6$, $C_6$-$C_8$, $C_6$-$C_7$ and $C_7$-$C_8$.

For example, "$C_3$-$C_6$" is intended to encompass $C_3$, $C_4$, $C_5$, $C_6$, $C_3$-$C_6$, $C_3$-$C_5$, $C_3$-$C_4$, $C_4$-$C_6$, $C_4$-$C_5$, and $C_5$-$C_6$.

For example, "$C_4$-$C_8$" is intended to encompass $C_4$, $C_5$, $C_6$, $C_7$, $C_8$, $C_4$-$C_8$, $C_4$-$C_7$, $C_4$-$C_6$, $C_4$-$C_5$, $C_5$-$C_8$, $C_5$-$C_7$, $C_5$-$C_6$, $C_6$-$C_8$, $C_6$-$C_7$ and $C_7$-$C_8$.

For example, "$C_4$-$C_7$" is intended to encompass $C_4$, $C_5$, $C_6$, $C_7$, $C_4$-$C_7$, $C_4$-$C_6$, $C_4$-$C_5$, $C_5$-$C_7$, $C_5$-$C_6$ and $C_6$-$C_7$.

For example, "$C_4$-$C_6$" is intended to encompass $C_4$, $C_5$, $C_6$, $C_4$-$C_6$, $C_4$-$C_5$ and $C_5$-$C_6$.

For example, "$C_4$-$C_{10}$" is intended to encompass $C_5$, $C_6$, $C_7$, $C_8$, $C_9$, $C_{10}$, $C_5$-$C_{10}$, $C_5$-$C_9$, $C_5$-$C_8$, $C_5$-$C_7$, $C_5$-$C_6$, $C_6$-$C_{10}$, $C_6$-$C_9$, $C_6$-$C_8$, $C_6$-$C_7$, $C_7$-$C_{10}$, $C_7$-$C_9$, $C_7$-$C_8$, $C_8$-$C_{10}$, $C_8$-$C_9$ and $C_9$-$C_{10}$.

For example, "$C_6$-$C_{10}$" is intended to encompass $C_6$, $C_7$, $C_8$, $C_9$, $C_{10}$, $C_6$-$C_{10}$, $C_6$-$C_9$, $C_6$-$C_8$, $C_6$-$C_7$, $C_7$-$C_{10}$, $C_7$-$C_9$, $C_7$-$C_8$, $C_8$-$C_{10}$, $C_8$-$C_9$ and $C_9$-$C_{10}$.

As used herein, the term "leaving group" refers to an atom or a group of atoms that is displaced in a chemical reaction as stable species taking with it the bonding electrons. Preferably, a leaving group is selected from the group comprising: halide, in particular fluoride, chloride, bromide or iodide, (methylsulfonyl)oxy, [(trifluoromethyl)sulfonyl]oxy, [(nonafluorobutyl)sulfonyl]oxy, (phenylsulfonyl)oxy, [(4-methylphenyl) sulfonyl]oxy, [(4-bromophenyl)sulfonyl]oxy, [(4-nitro-phenyl)sulfonyl]oxy, [(2-nitrophenyl)sulfonyl]oxy, [(4-isopropylphenyl)sulfonyl]oxy, [(2,4,6-triisopropylphenyl)sulfonyl]oxy, [(2,4,6-trimethylphenyl)sulfonyl]oxy, [(4-tert-butylphenyl)sulfonyl]oxy and [(4-methoxyphenyl)sulfonyl]oxy.

A symbol * at a bond indicates the point of attachment in the molecule.

A symbol # at a carbon atom indicates that the compound is present in enantiomerically pure form in respect of the configuration at said carbon atom, which, in the context of the present invention, is understood as meaning an enantiomeric excess of more than 90% (>90% ee).

In some embodiments, the present invention relates to compounds of general formula (I) in which the halogen atom of $R^1$ is a chlorine atom.

In other embodiments the present invention relates to compounds of general formula (I) in which $R^2$ is a hydroxyalkyl group.

In further embodiments the present invention relates to compounds of general formula (I) in which $R^2$ is a —$C_{1-3}$-alkylen-NH-heterocycloalkyl group which is optionally substituted independently from each occurrence one or more times with $C_{1-4}$-alkyl, halogen, benzyl, $C(O)R^7$.

In other embodiments the present invention relates to compounds of general formula (I) in which $R^2$ is hydroxyalkyl group or a —$C_{1-3}$-alkylen-NH-heterocycloalkyl group which is optionally substituted independently from each occurrence one or more times with $C_{1-4}$-alkyl, halogen, benzyl, $C(O)R^7$.

In further embodiments the present invention relates to compounds of general formula (I) in which $R^2$ is a —$C_{1-3}$-alkylen-heterocycloalkyl group which is optionally one or more times substituted with $C_{1-3}$-alkyl.

In certain embodiments, the present invention relates to compounds of general formula (I), in which $R^2$ represents a $C_{1-5}$-hydroxyalkylen group or a —$C_{1-3}$alkylen-heterocycloalkyl group of which the hetrocycloalkyl part is optionally substituted once or twice by methyl.

In certain such embodiments, the present invention relates to compounds of general formula (I), in which $R^2$ represents a $C_{1-5}$-hydroxyalkylen group or a —$C_{1-3}$alkylen-heterocycloalkyl group of which the hetrocycloalkyl part is optionally substituted once or twice by methyl or a —$C_{1-3}$-alkylen-heterocycloalkyl group which is optionally one or more times substituted with $C_{1-3}$-alkyl.

In certain embodiments, the present invention relates to compounds of general formula (I), in which $R^3$ represents a —$CH_2$-(4-cyano-phenyl) group.

In certain other embodiments, the present invention relates to compounds of general formula (I), in which $R^3$ represents a —CH2-phenyl group which is substituted one, two or three times independently with cyano, methyl, fluorine, iodine, methoxy, amino, aminocarbonyl, with the provision that within one compound if there occur more than one substituent the substitutents of said phenyl ring are different from each other.

In certain embodiments, the present invention relates to compounds of general formula (I), in which $R^4$ represents a chlorine atom.

In certain embodiments, the present invention relates to compounds of general formula (I), in which $R^5$ represents a hydrogen atom or a fluorine atom.

In certain embodiments, the present invention relates to compounds of general formula (I), in which $R^5$ represents a hydrogen atom.

In certain preferred embodiments, the present invention relates to compounds of general formula (I), in which $R^5$ represents a fluorine atom.

In certain embodiments, the present invention relates to compounds of general formula (I), in which $R^6$ represents a halogen atom, preferably a chlorine atom, a hydroxy group or a $C_{1-3}$-alkyoxy group.

In certain embodiments, the present invention relates to compounds of general formula (I), in which $R^6$ represents a hydrogen atom.

In certain embodiments, the present invention relates to compounds of general formula (I), in which $R^8$ and $R^9$ represent a hydrogen atom or a methyl group.

In certain embodiments, the present invention relates to compounds of general formula (I), especially the salts, solvates or solvates of the salts of the embodiments mentioned above.

It is possible for the compounds of general formula (I) to exist as isotopic variants. The invention therefore includes one or more isotopic variant(s) of the compounds of general formula (I), particularly deuterium-containing compounds of general formula (I).

By "stable compound" or "stable structure" is meant a compound that is sufficiently robust to survive isolation to a useful degree of purity from a reaction mixture, and formulation into an efficacious therapeutic agent.

The term "Isotopic variant" of a compound or a reagent is defined as a compound exhibiting an unnatural proportion of one or more of the isotopes that constitute such a compound.

The term "Isotopic variant of the compound of general formula (I)" is defined as a compound of general formula (I) exhibiting an unnatural proportion of one or more of the isotopes that constitute such a compound.

The expression "unnatural proportion" means a proportion of such isotope which is higher than its natural abundance. The natural abundances of isotopes to be applied in this context are described in "Isotopic Compositions of the Elements 1997", Pure Appl. Chem., 70(1), 217-235, 1998.

Examples of such isotopes include stable and radioactive isotopes of hydrogen, carbon, nitrogen, oxygen, phosphorus, sulfur, fluorine, chlorine, bromine and iodine, such as $^2H$ (deuterium), $^3H$ (tritium), $^{11}C$, $^{13}C$, $^{14}C$, $^{15}N$, $^{17}O$, $^{18}O$, $^{32}P$, $^{33}P$, $^{33}S$, $^{34}S$, $^{35}S$, $^{36}S$, $^{18}F$, $^{36}Cl$, $^{82}Br$, $^{123}I$, $^{124}I$, $^{125}I$, $^{129}I$ and $^{131}I$, respectively.

With respect to the treatment and/or prophylaxis of the disorders specified herein the isotopic variant(s) of the compounds of general formula (I) preferably contain deuterium ("deuterium-containing compounds of general formula (I)"). Isotopic variants of the compounds of general formula (I) in which one or more radioactive isotopes, such as $^3H$ or $^{14}C$, are incorporated are useful e.g. in drug and/or substrate tissue distribution studies. These isotopes are particularly preferred for the ease of their incorporation and detectability. Positron emitting isotopes such as $^{18}F$ or $^{11}C$ may be incorporated into a compound of general formula (I). These isotopic variants of the compounds of general formula (I) are useful for in vivo imaging applications. Deuterium-containing and $^{13}C$-containing compounds of general formula (I) can be used in mass spectrometry analyses in the context of preclinical or clinical studies.

Isotopic variants of the compounds of general formula (I) can generally be prepared by methods known to a person skilled in the art, such as those described in the schemes and/or examples herein, by substituting a reagent for an isotopic variant of said reagent, preferably for a deuterium-containing reagent. Depending on the desired sites of deuteration, in some cases deuterium from $D_2O$ can be incorporated either directly into the compounds or into reagents that are useful for synthesizing such compounds. Deuterium gas is also a useful reagent for incorporating deuterium into molecules. Catalytic deuteration of olefinic bonds and acetylenic bonds is a rapid route for incorporation of deuterium. Metal catalysts (i.e. Pd, Pt, and Rh) in the presence of deuterium gas can be used to directly exchange deuterium for hydrogen in functional groups containing hydrocarbons. A variety of deuterated reagents and synthetic building blocks are commercially available from companies such as for example C/D/N Isotopes, Quebec, Canada; Cambridge Isotope Laboratories Inc., Andover, Mass., USA; and CombiPhos Catalysts, Inc., Princeton, N.J., USA.

The term "deuterium-containing compound of general formula (I)" is defined as a compound of general formula (I), in which one or more hydrogen atom(s) is/are replaced by one or more deuterium atom(s) and in which the abundance of deuterium at each deuterated position of the compound of general formula (I) is higher than the natural abundance of deuterium, which is about 0.015%. Particularly, in a deuterium-containing compound of general formula (I) the abundance of deuterium at each deuterated position of the compound of general formula (I) is higher than 10%, 20%, 30%, 40%, 50%, 60%, 70% or 80%, preferably higher than 90%, 95%, 96% or 97%, even more preferably higher than 98% or 99% at said position(s). It is understood that the abundance of deuterium at each deuterated position is independent of the abundance of deuterium at other deuterated position(s).

The selective incorporation of one or more deuterium atom(s) into a compound of general formula (I) may alter the physicochemical properties (such as for example acidity [C. L. Perrin, et al., J. Am. Chem. Soc., 2007, 129, 4490], basicity [C. L. Perrin et al., J. Am. Chem. Soc., 2005, 127, 9641], lipophilicity [B. Testa et al., Int. J. Pharm., 1984, 19(3), 271]) and/or the metabolic profile of the molecule and may result in changes in the ratio of parent compound to metabolites or in the amounts of metabolites formed. Such changes may result in certain therapeutic advantages and hence may be preferred in some circumstances. Reduced rates of metabolism and metabolic switching, where the ratio of metabolites is changed, have been reported (A. E. Mutlib et al., Toxicol. Appl. Pharmacol., 2000, 169, 102). These changes in the exposure to parent drug and metabolites can have important consequences with respect to the pharmacodynamics, tolerability and efficacy of a deuterium-containing compound of general formula (I). In some cases deuterium substitution reduces or eliminates the formation of an undesired or toxic metabolite and enhances the formation of a desired metabolite (e.g. Nevirapine: A. M. Sharma et al., Chem. Res. Toxicol., 2013, 26, 410; Efavirenz: A. E. Mutlib et al., Toxicol. Appl. Pharmacol., 2000, 169, 102). In other cases the major effect of deuteration is to reduce the rate of systemic clearance. As a result, the biological half-life of the compound is increased. The potential clinical benefits would include the ability to maintain similar systemic exposure with decreased peak levels and increased trough levels. This could result in lower side effects and enhanced efficacy, depending on the particular compound's pharmacokinetic/pharmacodynamic relationship. ML-337 (C. J. Wenthur et al., J. Med. Chem., 2013, 56, 5208) and Odanacatib (K. Kassahun et al., WO2012/112363) are examples for this deuterium effect. Still other cases have been reported in which reduced rates of metabolism result in an increase in exposure of the drug without changing the rate of systemic clearance (e.g. Rofecoxib: F. Schneider et al., Arzneim. Forsch./Drug. Res., 2006, 56, 295; Telaprevir: F. Maltais et al., J. Med. Chem., 2009, 52, 7993). Deuterated drugs showing this effect may have reduced dosing requirements (e.g. lower number of doses or lower dosage to achieve the desired effect) and/or may produce lower metabolite loads.

A compound of general formula (I) may have multiple potential sites of attack for metabolism. To optimize the above-described effects on physicochemical properties and metabolic profile, deuterium-containing compounds of general formula (I) having a certain pattern of one or more deuterium-hydrogen exchange(s) can be selected. Particularly, the deuterium atom(s) of deuterium-containing compound(s) of general formula (I) is/are attached to a carbon atom and/or is/are located at those positions of the compound of general formula (I), which are sites of attack for metabolizing enzymes such as e.g. cytochrome $P_{450}$.

The compounds of the present invention contain one or more asymmetric centres, depending upon the location and nature of the various substituents desired. It is possible that one or more asymmetric carbon atoms are present in the (R) or (S) configuration, which can result in racemic mixtures in the case of a single asymmetric centre, and in diastereomeric mixtures in the case of multiple asymmetric centres. In certain instances, it is possible that asymmetry also be present due to restricted rotation about a given bond, for example, the central bond adjoining two substituted aromatic rings of the specified compounds.

Preferred compounds are those which produce the more desirable biological activity if both enantiomers or diastereomers show different activity. Separated, pure or partially purified isomers and stereoisomers or racemic or diastereomeric mixtures of the compounds of the present invention are also included within the scope of the present invention. The purification and the separation of such materials can be accomplished by standard techniques known in the art.

These separated, pure or partially purified isomers or racemic mixtures of the compounds of this invention are also included within the scope of the present invention. The purification and the separation of such materials can be accomplished by standard techniques known in the art.

The optical isomers can be obtained by resolution of the racemic mixtures according to conventional processes, for example, by the formation of diastereoisomeric salts using an optically active acid or base or formation of covalent diastereomers. Examples of appropriate acids are tartaric, diacetyltartaric, ditoluoyltartaric and camphorsulfonic acid. Mixtures of diastereoisomers can be separated into their individual diastereomers on the basis of their physical and/or chemical differences by methods known in the art, for example, by chromatography or fractional crystallisation. The optically active bases or acids are then liberated from the separated diastereomeric salts. A different process for separation of optical isomers involves the use of chiral chromatography (e.g., HPLC columns using a chiral phase), with or without conventional derivatisation, optimally chosen to maximise the separation of the enantiomers. Suitable HPLC columns using a chiral phase are commercially available, such as those manufactured by Daicel, e.g., Chiracel OD and Chiracel OJ, for example, among many others, which are all routinely selectable. Enzymatic separations, with or without derivatisation, are also useful. The optically active compounds of the present invention can likewise be obtained by chiral syntheses utilizing optically active starting materials.

In order to distinguish different types of isomers from each other reference is made to IUPAC Rules Section E (Pure Appl Chem 45, 11-30, 1976).

The present invention includes all possible stereoisomers of the compounds of the present invention as single stereoisomers, or as any mixture of said stereoisomers, e.g. (R)- or (S)-isomers, in any ratio. Isolation of a single stereoisomer, e.g. a single enantiomer or a single diastereomer, of a compound of the present invention is achieved by any suitable state of the art method, such as chromatography, especially chiral chromatography, for example.

Further, it is possible for the compounds of the present invention to exist as tautomers. For example, any compound of the present invention which contains an imidazopyridine moiety as a heteroaryl group for example can exist as a 1H tautomer, or a 3H tautomer, or even a mixture in any amount of the two tautomers, namely:

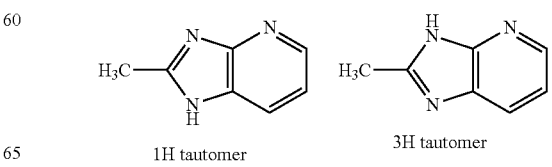

1H tautomer     3H tautomer

The present invention includes all possible tautomers of the compounds of the present invention as single tautomers, or as any mixture of said tautomers, in any ratio.

The present invention also covers useful forms of the compounds of the present invention, such as metabolites, hydrates, solvates, prodrugs, salts, in particular pharmaceutically acceptable salts, and/or co-precipitates.

The compounds of the present invention can exist as a hydrate, or as a solvate, wherein the compounds of the present invention contain polar solvents, in particular water, methanol or ethanol for example, as structural element of the crystal lattice of the compounds. It is possible for the amount of polar solvents, in particular water, to exist in a stoichiometric or non-stoichiometric ratio. In the case of stoichiometric solvates, e.g. a hydrate, hemi-, (semi-), mono-, sesqui-, di-, tri-, tetra-, penta-etc. solvates or hydrates, respectively, are possible. The present invention includes all such hydrates or solvates.

Further, it is possible for the compounds of the present invention to exist in free form, e.g. as a free base, or as a free acid, or as a zwitterion, or to exist in the form of a salt. Said salt may be any salt, either an organic or inorganic addition salt, particularly any pharmaceutically acceptable organic or inorganic addition salt, which is customarily used in pharmacy, or which is used, for example, for isolating or purifying the compounds of the present invention.

The term "pharmaceutically acceptable salt" refers to an inorganic or organic acid addition salt of a compound of the present invention. For example, see S. M. Berge, et al. "Pharmaceutical Salts," J. Pharm. Sci. 1977, 66, 1-19.

A suitable pharmaceutically acceptable salt of the compounds of the present invention may be, for example, an acid-addition salt of a compound of the present invention bearing a nitrogen atom, in a chain or in a ring, for example, which is sufficiently basic, such as an acid-addition salt with an inorganic acid, or "mineral acid", such as hydrochloric, hydrobromic, hydroiodic, sulfuric, sulfamic, bisulfuric, phosphoric, or nitric acid, for example, or with an organic acid, such as formic, acetic, acetoacetic, pyruvic, trifluoroacetic, propionic, butyric, hexanoic, heptanoic, undecanoic, lauric, benzoic, salicylic, 2-(4-hydroxybenzoyl)-benzoic, camphoric, cinnamic, cyclopentanepropionic, digluconic, 3-hydroxy-2-naphthoic, nicotinic, pamoic, pectinic, 3-phenylpropionic, pivalic, 2-hydroxyethanesulfonic, itaconic, trifluoromethanesulfonic, dodecylsulfuric, ethanesulfonic, benzenesulfonic, para-toluenesulfonic, methanesulfonic, 2-naphthalenesulfonic, naphthalinedisulfonic, camphorsulfonic acid, citric, tartaric, stearic, lactic, oxalic, malonic, succinic, malic, adipic, alginic, maleic, fumaric, D-gluconic, mandelic, ascorbic, glucoheptanoic, glycerophosphoric, aspartic, sulfosalicylic, or thiocyanic acid, for example.

Further, another suitably pharmaceutically acceptable salt of a compound of the present invention which is sufficiently acidic, is an alkali metal salt, for example a sodium or potassium salt, an alkaline earth metal salt, for example a calcium, magnesium or strontium salt, or an aluminium or a zinc salt, or an ammonium salt derived from ammonia or from an organic primary, secondary or tertiary amine having 1 to 20 carbon atoms, such as ethylamine, diethylamine, triethylamine, ethyldiisopropylamine, monoethanolamine, diethanolamine, triethanolamine, dicyclohexylamine, dimethylaminoethanol, diethylaminoethanol, tris(hydroxymethyl)aminomethane, procaine, dibenzylamine, N-methylmorpholine, arginine, lysine, 1,2-ethylenediamine, N-methylpiperidine, N-methyl-glucamine, N,N-dimethyl-glucamine, N-ethyl-glucamine, 1,6-hexanediamine, glucosamine, sarcosine, serinol, 2-amino-1,3-propanediol, 3-amino-1,2-propanediol, 4-amino-1,2,3-butanetriol, or a salt with a quarternary ammonium ion having 1 to 20 carbon atoms, such as tetramethylammonium, tetraethylammonium, tetra(n-propyl)ammonium, tetra(n-butyl)ammonium, N-benzyl-N,N,N-trimethylammonium, choline or benzalkonium.

Those skilled in the art will further recognise that it is possible for acid addition salts of the claimed compounds to be prepared by reaction of the compounds with the appropriate inorganic or organic acid via any of a number of known methods. Alternatively, alkali and alkaline earth metal salts of acidic compounds of the present invention are prepared by reacting the compounds of the present invention with the appropriate base via a variety of known methods.

The present invention includes all possible salts of the compounds of the present invention as single salts, or as any mixture of said salts, in any ratio.

Syntheses of Compounds (Overview)

The following schemes and general procedures illustrate general synthetic routes to the compounds of general formula (I) of the invention and are not intended to be limiting. It is obvious to the person skilled in the art that the order of transformations as exemplified in Schemes 1, 2, 3, 4 and 5 can be modified in various ways. The order of transformations exemplified in the Schemes is therefore not intended to be limiting. In addition, interconversion of substituents, for example of residues $R^1$, $R^2$, $R^3$, $R^4$ and $R^5$ can be achieved before and/or after the exemplified transformations. These modifications can be such as the introduction of protecting groups, cleavage of protecting groups, reduction or oxidation of functional groups, halogenation, metallation, substitution or other reactions known to the person skilled in the art. These transformations include those which introduce a functionality which allows for further interconversion of substituents. Appropriate protecting groups and their introduction and cleavage are well-known to the person skilled in the art (see for example T. W. Greene and P. G. M. Wuts, *Protective Groups in Organic Synthesis,* 3rd edition, Wiley 1999).

Specific examples are described in the subsequent paragraphs. Further, it is possible that two or more successive steps may be performed without work-up being performed between said steps, e.g. in a "one-pot" reaction, as it is well-known to a person skilled in the art. For the purposes of the processes and intermediates as described below the meaning of the residues on the reactants if not defined specifically here can be derived from the disclosure in the specification and claims.

Scheme 1:

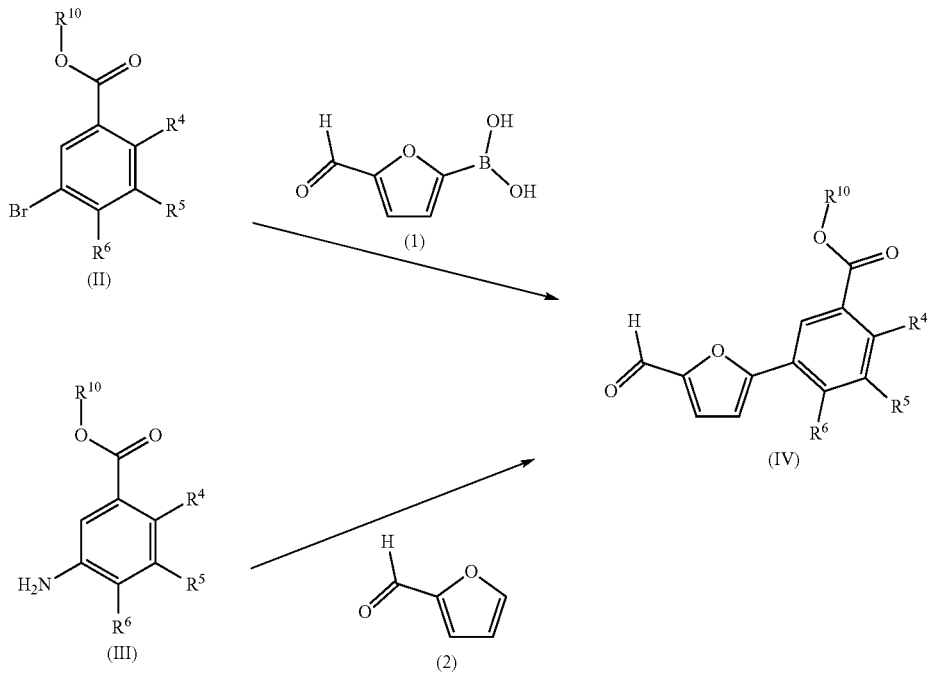

Scheme 1:

Preparation of intermediates of the general formula (IV), starting from bromo benzoic esters of general formula (II) and amino benzoic esters of general formula (III), wherein $R^4$, $R^5$ and $R^6$ are as defined for the compounds of general formula (I) in claim 1, and $R^{10}$ represents a $C_1$-$C_4$-alkyl group, especially a tert.butyl group or a benzyl group.

The compounds of the formula (IV) can be prepared analogously to processes which are well-known to the person skilled in the art, for example by a Suzuky-Miyaura coupling of 5-formylfuran-2-ylboronic acid (1) with the bromo benzoic esters of general formula (II) under palladium catalysis, as described by A. R. Katritzky, et al. Journal of Medicinal Chemistry 2009, 52, 7631-7639, or by a Meerwein arylation process of 2-furfuraldehyde (2) with the amino benzoic esters of general formula (III) using sodium nitrite and copper dichloride as described by L. He et al. Journal of Medicinal Chemistry 2009, 52, 2465ff.

The bromo benzoic esters of general formula (II) and the amino benzoic esters of general formula (III) are either commercially available or can be prepared by methods which are well-known to the person skilled in the art.

Scheme 2:

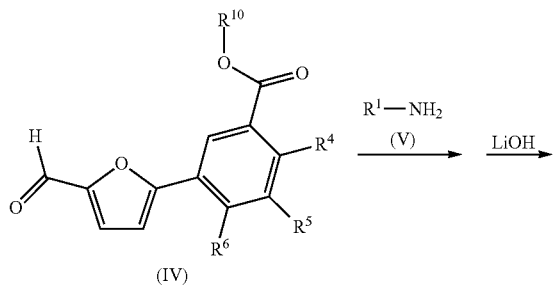

-continued

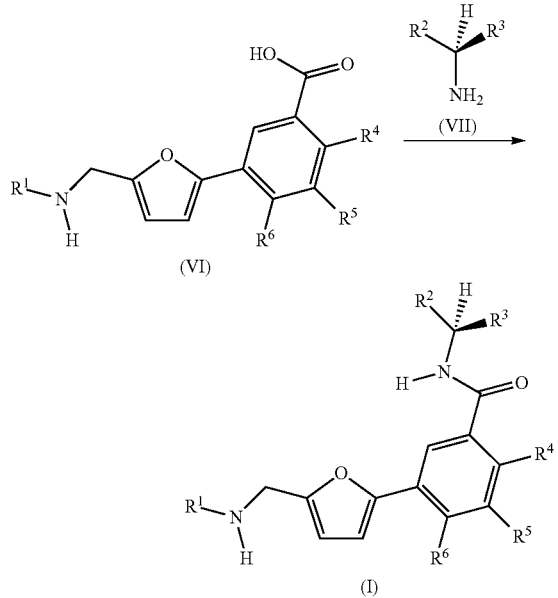

Scheme 2:

Preparation of compounds of the general formula (I), starting from furan-carbaldehyde derivatives of general formula (IV), wherein $R^1$, $R^2$, $R^3$, $R^4$, $R^5$ and $R^6$ are as defined for the compounds of general formula (I) supra, and $R^{10}$ represents a $C_1$-$C_4$-alkyl group or a benzyl group.

Scheme 2 outlines the preparation of compounds of the formula (I), in which $R^1$, $R^2$, $R^3$, $R^4$, $R^5$ and $R^6$ are as defined supra, starting from furan-carbaldehyde derivatives of general formula (IV), which can be converted into the compounds of general formula (VI) by means of a reductive amination of the aldehyde formula (IV) by the corresponding amine of general formula (V), wherein $R^1$ is as defined for the compounds of general formula (I) supra, using reducing agents which are well-known to the person skilled in the art, such as for example sodium triacetoxy borohydride, as described by A. F. Abdel-Magid and S. J. Mehrman in Organic Process Research & Development 2006, 10, 971ff, followed by basic saponification of the ester moiety, using a base such as for example lithium hydroxide or sodium hydroxide in a solvent system, such as for example a mixture of water with tetrahydrofuran or with methanol or with both.

The compounds of the general formula (I) can be prepared by coupling of the carboxylic acids of general formula (VI) with the amines of general formula (VII), employing coupling reagents which are well-known to the person skilled in the art, such as for example O-(Benzotriazol-1-yl)-N,N,N',N'-tetramethyluroniumtetra-fluoroborate (TBTU) or [O-(7-Azabenzotriazol-1-yl)-N,N,N',N'-tetramethyluronium-hexafluorphosphate] (HATU), as described for example by I. Abdelmoty et al in Lett. Pept. Sci. 1994, 1, 57 and F. Albericio et al. in J. Org. Chem. 1998, 63, 9678ff. Alternatively, the amide coupling reaction can be performed by reaction of the corresponding acid chlorides of the carboxylic acids of general formula (VI) with the amines of general formula (VII). Methods for the preparation of acid chlorides from carboxylic acid are well-known to the person skilled in the art.

Scheme 3:

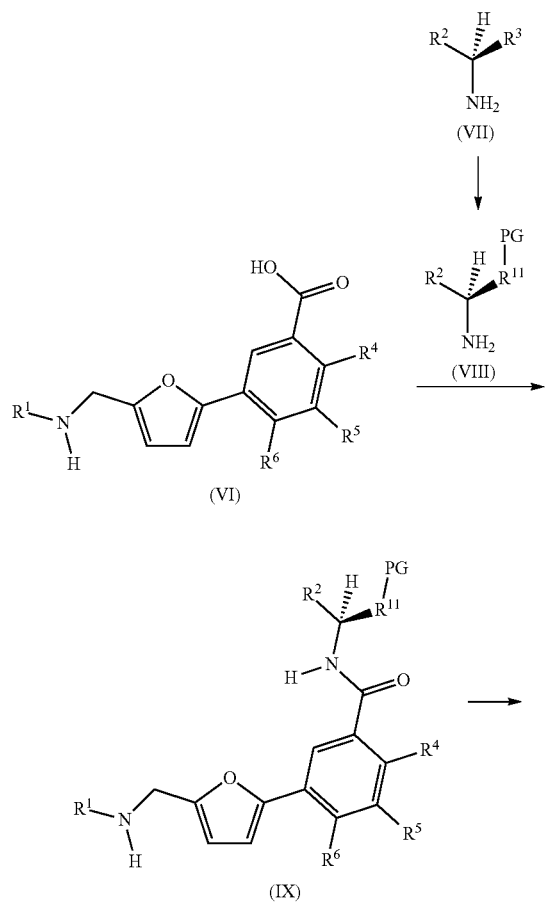

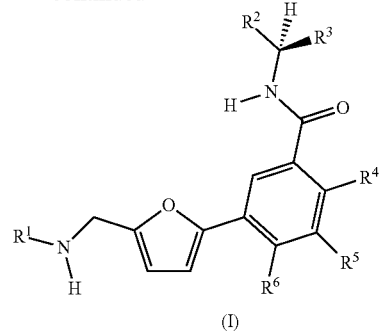

Scheme 3:

Preparation of compounds of the general formula (I), starting from carboxylic acids of general formula (VI) and amines of general formula (VIII), wherein $R^1$, $R^2$, $R^3$, $R^4$, $R^5$ and $R^6$ are as defined for the compounds of general formula (I) supra, and wherein $R^{11}$—PG represents a group $R^3$ which contains a primary or secondary amino group, as defined for the compounds of general formula (I) supra, which primary or secondary amino group is masked with a protective group.

The respective primary or secondary amino group of $R^3$ of the compounds of general formula (VII) can be protected in several ways, which are well-known to the person skilled in the art, for example with a tert-butoxycarbonyl (BOC) group or as a phtalimide to yield compounds of the general formula (VIII).

The compounds of the general formula (IX) can be prepared by coupling of the carboxylic acids of general formula (VI) with the protected amines of general formula (VIII), employing coupling reagents, which are well-known to the person skilled in the art, such as for example TBTU or HATU, as described by I. Abdelmoty et al in Lett. Pept. Sci. 1994, 1, 57 and F. Albericio et al. in J. Org. Chem. 1998, 63, 9678ff.

Alternatively, the amide coupling reaction can be performed by reaction of the corresponding acid chlorides of the carboxylic acids of general formula (VI) with the amines of general formula (VIII). Methods for the preparation of acid chlorides from carboxylic acid are well-known to the person skilled in the art.

The compounds of general formula (I) can be prepared from the compounds of general formula (IX) by cleavage of the protecting groups. This can be achieved by standard procedures, which are well-known to the person skilled in the art (see for example T. W. Greene and P. G. M. Wuts, Protective Groups in Organic Synthesis, 3rd edition, Wiley 1999). BOC groups can be cleaved for example by treatment with strong acids, such as trifluoroacetic acid, in solvents such as for example dichloromethane, or by treatment with hydrochloric acid in solvents, such as for example methanol or 1,4-dioxane or mixtures thereof. Phtalimides can be cleaved for example by treatment with hydrazine, in solvents such as for example ethanol or tetrahydrofuran or mixtures thereof.

Scheme 4:

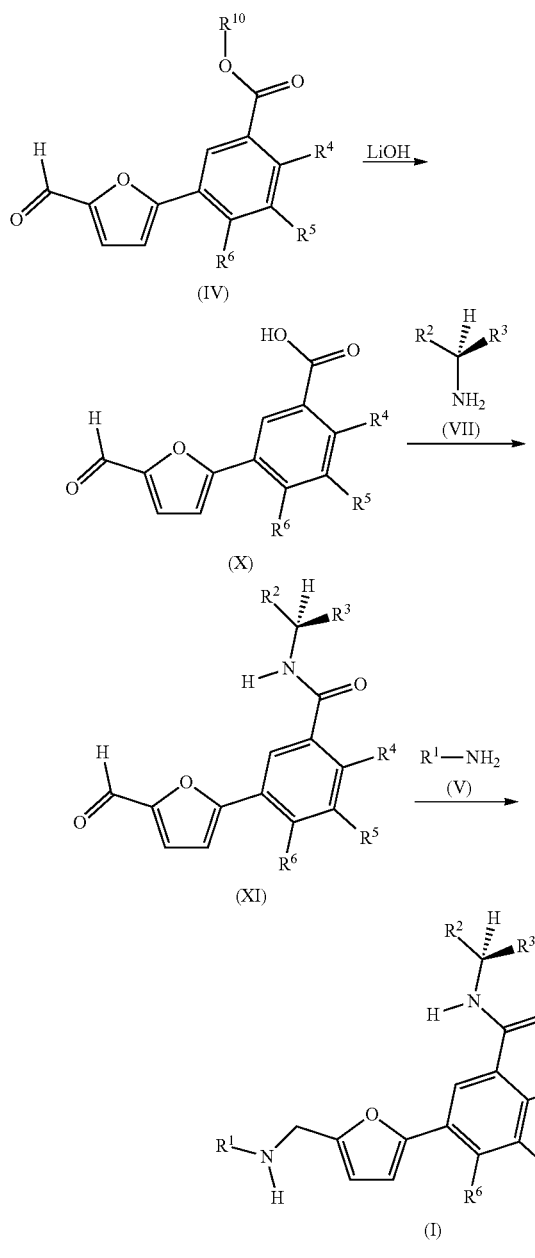

Scheme 4:

Alternative preparation of compounds of the general formula (I), starting from furan-carbaldehyde derivatives of general formula (IV), wherein $R^1$, $R^2$, $R^3$, $R^4$, $R^5$ and $R^6$ are as defined for the compounds of general formula (I) supra, and $R^{10}$ represents a $C_1$-$C_4$-alkyl group or a benzyl group.

Scheme 4 outlines the preparation of compounds of the formula (I), in which $R^1$, $R^2$, $R^3$, $R^4$, $R^5$ and $R^6$ are as defined supra, starting from furan-carbaldehyde derivatives of general formula (IV), which can be converted into the compounds of general formula (X) by basic saponification of the ester moiety, using a base such as for example lithium hydroxide or sodium hydroxide in a solvent system, such as for example a mixture of water with tetrahydrofuran or with methanol or with both.

The compounds of the general formula (XI) can be prepared by coupling of the carboxylic acids of general formula (X) with the amines of general formula (VII), employing coupling reagents which are well-known to the person skilled in the art, such as for example TBTU or HATU, as described for example by I. Abdelmoty et al in Lett. Pept. Sci. 1994, 1, 57 and F. Albericio et al. in J. Org. Chem. 1998, 63, 9678ff.

Alternatively, the amide coupling reaction can be performed by reaction of the corresponding acid chlorides of the carboxylic acids of general formula (X) with the amines of general formula (VII). Methods for the preparation of acid chlorides from carboxylic acid are well-known to the person skilled in the art.

The compounds of the general formula (I) can be prepared by means of a reductive amination of the aldehyde formula (XI) by the corresponding amine of general formula (V), wherein $R^1$ is as defined for the compounds of general formula (I) supra, using reducing agents which are well-known to the person skilled in the art, such as for example sodium triacetoxy borohydride, as described by A. F. Abdel-Magid and S. J. Mehrman in Organic Process Research & Development 2006, 10, 971ff.

Scheme 5:

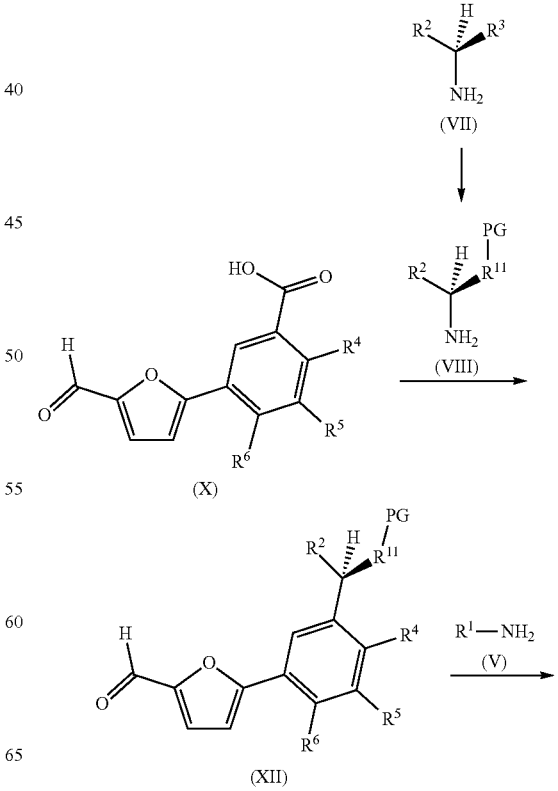

-continued

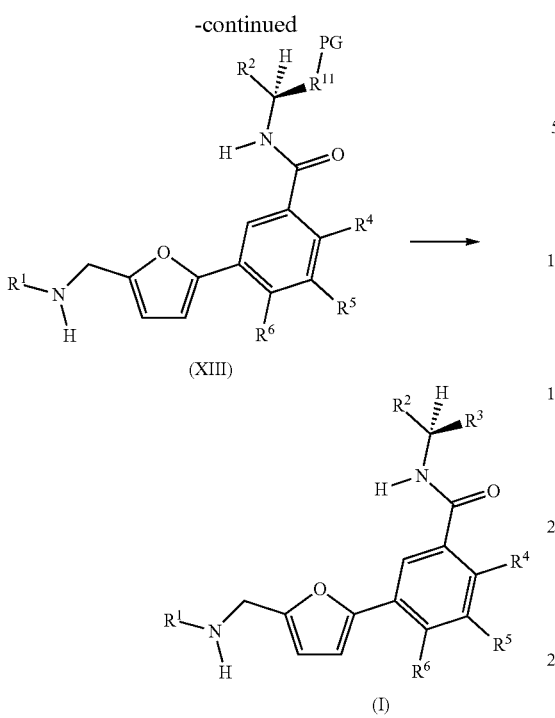

Scheme 5:

Preparation of compounds of the general formula (I), starting from carboxylic acids of general formula (X) and amines of general formula (VIII), wherein $R^1$, $R^2$, $R^3$, $R^4$, $R^5$ and $R^6$ are as defined for the compounds of general formula (I) supra, and wherein $R^{11}$—PG represents a group $R^3$ which contains a primary or secondary amino group, as defined for the compounds of general formula (I) supra, which primary or secondary amino group is masked with a protective group.

The respective primary or secondary amino group of $R^3$ of the compounds of general formula (VII) can be protected in several ways, which are well-known to the person skilled in the art, for example with a tert-butoxycarbonyl (BOC) group or as a phtalimide to yield compounds of the general formula (VIII).

The compounds of the general formula (XII) can be prepared by coupling of the carboxylic acids of general formula (X) with the protected amines of general formula (VIII), employing coupling reagents, which are well-known to the person skilled in the art, such as for example TBTU or HATU, as described by I. Abdelmoty et al in Lett. Pept. Sci. 1994, 1, 57 and F. Albericio et al. in J. Org. Chem. 1998, 63, 9678ff.

Alternatively, the amide coupling reaction can be performed by reaction of the corresponding acid chlorides of the carboxylic acids of general formula (X) with the amines of general formula (VIII). Methods for the preparation of acid chlorides from carboxylic acid are well-known to the person skilled in the art.

The compounds of the general formula (XIII) can be prepared by means of a reductive amination of the aldehyde formula (XII) by the corresponding amine of general formula (V), wherein $R^1$ is as defined for the compounds of general formula (I) supra, using reducing agents which are well-known to the person skilled in the art, such as for example sodium triacetoxy borohydride, as described by A. F. Abdel-Magid and S. J. Mehrman in Organic Process Research & Development 2006, 10, 971ff.

The compounds of general formula (I) can be prepared from the compounds of general formula (XII) by cleavage of the protecting groups. This can be achieved by standard procedures, which are well-known to the person skilled in the art (see for example T. W. Greene and P. G. M. Wuts, Protective Groups in Organic Synthesis, 3rd edition, Wiley 1999). BOC groups can be cleaved for example by treatment with strong acids, such as trifluoroacetic acid, in solvents such as for example dichloromethane, or by treatment with hydrochloric acid in solvents, such as for example methanol or 1,4-dioxane or mixtures thereof. Phtalimides can be cleaved for example by treatment with hydrazine, in solvents such as for example ethanol or tetrahydrofuran or mixtures thereof.

In accordance with a further aspect, the present invention also relates to a method of preparing a compound of general formula (I) as defined supra, said method comprising the step of allowing an intermediate compound of general formula (VI):

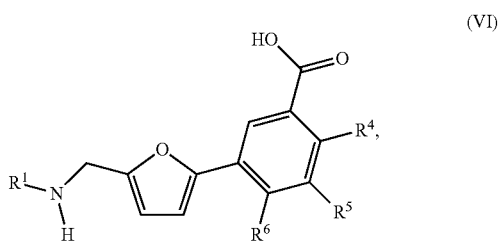

in which $R^1$, $R^4$, $R^5$ and $R^6$ are as defined for the compound of general formula (I) supra, to react with a compound of general formula (VII):

in which $R^2$ and $R^3$ are as defined for the compound of general formula (I) supra, thus providing a compound of general formula (I):

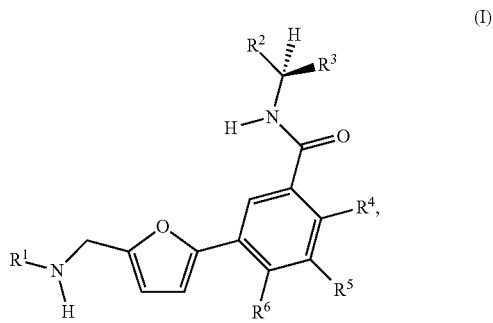

in which $R^1$, $R^2$, $R^3$, $R^4$ and $R^5$ are as defined for the compound of general formula (I) supra.

In a further aspect of the invention the meaning of the residues cited in the above mentioned process are limited as disclosed in subclaims 2-3.

In accordance with a further aspect, the present invention also relates to a method of preparing a compound of general formula (I) as defined supra, said method comprising the step of allowing an intermediate compound of general formula (VI):

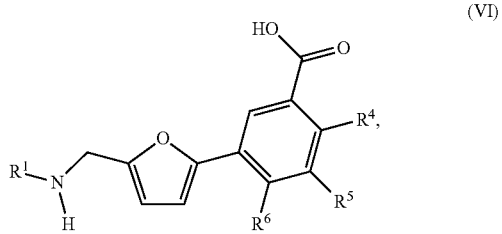

(VI)

in which $R^1$, $R^4$, $R^5$ and $R^6$ are as defined for the compound of general formula (I) supra, to react with a compound of general formula (VIII):

(VIII)

in which $R^2$ is as defined for the compound of general formula (I) supra, and in which $R^{11}$—PG represents a group $R^3$ which contains a primary or secondary amino group, as defined for the compounds of general formula (I) supra, which primary or secondary amino group is masked with a protective group, such as for example tert-butoxycarbonyloxy (BOC) or masked as a phtalimide, thus providing a compound of general formula (IX)

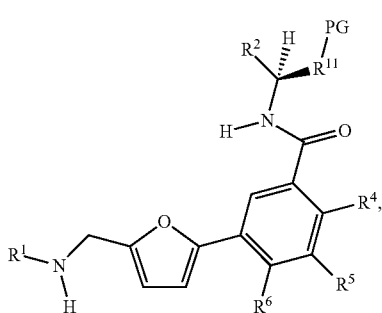

(IX)

in which $R^1$, $R^2$, $R^4$, $R^5$ and $R^6$ are as defined for the compound of general formula (I) supra, and in which $R^{11}$—PG represents a group $R^3$ which contains a primary or secondary amino group, as defined for the compounds of general formula (I) supra, whereby said primary or secondary amino group is masked with a protective group, such as for example tert-butoxycarbonyloxy (BOC) or masked as a phtalimide.

In accordance with a further aspect, the present invention also relates to a method of preparing a compound of general formula (I) as defined supra, said method comprising the step of allowing an intermediate compound of general formula (IX):

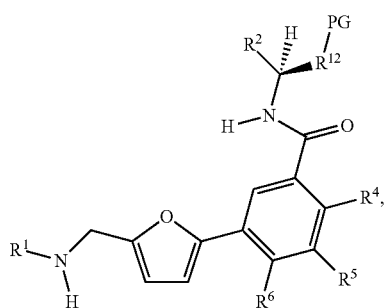

(IX)

in which $R^1$, $R^2$, $R^4$, $R^5$ and $R^6$ are as defined for the compound of general formula (I) supra, and in which $R^{12}$—PG represents a group $R^3$ which contains a primary or secondary amino group, as defined for the compounds of general formula (I) supra, which primary or secondary amino group is masked with a protective group, such as for example tert-butoxycarbonyloxy (BOC) or as a phtalimide, to react with an acid, such as for example hydrochloric acid, for the cleavage of a BOC-group, or to react with hydrazine for cleavage of a phtalimide group, thus providing a compound of general formula (I):

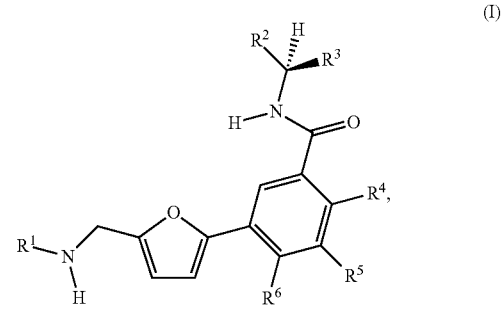

(I)

in which $R^1$, $R^2$, $R^3$, $R^4$, $R^5$ and $R^6$ are as defined for the compound of general formula (I) supra.

In accordance with a further aspect, the present invention also relates to a method of preparing a compound of general formula (I) as defined supra, said method comprising the step of allowing an intermediate compound of general formula (XI):

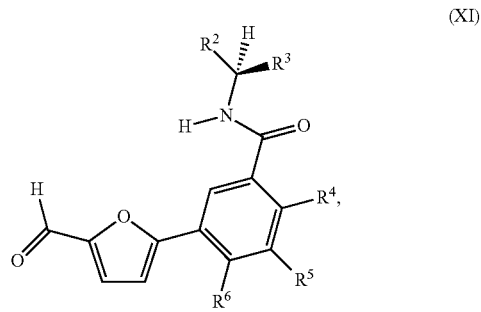

(XI)

in which $R^2$, $R^3$, $R^4$ and $R^5$ are as defined for the compound of general formula (I) supra, to react with a compound of general formula (V):

$$R^1—NH_2, \quad (V)$$

in which $R^1$ is as defined for the compound of general formula (I) supra, thus providing a compound of general formula (I):

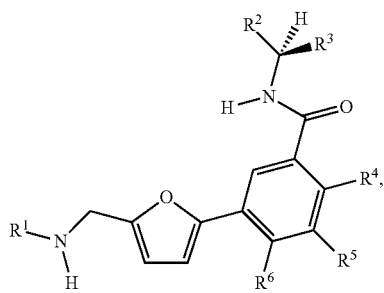

(I)

in which $R^1$, $R^2$, $R^3$, $R^4$, $R^5$ and $R^6$ are as defined for the compound of general formula (I) supra.

In accordance with a further aspect, the present invention also relates to a method of preparing a compound of general formula (I) as defined supra, said method comprising the step of allowing an intermediate compound of general formula (XII):

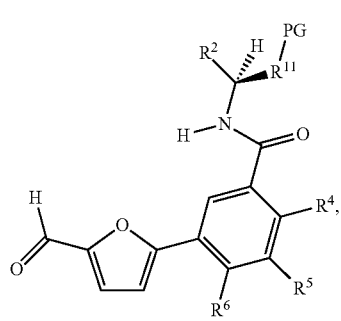

(XII)

in which $R^2$, $R^4$, $R^5$ and $R^6$ are as defined for the compound of general formula (I) supra, and in which $R^{11}$—PG represents a group $R^3$ which contains a primary or secondary amino group, as defined for the compounds of general formula (I) supra, which primary or secondary amino group is masked with a protective group, such as for example tert-butoxycarbonyloxy (BOC) or masked as a phtalimide, to react with a compound of general formula (VIII):

$$R^1—NH_2, \quad (V)$$

in which $R^1$ is as defined for the compound of general formula (I) supra, thus providing a compound of general formula (XIII):

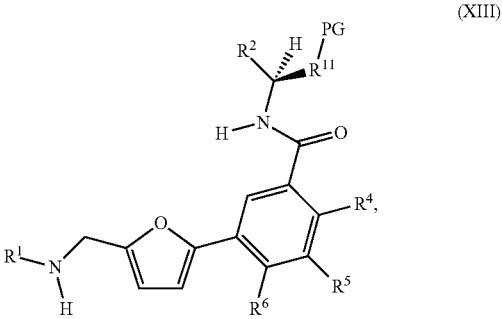

(XIII)

in which $R^1$, $R^2$, $R^4$, $R^5$ and $R^6$ are as defined for the compound of general formula (I) supra, and in which $R^{11}$—PG represents a group $R^3$ which contains a primary or secondary amino group, as defined for the compounds of general formula (I) supra, which primary or secondary amino group is masked with a protective group, such as for example tert-butoxycarbonyloxy (BOC) or masked as a phtalimide.

In accordance with a further aspect, the present invention also relates to a method of preparing a compound of general formula (I) as defined supra, said method comprising the step of allowing an intermediate compound of general formula (XIII):

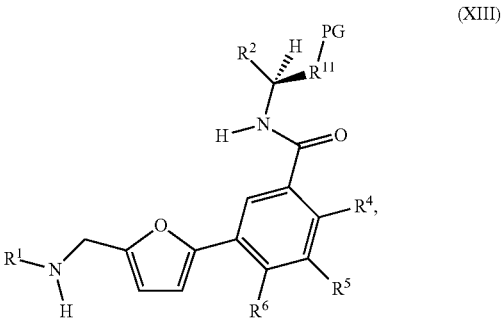

(XIII)

in which $R^2$, $R^4$, $R^5$ and $R^6$ are as defined for the compound of general formula (I) supra, and in which $R^{11}$—PG represents a group $R^3$ which contains a primary or secondary amino group, as defined for the compounds of general formula (I) supra, which primary or secondary amino group is masked with a protective group, such as for example tert-butoxycarbonyloxy (BOC) or masked as a phtalimide, to react with an acid, such as for example hydrochloric acid, for the cleavage of a BOC-group, or to react with hydrazine for cleavage of a phtalimide group, thereby giving a compound of general formula (I):

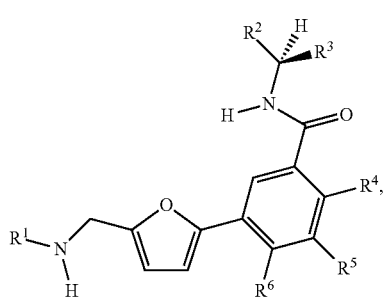
(I)

in which $R^1$, $R^2$, $R^3$, $R^4$, $R^5$ and $R^6$ are as defined for the compound of general formula (I) supra.

In another preferred embodiment the present invention covers the intermediate compounds which are disclosed in the Example section of this text, infra.

More particularly still, the present invention covers compounds of general formula (IV), (V), (VI), (VII), (VIII), (IX), (X) and (XI) which are disclosed in the Example section of this text, infra and their use for the preparation of the compounds of formula (I).

In particular in accordance with a further aspect, the present invention covers the use of the intermediate compounds of general formula (IV):

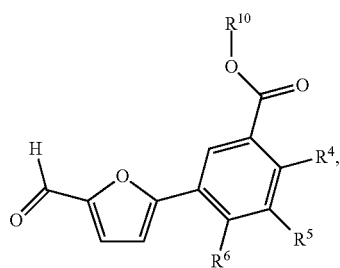
(IV)

in which $R^4$, $R^5$ and $R^6$ are as defined for the compound of general formula (I) supra, and $R^{10}$ represents a $C_1$-$C_4$-alkyl group or a benzyl group, for the preparation of a compound of general formula (I) as defined supra.

In accordance with a further aspect, the present invention covers the use of the intermediate compounds of general formula (V):

(V)

in which $R^1$ is as defined for the compound of general formula (I) supra, for the preparation of a compound of general formula (I) as defined supra.

In accordance with a further aspect, the present invention covers the use of the intermediate compounds of general formula (VI):

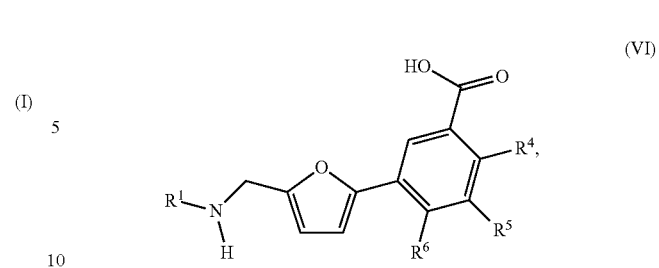
(VI)

in which $R^1$, $R^4$, $R^5$ and $R^6$ are as defined for the compound of general formula (I) supra, for the preparation of a compound of general formula (I) as defined supra.

In accordance with a further aspect, the present invention covers the use of the intermediate compounds of general formula (VII):

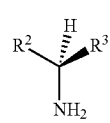
(VII)

in which $R^2$ and $R^3$ are as defined for the compound of general formula (I) supra, for the preparation of a compound of general formula (I) as defined supra.

In accordance with a further aspect, the present invention covers the use of the intermediate compounds of general formula (VIII):

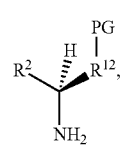
(VIII)

in which $R^2$ is as defined for the compound of general formula (I) supra, and in which $R^{11}$—PG represents a group $R^3$ which contains a primary or secondary amino group, as defined for the compounds of general formula (I) supra, which primary or secondary amino group is masked with a protective group, such as for example tert-butoxycarbonyloxy (BOC) or as a phtalimide, for the preparation of a compound of general formula (I) as defined supra.

In accordance with a further aspect, the present invention covers the use of the intermediate compounds of general formula (IX):

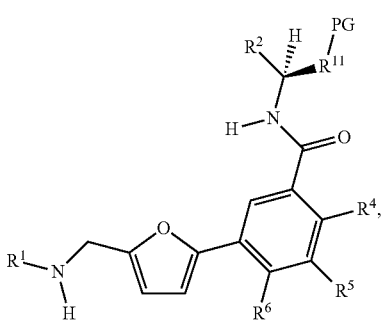
(IX)

in which $R^1$, $R^2$, $R^4$, $R^5$ and $R^6$ are as defined for the compound of general formula (I) supra, and in which $R^{11}$—PG represents a group $R^3$ which contains a primary or secondary amino group, as defined for the compounds of general formula (I) supra, which primary or secondary amino group is masked with a protective group, such as for example tert-butoxycarbonyloxy (BOC) or as a phtalimide, for the preparation of a compound of general formula (I) as defined supra.

In accordance with a further aspect, the present invention covers the use of the intermediate compounds of general formula (X):

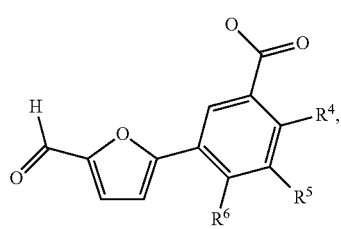

(X)

in which $R^4$, $R^5$ and $R^6$ are as defined for the compound of general formula (I) supra, for the preparation of a compound of general formula (I) as defined supra.

In accordance with a further aspect, the present invention covers the use of the intermediate compounds of general formula (XI):

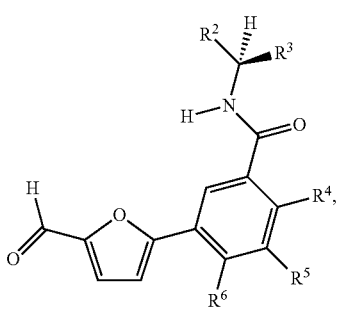

(XI)

in which $R^2$, $R^3$, $R^4$, $R^5$ and $R^6$ are as defined for the compound of general formula (I) supra, for the preparation of a compound of general formula (I) as defined supra.

In accordance with a further aspect, the present invention covers the use of the intermediate compounds of general formula (XII):

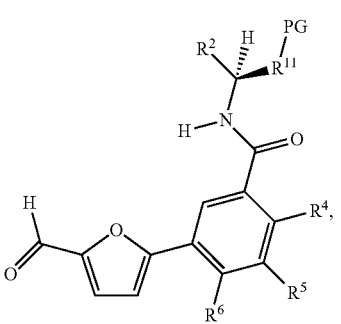

(XII)

in which $R^2$, $R^4$, $R^5$ and $R^6$ are as defined for the compound of general formula (I) supra, and in which $R^{11}$—PG represents a group $R^3$ which contains a primary or secondary amino group, as defined for the compounds of general formula (I) supra, which primary or secondary amino group is masked with a protective group, such as for example tert-butoxycarbonyloxy (BOC) or as a phtalimide, for the preparation of a compound of general formula (I) as defined supra.

In accordance with a further aspect, the present invention covers the use of the intermediate compounds of general formula (XIII):

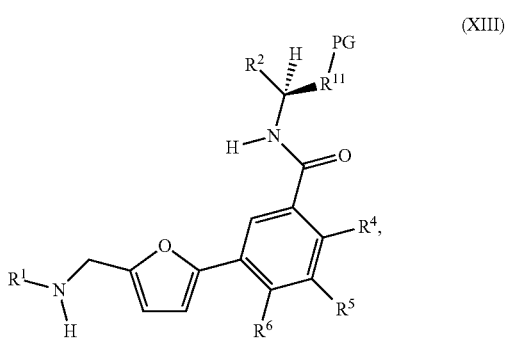

(XIII)

in which $R^1$, $R^2$, $R^4$, $R^5$ and $R^6$ are as defined for the compound of general formula (I) supra, and in which $R^{11}$—PG represents a group $R^3$ which contains a primary or secondary amino group, as defined for the compounds of general formula (I) supra, which primary or secondary amino group is masked with a protective group, such as for example tert-carbonyloxy BOC or as a phtalimide, for the preparation of a compound of general formula (I) as defined supra.

The definitions of radicals mentioned herein above in general terms or in preferred ranges apply not only to the end products of the formula (I), but also, analogously, to the intermediates or starting materials required in each case for the preparation.

The compounds of general formula (I) of the present invention can be converted to any salt, preferably pharmaceutically acceptable salts, as described herein, by any method which is known to the person skilled in the art. Similarly, any salt of a compound of general formula (I) of the present invention can be converted into the free compound, by any method which is known to the person skilled in the art.

Commercial Utility

As has been discussed in the Background section ATAD2 was shown to function as a co-factor of several oncogenic transcriptional factors in order to activate the expression of their target genes involved in cell proliferation and survival. In large number of tumour types ATAD2 is frequently amplified and highly overexpressed, and its expression correlates with the advanced progression, metastasis and poor prognosis. As down-regulation of ATAD2 by RNAi in cancer cells was shown to inhibit the proliferation and invasiveness of several cancer cells ATAD2 is considered to be suitable target for the treatment of diseases encompanied with uncontrolled cell proliferation and/or cell division such as hyperproliferative disorders, in particular cancer.

Hyperproliferative disorders include, but are not limited to, for example: psoriasis, keloids, and other hyperplasias affecting the skin, benign prostate hyperplasia (BPH), solid tumours, such as cancers of the breast, respiratory tract, brain, reproductive organs, digestive tract, urinary tract, eye, liver, skin, head and neck, thyroid, parathyroid and their distant metastases. Those disorders also include lymphomas, sarcomas, and leukaemias.

Examples of breast cancers include, but are not limited to, invasive ductal carcinoma, invasive lobular carcinoma, ductal carcinoma in situ, and lobular carcinoma in situ.

Examples of cancers of the respiratory tract include, but are not limited to, small-cell and non-small-cell lung carcinoma, as well as bronchial adenoma and pleuropulmonary blastoma.

Examples of brain cancers include, but are not limited to, brain stem and hypophtalmic glioma, cerebellar and cerebral astrocytoma, medulloblastoma, ependymoma, as well as neuroectodermal and pineal tumour.

Tumours of the male reproductive organs include, but are not limited to, prostate and testicular cancer.

Tumours of the female reproductive organs include, but are not limited to, endometrial, cervical, ovarian, vaginal, and vulvar cancer, as well as sarcoma of the uterus.

Tumours of the digestive tract include, but are not limited to, anal, colon, colorectal, oesophageal, gallbladder, gastric, pancreatic, rectal, small-intestine, and salivary gland cancers.

Tumours of the urinary tract include, but are not limited to, bladder, penile, kidney, renal pelvis, ureter, urethral and human papillary renal cancers.

Eye cancers include, but are not limited to, intraocular melanoma and retinoblastoma.

Examples of liver cancers include, but are not limited to, hepatocellular carcinoma (liver cell carcinomas with or without fibrolamellar variant), cholangiocarcinoma (intrahepatic bile duct carcinoma), and mixed hepatocellular cholangiocarcinoma.

Skin cancers include, but are not limited to, squamous cell carcinoma, Kaposi's sarcoma, malignant melanoma, Merkel cell skin cancer, and non-melanoma skin cancer.

Head-and-neck cancers include, but are not limited to, laryngeal, hypopharyngeal, nasopharyngeal, oropharyngeal cancer, lip and oral cavity cancer and squamous cell.

Lymphomas include, but are not limited to, AIDS-related lymphoma, non-Hodgkin's lymphoma, cutaneous T-cell lymphoma, Burkitt lymphoma, Hodgkin's disease, and lymphoma of the central nervous system.

Sarcomas include, but are not limited to, sarcoma of the soft tissue, osteosarcoma, malignant fibrous histiocytoma, lymphosarcoma, and rhabdomyosarcoma.

Leukemias include, but are not limited to, acute myeloid leukemia, acute lymphoblastic leukemia, chronic lymphocytic leukemia, chronic myelogenous leukemia, and hairy cell leukemia.

The present invention also provides methods of treating angiogenic disorders including diseases associated with excessive and/or abnormal angiogenesis.

Inappropriate and ectopic expression of angiogenesis can be deleterious to an organism. A number of pathological conditions are associated with the growth of extraneous blood vessels. These include, for example, diabetic retinopathy, ischemic retinal-vein occlusion, and retinopathy of prematurity [Aiello et al., New Engl. J. Med., 1994, 331, 1480; Peer et al., Lab. Invest., 1995, 72, 638], age-related macular degeneration (AMD) [Lopez et al., Invest. Opththalmol. Vis. Sci., 1996, 37, 855], neovascular glaucoma, psoriasis, retrolental fibroplasias, angiofibroma, inflammation, rheumatoid arthritis (RA), restenosis, in-stent restenosis, vascular graft restenosis, etc. In addition, the increased blood supply associated with cancerous and neoplastic tissue, encourages growth, leading to rapid tumour enlargement and metastasis. Moreover, the growth of new blood and lymph vessels in a tumour provides an escape route for renegade cells, encouraging metastasis and the consequence spread of the cancer. Thus, compounds of general formula (I) of the present invention can be utilized to treat and/or prevent any of the aforementioned angiogenesis disorders, for example by inhibiting and/or reducing blood vessel formation; by inhibiting, blocking, reducing, decreasing, etc. endothelial cell proliferation, or other types involved in angiogenesis, as well as causing cell death or apoptosis of such cell types.

These disorders have been well characterized in humans, but also exist with a similar etiology in other mammals, and can be treated by administering pharmaceutical compositions of the present invention.

The term "treating" or "treatment" as stated throughout this document is used conventionally, for example the management or care of a subject for the purpose of combating, alleviating, reducing, relieving, improving the condition of a disease or disorder, such as a carcinoma.

The compounds of the present invention can be used in particular in therapy and prevention, i.e. prophylaxis, of tumour growth and metastases, especially in solid tumours of all indications and stages with or without pre-treatment of the tumour growth.

The compounds of the present invention are therefore suitable for the treatment and/or prophylaxis of diseases in humans and animals. The treatment is preferred for the uses and methods described below.

Consequently one aspect of the invention is the use of the compounds of formula (I) for the treatment and/or prophylaxis of diseases.

A further aspect of the invention is a compound of formula (I) according to any one of the claims 1 to 4 for inhibiting proliferation of a cell, comprising contacting the cell with said compound.

Yet another aspect of the invention is a compound for use of formula (I) for the treatment and/or prophylaxis of diseases, wherein the disease is a hyperproliferative diseases, more particularly cancer.

Another aspect of the invention is a method of treatment and/or prophylaxis of diseases comprising administering a compound of formula (I) according to any one of the claims 1-4 to a patient in need thereof.

Yet another aspect of the invention is a method of treatment comprising administering a pharmaceutically effective amount of a compound of formula (I).

A further aspect of the invention is a method of inhibiting proliferation of a cell, comprising contacting the cell with a compound of formula (I) according to any one of claims 1-4.

Another aspect of the invention is a method of treating a hyperproliferative disease, particularly cancer, comprising administering an effective amount of at least one compound of formula (I) according to any one of claims 1-4 to a patient in need thereof.

As used herein, "prophylaxis" includes a use of the compound that, in a statistical sample, reduces the occurrence of the disorder or condition in the treated sample relative to an untreated control sample, or delays the onset or reduces the severity of one or more symptoms of the disorder or condition relative to the untreated control sample, when administered to prior to the onset of the disorder or condition.

The invention furthermore relates to the use of the compound according to the invention for the treatment and/or prophylaxis of diseases, preferably of hyperproliferative diseases, in particular of cancer.

The present invention furthermore relates to the use of the compounds according to the invention for the preparation of a pharmaceutical composition for the treatment and/or prophylaxis of diseases, in particular of the above mentioned diseases.

A further aspect of the invention are pharmaceutical compositions comprising at least a compound of general formula (I) together with one or more excipients, especially for the treatment and/or prophylaxis of the diseases mentioned above.

In accordance with a further aspect, the present invention covers pharmaceutical compositions, in particular a medicament, comprising a compound of general formula (I), as described supra, or a stereoisomer, a tautomer, a hydrate, a solvate, a salt thereof, particularly a pharmaceutically acceptable salt, or a mixture of same, and one or more excipients), in particular one or more pharmaceutically acceptable excipient(s). Conventional procedures for preparing such pharmaceutical compositions in appropriate dosage forms can be utilized.

The present invention furthermore covers pharmaceutical compositions, in particular medicaments, which comprise at least one compound according to the invention, conventionally together with one or more pharmaceutically suitable excipients, and to their use for the above mentioned purposes.

It is possible for the compounds according to the invention to have systemic and/or local activity. For this purpose, they can be administered in a suitable manner, such as, for example, via the oral, parenteral, pulmonary, nasal, sublingual, lingual, buccal, rectal, vaginal, dermal, transdermal, conjunctival, otic route or as an implant or stent.

For these administration routes, it is possible for the compounds according to the invention to be administered in suitable administration forms.

For oral administration, it is possible to formulate the compounds according to the invention to dosage forms known in the art that deliver the compounds of the invention rapidly and/or in a modified manner, such as, for example, tablets (uncoated or coated tablets, for example with enteric or controlled release coatings that dissolve with a delay or are insoluble), orally-disintegrating tablets, films/wafers, films/lyophylisates, capsules (for example hard or soft gelatine capsules), sugar-coated tablets, granules, pellets, powders, emulsions, suspensions, aerosols or solutions. It is possible to incorporate the compounds according to the invention in crystalline and/or amorphised and/or dissolved form into said dosage forms.

Parenteral administration can be effected with avoidance of an absorption step (for example intravenous, intraarterial, intracardial, intraspinal or intralumbal) or with inclusion of absorption (for example intramuscular, subcutaneous, intracutaneous, percutaneous or intraperitoneal). Administration forms which are suitable for parenteral administration are, inter alia, preparations for injection and infusion in the form of solutions, suspensions, emulsions, lyophylisates or sterile powders.

Examples which are suitable for other administration routes are pharmaceutical forms for inhalation [inter alia powder inhalers, nebulizers], nasal drops, nasal solutions, nasal sprays; tablets/films/wafers/capsules for lingual, sublingual or buccal administration; suppositories; eye drops, eye ointments, eye baths, ocular inserts, ear drops, ear sprays, ear powders, ear-rinses, ear tampons; vaginal capsules, aqueous suspensions (lotions, mixturae agitandae), lipophilic suspensions, emulsions, ointments, creams, transdermal therapeutic systems (such as, for example, patches), milk, pastes, foams, dusting powders, implants or stents.

The compounds according to the invention can be incorporated into the stated administration forms. This can be effected in a manner known per se by mixing with pharmaceutically suitable excipients. Pharmaceutically suitable excipients include, inter alia, fillers and carriers (for example cellulose, microcrystalline cellulose (such as, for example, Avicel®), lactose, mannitol, starch, calcium phosphate (such as, for example, Di-Cafos®)), ointment bases (for example petroleum jelly, paraffins, triglycerides, waxes, wool wax, wool wax alcohols, lanolin, hydrophilic ointment, polyethylene glycols), bases for suppositories (for example polyethylene glycols, cacao butter, hard fat), solvents (for example water, ethanol, isopropanol, glycerol, propylene glycol, medium chain-length triglycerides fatty oils, liquid polyethylene glycols, paraffins), surfactants, emulsifiers, dispersants or wetters (for example sodium dodecyl sulfate), lecithin, phospholipids, fatty alcohols (such as, for example, Lanette®), sorbitan fatty acid esters (such as, for example, Span®), polyoxyethylene sorbitan fatty acid esters (such as, for example, Tween®), polyoxyethylene fatty acid glycerides (such as, for example, Cremophor®), polyoxethylene fatty acid esters, polyoxyethylene fatty alcohol ethers, glycerol fatty acid esters, poloxamers (such as, for example, Pluronic®), buffers, acids and bases (for example phosphates, carbonates, citric acid, acetic acid, hydrochloric acid, sodium hydroxide solution, ammonium carbonate, trometamol, triethanolamine), isotonicity agents (for example glucose, sodium chloride), adsorbents (for example highly-disperse silicas), viscosity-increasing agents, gel formers, thickeners and/or binders (for example polyvinylpyrrolidone, methylcellulose, hydroxypropylmethylcellulose, hydroxypropylcellulose, carboxymethylcellulose-sodium, starch, carbomers, polyacrylic acids (such as, for example, Carbopol®); alginates, gelatine), disintegrants (for example modified starch, carboxymethylcellulose-sodium, sodium starch glycolate (such as, for example, Explotab®), cross-linked polyvinylpyrrolidone, croscarmellose-sodium (such as, for example, AcDiSol®)), flow regulators, lubricants, glidants and mould release agents (for example magnesium stearate, stearic acid, talc, highly-disperse silicas (such as, for example, Aerosil®)), coating materials (for example sugar, shellac) and film formers for films or diffusion membranes which dissolve rapidly or in a modified manner (for example polyvinylpyrrolidones (such as, for example, Kollidon®), polyvinyl alcohol, hydroxypropylmethylcellulose, hydroxypropylcellulose, ethylcellulose, hydroxypropylmethylcellulose phthalate, cellulose acetate, cellulose acetate phthalate, polyacrylates, polymethacrylates such as, for example, Eudragit®)), capsule materials (for example gelatine, hydroxypropylmethylcellulose), synthetic polymers (for example polylactides, polyglycolides, polyacrylates, polymethacrylates (such as, for example, Eudragit®), polyvinylpyrrolidones (such as, for example, Kollidon®), polyvinyl alcohols, polyvinyl acetates, polyethylene oxides, polyethylene glycols and their copolymers and blockcopolymers), plasticizers (for example polyethylene glycols, propylene glycol, glycerol, triacetine, triacetyl citrate, dibutyl phthalate), penetration enhancers, stabilisers (for example antioxidants such as, for example, ascorbic acid, ascorbyl palmitate, sodium ascorbate, butylhydroxyanisole, butylhydroxytoluene, propyl gallate), preservatives (for example parabens, sorbic acid, thiomersal, benzalkonium chloride, chlorhexidine acetate, sodium benzoate), colourants (for example inorganic pigments such as, for example, iron oxides, titanium dioxide), flavourings, sweeteners, flavour- and/or odour-masking agents.

The present invention furthermore relates to a pharmaceutical composition comprising at least one compound according to the invention, conventionally together with one or more pharmaceutically suitable excipient(s), and to their use according to the present invention and to their use for the above mentioned purposes.

The present invention furthermore relates to pharmaceutical compositions comprising at least one compound according to the invention and at least one or more further chemotherapeutic agents and/or anti-cancer agents, in particular for the treatment and/or prophylaxis of the above mentioned diseases.

Generally, the use of chemotherapeutic agents and/or anti-cancer agents in combination with a compound or pharmaceutical composition of the present invention will serve to:

1. yield better efficacy in reducing the growth of a tumour or even eliminate the tumour as compared to administration of either agent alone,
2. provide for the administration of lesser amounts of the administered chemotherapeutic agents,
3. provide for a chemotherapeutic treatment that is well tolerated in the patient with fewer deleterious pharmacological complications than observed with single agent chemotherapies and certain other combined therapies,
4. provide for treating a broader spectrum of different cancer types in mammals, especially humans,
5. provide for a higher response rate among treated patients,
6. provide for a longer survival time among treated patients compared to standard chemotherapy treatments,
7. provide a longer time for tumour progression, and/or
8. yield efficacy and tolerability results at least as good as those of the agents used alone, compared to known instances where other anti-cancer agent combinations produce antagonistic effects.

In addition, the compounds of general formula (I) of the present invention can also be used in combination with radiotherapy and/or surgical intervention.

In accordance with another aspect, the present invention covers pharmaceutical combinations, in particular medicaments, comprising at least one compound of general formula (I) of the present invention and at least one or more further active ingredients, in particular for the treatment and/or prophylaxis of hyperproliferative disorders, in particular cancer.

Particularly, the present invention covers a pharmaceutical combination, which comprises:
one or more first active ingredients, in particular compounds of general formula (I) as defined supra, and
one or more further active ingredients, in particular hyperproliferative disorders, in particular cancer.

The term "combination" in the present invention is used as known to persons skilled in the art and may be present as a fixed combination, a non-fixed combination or kit-of-parts.

A "fixed combination" in the present invention is used as known to persons skilled in the art and is defined as a combination wherein the said first active ingredient and the said second active ingredient are present together in one unit dosage or in a single entity. One example of a "fixed combination" is a pharmaceutical composition wherein the said first active ingredient and the said second active ingredient are present in admixture for simultaneous administration, such as in a formulation. Another example of a "fixed combination" is a pharmaceutical combination wherein the said first active ingredient and the said second active ingredient are present in one unit without being in admixture.

A non-fixed combination or "kit-of-parts" in the present invention is used as known to persons skilled in the art and is defined as a combination wherein the said first active ingredient and the said second active ingredient are present in more than one unit. One example of a non-fixed combination or kit-of-parts is a combination wherein the said first active ingredient and the said second active ingredient are present separately. The components of the non-fixed combination or kit-of-parts may be administered separately, sequentially, simultaneously, concurrently or chronologically staggered.

Suitable active ingredients for combinations which may be mentioned by way of example and by preference are:

Anti-cancer agents are comprising chemotherapeutic anti-cancer agents and target specific anti-cancer agents, "Chemotherapeutic anti-cancer agents", including but is not limited to (i) alkylating/carbamoylating agents,
(ii) platinum derivatives,
(iii) antimitotic agents/tubulin inhibitors,
(iv) topoisomerase inhibitors,
(v) pyrimidine antagonists,
(vi) purine antagonists,
(vii) folic acid antagonists, target specific anti-cancer agents, including but is not limited to (i) kinase inhibitors
(ii) proteasome inhibitors
(iii) histone deacetylase inhibitors
(iv) heat shock protein 90 inhibitors
(v) vascular targeting agents
(vi) monoclonal antibodies and antibody fragments;
(vii) oligonucleotide based therapeutics
(viii) Toll-like receptor/TLR 9 agonists, TLR 7 agonists or TLR 7/8 agonists as well as immunostimulatory RNA as TLR 7/8 agonists;
(ix) protease inhibitors;
(x) hormonal therapeutics and other "target specific anti-cancer agents" including bleomycin, retinoids, DNA methyltransferase inhibitors and 5-azacytidine, cytokines, bcl2 antagonists, death receptor agonists, DR4/5 agonistic antibodies, FasL and TNF-R agonists.

In particular the compound of the present invention can be combined with the compounds of the following list comprising specific examples for the classes of inhibitors mentioned above, such as 131I-chTNT, abarelix, abiraterone, aclarubicin, adalimumab, ado-trastuzumab emtansine, afatinib, aflibercept, aldesleukin, alectinib, alemtuzumab, alendronic acid, alitretinoin, altretamine, amifostine, aminoglutethimide, hexyl arninolevulinate, amrubicin, amsacrine, anastrozole, ancestim, anethole dithiolethione, anetumab ravtansine, angiotensin II, antithrombin III, aprepitant, arcitumomab, arglabin, arsenic trioxide, asparaginase, atezolizumab, axitinib, azacitidine, basiliximab, belotecan, bendamustine, besilesomab, belinostat, bevacizumab, bexarotene, bicalutamide, bisantrene, bleomycin, blinatumomab, bortezomib, buserelin, bosutinib, brentuximab vedotin, busulfan, cabazitaxel, cabozantinib, calcitonine, calcium folinate, calcium levofolinate, capecitabine, capromab, carbamazepine carboplatin, carboquone, carfilzomib, carmofur, carmustine, catumaxomab, celecoxib, celmoleukin, ceritinib, cetuximab, chlorambucil, chlormadinone, chlormethine, cidofovir, cinacalcet, cisplatin, cladribine, clodronic acid, clofarabine, cobimetinib, copanlisib, crisantaspase, crizotinib, cyclophosphamide, cyproterone, cytarabine, dacarbazine, dactinomycin, daratumumab, darbepoetin alfa, dabrafenib, dasatinib, daunorubicin, decitabine, degarelix, denileukin diftitox, denosumab, depreotide, deslorelin, dianhydrogalactitol, dexrazoxane, dibrospidium chloride, dianhydrogalactitol, diclofenac, dinutuximab, docetaxel, dolasetron, doxifluridine, doxorubicin, doxorubicin+estrone, dronabinol, eculizumab, edrecolomab, elliptinium acetate, elotuzumab, eltrombopag, endostatin, enocitabine, enzalutamide, epirubicin, epitiostanol, epoetin alfa, epoetin beta, epoetin zeta, eptaplatin, eribulin, erlotinib, esomeprazole, estradiol, estramustine, ethinylestradiol, etoposide, everolimus, exemestane, fadrozole, fentanyl, filgrastim, fluoxymesterone, floxuridine, fludarabine, fluorouracil, flutamide, folinic acid, formestane, fosaprepitant, fotemustine, fulvestrant, gadobutrol, gadoteridol, gadoteric acid meglumine, gadoversetamide, gadoxetic acid, gallium nitrate, ganirelix, gefitinib, gemcitabine, gemtuzumab, Glucarpidase, glutoxim, GM-CSF, goserelin, granisetron, granulocyte colony stimulating factor, histamine dihydrochloride, histrelin, hydroxycarbamide, I-125 seeds, lansoprazole, ibandronic acid, ibritumomab tiuxetan, ibrutinib, idarubicin, ifosfamide, imatinib, imiquimod, improsulfan, indisetron, incadronic acid, ingenol mebutate, interferon alfa, interferon beta, interferon gamma, iobitridol, iobenguane (123I), iomeprol, ipilimumab, irinotecan, Itraconazole, ixabepilone, ixazomib, lanreotide, lansoprazole, lapatinib, lasocholine, lenalidomide, lenvatinib, lenograstim, lentinan, letrozole, leuprorelin, levamisole, levonorgestrel, levothyroxine sodium, lisuride, lobaplatin, lomustine, lonidamine, masoprocol, medroxyprogesterone, megestrol, melarsoprol, melphalan, mepitiostane, mercaptopurine, mesna, methadone, methotrexate, methoxsalen, methylamino-levulinate, methylprednisolone, methyltestosterone, metirosine, mifamurtide, miltefosine, miriplatin, mitobronitol, mitoguazone, mitolactol, mitomycin, mitotane, mitoxantrone, mogamulizumab, molgramostim, mopidamol, morphine hydrochloride, morphine sulfate, nabilone, nabiximols, nafarelin, naloxone+pentazocine, naltrexone, nartograstim, necitumumab, nedaplatin, nelarabine, neridronic acid, netupitant/palonosetron, nivolumab, pentetreotide, nilotinib, nilutamide, nimorazole, nimotuzumab, nimustine, nintedanib, nitracrine, nivolumab, obinutuzumab, octreotide, ofatumumab, olaparib, olaratumab, omacetaxine mepesuccinate, omeprazole, ondansetron, oprelvekin, orgotein, orilotimod, osimertinib, oxaliplatin, oxycodone, oxymetholone, ozogamicine, p53 gene therapy, paclitaxel, palbociclib, palifermin, palladium-103 seed, palonosetron, pamidronic acid, panitumumab, panobinostat, pantoprazole, pazopanib, pegaspargase, PEG-epoetin beta (methoxy PEG-epoetin beta), pembrolizumab, pegfilgrastim, peginterferon alfa-2b, pembrolizumab, pemetrexed, pentazocine, pentostatin, peplomycin, Perflubutane, perfosfamide, Pertuzumab, picibanil, pilocarpine, pirarubicin, pixantrone, plerixafor, plicamycin, poliglusam, polyestradiol phosphate, polyvinylpyrrolidone+sodium hyaluronate, polysaccharide-K, pomalidomide, ponatinib, porfimer sodium, pralatrexate, prednimustine, prednisone, procarbazine, procodazole, propranolol, quinagolide, rabeprazole, racotumomab, radium-223 chloride, radotinib, raloxifene, raltitrexed, ramosetron, ramucirumab, ranimustine, rasburicase, razoxane, refametinib, regorafenib, risedronic acid, rhenium-186 etidronate, rituximab, rolapitant, romidepsin, romiplostim, romurtide, roniciclib, samarium (153Sm) lexidronam, sargramostim, satumomab, secretin, siltuximab, sipuleucel-T, sizofiran, sobuzoxane, sodium glycididazole, sonidegib, sorafenib, stanozolol, streptozocin, sunitinib, talaporfin, talimogene laherparepvec, tamibarotene, tamoxifen, tapentadol, tasonermin, teceleukin, technetium (99mTc) nofetumomab merpentan, 99mTc-HYNIC-[Tyr3]-octreotide, tegafur, tegafur+gimeracil+oteracil, temoporfin, temozolomide, temsirolimus, teniposide, testosterone, tetrofosmin, thalidomide, thiotepa, thymalfasin, thyrotropin alfa, tioguanine, tocilizumab, topotecan, toremifene, tositumomab, trabectedin, trametinib, tramadol, trastuzumab, trastuzumab emtansine, treosulfan, tretinoin, trifluridine+tipiracil, trilostane, triptorelin, trametinib, trofosfamide, thrombopoietin, tryptophan, ubenimex, valatinib, valrubicin, vandetanib, vapreotide, vemurafenib, vinblastine, vincristine, vindesine, vinflunine, vinorelbine, vismodegib, vorinostat, vorozole, yttrium-90 glass microspheres, zinostatin, zinostatin stimalamer, zoledronic acid, zorubicine.

Based upon standard laboratory techniques known to evaluate compounds useful for the treatment of generic disorders, by standard toxicity tests and by standard pharmacological assays for the determination of treatment of the conditions identified above in mammals, and by comparison of these results with the results of known active ingredients or medicaments that are used to treat these conditions, the effective dosage of the compounds of the present invention can readily be determined for treatment of each desired indication. The amount of the active ingredient to be administered in the treatment of one of these conditions can vary widely according to such considerations as the particular compound and dosage unit employed, the mode of administration, the period of treatment, the age and sex of the patient treated, and the nature and extent of the condition treated.

The total amount of the active ingredient to be administered will generally range from about 0.001 mg/kg to about 500 mg/kg body weight per day, and preferably from about 0.01 mg/kg to about 100 mg/kg body weight per day. Clinically useful dosing schedules will range from one to three times a day dosing to once every four weeks dosing. In addition, it is possible for "drug holidays", in which a patient is not dosed with a drug for a certain period of time, to be beneficial to the overall balance between pharmacological effect and tolerability. It is possible for a unit dosage to contain from about 0.5 mg to about 1500 mg of active ingredient, and can be administered one or more times per day or less than once a day. The average daily dosage for administration by injection, including intravenous, intramuscular, subcutaneous and parenteral injections, and use of infusion techniques will preferably be from 0.01 to 500 mg/kg of total body weight.

Despite this, it may occasionally be necessary to deviate from the above mentioned amounts, as a function of the body weight, the route of administration, the individual behaviour towards the active substance, the type of preparation and the point in time or interval at which administration is affected. Thus, in some cases it may suffice to manage with less than the above mentioned minimum amount, while in other cases the above mentioned upper limit will have to be exceeded. In the event that relatively large amounts are administered, it is advisable to divide these into several individual doses over the course of the day.

Of course the specific initial and continuing dosage regimen for each patient will vary according to the nature and severity of the condition as determined by the attending diagnostician, the activity of the specific compound employed, the age and general condition of the patient, time of administration, route of administration, rate of excretion of the drug, drug combinations, and the like. The desired mode of treatment and number of doses of a compound of the present invention or a pharmaceutically acceptable salt or ester or composition thereof can be ascertained by those skilled in the art using conventional treatment tests.

In the following tests and examples, the percentages are, unless otherwise specified, percent by weight. Solvent ratios, dilution ratios and concentration data of liquid/liquid-solutions refer in each case to the volume.

A. Examples

The following table lists the abbreviations used in this paragraph and in the Intermediate Examples and Examples section as far as they are not explained within the text body.

| Abbreviation | Meaning |
| --- | --- |
| Ac | acetyl |
| app | apparent |
| δ | chemical shift |
| DCM | dichloromethane |
| DIPEA | diisopropylethylamine |
| DMF | N,N-dimethylformamide |
| DMSO | dimethyl sulfoxide |
| ELSD | evaporative light scattering detector |
| HATU | (1-[bis(dimethylamino)methylene]-1H-1,2,3-triazolo[4,5-b]pyridinium 3-oxid hexafluorophosphate) |
| HPLC | high-performance liquid chromatography |
| h | hour |
| LC-MS | liquid chromatography-mass spectrometry |
| min | minute(s) |
| mL | milliliter |
| μL | microliter |
| mmol | millimole |
| mg | milligram |
| MHz | megahertz |
| MS | mass spectrometry |
| MTBE | methyl tert-butyl ether |
| NMR | nuclear magnetic resonance |
| ppm | parts per million |
| $R_f$ | retention time |
| r.t. | room temperature |
| TBTU | O-(benzotriazol-1-yl)-N,N,N',N'-tetramethyluronium tetrafluoroborate |
| THF | tetrahydrofuran |
| TLC | Thin-layer chromatography |

Other abbreviations have their meanings customary per se to the skilled person.

In the present text, in particular in the Experimental Section, for the synthesis of intermediates and of examples of the present invention, when a compound is mentioned as a salt form with the corresponding base or acid, the exact stoichiometric composition of said salt form, as obtained by the respective preparation and/or purification process, is, in most cases, unknown.

Unless specified otherwise, suffixes to chemical names or structural formulae relating to salts, such as "hydrochloride", "trifluoroacetate", "sodium salt", or "x HCl", "x $CF_3COOH$", "x $Na^+$", for example, mean a salt form, the stoichiometry of which salt form not being specified.

This applies analogously to cases in which synthesis intermediates or example compounds or salts thereof have been obtained, by the preparation and/or purification processes described, as solvates, such as hydrates, with (if defined) unknown stoichiometric composition.

The $^1$H-NMR data of selected examples are listed in the form of $^1$H-NMR peaklists. For each signal peak the δ value in ppm is given, followed by the signal intensity, reported in round brackets. The δ value-signal intensity pairs from different peaks are separated by commas. Therefore, a peaklist is described by the general form: $δ_1$ (intensity$_1$), $δ_2$ (intensity$_2$), . . . , $δ_i$ (intensity$_1$), . . . , $δ_n$ (intensity$_n$).

The intensity of a sharp signal correlates with the height (in cm) of the signal in a printed NMR spectrum. When compared with other signals, this data can be correlated to the real ratios of the signal intensities. In the case of broad signals, more than one peak, or the center of the signal along with their relative intensity, compared to the most intense signal displayed in the spectrum, are shown. A $^1$H-NMR peaklist is similar to a classical $^1$H-NMR readout, and thus usually contains all the peaks listed in a classical NMR interpretation. Moreover, similar to classical $^1$H-NMR printouts, peaklists can show solvent signals, signals derived from stereoisomers of target compounds (also the subject of the invention), and/or peaks of impurities. The peaks of stereoisomers, and/or peaks of impurities are typically displayed with a lower intensity compared to the peaks of the target compounds (e.g., with a purity of >90%). Such stereoisomers and/or impurities may be typical for the particular manufacturing process, and therefore their peaks may help to identify the reproduction of our manufacturing process on the basis of "by-product fingerprints". An expert who calculates the peaks of the target compounds by known methods (MestReC, ACD simulation, or by use of empirically evaluated expectation values), can isolate the peaks of target compounds as required, optionally using additional intensity filters. Such an operation would be similar to peak-picking in classical $^1$H-NMR interpretation. A detailed description of the reporting of NMR data in the form of peaklists can be found in the publication "Citation of NMR Peaklist Data within Patent Applications" (cf. Research Disclosure Database Number 605005, 2014, 1 Aug. 2014, or http://www.researchdisclosure.com/searching-disclosures).

In the peak picking routine, as described in the Research Disclosure Database Number 605005, the parameter "MinimumHeight" can be adjusted between 1% and 4%. Depending on the chemical structure and/or depending on the concentration of the measured compound it may be reasonable to set the parameter "MinimumHeight"<1%.

LC-MS Methods:
Method 1 (Standard 6 Min):
MS instrument type: Micromass ZQ; HPLC instrument type: Waters Alliance 2695; UV PDA 2996 Waters detector; column: Waters SunFire C18 2.1×50 mm, 3.5 μm; mobile phase A: 10 mM formic acid in water, mobile phase B: acetonitrile; gradient: 0.0 min 100% A→3.1 min 0% A→3.8 min 0% A→4.8 min 100% A→6.0 min 100% A; flow rate: 0.7 ml/min; ELSD detection: Sedere Sedex 90.

Method 8 (Polar Compounds, 8 Min):
MS instrument type: Micromass ZQ; HPLC instrument type: Waters Alliance 2695; UV PDA 2996 Waters detector; column: Waters SunFire C18 2.1×50 mm, 3.5 µm; mobile phase A: 10 mM formic acid in water, mobile phase B: acetonitrile; gradient: 0.0 min 100% A→0.5 min 100% A→5.5 min 20% A→6.0 min 0% A→6.5 min 0% A→7.0 min 100% A→8.0 min 100% A; flow rate: 0.7 ml/min; ELSD detection: Sedere Sedex 90.
Method 9 (Standard 18 Min):
MS instrument type: Micromass ZQ; HPLC instrument type: Waters Alliance 2695; UV PDA 2996 Waters detector; column: Waters SunFire C18 2.1×50 mm, 3.5 m; mobile phase A: 10 mM formic acid in water, mobile phase B: acetonitrile; gradient: 0.0 min 95% A→0.5 min 95% A→14 min 5% A→15 min 5% A→16 min 95% A→18.0 min 95% A; flow rate: 0.7 ml/min; ELSD detection: Sedere Sedex 90.
Method 12 (Basic 6 Min)
MS instrument type: Agilent 6120 Quadrupole LC/MS; HPLC instrument type: Agilent 1260 Infinity; DAD detector Agilent 1260 Infinity; Column heater Agilent 1260 Infinity column: Waters XSelect CSH C18 2.1×50 mm, 3.5 µm; mobile phase A: 10 mM ammonium hydroxide in water, mobile phase D: acetonitrile; gradient: 0.0 min 95% A→0.1 min 95% A→0.3 min 50% A→4.5 min 2% A→5.0 min 2% A→5.1 min 95% A→6.0 min 95% A; flow rate: 0.7 ml/min.
UHPLC-MS Methods:
Method 2 (Standard 2.5 Min Acid):
MS instrument type: Waters 3100; UHPLC instrument type: Waters Acquity HClass; UV PDA eλ Detector; column: Waters XSelect C18 CSH, 2.1×50 mm, 2.5 µm; mobile phase A: 10 mM formic acid in water, mobile phase B: acetonitrile; gradient: 0.0 min 95% A→0.5 min 95% A→1.67 min 2% A→1.92 min 2% A→2.15 min 95% A→2.5 min 95% A; flow rate: 1.0 ml/min; detection Thermo Corona Ultra RS.
Method 3 (Standard 2.5 Min Basic):
MS instrument type: Waters 3100; UHPLC instrument type: Waters Acquity HClass; UV PDA eλ Detector; column: Waters XSelect C18 CSH, 2.1×50 mm, 2.5 µm; mobile phase A: 10 mM ammonia in water, mobile phase B: acetonitrile; gradient: 0.0 min 95% A→0.5 min 95% A→1.67 min 2% A→1.92 min 2% A→2.15 min 95% A→2.5 min 95% A; flow rate: 1.0 ml/min; detection Thermo Corona Ultra RS.
Method 4 (Standard 4.0 Min Acid):
MS instrument type: Waters 3100; UHPLC instrument type: Waters Acquity HClass; UV PDA eλ Detector; column: Waters XSelect C18 CSH, 2.1×50 mm, 2.5 µm; mobile phase A: 10 mM formic acid in water, mobile phase B: acetonitrile; gradient: 0.0 min 95% A→0.5 min 95% A→3.15 min 2% A→3.42 min 2% A→3.67 min 95% A 4.0 min 95% A; flow rate: 1.0 ml/min; detection Thermo Corona Ultra RS.
Method 5 (Standard 4.0 Min Basic):
MS instrument type: Waters 3100; UHPLC instrument type: Waters Acquity HClass; UV PDA eλ Detector; column: Waters XSelect C18 CSH, 2.1×50 mm, 2.5 m; mobile phase A: 10 mM ammonia in water, mobile phase B: acetonitrile; gradient: 0.0 min 95% A→0.5 min 95% A→3.15 min 2% A→3.42 min 2% A→3.67 min 95% A→4.0 min 95% A; flow rate: 1.0 ml/min; detection Thermo Corona Ultra RS.
Method 10 (15.0 Min Basic):
MS instrument type: Waters 3100; UHPLC instrument type: Waters Acquity HClass; UV PDA eλ Detector; column: Waters XSelect C18 CSH, 2.1×50 mm, 2.5 µm; mobile phase A: 10 mM ammonia in water, mobile phase B: acetonitrile; gradient: 0.0 min 95% A→1 min 95% A→13.2 min 20% A→13.65 min 20% A→13.75 min 2% A→14.3 min 2% A→14.65 min 95% A→15 min 95% A; flow rate: 1.0 ml/min; detection Thermo Corona Ultra RS.
Method 11 (3.5 Min Basic Apolaire):
MS instrument type: Waters 3100; UHPLC instrument type: Waters Acquity HClass; UV PDA eλ Detector; column: Waters XSelect C18 CSH, 2.1×50 mm, 2.5 m; mobile phase A: 10 mM ammonia in water, mobile phase B: acetonitrile; gradient: 0.0 min 50% A→0.2 min 50% A→2.2 min 2% A→2.9 min 2% A→3.15 min 50% A→3.5 min 50% A; flow rate: 1.0 ml/min; detection Thermo Corona Ultra RS.
Semi Preparative Methods:
Method 6: (Semi Preparative LC-MS, Basic Conditions)
MS instrument type: Waters ZQ Micromass (ESI source); HPLC instrument type: Waters 2525 with «Make up» and «At column» pumps 515; Photodiode Array Detector Waters 996; column: Waters XBridge C18 OBD, 30×50 mm, 5 µm; mobile phase A: 10 mM ammonia in water, mobile phase B: acetonitrile; flow rate: 60 ml/min; injection loop volume: 2 mL.
Method 7: (Semi Preparative LC-MS, Acidic Conditions)
MS instrument type: Waters ZQ Micromass (ESI source); HPLC instrument type: Waters 2525 with «Make up» and «At column» pumps 515; Photodiode Array Detector Waters 996; column: Waters Sunfire C18 OBD, 30×50 mm, 5 µm; mobile phase A: 10 mM formic acid in water, mobile phase B: acetonitrile; flow rate: 60 ml/min; injection loop volume: 2 mL.

In the present text, in particular in the Experimental Section, for the synthesis of intermediates and of examples of the present invention, when a compound is mentioned as a salt form with the corresponding base or acid, the exact stoichiometric composition of said salt form, as obtained by the respective preparation and/or purification process, is, in most cases, unknown.

Unless specified otherwise, suffixes to chemical names or structural formulae such as "hydrochloride", "trifluoroacetate", "sodium salt", or "x HCl", "x CF3COOH", "x Na+", for example, are to be understood as not a stoichiometric specification, but solely as a salt form.

This applies analogously to cases in which synthesis intermediates or example compounds or salts thereof have been obtained, by the preparation and/or purification processes described, as solvates, such as hydrates with (if defined) unknown stoichiometric composition.

Starting Material to be Synthesized and Intermediates

Carboxylic Acid Intermediates (A)

Intermediate 1A 2-chloro-5-[5-({[(1R)-1-(4-methylphenyl)ethyl]amino}methyl)-2-furyl]benzoic acid

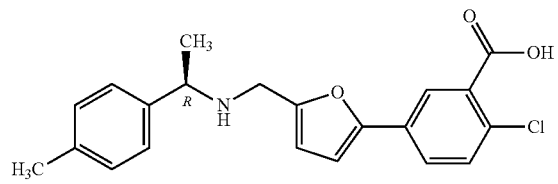

Ethyl 5-amino-2-chlorobenzoate

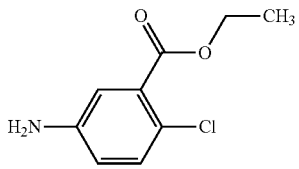

To a stirred solution of 5-amino-2-chlorobenzoic acid, 20 g (85% purity, 99 mmol) in dry ethanol (400 mL) was added thionyl chloride, 14.5 mL (198 mmol, 2.0 eq.) over 30 min at 0° C. The resulting suspension was then allowed to warm to r.t., stirred for 1 h and then heated at 90° C. for 3 h. After cooling to r.t., the mixture was concentrated in vacuum and the resulting purple slurry was partitioned between ethyl acetate and water. The layers were separated and the aqueous phase was washed with ethyl acetate. The aqueous acidic phase was basified with solid sodium hydrogen carbonate and extracted with ethyl acetate. The combined organic extracts were washed with brine, dried over sodium sulfate and concentrated under reduced pressure to yield the product, 18.0 g (91%) as a purple oil.

LC-MS (Method 1): $R_t$=2.95 min; MS (ES+): m/z=200 (M+H)$^+$, 241 ([M+acetonitrile]+H)$^+$.

$^1$H-NMR (500 MHz, CDCl$_3$) δ [ppm]=1.39 (t, 3H), 4.37 (q, 2H), 6.71 (dd, 1H), 7.10 (d, 1H), 7.19 (d, 1H).

Ethyl 2-chloro-5-(5-formylfuran-2-yl)benzoate

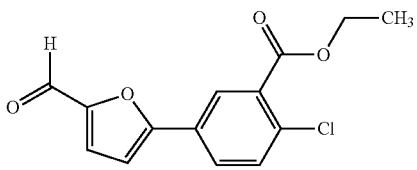 [SMILES: CCOC(=O)c1cc(-c2ccc(C=O)o2)ccc1Cl]

A mixture of ethyl 5-amino-2-chlorobenzoate, 18.0 g (90 mmol) in aq. hydrochloric acid, 150 mL (1.5N, 225 mmol, 2.5 eq.) was heated to 80° C. for 1 h. The solution was then cooled to 0° C. and sodium nitrite, 6.53 g (95 mmol, 1.05 eq.) in water (20 mL) was added slowly. After 2 h at 0° C., the mixture was filtered and the filtrate was treated with 2-furfuraldehyde, 7.5 mL (42.1 mmol). An aqueous solution of cupric chloride, 2.42 g (18 mmol, 0.2 eq.) in water (10 mL) was then added dropwise at r.t. and the resulting mixture was stirred at r.t. for 18 h. The mixture was then extracted with ethyl acetate and the combined organic phase was washed with brine, dried over sodium sulfate and concentrated under reduced pressure to give the product, 18.9 g (74%) as a dark brown oily solid.

LC-MS (Method 1): $R_t$=3.46 min; MS (ES+): m/z=279/281 (M+H)$^+$.

$^1$H-NMR (500 MHz, CDCl$_3$)=1.44 (t, 3H), 4.45 (q, 2H), 6.89 (d, 1H), 7.33 (d, 1H), 7.53 (d, 1H), 7.84 (dd, 1H), 8.21 (d, 1H), 9.68 (s, 1H).

2-Chloro-5-(5-formyl-2-furyl)benzoic acid

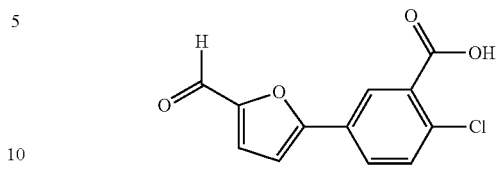

To a solution of ester ethyl 2-chloro-5-(5-formylfuran-2-yl)benzoate, 2.0 g (7.17 mmol) in THF (290 mL) at 0° C. was added lithium hydroxide, 361 mg (8.61 mmol, 1.2 eq) in water (70 mL). The solution was stirred at 0° C. for 6 h, then stored at 4° C. overnight. LC-MS analysis showed full conversion. The mixture was diluted with water (70 mL), then acidified using 1N hydrochloric acid aqueous solution. The aqueous phase was extracted with ethyl acetate. The combined organics were dried over sodium sulfate and concentrated to an orange solid. The solid was triturated in ethyl acetate, filtered, rinse with ethyl acetate and dried under reduced pressure to give the product, 1.25 g (64%) as an orange solid.

LC-MS (Method 1): $R_t$=2.99 min; MS (ES-): m/z=249/251 (M-H)$^-$ $^1$H-NMR (500 MHz, DMSO-d6) δ [ppm]=7.44 (d, 1H), 7.66 (d, 1H), 7.69 (d, 1H), 8.01 (dd, 1H), 8.23 (d, 1H), 9.64 (s, 1H), 13.70 (br s, 1H).

Ethyl 2-chloro-5-[5-({[(1R)-1-(4-methylphenyl)ethyl]amino}methyl)furan-2-yl]-benzoate

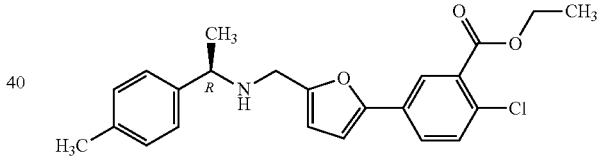

To a stirred solution of ethyl 2-chloro-5-(5-formylfuran-2-yl)benzoate, 2.50 g (8.97 mmol) in dichloroethane (83 mL) at r.t. was added (R)-(+)-1-(4-methylphenyl)ethylamine, 1.58 mL (10.8 mmol, 1.2 eq.). The mixture was stirred at r.t. 1 h, and then sodium triacetoxyborohydride, 2.85 g (13.46 mmol, 1.5 eq.) was added in three portions over a 4 h period. The mixture was stirred at r.t. overnight. The mixture was poured into aq. sat. sodium hydrogen carbonate and the layers were separated. The aqueous phase was extracted with DCM (2×) and the combined organic extracts were dried over sodium sulfate, filtered and the solvent was removed under reduced pressure. The residue was purified by flash column chromatography on silica gel (Companion, 80 g column, cyclohexane/ethyl acetate 1/0 to 1/1) to give the product, 2.42 g (64%) as a brown oil.

LC-MS (Method 1): $R_t$=2.57 min; MS (ES+): m/z=398/400 (M+H)$^+$.

$^1$H-NMR (500 MHz, CDCl$_3$) δ [ppm]=1.38 (d, 3H), 1.43 (t, 3H), 1.75 (br s, 1H), 2.35 (s, 3H), 3.64 & 3.72 (2 d, AB, 2H), 3.82 (q, 1H), 4.44 (q, 2H), 6.21 (d, 1H), 6.61 (d, 1H), 7.16 (d, 2H), 7.25 (d, 2H), 7.43 (d, 1H), 7.64 (dd, 1H), 8.03 (d, 1H).

2-Chloro-5-[5-({[(1R)-1-(4-methylphenyl)ethyl]amino}methyl)-2-furyl]benzoic acid To a stirred solution of ethyl 2-chloro-5-[5-({[(1R)-1-(4-methylphenyl)ethyl]-amino}methyl)furan-2-yl]benzoate, 1.0 g (2.5 mmol) in a mixture tetrahydro-furan/methanol/water (24 mL, 1/1/1) was added lithium hydroxide monohydrate, 211 mg (5.0 mmol, 2 eq.) at 0° C. and the resulting mixture was stirred at r.t. for 2.5 h. The volatiles were removed under reduced pressure, water (20 mL) was added and the mixture was acidified to pH~7 by dropwise addition of aq. 1N hydrochloric acid. The resulting solid was filtered, washed with water, THF, MTBE and dried under reduced pressure to give the product, 0.77 g (79%) as a light brown solid.

LC-MS (Method 1): $R_t$=2.41 min; MS (ES+): m/z=370/372 (M+H)$^+$ $^1$H-NMR (500 MHz, CD$_3$OD) δ [ppm]=1.68 (d, 3H), 2.37 (s, 3H), 4.04 & 4.18 (2 d, AB, 2H), 4.37 (q, 1H), 6.59 (d, 1H), 6.80 (d, 1H), 7.31 (d, 2H), 7.37 (d, 2H), 7.38 (d, 1H), 7.58 (dd, 1H), 7.82 (d, 1H).

Intermediate 2A 2-fluoro-5-[5-({[(1R)-1-(4-methylphenyl)ethyl]amino}methyl)furan-2-yl]benzoic acid

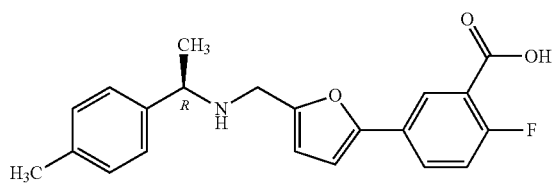

Ethyl 5-amino-2-fluorobenzoate

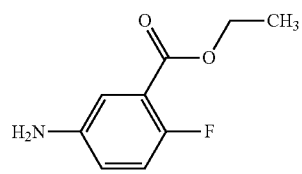

Thionyl chloride, 4.7 mL (64 mmol, 2.0 eq.) was added dropwise to a cold (0° C.) solution of 5-amino-2-fluorobenzoic acid, 5.0 g (32 mmol) in dry ethanol (100 mL) over 10 min. The resulting solution was then allowed to warm to r.t. over 1 h and then heated to reflux for 4 h. The mixture was then concentrated in vacuo and water was added until a clear solution was obtained (200 mL). The obtained purple acidic solution was washed with an ethyl acetate/cyclohexane mixture (1/1). The organic phase was further extracted with 0.5 N aqueous hydrochloric acid. The combined aqueous acidic phase was further washed with an ethyl acetate-cyclohexane mixture (1/1), cooled at 0° C., basified using solid sodium hydrogen carbonate and then extracted with ethyl acetate. The combined organic phase was washed with brine, dried over sodium sulfate, filtered and concentrated under reduced pressure to yield ethyl 5-amino-2-fluorobenzoate, 5.3 g (90%) as a purple oil.

LC-MS (Method 1): $R_t$=2.55 min; (ES+): m/z=184 (M+H)$^+$.

$^1$H-NMR (500 MHz, CDCl$_3$): δ [ppm]=1.38 (t, 3H), 4.37 (q, 2H), 6.79 (dd, 1H), 6.92 (dd, 1H), 7.19 (dd, 1H).

Ethyl 2-fluoro-5-(5-formylfuran-2-yl)benzoate

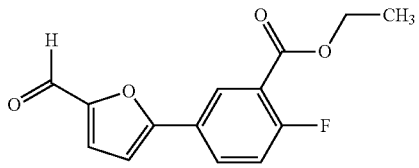 [SMILES: CCOC(=O)c1cc(-c2ccc(C=O)o2)ccc1F]

A solution of Ethyl 5-amino-2-fluorobenzoate, 5.4 g (29.5 mmol) in hydrochloric acid (1.5N, 50 mL, 2.5 eq.) was cooled to 0° C. (a solid precipitated) and was diazotized by the addition of sodium nitrite, 2.14 g (31.0 mmol, 1.05 eq.) in water (6.5 mL). After 2 h stirring at 0° C., the mixture was filtered and the filtrate containing the diazonium salt was treated with 2-furfuraldehyde, 2.44 mL (29.5 mmol) and water (14 mL). To this mixture, an aqueous solution of cupric chloride, 793 mg (5.9 mmol, 0.2 eq.) in 3.5 mL of water was added dropwise with stirring. Stirring was continued overnight at room temperature. The mixture was extracted with ethyl acetate and then the organic phase was washed with water, aq. Sat. sodium hydrogen carbonate, brine, dried over sodium sulfate and concentrated. The dark brown residue was purified by flash chromatography (Companion, 80 g column, eluent: cyclohexane/ethyl acetate 1/0 to 7/3) to give the desired product, 120 mg (1%) as a dark brown solid.

LC-MS (Method 1): $R_t$=3.30 min; (ES+) nm/z=263 (M+H)$^+$ $^1$H-NMR (500 MHz, CDCl$_3$): δ [ppm]=1.44 (t, 3H), 4.45 (q, 2H), 6.87 (d, 1H), 7.24 (dd, 1H), 7.33 (d, 1H), 7.98 (ddd, 1H), 8.35 (dd, 1H), 9.68 (s, 1H).

$R_f$=0.28 (cyclohexane/ethyl acetate 4/1).

Ethyl 2-fluoro-5-[5-({[(1R)-1-(4-methylphenyl)ethyl]amino}methyl)furan-2-yl]benzoate

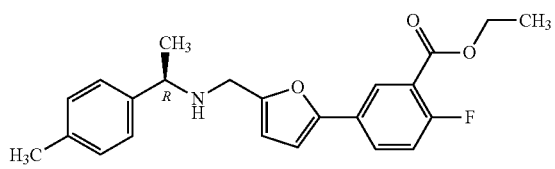

To a stirred solution of ethyl 2-fluoro-5-(5-formylfuran-2-yl)benzoate, 120 mg (0.46 mmol) in dichloroethane (4 mL) at r.t. was added (R)-(+)-1-(4-Methylphenyl)-ethylamine, 0.081 mL (0.55 mmol, 1.2 eq.). The mixture was stirred at r.t. 1 h, and then sodium triacetoxyborohydride, 146 mg (0.69 mmol, 1.5 eq.) was added in one portion. The mixture was stirred at r.t. overnight. The mixture was poured into aq. sat. sodium hydrogen carbonate and the layers were separated. The aqueous phase was extracted with DCM and the combined organic phase was dried over sodium sulfate, filtered and the solvent was removed under reduced pressure. The residue was purified by flash column chromatography on silica gel (Companion, 12 g column, cyclohexane/ethyl acetate 9/1 to 7/3) to give the product, 133 mg (70%) as a brown oil.

LC-MS (Method 1): $R_t$=2.49; MS (ES+): m/z=382 (M+H)$^+$ $^1$H-NMR (CDCl$_3$, 500 MHz): δ [ppm]=1.43 (t, 3H), 1.44 (t, 3H), 2.36 (s, 3H), 3.68 & 3.79 (2d, AB, 2H), 3.88 (m, 1H), 4.44 (q, 2H), 6.28 (br s, 1H), 6.58 (d, 1H), 7.11-7.35 (m, 5H), 7.80 (m, 1H), 8.18 (dd, 1H)

2-fluoro-5-[5-({[(1R)-1-(4-methylphenyl)ethyl]amino}methyl)furan-2-yl]benzoic acid To a stirred solution of ethyl 2-fluoro-5-[5-({[(1R)-1-(4-methylphenyl)ethyl]-amino}methyl)furan-2-yl]benzoate, 130 mg (0.34 mmol) in a mixture tetrahydrofuran/methanol (3 mL, 1:1) was added lithium hydroxide monohydrate, 29 mg (0.68 mmol, 2 eq.) in water (1.5 mL). The resulting mixture was stirred at r.t. for 5 h. The volatiles were removed under reduced pressure, water (4 mL) was added and the solution was acidified to pH~7 by dropwise addition of aq. 1N hydrochloric acid. The resulting solid was filtered, washed with water and dried under reduced pressure to give the product 2A, 100 mg (78%) as a light orange solid.

LC-MS (Method 1): $R_t$=2.33 min; MS (ES-): m/z=352 (M-H)-.

$^1$H-NMR (500 MHz, DMSO-d6) δ [ppm]=1.31 (d, 3H), 2.28 (s, 3H), 3.61 (m, 2H), 3.85 (q, 1H), 6.37 (d, 1H), 6.92 (d, 1H), 7.15 (d, 2H), 7.28 (d, 2H), 7.34 (dd, 1H), 7.88 (ddd, 1H), 8.09 (dd, 1H)

Intermediate 3A 2-chloro-3-fluoro-5-[5-({[(1R)-1-(4-methylphenyl)ethyl]amino}methyl)-2-furyl]-benzoic acid

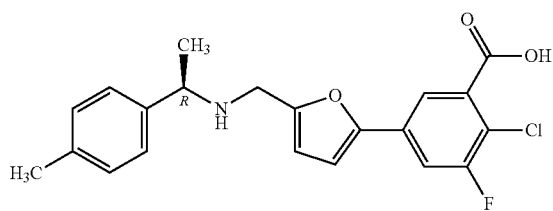

Methyl 2-chloro-3-fluoro-5-(5-formyl-2-furyl)benzoate

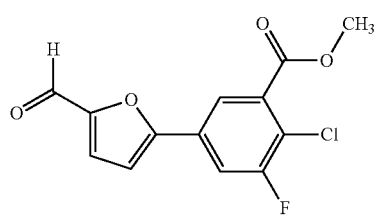 [SMILES: COC(=O)c1cc(-c2ccc(C=O)o2)cc(F)c1Cl]

A mixture of 5-amino-2-chloro-3-fluoro-benzoic acid methyl ester, 0.20 g (0.84 mmol), hydrochloric acid (1N, 1.7 mL, 2 eq.), water (1.4 mL) and acetonitrile (1 mL) was cooled to 0° C. and sodium nitrite, 72 mg (1.04 mmol, 1.25 eq.) in water (0.2 mL) was added slowly. After 2 h stirring at 0° C., the suspension was treated with 2-furfuraldehyde, 0.104 mL (1.25 mmol, 1.5 eq.) and an aqueous solution of cupric chloride (23 mg in 0.2 mL of water, 0.017 mmol, 0.2 eq.). Stirring was continued overnight at room temperature. The resulting heterogeneous mixture (a gum has formed) was then extracted using ethyl acetate. The combined organic phase was dried over sodium sulfate and concentrated. The residue was purified by flash chromatography (companion, 12 g column, cyclohexane/ethyl acetate 0/1>6/4) to give the product, 80 mg (29%) as a yellow solid.

LC-MS (Method 1): $R_t$=3.47 min; MS (ES+): m/z=283 (M+H)$^+$.

$^1$H-NMR (500 MHz, CDCl$_3$) δ [ppm]=4.00 (s, 3H), 6.93 (d, 1H), 7.34 (d, 1H), 7.73 (dd, 1H), 8.06 (dd, 1H), 9.71 (s, 1H).

Methyl 2-chloro-3-fluoro-5-[5-({[(1R)-1-(4-methylphenyl)ethyl]amino}methyl)-2-furyl]benzoate

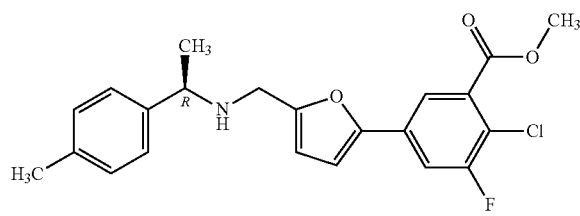

To a stirred solution of methyl 2-chloro-3-fluoro-5-(5-formyl-2-furyl)benzoate, 100 mg (0.35 mmol) in dichloroethane (3 mL) were added (R)-1-4-tolylethanamine, 0.062 mL (0.43 mmol) followed by acetic acid, 0.041 mL (0.71 mmol, 2 eq.) and the mixture was stirred at r.t. for 15 min. Sodium triacetoxyborohydride, 113 mg (0.53 mmol, 1.5 eq.) was added in one portion and the resulting mixture was stirred at r.t. for 16 h. The mixture was poured into aq. sat. sodium hydrogen carbonate and extracted with dichloromethane (3×). The combined organic phases were dried over sodium sulfate, filtered and concentrated. The residue was purified by flash column chromatography on silica gel (eluent: cyclohexane/ethyl acetate 1/0 to 0/1) to give the product, 140 mg (96%) as a brown oil.

LC-MS (Method 1): $R_t$=2.57 min; MS (ES+): m/z=402/404 (M+H)$^+$.

$^1$H-NMR (500 MHz, DMSO-d6) δ [ppm]=1.25 (d, 3H), 2.28 (s, 3H), 3.50 & 3.57 (2d, AB, 2H), 3.70 (q, 1H), 3.93 (s, 3H), 6.35 (d, 1H), 7.12 (d, 1H), 7.13 (d, 2H), 7.24 (d, 2H), 7.88-7.93 (m, 2H).

2-chloro-3-fluoro-5-[5-({[(1R)-1-(4-methylphenyl)ethyl]amino}methyl)-2-furyl]benzoic acid To stirred solution of methyl 2-chloro-3-fluoro-5-[5-({[(1R)-1-(4-methylphenyl)-ethyl]amino}methyl)-2-furyl]benzoate, 140 mg (0.35 mmol) in a mixture tetrahydrofuran/methanol (3.0 mL, 1/1) was added lithium hydroxide monohydrate, 22 mg (0.52 mmol, 1.5 eq.) in water (1.5 mL) at 0° C. and the resulting mixture was stirred at r.t. for 18 h. The volatiles were removed under reduced pressure, water (5 mL) was added and the mixture was neutralised to pH~7 by dropwise addition of aq. 1N hydrochloric acid. The solid formed was filtered, rinsed with water and dried in vacuo, then over phosphorus pentoxide to give the crude product 3A, 90 mg (67%) as a light yellow solid.

LC-MS (Method 1): $R_t$=2.49 min; MS (ES-): m/z=386/388 (M-H)$^-$.

$^1$H-NMR (500 MHz, DMSO-d6) δ [ppm]=1.34 (s, 3H), 2.30 (s, 3H), 3.68 (br s, 2H), 3.88 (m, 1H), 6.42 (d, 1H), 7.09 (d, 1H), 7.17 (d, 2H), 7.19 (d, 2H), 7.75-7.79 (m, 2H).

Intermediate 4A 2-chloro-5-{5-[({2-[4-(trifluoromethyl)phenyl]propan-2-yl}amino)methyl]-2-furyl}benzoic acid

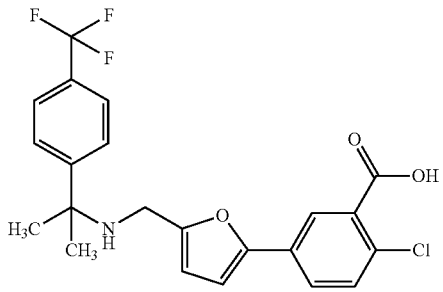 [SMILES: CC(C)(NCc1ccc(-c2ccc(Cl)c(C(=O)O)c2)o1)c1ccc(C(F)(F)F)cc1]

Ethyl 2-chloro-5-{5-[({2-[4-(trifluoromethyl)phenyl]propan-2-yl}amino)methyl]-2-furyl}benzoate

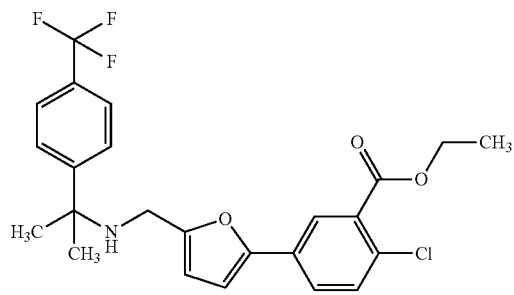 [SMILES: CCOC(=O)c1cc(-c2ccc(CNC(C)(C)c3ccc(C(F)(F)F)cc3)o2)ccc1Cl]

A solution of ethyl 2-chloro-5-(5-formylfuran-2-yl)benzoate, 194 mg (0.70 mmol) in 1,2-dichloroethane (7 mL) was treated with 1-[4-(trifluoromethyl)phenyl]-1-methylethylamine hydrochloride, 250 mg (1.04 mmol) and triethylamine, 0.15 mL (1.04 mmol). The brown mixture was stirred at r.t. for 45 minutes before addition of sodium triacetoxyborohydride, 295 mg (1.39 mmol). The resulting brown reaction medium was stirred at r.t. overnight. Sodium triacetoxyborohydride, 74 mg (0.35 mmol) was added and the mixture was stirred at r.t. for 1 h and then at 50° C. for 2 h. The reaction medium was diluted with DCM and washed with sat. aq. sodium bicarbonate solution (×2). The aqueous layer was extracted with dichloromethane (×3) and combined organics were dried over sodium sulfate, filtered and concentrated. The residue was purified by flash chromatography with combiflash (12 g column, eluent: cyclohexane/ethyl acetate 1/0 to 7/3) to give the product, 159 mg (43%) as a brown thick oil.

LC-MS (Method 1): $R_t$=2.86 min; MS (ES+): m/z=466/468 (M+H)$^+$.

$^1$H-NMR (500 MHz, CD$_3$OD) δ [ppm]=1.42 (t, 3H), 1.56 (s, 6H), 3.54 (s, 2H), 4.42 (q, 2H), 6.27 (d, 1H), 6.73 (d, 1H), 7.49 (d, 1H), 7.62 (d, 2H), 7.72-7.76 (m, 3H), 8.03 (d, 1H).

2-chloro-5-{5-[({2-[4-(trifluoromethyl)phenyl]propan-2-yl}amino)methyl]-2-furyl}-benzoic acid To a stirred solution of ethyl 2-chloro-5-{5-[({2-[4-(trifluoromethyl)phenyl]propan-2-yl}amino)methyl]-2-furyl}benzoate, 155 mg (0.33 mmol) in a mixture tetrahydrofuran/methanol/water (1/1/1, 3.6 mL) was added lithium hydroxide monohydrate, 28 mg (0.67 mmol, 2.0 eq.) and the resulting mixture was stirred at r.t. overnight. The volatiles were removed under reduced pressure. The resulting orange aqueous solution was then acidified to pH~4 by dropwise addition of aq. 1N hydrochloric acid. The precipitate formed was filtered and washed with water. The residual solid was then triturated in MTBE but the whole solid dissolved. The MTBE solution was concentrated to dryness to afford the product 4A, 155 mg (93%) as an orange solid.

LC-MS (Method 1): $R_t$=2.58 min; MS (ES+): m/z=438/440 (M+H)$^+$ $^1$H-NMR (500 MHz, DMSO-d$_6$) δ [ppm]=1.75 (s, 6H), 3.93 (s, 2H), 6.59 (s, 1H), 7.03 (d, 1H), 7.62 (d, 1H), 7.79 (d, 2H), 7.82 (dd, 1H), 7.86 (d, 2H), 8.06 (d, 1H).

Intermediate 5A 2,4-dichloro-5-[5-({[(1R)-1-(4-methylphenyl)ethyl]amino}methyl)-2-furyl]benzoic acid

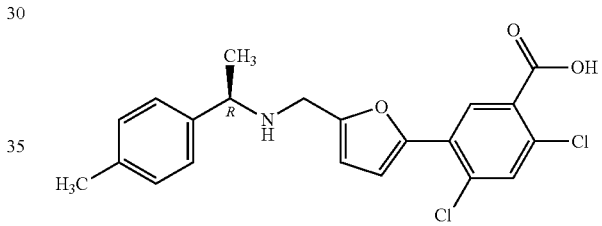

2,4-dichloro-5-(5-formyl-2-furyl)benzoic acid

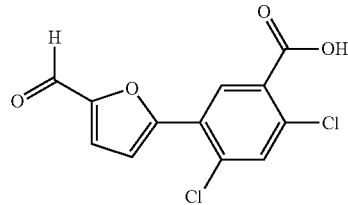 [SMILES: O=Cc1ccc(-c2cc(C(=O)O)c(Cl)cc2Cl)o1]

A mixture of 5-amino-2,4-dichlorobenzoic acid, 250 mg (1.21 mmol) in aq. hydrochloric acid, 2 mL (1.5N, 3.03 mmol, 2.5 eq.) and acetic acid (0.5 mL) was heated to 80° C. for 1 h. The solution was then cooled to 0° C. and sodium nitrite, 88 mg (1.27 mmol, 1.05 eq.) in water (0.6 mL) was added slowly. After 2 h at 0° C., 2-furfuraldehyde, 0.10 mL (1.21 mmol) followed by an aqueous solution of copper(II) chloride, 33 mg (0.243 mmol, 0.2 eq.) in water (0.3 mL) were added dropwise at r.t. and the resulting mixture was stirred at r.t. for 18 h. The mixture was then extracted with ethyl acetate (3×) and the combined organic phases were washed with brine, dried over sodium sulfate and concentrated under reduced pressure to give the crude product 5A, 267 mg (63%) as a brown solid.

LC-MS (Method 1): R$_t$=3.42 min; MS (ES−): m/z=283/ 285 (M−H)$^-$.

$^1$H-NMR (500 MHz, DMSO-d$_6$) δ [ppm]=7.47 (d, 1H), 7.70 (d, 1H), 7.96 (s, 1H), 8.33 (s, 1H), 9.70 (s, 1H).

2,4-dichloro-5-[5-({[(1R)-1-(4-methylphenyl)ethyl]amino}methyl)-2-furyl]benzoic acid To a stirred solution of 2,4-dichloro-5-(5-formyl-2-furyl)benzoic acid, 265 mg (0.762 mmol) in dichloromethane (7.5 mL) were added (R)-1-4-tolylethanamine, 0.12 mL (0.84 mmol, 1.1 eq.) followed by acetic acid, 0.22 mL (3.81 mmol, 5 eq.) and the mixture was stirred at r.t. for 30 min. Sodium triacetoxyborohydride, 242 mg (1.14 mmol, 1.5 eq.) was added in one portion and the resulting mixture was stirred at r.t. for 18 h. The mixture was poured into aq. sat. sodium hydrogen carbonate and extracted with dichloromethane (3×). The combined organic extracts were dried over sodium sulfate, filtered and concentrated. The residue (337 mg, brown oil) was triturated in methyl tert-butyl ether, filtered, washed with methyl tert-butyl ether and dried to give a first batch, 48 mg (15%) as a beige solid. The filtrate was concentrated and dissolved in ethyl acetate (30 mL). The organic layer was washed with aq. 1N hydrochloric acid (2×), brine, dried over sodium sulfate and concentrated to give a second batch, 217 mg (63%) as a brown solid. Combined yield=78%.

LC-MS (Method 1): R$_t$=2.54 min; MS (ES+): m/z=404/ 406 (M+H)$^+$.

$^1$H-NMR (500 MHz, DMSO-d$_6$) δ [ppm]=1.29 (d, 3H), 2.28 (s, 3H), 3.61 (d, 1H), 3.66 (d, 1H), 3.82 (q, 1H), 6.43 (d, 1H), 7.12 (d, 1H), 7.15 (d, 2H), 7.27 (d, 2H), 7.72 (s, 1H), 8.11 (s, 1H).

Intermediate 6A 4-cyano-3-[5-({[(1R)-1-(4-methylphenyl)ethyl]amino}methyl)-2-furyl]benzoic acid

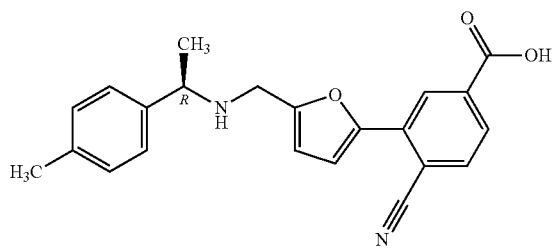

Ethyl 4-cyano-3-(5-formyl-2-furyl)benzoate

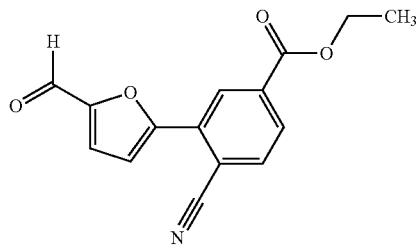 [SMILES: CCOC(=O)c1ccc(C#N)c(-c2ccc(C=O)o2)c1]

To a stirred solution of ethyl-3-bromo-4-cyanobenzoate, 1.50 g (5.90 mmol), 5-formylfuran-2-ylboronic acid, 1.24 g (8.85 mmol, 1.5 eq.) and [1,1'-Bis(diphenyl-phosphino)ferrocene]dichloropalladium(II), complex with dichloromethane, 723 mg (0.88 mmol, 15 mol %) in degazed tetrahydrofuran (90 mL) was added a solution of sodium carbonate, 1.25 g (11.8 mmol, 2.0 eq.) in degazed water (45 mL) and the resulting mixture was stirred at 50° C. for 18 h. After cooling to r.t., the solvent was removed under reduced pressure, water and ethyl acetate were added and the mixture was filtered through Celite. The phases were separated and the aqueous layer was extracted with ethyl acetate (2×). The combined organic extracts were washed with brine, dried over sodium sulfate, filtered and concentrated to give the product, 2.10 g (quantitative yield) as a dark brown solid.

LC-MS (Method 1): R$_t$=3.30 min; MS (ES+): m/z=270 (M+H)$^+$.

$^1$H-NMR (500 MHz, CDCl$_3$) δ [ppm]=1.44 (t, 3H), 4.47 (q, 2H), 7.39 (d, 1H), 7.54 (d, 1H), 7.86 (dd, 1H), 8.12 (dd, 1H), 8.68 (d, 1H), 9.79 (s, 1H).

Ethyl 4-cyano-3-[5-({[(1R)-1-(4-methylphenyl)ethyl]amino}methyl)-2-furyl]benzoate

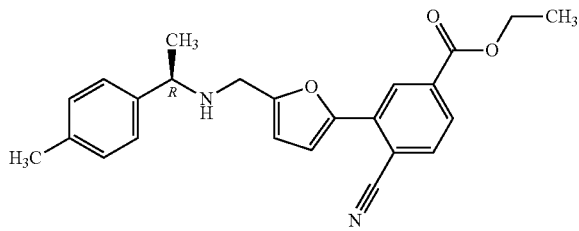

To a stirred solution of ethyl 4-cyano-3-(5-formyl-2-furyl)benzoate, 2.10 g (6.16 mmol) in dichloromethane (60 mL) were added successively acetic acid, 1.76 mL (30.8 mmol, 5 eq.) and (R)-(+)-1-(4-methylphenyl)ethylamine, 0.91 mL (6.16 mmol) and the resulting mixture was stirred at r.t. for 30 min. Sodium triacetoxyborohydride, 1.83 mg (8.63 mmol, 1.4 eq.) was added in one portion and the resulting mixture was stirred at r.t. for 18 h. Aq. sat. sodium hydrogen carbonate was added and the mixture was extracted with dichloromethane (3×). The combined organic extracts were dried over sodium sulfate, filtered and concentrated. The residue was purified by flash column chromatography on silica gel (eluent: dichloromethane/methanol, 99/1) to give the product, 1.18 g (49%) as a brown oil.

LC-MS (Method 1): R$_t$=2.52 min; MS (ES+): m/z=389 (M+H)$^+$.

$^1$H-NMR (500 MHz, CDCl$_3$) δ [ppm]=1.40 (d, 3H), 1.43 (t, 3H), 2.34 (s, 3H), 3.69 (d, 1H), 3.78 (d, 1H), 3.85 (q, 1H), 4.45 (q, 2H), 6.32 (d, 1H), 7.17 (d, 2H), 7.26 (d, 1H), 7.28 (d, 2H), 7.75 (dd, 1H), 7.93 (dd, 1H), 8.47 (d, 1H).

4-cyano-3-[5-({[(1R)-1-(4-methylphenyl)ethyl]amino}methyl)-2-furyl]benzoic acid

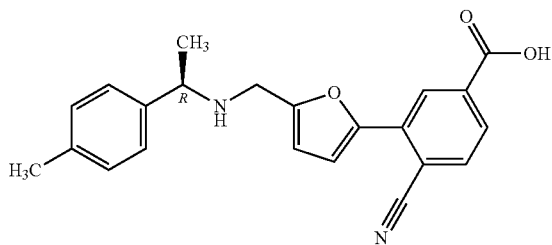

To a stirred solution of ethyl 4-cyano-3-[5-({[(1R)-1-(4-methylphenyl)ethyl]-amino}methyl)-2-furyl]benzoate, 268 mg (0.69 mmol) in a mixture of tetra-hydrofuran/methanol/water (10.5 mL, 1/1/1) was added lithium hydroxide monohydrate, 58 mg (1.38 mmol, 2 eq.) at 0° C. and the resulting mixture was stirred at r.t. for 18 h. The volatiles were removed under reduced pressure, water was added and the mixture was acidified to pH~4 with aq. 1N hydrochloric acid. The aqueous layer was extracted with ethyl acetate (3×), the combined organic layers were washed with brine, dried over sodium sulfate, filtered and concentrated to give the crude product 6A, 211 mg (85%) as a light yellow solid.

LC-MS (Method 1): $R_t$=2.38 min; MS (ES+): m/z=361 (M+H)$^+$.

$^1$H-NMR (500 MHz, DMSO-d$_6$) δ [ppm]=1.35 (d, 3H), 2.28 (s, 3H), 3.77 (s, 2H), 3.95 (m, 1H), 6.56 (d, 1H), 7.17 (d, 2H), 7.27 (d, 1H), 7.31 (d, 2H), 7.93 (dd, 1H), 8.02 (d, 1H), 8.38 (d, 1H).

Intermediate 7A 4-methoxy-2-methyl-5-[5-({[(1R)-1-(4-methylphenyl)ethyl]amino}methyl)-2-furyl]-benzoic acid

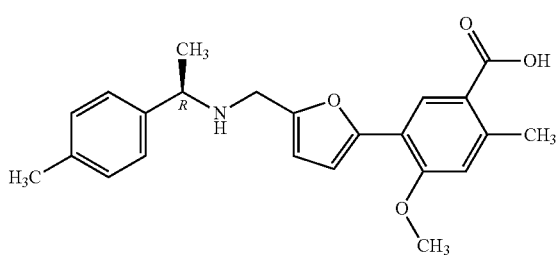

Methyl 5-(5-formyl-2-furyl)-4-methoxy-2-methylbenzoate

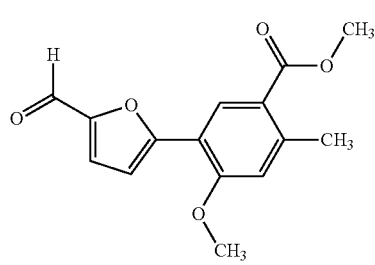 [SMILES: COC(=O)c1cc(-c2ccc(C=O)o2)c(OC)cc1C]

To a stirred solution of methyl 5-bromo-4-methoxy-2-methylbenzoate, 200 mg (0.772 mmol), 5-formylfuran-2-ylboronic acid, 162 mg (1.16 mmol, 1.5 eq.) and [1,1'-Bis(diphenylphosphino)ferrocene]dichloropalladium(II), complex with dichloromethane, 95 mg (0.116 mmol, 15 mol %) in degazed tetrahydrofuran (5 mL) was added a solution of sodium carbonate, 164 mg (1.54 mmol, 2.0 eq.) in degazed water (2.5 mL) and the resulting mixture was stirred at 50° C. for 18 h. After cooling to r.t., the solvent was removed under reduced pressure, water and ethyl acetate were added and the mixture was filtered through Celite. The phases were separated and the aqueous layer was extracted with ethyl acetate (2×). The combined organic extracts were washed with brine, dried over sodium sulfate, filtered and concentrated to give the crude product, 242 mg (95%) as a brown solid.

LC-MS (Method 1): $R_t$=3.37 min; MS (ES+): m/z=275 (M+H)$^+$.

$^1$H-NMR (500 MHz, CDCl$_3$) δ [ppm]=2.68 (s, 3H), 3.92 (s, 3H), 4.01 (s, 3H), 6.83 (s, 1H), 7.09 (d, 1H), 7.32 (d, 1H), 8.60 (s, 1H), 9.68 (s, 1H).

Methyl 4-methoxy-2-methyl-5-[5-({[(1R)-1-(4-methylphenyl)ethyl]amino}methyl)-2-furyl]benzoate

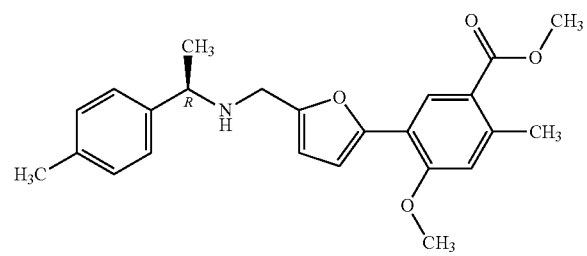

To a stirred solution of methyl 5-(5-formyl-2-furyl)-4-methoxy-2-methylbenzoate, 240 mg (0.726 mmol) in dichloromethane (7 mL) were added (R)-1-4-tolylethanamine, 0.12 mL (0.80 mmol, 1.1 eq.) followed by acetic acid, 0.21 mL (3.63 mmol, 5 eq.) and the mixture was stirred at r.t. for 30 min. Sodium triacetoxyborohydride, 231 mg (1.09 mmol, 1.5 eq.) was added in one portion and the resulting mixture was stirred at r.t. for 4 h. The mixture was poured into aq. sat. sodium hydrogen carbonate and extracted with dichloromethane (3×). The combined organic extracts were washed with brine, dried over sodium sulfate, filtered and concentrated. The residue was purified by flash column chromatography on silica gel (eluent: dichloromethane/methanol, 98:2) to give the product, 240 mg (76%) as a brown oil.

LC-MS (Method 1): $R_t$=2.51 min; MS (ES+): m/z=394 (M+H)$^+$, 259.

$^1$H-NMR (500 MHz, CDCl$_3$) δ [ppm]=1.48 (br d, 3H), 2.35 (s, 3H), 2.65 (s, 3H), 3.69 (d, 1H), 3.84 (m, 1H), 3.92 (s, 3H), 3.97 (s, 3H), 3.99 (m, 1H), 6.35 (br s, 1H), 6.77 (s, 1H), 6.81 (d, 1H), 7.18 (d, 2H), 7.34 (d, 2H), 8.42 (s, 1H).

4-methoxy-2-methyl-5-[5-({[(1R)-1-(4-methylphenyl)ethyl]amino}methyl)-2-furyl]-benzoic acid To a stirred solution of methyl 4-methoxy-2-methyl-5-[5-({[(1R)-1-(4-methyl-phenyl)ethyl]amino}methyl)-2-furyl]benzoate, 240 mg (0.61 mmol) in a mixture tetrahydrofuran/methanol/water (6 mL, 1/1/1) was added lithium hydroxide monohydrate, 51 mg (1.22 mmol, 2 eq.) at 0° C. and the resulting mixture was stirred at r.t. for 18 h. The volatiles were removed under reduced pressure, water (20 mL) was added and the mixture was acidified to pH~7 by dropwise addition of aq. 1N hydrochloric acid. The resulting solid was filtered, washed with water and dried under reduced pressure to give the product 7A, 175 mg (71%) as a red solid.

LC-MS (Method 1): R$_t$=2.37 min; MS (ES+): m/z=380 (M+H)$^+$.

$^1$H-NMR (500 MHz, DMSO-d$_6$) δ [ppm]=1.23 (d, 3H), 2.28 (s, 3H), 2.58 (s, 3H), 3.48 (d, 1H), 3.57 (d, 1H), 3.73 (q, 1H), 3.96 (s, 3H), 6.27 (d, 1H), 6.79 (d, 1H), 7.02 (s, 1H), 7.14 (d, 2H), 7.25 (d, 2H), 8.26 (s, 1H).

Intermediate 8A 2-chloro-4-methoxy-5-[5-({[(1R)-1-(4-methylphenyl)ethyl]amino}methyl)-2-furyl]-benzoic acid

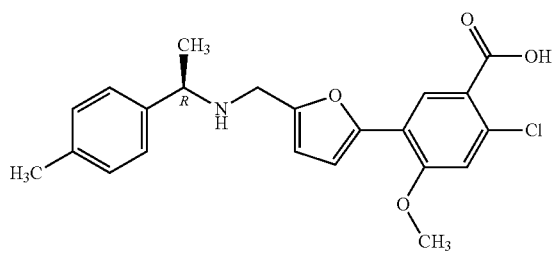

5-bromo-2-chloro-4-hydroxybenzonitrile

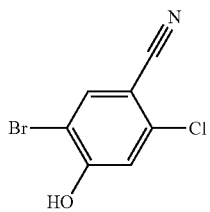 [SMILES: N#Cc1cc(Br)c(O)cc1Cl]

To a stirred solution of 2-chloro-4-hydroxybenzonitrile, 5.0 g (32.5 mmol) in acetonitrile (100 mL) was added dropwise trifluoromethanesulfonic acid, 3.17 mL (35.8 mmol, 1.1 eq.) at −30° C. After 10 min at −30° C., N-bromosuccinimide, 8.11 g (45.6 mmol, 1.4 eq.) was added and the resulting mixture was stirred at r.t. for 18 h. Most of the solvent was removed under reduced pressure and the residue was partitioned between aq. sat. sodium hydrogen carbonate and ethyl acetate. The layers were separated and the aqueous phase was extracted with ethyl acetate. The combined organic layers were washed with brine, dried over sodium sulfate, filtered and concentrated. The residue was purified by flash column chromatography on silica gel (eluent: cyclohexane/ethyl acetate, 4/1) to give the desired product, 1.26 g (16%) as a white solid, and a mixture fraction containing 50% of the desired product together with the starting material and a regioisomer, 1.13 g (8%) as a white solid.

LC-MS (Method 1): R$_t$=3.03 min; MS (ES−): m/z=230/232 (M−H)$^-$.

$^1$H-NMR (500 MHz, CD$_3$OD) δ [ppm]=7.06 (s, 1H), 7.93 (s, 1H).

5-bromo-2-chloro-4-hydroxybenzoic acid

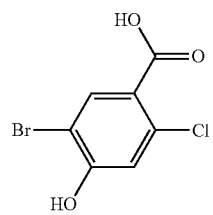 [SMILES: O=C(O)c1cc(Br)c(O)cc1Cl]

A stirred solution of 5-bromo-2-chloro-4-hydroxybenzonitrile, 1.20 g (5.16 mmol) in ethanol (6 mL) and aq. 30% potassium hydroxide (18 mL) was stirred at 100° C. for 18 h. After cooling to 0° C., the mixture was acidified with aq. 10% hydrochloric acid and the resulting solid was filtered, washed with water and dried under reduced pressure to give the product, 1.06 g (81%) as a white solid.

LC-MS (Method 1): R$_t$=2.62 min; MS (ES−): m/z=249/251 (M−H)$^-$.

$^1$H-NMR (500 MHz, CD$_3$OD) δ [ppm]=7.00 (s, 1H), 8.10 (s, 1H).

Methyl 5-bromo-2-chloro-4-methoxybenzoate

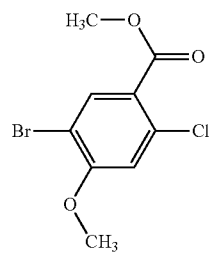

To a stirred solution of 5-bromo-2-chloro-4-hydroxybenzoic acid, 700 mg (2.78 mmol) in N,N-dimethylformamide (10 mL) was added potassium carbonate, 1.15 g (8.35 mmol, 3 eq.) followed by methyl iodide, 0.38 mL (6.12 mmol, 2.2 eq.) at r.t. and the resulting mixture was stirred at r.t. for 4 h. The mixture was poured into water, the resulting solid was filtered, washed with water and dried under reduced pressure to give the product, 715 mg (92%) as a white solid.

LC-MS (Method 1): R$_t$=3.51 min; no ionisation.

$^1$H-NMR (500 MHz, CDCl$_3$) δ [ppm]=3.91 (s, 3H), 3.95 (s, 3H), 6.94 (s, 1H), 8.14 (s, 1H).

Methyl 2-chloro-5-(5-formyl-2-furyl)-4-methoxybenzoate

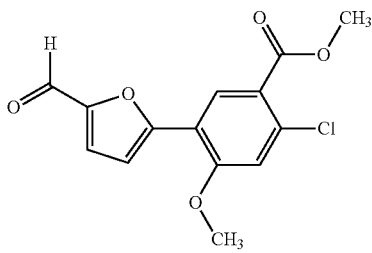 [SMILES: COC(=O)c1cc(-c2ccc(C=O)o2)c(OC)cc1Cl]

To a stirred solution of methyl 5-bromo-2-chloro-4-methoxybenzoate, 250 mg (0.894 mmol), 5-formylfuran-2-ylboronic acid, 188 mg (1.34 mmol, 1.5 eq.) and [1,1'-bis(diphenylphosphino)ferrocene]dichloropalladium(II), complex with dichloromethane, 110 mg (0.134 mmol, 15 mol %) in degazed tetrahydrofuran (6 mL) was added a solution of sodium carbonate, 190 mg (1.79 mmol, 2.0 eq.) in degazed water (3 mL) and the resulting mixture was stirred at 50° C. for 18 h. After cooling to r.t., the solvent was removed under reduced pressure, water and ethyl acetate were added and the mixture was filtered through Celite. The phases were separated and the aqueous layer was extracted with ethyl acetate (2×). The combined organic extracts were washed with brine, dried over sodium sulfate, filtered and concentrated to give the crude product, 225 mg (84%) as a brown solid.

LC-MS (Method 1): $R_t$=3.34 min; MS (ES+): m/z=295/297 (M+H)$^+$.

$^1$H-NMR (500 MHz, CDCl$_3$) δ [ppm]=3.94 (s, 3H), 3.95 (s, 3H), 7.07 (s, 1H), 7.12 (d, 1H), 7.32 (d, 1H), 8.56 (s, 1H), 9.69 (s, 1H).

Methyl 2-chloro-4-methoxy-5-[5-({[(1R)-1-(4-methylphenyl)ethyl]amino}methyl)-2-furyl]benzoate

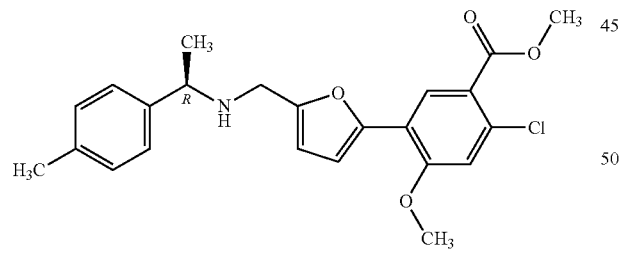

To a stirred solution of methyl 2-chloro-5-(5-formyl-2-furyl)-4-methoxybenzoate, 223 mg (0.757 mmol) in dichloromethane (8 mL) were added (R)-1-4-tolylethanamine, 0.12 mL (0.832 mmol, 1.1 eq.) followed by acetic acid, 0.22 mL (3.78 mmol, 5 eq.) and the mixture was stirred at r.t. for 30 min. Sodium triacetoxyborohydride, 240 mg (1.13 mmol, 1.5 eq.) was added in one portion and the resulting mixture was stirred at r.t. for 4 h. The mixture was poured into aq. sat. sodium hydrogen carbonate and extracted with dichloromethane (3×). The combined organic extracts were washed with brine, dried over sodium sulfate, filtered and concentrated. The residue was purified by flash column chromatography on silica gel (eluent: dichloromethane/methanol, 98:2) to give the product, 110 mg (35%) as a brown oil.

LC-MS (Method 1): $R_t$=2.55 min; MS (ES+): m/z=414/416 (M+H)$^+$.

$^1$H-NMR (500 MHz, CDCl$_3$) δ [ppm]=1.36 (d, 3H), 2.35 (s, 3H), 3.64 (d, 1H), 3.74 (d, 1H), 3.83 (q, 1H), 3.95 (s, 3H), 3.98 (s, 3H), 6.21 (d, 1H), 6.85 (d, 1H), 6.99 (s, 1H), 7.16 (d, 2H), 7.25 (d, 2H), 8.35 (s, 1H).

2-chloro-4-methoxy-5-[5-({[(1R)-1-(4-methylphenyl)ethyl]amino}methyl)-2-furyl]-benzoic acid To a stirred solution of methyl 2-chloro-4-methoxy-5-[5-({[(1R)-1-(4-methylphenyl)-ethyl]amino}methyl)-2-furyl]benzoate, 110 mg (0.266 mmol) in a mixture tetrahydrofuran/methanol/water (3 mL, 1/1/1) was added lithium hydroxide monohydrate, 22 mg (0.532 mmol, 2 eq.) at 0° C. and the resulting mixture was stirred at r.t. for 18 h. The volatiles were removed under reduced pressure, water was added and the mixture was acidified to pH~7 by dropwise addition of aq. 1N hydrochloric acid. The resulting solid was filtered, washed with water and dried to give the crude product 8A, 73 mg (69%) as a beige solid.

LC-MS (Method 1): $R_t$=2.40 min; MS (ES+): m/z=400/402 (M+H)$^+$.

$^1$H-NMR (500 MHz, DMSO-d$_6$) δ [ppm]=1.24 (d, 3H), 2.28 (s, 3H), 3.51 (d, 1H), 3.59 (d, 1H), 3.74 (q, 1H), 3.99 (s, 3H), 6.32 (d, 1H), 6.87 (d, 1H), 7.14 (d, 2H), 7.23 (d, 2H), 7.26 (s, 1H), 8.20 (s, 1H).

Amine Intermediates (B)

Intermediate 1B

(3R)-3-amino-4-(4-cyanophenyl)-N-methylbutanamide

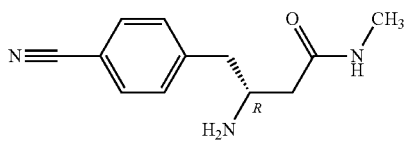

Tert-butyl [(2R)-1-(4-cyanophenyl)-4-(methylamino)-4-oxobutan-2-yl]carbamate (Intermediate 1B$^{Boc}$)

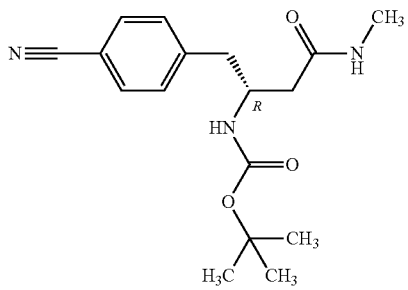

To a stirred solution of (3R)-3-(tert-butoxycarbonylamino)-4-(4-cyanophenyl)butanoic acid, 3.0 g (9.86 mmol) in tetrahydrofuran (100 mL) at r.t. was added TBTU, 3.17 g (9.86 mmol) followed by triethylamine, 2.75 mL (19.7 mmol, 2 eq.). After 30 min, methylamine, 5.91 mL (2N in tetrahydrofuran, 11.8 mmol, 1.2 eq.) was added, and the resulting solution was stirred at r.t. for 16 h. More TBTU, 633 mg (0.2 eq) was added, and after 20 min of stirring at r.t., methylamine, 2.0 mL (2N in tetrahydrofuran, 3.9 mmol, 0.4 eq.) was added. The mixture was stirred at r.t. for 4 h. Most of the solvent was removed under reduced pressure and the residue was triturated in ethyl acetate (75 mL), filtered, washed with ethyl acetate (10 mL) and then with pentane. The solid was dried under high vacuum to give the expected product, 2.9 g (93%) as a white solid.

LC-MS (Method 1): $R_t$=2.77 min; MS (ES+): m/z=318 $(M+H)^+$, 262 $([M-tBu]+H)^+$, 218 $([M-Boc]+H)^+$.

$^1$H-NMR (500 MHz, DMSO-d6) δ [ppm]=1.28 (s, 9H), 2.23 (m, 2H), 2.55 (d, 3H), 2.69 (dd, 1H), 2.81 (dd, 1H), 3.97 (m, 1H), 6.73 (d, 1H), 7.35 (d, 2H), 7.73 (m, 3H)

(3R)-3-amino-4-(4-cyanophenyl)-N-methylbutanamide

To a stirred suspension of tert-butyl [(2R)-1-(4-cyanophenyl)-4-(methylamino)-4-oxobutan-2-yl]carbamate, 4.11 g (12.9 mmol) in dichloromethane (170 mL) was added slowly hydrochloric acid, 32 mL (4N in dioxane, 129 mmol, 10 eq.) at r.t. and the resulting mixture was stirred at r.t. for 16 h. The resulting suspension was cooled at 0° C., 80 mL of aq. sat. sodium hydrogen carbonate was slowly added, followed by solid potassium carbonate until basic pH was obtained. The aqueous phase was saturated with sodium chloride, then extracted using a DCM/methanol mixture (95:5, 5×100 mL). The combined organics were dried over sodium sulfate, concentrated and dried to provide the product as an off white solid, 2.60 g (92%).

LC-MS (Method 1): $R_1$=0.43 min; MS (ES+): m/z=218 $(M+H)^+$.

$^1$H-NMR (500 MHz, DMSO-d6) δ [ppm]=1.49 (br s, 2H), 2.01 (dd, 1H), 2.11 (dd, 1H), 2.55 (d, 3H), 2.60 (dd, 1H), 2.71 (dd, 1H), 3.23 (m, 1H), 7.40 (d, 2H), 7.74 (d, 2H), 7.80 (br s, 1H).

Using the same procedure, the following examples have been prepared from corresponding N-Boc derivatives:

| Intermediate | Structure/Name | Analytics |
|---|---|---|
| 2B | 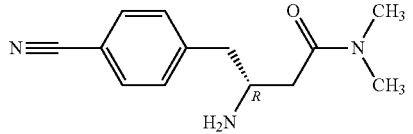<br>(3R)-3-amino-4-(4-cyanophenyl)-N,N-dimethylbutanamide | LC-MS (Method 1): $R_t$ = 0.43 min; MS (ES+): m/z = 232 (M + H)$^+$.<br>$^1$H-NMR (500 MHz, DMSO-d$_6$) δ [ppm] = 2.30 (m, 2H), 2.61 (dd, 1H), 2.77 (dd, 1H), 2.80 (s, 3H), 2.91 (s, 3H), 3.29 (m, 1H), 7.42 (d, 2H), 7.74 (d, 2H) |
| 3B | 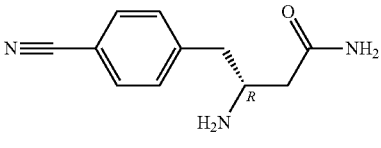<br>(3R)-3-amino-4-(4-cyanophenyl)butanamide | LC-MS (Method 1): $R_t$ = 0.43 min; MS (ES+): m/z = 204 (M + H)$^+$.<br>$^1$H-NMR (500 MHz, CD$_3$OD) δ [ppm] = 2.23 (dd, 1H), 2.34 (dd, 1H), 2.74 (dd, 1H), 2.85 (dd, 1H), 3.43 (m, 1H), 7.43 (d, 2H), 7.67 (d, 2H). |
| 4B | 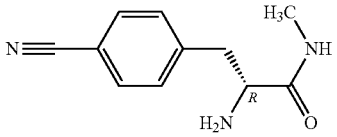<br>4-cyano-N-methyl-D-phenylalaninamide | LC-MS (Method 1): $R_t$ = 0.40 min; MS (ES+): m/z = 204 (M + H)$^+$.<br>$^1$H-NMR (500 MHz, CD$_3$OD) δ [ppm] = 2.66 (s, 3H), 2.89 (dd, 1H), 3.05 (dd, 1H), 3.52 (m, 1H), 7.39 (d, 2H), 7.65 (d, 2H) |
| 5B | 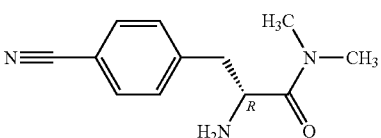<br>4-cyano-N,N-dimethyl-D-phenylalaninamide | LC-MS (Method 1): $R_t$ = 0.40 min; MS (ES+): m/z = 218 (M + H)$^+$.<br>$^1$H-NMR (500 MHz, CDCl$_3$) δ [ppm] = 2.80 (s, 3H), 2.91 (s, 3H), 2.96 (dd, 1H), 3.05 (dd, 1H), 4.10 (m, 1H), 7.35 (d, 2H), 7.59 (d, 2H) |

-continued

| Intermediate | Structure/Name | Analytics |
|---|---|---|
| 6B | 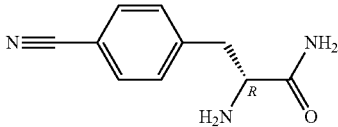  4-cyano-D-phenylalaninamide | LC-MS (Method 1): $R_t$ = 0.40 min; MS (ES+): m/z = 190 (M + H)$^+$. $^1$H-NMR (500 MHz, CD$_3$OD) δ [ppm] = 2.90 (dd, 1H), 3.08 (dd, 1H), 3.58 (m, 1H), 7.43 (d, 2H), 7.66 (d, 2H) |
| 7B | 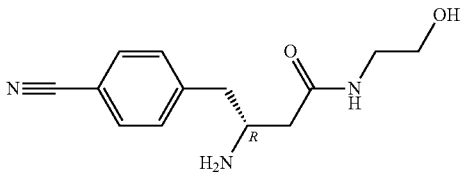  (3R)-3-amino-4-(4-cyanophenyl)-N-(2-hydroxyethyl)butanamide | LC-MS (Method 1): $R_t$ = 0.39 min; MS (ES+): m/z = 248 (M + H)$^+$. $^1$H-NMR (500 MHz, DMSO-d$_6$) δ [ppm] = 2.02 (dd, 1H), 2.14 (dd, 1H), 2.61 (dd, 1H), 2.71 (dd, 1H), 3.08-3.12 (m, 2H), 3.22 (m, 1H), 3.31 (br s, 2H), 3.38 (t, 2H), 7.40 (d, 2H), 7.74 (d, 2H), 7.93 (m, 1H). |
| 8B | 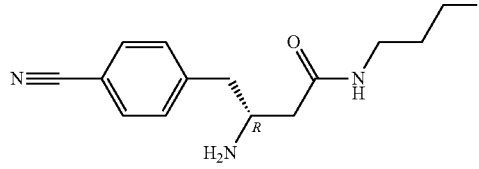  (3R)-3-amino-4-(4-cyanophenyl)-N-(3-hydroxypropyl)butanamide | LC-MS (Method 1): $R_t$ = 0.39 min; MS (ES+): m/z = 262 (M + H)$^+$. $^1$H-NMR (500 MHz, DMSO-d$_6$) δ [ppm] = 1.51-1.56 (m, 2H), 2.02 (dd, 1H), 2.13 (dd, 1H), 2.61 (dd, 1H), 2.72 (dd, 1H), 3.07-3.11 (m, 2H), 3.25 (m, 1H), 3.31 (br s, 2H), 3.40 (t, 2H), 7.41 (d, 2H), 7.75 (d, 2H), 7.88 (m, 1H). |
| 9B | 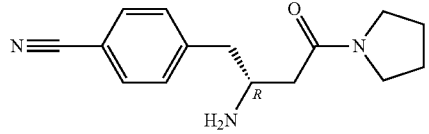  4-[(2R)-2-amino-4-oxo-4-(pyrrolidin-1-yl)butyl]benzonitrile | LC-MS (Method 1): $R_t$ = 0.40, 1.75 min; MS (ES+): m/z = 258 (M + H)$^+$. $^1$H-NMR (500 MHz, CDCl$_3$) δ [ppm] = 1.83-1.87 (m, 2H), 1.91-1.97 (m, 4H), 2.28 (dd, 1H), 2.39 (dd, 1H), 2.75 (dd, 1H), 2.87 (dd, 1H), 3.30 (m, 1H), 3.36 (m, 1H), 3.45 (t, 2H), 3.61 (m, 1H), 7.34 (d, 2H), 7.59 (d, 2H). |
| 10B | 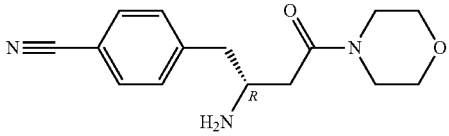  4-[(2R)-2-amino-4-(morpholin-4-yl)-4-oxobutyl]benzonitrile | LC-MS (Method 1): $R_t$ = 0.40, 1.63 min; MS (ES+): m/z = 274 (M + H)$^+$. $^1$H-NMR (500 MHz, CDCl$_3$) δ [ppm] = 2.10 (br s, 2H), 2.36 (dd, 1H), 2.43 (dd, 1H), 2.79 (dd, 1H), 2.89 (dd, 1H), 3.37-3.44 (m, 2H), 3.58-3.67 (m, 7H), 7.34 (d, 2H), 7.61 (d, 2H). |
| 11B | 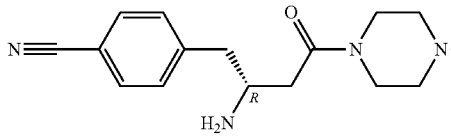  4-[(2R)-2-amino-4-(4-methylpiperazin-1-yl)-4-oxobutyl]benzonitrile | LC-MS (Method 1): $R_t$ = 0.33, min; MS (ES+): m/z = 287 (M + H)$^+$. $^1$H-NMR (500 MHz, CDCl$_3$) δ [ppm] = 2.30 (s, 3H), 2.35-2.40 (m, 4H), 2.40 (dd, 1H), 2.46 (dd, 1H), 2.57 (br s, 2H), 2.86-2.94 (m, 2H), 3.36-3.44 (m, 2H), 3.56-3.67 (m, 3H), 7.35 (d, 2H), 7.60 (d, 2H). |

Intermediate 12B (3R)-3-amino-4-(4-cyanophenyl)-N-methylbutanamide hydrochloride (1:1)

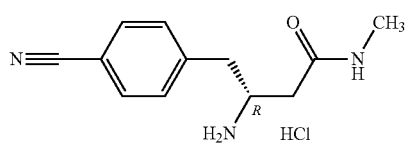

To a stirred suspension of tert-butyl [(2R)-1-(4-cyanophenyl)-4-(methylamino)-4-oxobutan-2-yl]carbamate, 6.72 g (21.2 mmol) in dichloromethane (275 mL) was added slowly hydrochloric acid, 53 mL (4M in dioxane, 212 mmol, 10 eq.) at r.t. and the resulting mixture was stirred at r.t. for 20 h. The mixture was concentrated to dryness, dried under high vacuum at 45° C. overnight to provide the desired product, 5.48 g (98%) as a white solid.

LC-MS (Method 1): $R_t$=0.44 min & 0.86 min; MS (ES+): m/z=218 (M+H)$^+$.

$^1$H-NMR (500 MHz, DMSO-d6) δ [ppm]=2.40 (m, 2H), 2.53 (d, 3H), 2.90 (dd, 1H), 3.11 (dd, 1H), 3.70 (br s, 1H), 7.47 (d, 2H), 7.81 (d, 2H), 8.11 (d, 1H), 8.22 (br s, 3H).

Intermediate 13B (3R)-3-amino-4-(4-cyanophenyl)butanamide hydrochloride (1:1)

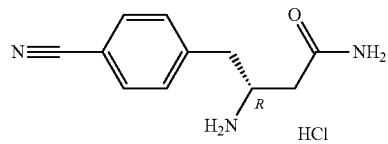

To a stirred suspension of tert-butyl [(2R)-4-amino-1-(4-cyanophenyl)-4-oxobutan-2-yl]carbamate, 3B$^{Boc}$, 2.80 g (9.2 mmol) in dichloromethane (94 mL) was added slowly 4M hydrochloric acid in 1,4-dioxane, 18.5 mL (74 mmol, 8.0 eq.) at 0° C. and the resulting mixture was stirred at r.t. for 18 h. Approximately half of the solvent was removed under vacuum (bath at 25° C.) and then the mixture was diluted with MTBE. The suspension was filtered, rinsed with MTBE, then pentane, and dried to give the product, 2.10 g (90%) as a white solid.

LC-MS (Method 1): $R_t$=0.45 min; MS (ES+): m/z=204 (M+H)$^+$.

$^1$H-NMR (500 MHz, DMSO-d6) δ [ppm]=2.38 (dd, 1H), 2.43 (dd, 1H), 2.92 (dd, 1H), 3.11 (dd, 1H), 3.68 (m, 1H), 7.14 (br s, 1H), 7.48 (d, 2H), 7.63 (br s, 1H), 7.81 (d, 2H), 8.20 (br s, 3H).

Using the same procedure, the following examples were prepared from corresponding N-Boc derivatives:

| Intermediate | Structure/Name | Analytics |
|---|---|---|
| 14B | ![structure] (3R)-3-amino-4-(4-cyanophenyl)-N-isopropylbutanamide hydrochloride (1:1) | LC-MS (Method 1): $R_t$ = 1.75 min; MS (ES+): m/z = 246 (M + H)$^+$. $^1$H-NMR (500 MHz, DMSO-d$_6$) δ [ppm] = 1.00 (d, 3H), 1.03 (d, 3H), 2.35 (d, 2H), 2.87 (dd, 1H), 3.08 (dd, 1H), 3.71 (m, 1H), 3.79 (m, 1H), 7.46 (d, 2H), 7.82 (d, 2H), 8.01 (d, 1H), 8.11 (br s, 3H). |
| 15B | ![structure] 4-[(2R)-2-amino-3-hydroxypropyl]benzonitrile hydrochloride (1:1) | LC-MS (Method 1): $R_t$ = 0.57 min; MS (ES+): m/z = 177 (M + H)$^+$. $^1$H-NMR (500 MHz, DMSO-d$_6$) δ [ppm] = 2.93 (dd, 1H), 3.00 (dd, 1H), 3.37-3.40 (m, 2H), 3.51 (m, 1H), 5.38 (br s, 1H), 7.50 (d, 2H), 7.81 (d, 2H), 8.10 (br s, 3H). |
| 16B | ![structure] 4-[(2S)-2-aminopropyl]benzonitrile hydrochloride (1:1) | LC-MS (Method 1): Rt = 0.43 min; MS (ES+): m/z = 161 (M + H)$^+$. |

| Intermediate | Structure/Name | Analytics |
|---|---|---|
| 17B | N-[(2R)-2-amino-3-(4-cyanophenyl)propyl]acetamide hydrochloride (1:1) | LC-MS (Method 1): $R_t$ = 0.43 min; MS (ES+): m/z = 218 (M + H)$^+$. |
| 18B | 4-[(2R)-2-amino-3-hydroxy-3-methylbutyl]benzonitrile hydrochloride (1:1) | LC-MS (Method 1): $R_t$ = 1.56 min; MS (ES+): m/z = 205 (M + H)$^+$, 187 ([M − H$_2$O] + H)$^+$.<br>$^1$H-NMR (500 MHz, DMSO-d$_6$) δ [ppm] = 1.17 (s, 3H), 1.23 (s, 3H), 2.78 (dd, 1H), 3.07 (dd, 1H), 3.19 (m, 1H), 5.34 (s, 1H), 7.56 (d, 2H), 7.79 (br s, 3H), 7.82 (d, 2H). |
| 19B | 4-[(2R)-2-amino-4-hydroxybutyl]benzonitrile | LC-MS (Method 1): $R_t$ = 0.44 min-1.02 min; MS (ES+): m/z = 191 (M + H)$^+$.<br>$^1$H-NMR (500 MHz, DMSO-d$_6$) δ [ppm] = 1.31-1.36 (m, 1H), 1.46-1.52 (m, 1H), 2.60 (dd, 1H), 2.72 (dd, 1H), 3.00 (m, 1H), 3.51 (t, 2H), 7.40 (d, 2H), 7.74 (d, 2H). |
| 20B | 4-[(2R)-2-amino-3-methoxypropyl]benzonitrile hydrochloride (1:1) | LC-MS (Method 1): $R_t$ = 0.44 & 0.86 min; MS (ES+): m/z = 191 (M + H)$^+$.<br>$^1$H-NMR (500 MHz, DMSO-d$_6$) δ [ppm] = 2.92 (dd, 1H), 3.02 (dd, 1H), 3.28 (s, 3H), 3.31 (dd, 1H), 3.42 (dd 1H), 3.58 (m, 1H), 7.49 (d, 2H), 7.82 (d, 2H), 8.15 (br s, 3H) |
| 21B | 3-[(2R)-2-amino-3-hydroxypropyl]benzonitrile hydrochloride (1:1) | LC-MS (Method 1): $R_t$ = 0.58 min; MS (ES+): m/z = 177 ([M − HCl] + H)$^+$.<br>$^1$H-NMR (500 MHz, DMSO-d$_6$) δ [ppm] = 2.91 (dd, 1H), 2.98 (dd, 1H), 3.38 (d, 2H), 3.52 (d, 1H), 5.38 (br s, 1H), 7.55 (t, 1H), 7.64 (d, 1H), 7.73 (d, 1H), 7.78 (s, 1H), 8.13 (br s, 3H). |

-continued

| Intermediate | Structure/Name | Analytics |
|---|---|---|
| 22B | 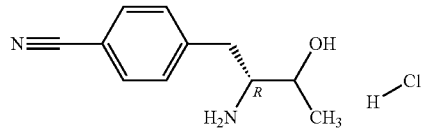<br>4-[(2R,3R)-2-amino-3-hydroxybutyl]benzonitrile hydrochloride (1:1) and 4-[(2R,3S)-2-amino-3-hydroxybutyl]benzonitrile hydrochloride (1:1) | LC-MS (Method 1): $R_t$ = 0.44 min; MS (ES+): m/z = 191 (M + H)+.<br>$^1$H-NMR (500 MHz, DMSO-$d_6$) δ [ppm] = 1.13 (t, 3H), 2.86 (dd, 0.5H), 2.91 (dd, 0.5H), 2.95-3.04 (m, 1H), 3.23 (m, 0.5H), 3.38 (m, 0.5H), 3.58-3.65 (m, 0.5H), 3.78-3.85 (m, 0.5H), 5.36 (d, 0.5H), 5.49 (d, 0.5 H), 7.52 (t, 2H), 7.79-7.94 (m, 5H) |
| 23B | 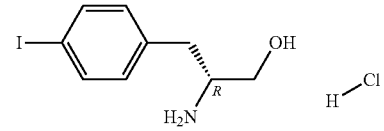<br>(2R)-2-amino-3-(4-iodophenyl)propan-1-ol hydrochloride (1:1) | LC-MS (Method 1): $R_t$ = 1.80 min; MS (ES+): m/z = 278 (M + H)+.<br>$^1$H-NMR (500 MHz, DMSO-$d_6$) δ [ppm] = 2.78 (dd, 1H), 2.86 (dd, 1H), 3.30-3.37 (m, 2H), 3.50 (d, 1H), 5.33 (s, 1H), 7.10 (d, 2H), 7.69 (d, 2H), 8.04 (s, 3H). |
| 24B | 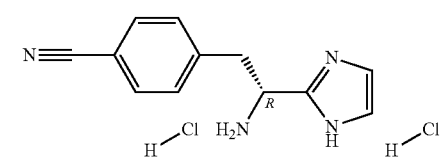<br>4-[(2R)-2-amino-2-(1H-imidazol-2-yl)ethyl]benzonitrile dihydrochloride | LC-MS (Method 1): $R_t$ = 0.47 min; MS (ES+): m/z = 213 (M + H)+ |
| 25B | 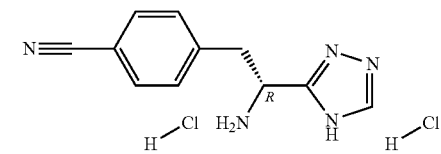<br>4-[(2R)-2-amino-2-(1H-1,2,4-triazol-5-yl)ethyl]benzonitrile dihydrochloride | LC-MS (Method 1): $R_t$ = 0.47 min; MS (ES+): m/z = 214 (M + H)+ |
| 26B | 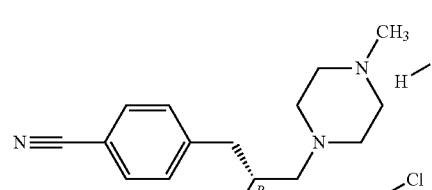<br>4-[(2R)-2-amino-3-(4-methylpiperazin-1-yl)propyl]benzonitrile dihydrochloride | LC-MS (Method 1): $R_t$ = 0.37 min; MS (ES+): m/z = 259 (M + H)+.<br>$^1$H-NMR (500 MHz, DMSO-$d_6$) δ [ppm] = 2.12 (s, 3H), 2.21-2.36 (m, 10H), 2.60 (dd, 1H), 2.91 (dd, 1H), 3.78 (m, 1H), 6.65 (d, 1H), 7.37 (d, 2H), 7.72 (d, 2H). |
| 27B | 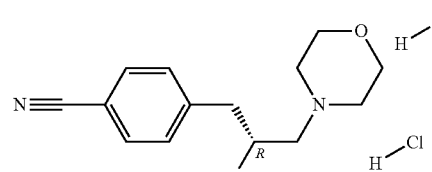<br>4-[(2R)-2-amino-3-(morpholin-4-yl)propyl]benzonitrile dihydrochloride | LC-MS (Method 1): $R_t$ = 0.46 & 1.60 min; MS (ES+): m/z = 246 (M + H)+. |

| Intermediate | Structure/Name | Analytics |
|---|---|---|
| 28B | 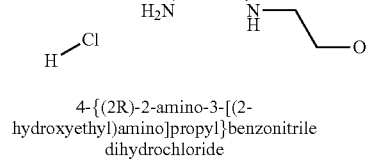<br>4-{(2R)-2-amino-3-[(2-hydroxyethyl)amino]propyl}benzonitrile dihydrochloride | LC-MS (Method 1): $R_t$ = 0.43 min; MS (ES+): m/z = 220 (M + H)+.<br>$^1$H-NMR (500 MHz, DMSO-$d_6$) δ [ppm] = 2.95-3.15 (m, 4H), 3.25-3.35 (m, 2H), 3.67 (t, 2H), 3.90 (m, 1H), 5.26 (br s, 1H), 7.55 (d, 2H), 7.85 (d, 2H), 8.60 (br s, 3H), 9.26 (br s, 2H). |
| 29B | 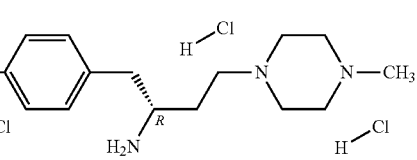<br>4-[(2R)-2-amino-4-(4-methylpiperazin-1-yl)butyl]benzonitrile trihydrochloride | LC-MS (Method 1): $R_t$ = 0.35 min; MS (ES+): m/z = 273 (M + H)+. |
| 30B | 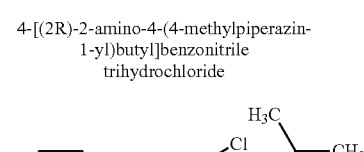<br>4-[(2R)-2-amino-4-(isopropylamino)butyl]benzonitrile dihydrochloride | LC-MS (Method 1): $R_t$ = 0.36 min; MS (ES+): m/z = 232 (M + H)+.<br>$^1$H-NMR (500 MHz, DMSO-$d_6$) δ [ppm] = 1.22 (d, 6H), 1.83-1.99 (m, 2H), 2.97 (dd, 1H), 3.08 (dd, 1H), 3.11 (m, 1H), 3.21 (m, 1H), 3.45 (br s, 1H), 3.64 (m, 1H), 7.55 (d, 2H), 7.84 (d, 2H), 8.32 (s, 3H), 8.87 (br d, 2H). |
| 31B | 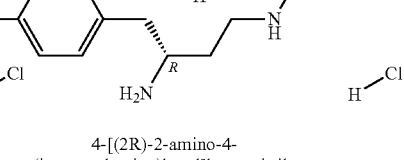<br>4-{(2R)-2-amino-4-[(3R)-3-methylpiperazin-1-yl]butyl}benzonitrile trihydrochloride | LC-MS (Method 1): $R_t$ = 0.38 min; MS (ES+): m/z = 273 (M + H)+. |
| 32B | 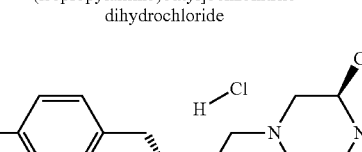<br>4-{(2R)-2-amino-4-[(3S)-3-methylpiperazin-1-yl]butyl}benzonitrile trihydrochloride | LC-MS (Method 1): $R_t$ = 0.39 min; MS (ES+): m/z = 273 (M + H)+. |
| 33B | 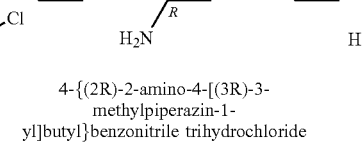<br>4-[(2R)-2-amino-4-(morpholin-4-yl)butyl]benzonitrile dihydrochloride | LC-MS (Method 1): $R_t$ = 0.37 min; MS (ES+): m/z = 260 (M + H)+. |

| Intermediate | Structure/Name | Analytics |
|---|---|---|
| 34B | 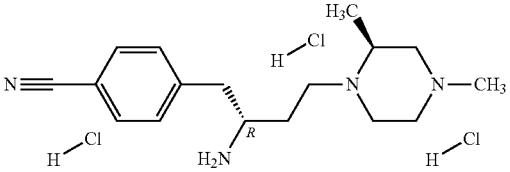<br>4-{(2R)-2-amino-4-[(2S)-2,4-dimethylpiperazin-1-yl]butyl}benzonitrile trihydrochloride | LC-MS (Method 1): $R_t$ = 0.41 min; MS (ES+): m/z = 287 (M + H)⁺. |
| 35B | 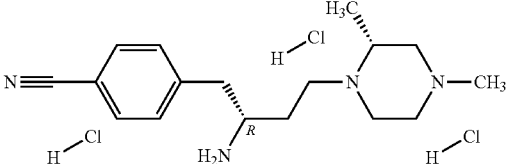<br>4-{(2R)-2-amino-4-[(2R)-2,4-dimethylpiperazin-1-yl]butyl}benzonitrile trihydrochloride | LC-MS (Method 1): $R_t$ = 0.39 min; MS (ES+): m/z = 287 (M + H)⁺. |
| 36B | 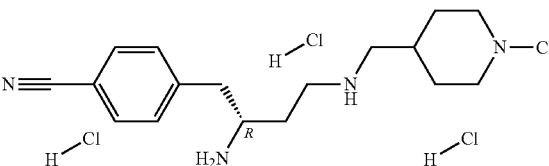<br>4-[(2R)-2-amino-4-{[(1-methylpiperidin-4-yl)methyl]amino}butyl]benzonitrile trihydrochloride | LC-MS (Method 1): $R_t$ = 0.31 min; MS (ES+): m/z = 301 (M + H)⁺. |
| 37B | 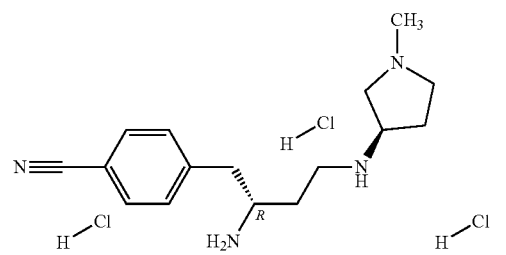<br>4-[(2R)-2-amino-4-{[(3R)-1-methylpyrrolidin-3-yl]amino}butyl]benzonitrile trihydrochloride | LC-MS (Method 1): $R_t$ = 0.38 min; MS (ES+): m/z = 273 (M + H)⁺. |
| 38B | 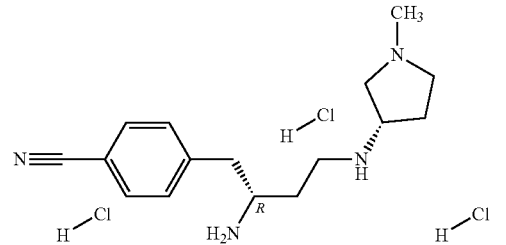<br>4-[(2R)-2-amino-4-{[(3S)-1-methylpyrrolidin-3-yl]amino}butyl]benzonitrile trihydrochloride | LC-MS (Method 1): $R_t$ = 0.34 min; MS (ES+): m/z = 273 (M + H)⁺. |

| Intermediate | Structure/Name | Analytics |
|---|---|---|
| 39B | 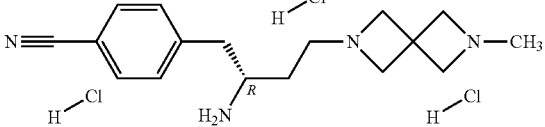<br>4-[(2R)-2-amino-4-(6-methyl-2,6-diazaspiro[3.3]hept-2-yl)butyl]benzonitrile trihydrochloride | LC-MS (Method 1): $R_t$ = 0.35 min; MS (ES+): m/z = 285 (M + H)$^+$. |
| 40B | 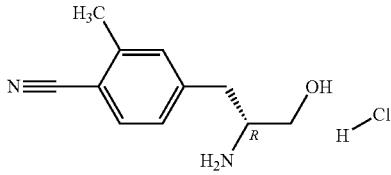<br>4-[(2R)-2-amino-3-hydroxypropyl]-2-methylbenzonitrile hydrochloride (1:1) | LC-MS (Method 1): $R_t$ = 0.39 min; MS (ES+): m/z = 191 (M + H)$^+$.<br>$^1$H-NMR (500 MHz, DMSO-$d_6$) δ [ppm] = 2.47 (s, 3H), 2.87 (dd, 1H), 2.93 (dd, 1H), 3.33-3.40 (m, 2H), 3.51 (dd, 1H), 5.36 (t, 1H), 7.29 (d, 1H), 7.38 (s, 1H), 7.74 (d, 1H), 8.00 (br s, 3H). |
| 41B | 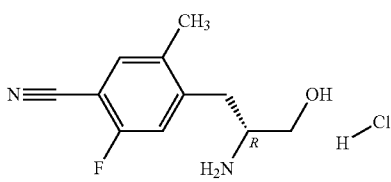<br>4-[(2R)-2-amino-3-hydroxypropyl]-2-fluoro-5-methylbenzonitrile hydrochloride (1:1) | LC-MS (Method 1): $R_t$ = 1.25 min; MS (ES+): m/z = 209 (M + H)$^+$.<br>$^1$H-NMR (500 MHz, DMSO-$d_6$) δ [ppm] = 2.31 (s, 3H), 2.91-2.99 (m, 2H), 3.38-3.42 (m, 2H), 3.55 (m, 1H), 5.42 (s, 1H), 7.44 (d, 1H), 7.77 (d, 1H), 8.06 (br s, 3H). |
| 42B | 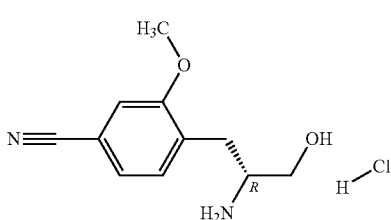<br>4-[(2R)-2-amino-3-hydroxypropyl]-3-methoxybenzonitrile hydrochloride (1:1) | LC-MS (Method 1): $R_t$ = 1.28 min; MS (ES+): m/z = 207 (M + H)$^+$.<br>$^1$H-NMR (500 MHz, DMSO-$d_6$) δ [ppm] = 2.85-2.93 (m, 2H), 3.34-3.38 (m, 2H), 3.48 (m, 1H), 3.86 (s, 3H), 5.33 (t, 1H), 7.40 (br s, 2H), 7.48 (s, 1H), 7.94 (br s, 3H). |
| 43B | 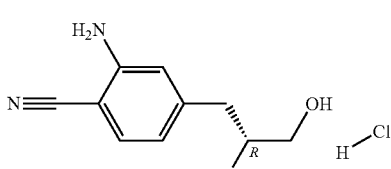<br>2-amino-4-[(2R)-2-amino-3-hydroxypropyl]benzonitrile hydrochloride (1:1) | LC-MS (Method 1): $R_t$ = 0.62 min; MS (ES+): m/z = 192 (M + H)$^+$.<br>$^1$H-NMR (500 MHz, DMSO-$d_6$) δ [ppm] = 2.71 (dd, 1H), 2.80 (dd, 1H), 3.26 (m, 1H), 3.36 (dd, 1H), 3.50 (dd, 1H), 6.13 (br s, 3H), 6.51 (dd, 1H), 6.65 (d, 1H), 7.34 (d, 1H), 8.04 (br s, 3H). |
| 44B | 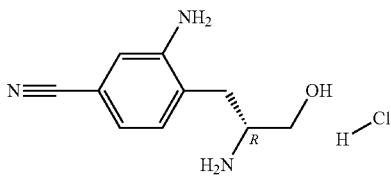<br>3-amino-4-[(2R)-2-amino-3-hydroxypropyl]benzonitrile | LC-MS (Method 1): $R_t$ = 0.38 min; MS (ES+): m/z = 192 (M + H)$^+$. |

-continued

| Intermediate | Structure/Name | Analytics |
|---|---|---|
| 45B | 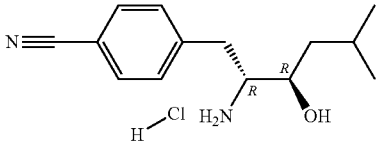<br>4-[(2R,3R)-2-amino-3-hydroxy-5-methylhexyl]benzonitrile hydrochloride (1:1) | LC-MS (Method 1): $R_t$ = 2.02 min; MS (ES+): m/z = 233 (M + H)+. |
| 46B | 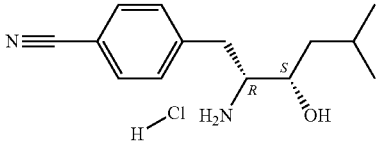<br>4-[(2R,3S)-2-amino-3-hydroxy-5-methylhexyl]benzonitrile hydrochloride (1:1) | LC-MS (Method 1): $R_t$ = 2.01 min; MS (ES+): m/z = 233 (M + H)+. |
| 47B | 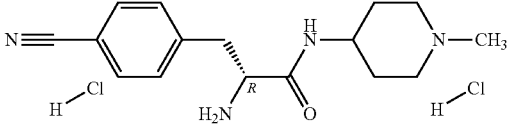<br>4-cyano-N-(1-methylpiperidin-4-yl)-D-phenylalaninamide dihydrochloride | LC-MS (Method 1): $R_t$ = 0.4 min; MS (ES+): m/z = 287 (M + H)+<br>$^1$H-NMR (500 MHz, DMSO-d$_6$) δ [ppm] = 1.48-1.61 (m, 1H), 1.66-1.80 (m, 2H), 1.84-1.92 (m, 1H), 2.68 (s, 3H), 2.94-3.05 (m, 2H), 3.11 (d, 2H), 3.32-3.40 (m, 2H), 3.74 (m, 1H), 3.98 (m, 1H), 7.45 (d, 2H), 7.82 (d, 2H), 8.34 (br s, 3H), 8.72 (d, 1H), 10.46 (s, 1H) |
| 48B | 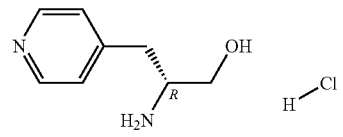<br>(2R)-2-amino-3-(pyridin-4-yl)propan-1-ol hydrochloride (1:1) | LC-MS (Method 1): $R_t$ = 0.35 min; MS (ES+): m/z = 153 ([M − HCl] + H)+.<br>$^1$H-NMR (500 MHz, DMSO-d6) δ [ppm] = 3.20-3.24 (m, 2H), 3.48 (dd, 1H), 3.52 (m, 1H), 3.60 (dd, 1H), 8.05 (d, 2H), 8.36 (br s, 3H), 8.87 (d, 2H). |
| 49B | 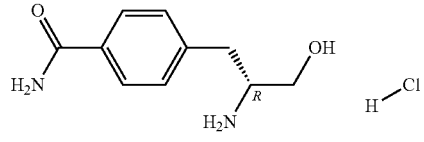<br>4-[(2R)-2-amino-3-hydroxypropyl]benzamide hydrochloride (1:1) | LC-MS (Method 1): $R_t$ = 0.38 min; MS (ES+): m/z = 195 (M + H)+.<br>$^1$H-NMR (500 MHz, DMSO-d$_6$) δ [ppm] = 2.87 (dd, 1H), 2.96 (dd, 1H), 3.36-3.39 (m, 2H), 3.51 (m, 1H), 5.34 (br s, 1H), 7.31 (s, 1H), 7.34 (d, 2H), 7.84 (d, 2H), 7.94 (s, 1H), 8.06 (br s, 3H). |
| 50B | 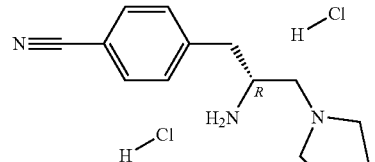<br>4-[(2R)-2-amino-3-(pyrrolidin-1-yl)propyl]benzonitrile dihydrochloride | LC-MS (Method 1): $R_t$ = 0.40 min; MS (ES+): m/z = 230 (M + H)+<br>$^1$H-NMR (500 MHz, DMSO-d$_6$) δ [ppm] = 1.78-2.05 (m, 4H), 2.83 (m, 1H), 3.07 (m, 1H), 3.10-3.22 (m, 2H), 3.23-3.29 (m, 1H), 3.52 (dd, 1H), 3.52-3.80 (m, 2H), 3.99 (m, 1H), 7.59 (d, 2H), 7.85 (d, 2H), 8.69 (m, 3H), 11.11 (br s, 1H) |

-continued

| Intermediate | Structure/Name | Analytics |
|---|---|---|
| 51B | 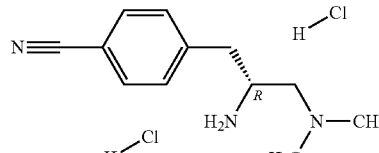<br>4-[(2R)-2-amino-3-(dimethylamino)propyl]benzonitrile dihydrochloride | 2.77 (br s, 6H), 3.10 (dd, 1H), 3.20 (dd, 1H), 3.41 (m, 2H), 4.08 (m, 1H), 7.59 (d, 2H), 7.84 (d, 2H), 8.71 (br s, 3H), 10.97 (br s, 1H). |
| 53B | 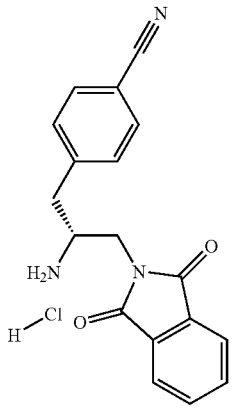<br>4-[(2R)-2-amino-3-(1,3-dioxo-1,3-dihydro-2H-isoindol-2-yl)propyl]benzonitrile hydrochloride (1:1) | LC-MS (Method 1): $R_t$ = 2.03 min; MS (ES+): m/z = 306 (M + H)+.<br>$^1$H-NMR (500 MHz, DMSO-d$_6$) δ [ppm] = 2.99 (dd, 1H), 3.24 (dd, 1H), 3.68 (dd, 1H), 3.78 (br s, 1H), 3.84 (dd, 1H), 7.53 (d, 2H), 7.76 (d, 2H), 7.84 (s, 4H), 8.43 (br s, 3H). |

Intermediate 53B

Methyl (3R)-3-amino-4-(4-cyanophenyl)butanoate hydrochloride (1:1)

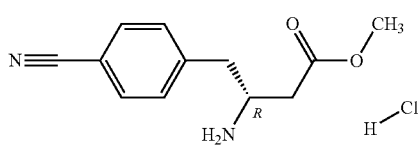

Under argon, thionyl chloride, 0.18 mL (2.5 mmol) was added slowly to methanol (4 mL) at 0° C. The solution was stirred at 0° C. for 5 min, then a suspension of (R)-3-amino-4-(4-cyano-phenyl)-butyric acid hydrochloride (ABCR AB166044), 150 mg (0.62 mmol, 1.2 eq.) was added. The mixture was allowed to reach r.t. and then stirred at 40° C. for 2 h. The mixture was then concentrated, co-evaporated with methanol, to leave the product, 170 mg (96%) as a white solid.

LC-MS (Method 1): $R_t$=1.60 min; MS (ES+) m/z=219.

$^1$H-NMR (500 MHz, DMSO-d6) δ [ppm]=2.60 (dd, 1H), 2.69 (dd, 1H), 2.95 (dd, 1H), 3.12 (dd, 1H), 3.56 (s, 3H), 3.74 (m, 1H), 7.50 (d, 2H), 7.83 (d, 2H), 8.25 (br s, 3H).

Intermediate 54B EDEL534

Methyl 4-cyano-D-phenylalaninate hydrochloride (1:1)

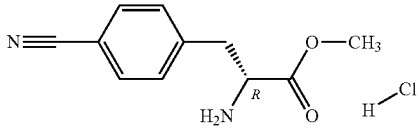

Under argon, thionyl chloride, 3.07 mL (42 mmol, 4 eq.) was added slowly to methanol (70 mL) at 0° C. The solution was stirred at 0° C. for 10 min, then solid (R)-2-amino-3-(4-cyanophenyl)propanoic acid (Fluorochem), 2.0 g (10.5 mmol) was added. The mixture was allowed to reach r.t. and then stirred at 30° C. for 16 h, and then at 40° C. for 2 h. The mixture was then concentrated and the residue was triturated in methyl tert-butyl ether, filtered, washed with methyl tert-butyl ether and dried to give the product, 2.34 g (86%) as a white solid.

LC-MS (Method 1): $R_t$=0.39 min; MS (ES+) m/z=205 (M+H)+.

$^1$H-NMR (500 MHz, DMSO-d$_6$) δ [ppm]=3.21 (dd, 1H), 3.26 (dd, 1H), 3.68 (s, 3H), 4.36 (t, 1H), 7.48 (d, 2H), 7.82 (d, 2H), 8.69 (br s, 3H).

Intermediate 55B

Methyl 4-[(2R)-2-amino-3-hydroxypropyl]benzoate

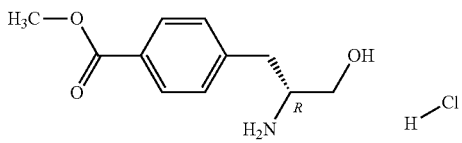

4-[(2R)-2-amino-3-hydroxypropyl]benzoic Acid Dihydrochloride Ammoniate

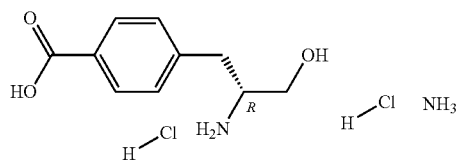

A stirred solution of 4-[(2R)-2-amino-3-hydroxypropyl]benzonitrile hydrochloride (1:1) 15B, 350 mg (1.65 mmol) in aq. 6N hydrochloric acid (10 mL) was stirred at 100° C. for 18 h. Water was removed under reduced pressure and the residue was triturated in methyl tert-butyl ether, filtered, washed with methyl tert-butyl ether and dried to give the product, 423 mg (90%) as a light yellow solid.

LC-MS (Method 1): $R_t$=0.57 min; MS (ES+): m/z=196 (M+H)$^+$.

$^1$H-NMR (500 MHz, DMSO-d$_6$) δ [ppm]=2.91 (dd, 1H), 3.01 (dd, 1H), 3.37-3.40 (m, 2H), 3.51 (m, 1H), 5.37 (s, 1H), 7.22 (s, 1H), 7.33 (s, 1H), 7.36 (s, 1H), 7.40 (d, 2H), 7.43 (s, 1H), 7.89 (d, 2H), 8.17 (br s, 3H), 12.88 (s, 1H).

Methyl 4-[(2R)-2-amino-3-hydroxypropyl]benzoate

Thionyl chloride, 0.21 mL (2.80 mmol, 4 eq.) was added slowly to methanol (5.0 mL) at 0° C. and the solution was stirred at 0° C. for 10 min. 4-[(2R)-2-amino-3-hydroxypropyl]benzoic acid dihydrochloride ammoniate, 200 mg (0.70 mmol) was added and the resulting mixture was allowed to reach r.t. and then stirred at 40° C. for 4 h. The mixture was then concentrated and the residue was dissolved in water. The mixture was basified with solid sodium hydrogen carbonate and extracted with dichloromethane (5×). The combined organic extracts were dried over sodium sulfate, filtered and concentrated to give intermediate 55B, 122 mg (83% yield) as a white solid.

LC-MS (Method 1): $R_t$=0.41 min; MS (ES+) m/z=210 (M+H)$^+$.

$^1$H-NMR (500 MHz, DMSO-d$_6$) δ [ppm]=2.63 (dd, 1H), 2.81 (dd, 1H), 3.03 (m, 1H), 3.24 (dd, 1H), 3.33 (dd, 1H), 3.84 (s, 3H), 4.05 (br s, 2H), 4.81 (br s, 1H), 7.38 (d, 2H), 7.89 (d, 2H).

Intermediate 56B

4-[(2R)-2-amino-3-(1,3-dioxo-1,3-dihydro-2H-isoindol-2-yl)propyl]-2-methylbenzonitrile hydrochloride (1:1)

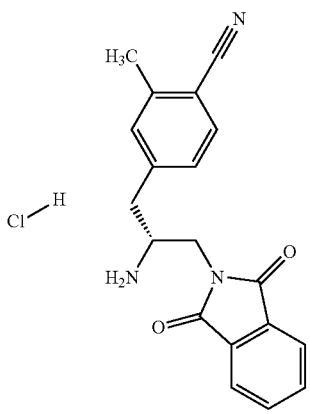 [SMILES: Cl ; Cc1cc(C[C@@H](N)CN2C(=O)c3ccccc3C2=O)ccc1C#N]

To a stirred solution of 56B$^{Boc}$, tert-butyl [(2R)-1-(4-cyano-3-methylphenyl)-3-(1,3-dioxo-1,3-dihydro-2H-isoindol-2-yl)propan-2-yl]carbamate, 370 mg (0.88 mmol) in dichloromethane (5 mL) was added slowly hydrochloric acid, 2.2 mL (4M in 1,4-dioxane, 8.8 mmol, 10 eq.) at r.t. and the resulting mixture was stirred at r.t. for 20 h. The volatiles were removed under reduced pressure and the residue was triturated in methyl tert-butyl ether, filtered, washed with methyl tert-butyl ether and dried under reduced pressure to give the product, 300 mg (95%) as a white solid.

LC-MS (Method 1): $R_t$=2.10 min; MS (ES+): m/z=320 (M+H)$^+$.

$^1$H-NMR (500 MHz, DMSO-d$_6$) δ [ppm]=2.39 (s, 3H), 2.92 (dd, 1H), 3.20 (dd, 1H), 3.71 (m, 1H), 3.84 (m, 2H), 7.30 (d, 1H), 7.36 (s, 1H), 7.65 (d, 1H), 7.83 (s, 4H), 8.43 (br s, 3H).

Protected Amine Intermediates (B$^{Boc}$)

Protected Intermediate 3B$^{Boc}$

Tert-butyl [(2R)-4-amino-1-(4-cyanophenyl)-4-oxobutan-2-yl]carbamate

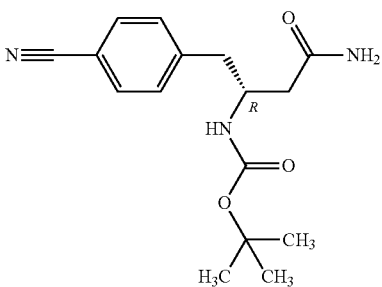

To a stirred solution of (3R)-3-(tert-butoxycarbonylamino)-4-(4-cyanophenyl)butanoic acid, 3.0 g (9.86 mmol) and triethylamine, 1.5 mL (10.8 mmol, 1.1 eq.) in tetrahydrofuran (45 mL, Acros Organics, extra dry, over 4A molecular sieve) was added dropwise ethyl chloroformate, 1.04 mL (10.8 mmol, 1.1 eq.) at −10° C. (ice/salt bath) and the resulting mixture was stirred at −10° C. for 1 h. To the resulting suspension was added slowly aq. ammonium hydroxide (3.9 mL, 30% aq. solution) at −10° C. A copious solid formed, and stirring was discontinued. The mixture was diluted with tetrahydrofuran (20 mL, Acros Organics, extra dry, over 4A molecular sieve), shacked, and stirring was continued at −10° C. for 4 h. The resulting mixture was then left without stirring at r.t. overnight. The solvent was removed under reduced pressure and the residue was triturated in water (50 mL). The solid was filtered, rinsed with water, and then dried over phosphorus pentoxide to give the expected product, 2.80 g (91%) as a white solid.

LC-MS (Method 1): $R_t$=2.70 min; MS (ES+): m/z=304 [M+H]$^+$, 248 ([M−tBu]+H)+, 204 ([M−Boc]+H)$^+$ $^1$H-NMR (500 MHz, DMSO-d6) δ [ppm]=1.28 (s, 9H), 2.23 (m, 2H), 2.69 (dd, 1H), 2.83 (dd, 1H), 3.96 (m, 1H), 6.72 (d, 1H), 6.83 (br s, 1H), 7.28 (br s, 1H), 7.35 (d, 2H), 7.73 (d, 2H).

Using the same procedure, the following examples have been prepared from corresponding N-Boc amino acids and amines (all commercially available):

| Intermediate | Structure | Name | Analytics |
|---|---|---|---|
| 2B$^{Boc}$ | 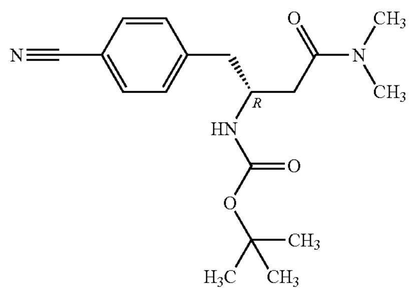 | tert-butyl [(2R)-1-(4-cyanophenyl)-4-(dimethylamino)-4-oxobutan-2-yl]carbamate | LC-MS (Method 1): $R_t$ = 2.98 min; MS (ES+): m/z = 332 (M + H)+, 276 ([M − tBu)] + H)$^+$, 232 ([M − Boc] + H)$^+$. $^1$H-NMR (500 MHz, CDCl$_3$) δ [ppm] = 1.36 (s, 9H), 2.50 (d, 2H), 2.91 (s, 3H), 2.96 (s, 3H), 2.97 (m, 1H), 3.11 (m, 1H), 4.12 (m, 1H), 7.32 (d, 2H), 7.58 (d, 2H). |
| 4B$^{Boc}$ | 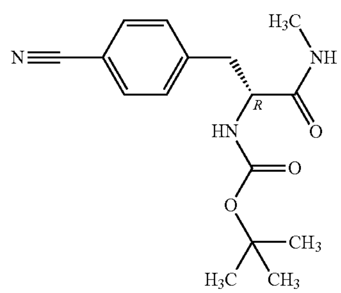 | tert-butyl N-[(1R)-1-[(4-cyanophenyl)methyl]-2-(methylamino)-2-oxo-ethyl]carbamate | LC-MS (Method 1): $R_t$ = 2.78 min; MS (ES+): m/z = 248 ([M − tBu)] + H)$^+$, 204 ([M − Boc)] + H)$^+$. $^1$H-NMR (500 MHz, CDCl$_3$) δ [ppm] = 1.39 (s, 9H), 2.76 (d, 3H), 3.04 (dd, 1H), 3.19 (dd, 1H), 4.32 (m, 1H), 4.97 (br s, 1H), 5.87 (br s, 1H), 7.32 (d, 2H), 7.59 (d, 2H). |
| 7B$^{Boc}$ | 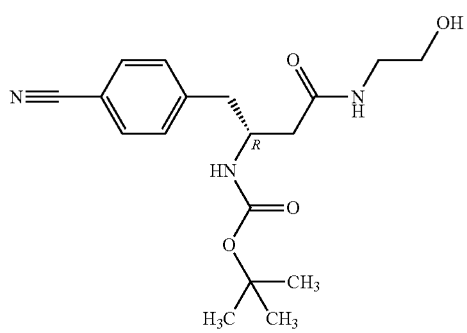 | tert-butyl {(2R)-1-(4-cyanophenyl)-4-[(2-hydroxyethyl)amino]-4-oxobutan-2-yl}carbamate | LC-MS (Method 1): $R_t$ = 2.62 min; MS (ES+): m/z = 348 (M + H)$^+$, 292 ([M − tBu)] + H)$^+$, 248 ([M − Boc] + H)$^+$. $^1$H-NMR (500 MHz, DMSO-d$_6$) δ [ppm] = 1.28 (s, 9H), 2.25 (d, 2H), 2.68 (dd, 1H), 2.82 (dd, 1H), 3.08-3.11 (m, 2H), 3.36-3.40 (m, 2H), 3.97 (m, 1H), 4.60 (m, 1H), 6.73 (d, 1H), 7.35 (d, 2H), 7.73 (d, 2H), 7.81 (m, 1H). |
| 8B$^{Boc}$ | 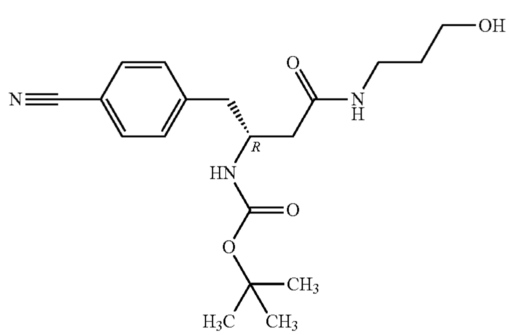 | tert-butyl {(2R)-1-(4-cyanophenyl)-4-[(3-hydroxypropyl)amino]-4-oxobutan-2-yl}carbamate | LC-MS (Method 1): $R_t$ = 2.64 min; MS (ES+): m/z = 362 (M + H)$^+$, 306 ([M − tBu)] + H)$^+$, 262 ([M − Boc)] + H)$^+$. $^1$H-NMR (500 MHz, CDCl$_3$) δ [ppm] = 1.37 (s, 9H), 1.67-1.72 (m, 2H), 2.36 (dd, 1H), 2.50 (dd, 1H), 2.91 (dd, 1H), 3.01 (m, 1H), 3.41-3.45 (m, 2H), 3.67 (t, 2H), 4.07 (m, 1H), 5.53 (br s, 1H), 6.15 (br s, 1H), 7.32 (d, 2H), 7.59 (d, 2H). |

-continued

| Intermediate | Structure | Name | Analytics |
|---|---|---|---|
| 9B$^{Boc}$ | 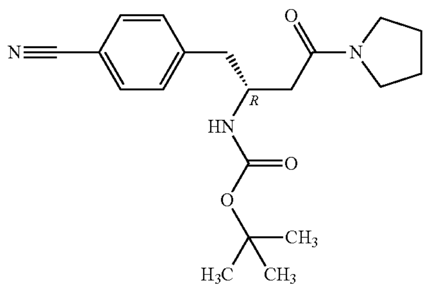 | tert-butyl [(2R)-1-(4-cyanophenyl)-4-oxo-4-(pyrrolidin-1-yl)butan-2-yl]carbamate | LC-MS (Method 1): R$_t$ = 3.05 min; MS (ES+): m/z = 358 (M + H)$^+$, 302 ([M − tBu)] + H)$^+$, 258 ([M − Boc)] + H)$^+$. $^1$H-NMR (500 MHz, CDCl$_3$) δ [ppm] = 1.36 (s, 9H), 1.84-1.89 (m, 2H), 1.91-1.96 (m, 2H), 2.43 (dd, 1H), 2.49 (dd, 1H), 2.97 (dd, 1H), 3.12 (m, 1H), 3.22 (m, 1H), 3.30 (m, 1H), 3.47 (t, 2H), 4.12 (m, 1H), 7.32 (d, 2H), 7.57 (d, 2H). |
| 10B$^{Boc}$ | 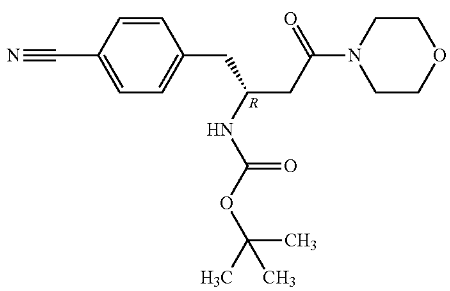 | tert-butyl [(2R)-1-(4-cyanophenyl)-4-(morpholin-4-yl)-4-oxobutan-2-yl]carbamate | LC-MS (Method 1): R$_t$ = 2.90 min; MS (ES+): m/z = 374 (M + H)$^+$, 318 ([M − tBu)] + H)$^+$, 274 ([M − Boc)] + H)$^+$. $^1$H-NMR (500 MHz, CDCl$_3$) δ [ppm] = 1.36 (s, 9H), 2.50 (dd, 1H), 2.54 (dd, 1H), 2.98 (dd, 1H), 3.10 (m, 1H), 3.37 (t, 2H), 3.62-3.68 (m, 6H), 4.12 (m, 1H), 5.47 (br s, 1H), 7.33 (d, 2H), 7.58 (d, 2H). |
| 11B$^{Boc}$ | 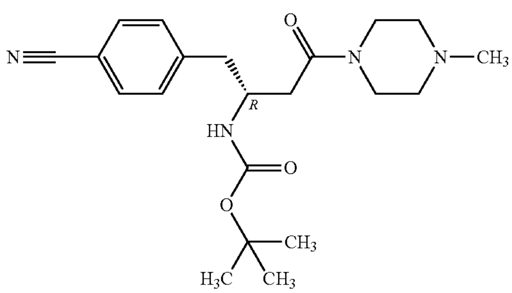 | tert-butyl [(2R)-1-(4-cyanophenyl)-4-(4-methylpiperazin-1-yl)-4-oxobutan-2-yl]carbamate | LC-MS (Method 1): R$_t$ = 2.09 min; MS (ES+): m/z = 387 (M + H)$^+$, 331 ([M − tBu)] + H)$^+$, 287 ([M − Boc)] + H)$^+$. $^1$H-NMR (500 MHz, CDCl$_3$) δ [ppm] = 1.36 (s, 9H), 2.36 (s, 3H), 2.40-2.48 (br m, 4H), 2.51-2.52 (m, 2H), 2.97 (dd, 1H), 3.09 (m, 1H), 3.43 (br s, 2H), 3.68 (br s, 2H), 4.11 (m, 1H), 5.51 (br d, 1H), 7.32 (d, 2H), 7.58 (d, 2H). |
| 14B$^{Boc}$ | 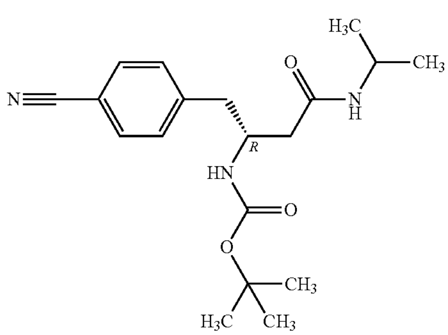 | tert-butyl [(2R)-1-(4-cyanophenyl)-4-(isopropylamino)-4-oxobutan-2-yl]carbamate | LC-MS (Method 1): R$_t$ = 3.03 min; MS (ES+): m/z = 346 (M + H)$^+$, 290 ([M − tBu)] + H)$^+$, 246 ([M − Boc)] + H)$^+$. $^1$H-NMR (500 MHz, CD$_3$OD) δ [ppm] = 1.11-1.14 (m, 6H), 1.33 (s, 9H), 2.29-2.38 (m, 2H), 2.79 (dd, 1H), 2.92 (dd, 1H), 3.95 (m, 1H), 4.12 (m, 1H), 7.41 (d, 2H), 7.63 (d, 2H). |

| Intermediate | Structure | Name | Analytics |
|---|---|---|---|
| 47B[Boc] | | N-(tert-butoxycarbonyl)-4-cyano-N-(1-methylpiperidin-4-yl)-D-phenylalaninamide | LC-MS (Method 1): $R_t$ = 2.12 min; MS (ES+): m/z = 387 (M + H)+, MS (ES−): m/z = 385 (M − H)−, 431 (M − H + HCO$_2$H)− $^1$H-NMR (500 MHz, CD$_3$OD) δ [ppm] = 1.37 (s, 9H), 1.46-1.56 (m, 1H), 1.67-1.74 (m, 1H), 1.80-1.87 (m, 2H), 2.04 (q, 2H), 2.26 (s, 3H), 2.72-2.86 (m, 2H), 2.92 (dd, 1H), 3.09 (dd, 1H), 3.61 (m, 1H), 4.28 (t, 1H), 7.42 (d, 2H), 7.65 (d, 2H) |

Tert-butyl [(2R)-1-(4-cyanophenyl)-3-hydroxypropan-2-yl]carbamate

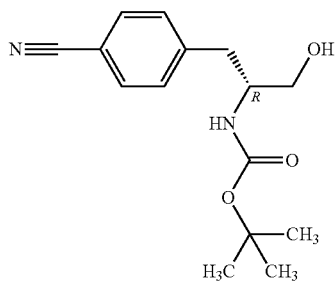

To a stirred solution of N-(tert-butoxycarbonyl)-4-cyano-D-phenylalanine, 8.44 g (29.1 mmol) in tetrahydrofuran (280 mL) was added 4-methylmorpholine, 3.51 mL (32 mmol, 1.1 eq.) followed by isobutyl chloroformate, 3.96 mL (30.5 mmol, 1.05 eq.) at 0° C. and the resulting mixture was stirred at 0° C. for 2 h. Sodium borohydride, 1.65 g (43.6 mmol, 1.5 eq.) in water (28 mL) was then added dropwise and the resulting mixture was stirred at 0° C. for 2 h and then at rt during the night. The mixture was partly evaporated, and the residue was diluted with ethyl acetate, cooled at 0° C. and quenched with aq. 1N hydrochloric acid. The resulting mixture was extracted with ethyl acetate. The combined organic layers were washed with aq. sat. sodium hydrogen carbonate, brine, dried over sodium sulfate, filtered and concentrated. The residue was triturated in pentane, filtered, washed with pentane and dried to give the product, 6.77 g (82%, white solid).

LC-MS (Method 1): $R_t$=2.87 min; MS (ES+): m/z=221 ([M−tBu)]+H)+, 177 ([M−Boc]+H)+

$^1$H-NMR (500 MHz, CDCl$_3$) δ [ppm]=1.40 (s, 9H), 2.91-2.96 (m, 2H), 3.56 (dd, 1H), 3.67 (dd, 1H), 3.88 (br s, 1H), 4.75 (br s, 1H), 7.34 (d, 2H), 7.59 (d, 2H) Using the same procedure, the following examples have been prepared from corresponding commercially available N-Boc amino acids derivatives:

| Intermediate No | Starting material | Structure/Name | Analytics |
|---|---|---|---|
| 19B[Boc] | (3R)-3-[(tert-butoxycarbonyl)amino]-4-(4-cyanophenyl)butanoic acid | tert-butyl [(2R)-1-(4-cyanophenyl)-4-hydroxybutan-2-yl]carbamate | LC-MS (Method 1): $R_t$ = 2.90 min; MS (ES+): m/z = 291 (M + H)+, 235 ([M − tBu)] + H)+, 191 ([M − Boc] + H)+. $^1$H-NMR (500 MHz, CDCl$_3$) δ [ppm] = 1.40 (s, 10H), 1.83-1.85 (m, 1H), 2.87 (d, 2H), 3.66 (d, 2H), 4.10 (br s, 1H), 4.46 (br s, 1H), 7.31 (d, 2H), 7.59 (d, 2H). |

-continued

| Intermediate No | Starting material | Structure/Name | Analytics |
|---|---|---|---|
| 21B$^{Boc}$ | N-Boc-3-cyano-D-phenylalanine | tert-butyl [(2R)-1-(3-cyanophenyl)-3-hydroxypropan-2-yl]carbamate | LC-MS (Method 1): R$_t$ = 2.90 min; MS (ES+): m/z = 221 ([M − tBu)] + H)$^+$, 177 ([M − Boc] + H)$^+$.<br>$^1$H-NMR (500 MHz, CDCl$_3$) δ [ppm] = 1.40 (s, 9H), 2.85-2.94 (m, 2H), 3.56 (dd, 1H), 3.67 (dd, 1H), 3.85 (br s, 1H), 4.76 (br s, 1H), 7.39-7.42 (m, 1H), 7.48 (d, 1H), 7.52-7.53 (m, 2H). |
| 23B$^{Boc}$ | (R)-2-((tert-butoxycarbonyl)amino)-3-(4-iodophenyl)propanoic acid | tert-butyl [(2R)-1-hydroxy-3-(4-iodophenyl)propan-2-yl]carbamate | LC-MS (Method 1): R$_t$ = 3.50 min; MS (ES+): m/z = 322 ([M − tBu)] + H)$^+$, 278 ([M − Boc] + H)$^+$. $^1$H-NMR (500 MHz, CDCl$_3$) δ [ppm] = 1.41 (s, 9H), 2.79 (d, 2H), 3.54 (dd, 1H), 3.65 (dd, 1H), 3.81 (br s, 1H), 4.70 (br s, 1H), 6.97 (d, 2H), 7.62 (d, 2H). |

Protected Intermediate 17B$^{Boc}$

Tert-butyl [(2R)-1-acetamido-3-(4-cyanophenyl)propan-2-yl]carbamate

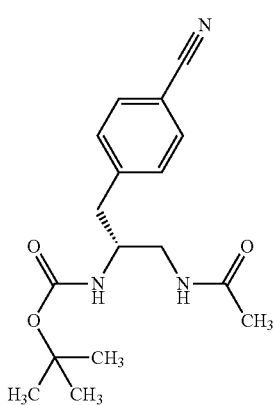

To a solution of tert-butyl [(2R)-1-amino-3-(4-cyanophenyl)propan-2-yl]carbamate, 80 mg (0.29 mmol) in THF (2 mL) was added triethylamine, 81 μL (0.58 mmol, 2.0 eq.) followed by acetic anhydride, 40 μL (0.44 mmol, 1.5 eq.). The resulting mixture was stirred at r.t. for 1 h, then diluted with ethyl acetate. The solution was washed with water, then with 1N hydrochloric acid and then with aq. sat. sodium hydrogencarbonate. The solution was dried over sodium sulfate and concentrated. The residue was purified by preparative TLC (silica, DCM/methanol 95/5) to provide the product, 36 mg (37%) as a beige solid.

LC-MS (Method 1): R$_t$=2.80 min; MS (ES+): m/z=318 (M+H)$^+$.

$^1$H-NMR (500 MHz, CDCl$_3$) δ [ppm]=1.40 (s, 9H), 1.99 (s, 3H), 2.83 (dd, 1H), 2.88 (m, 1H), 3.27 (m, 1H), 3.38 (m, 1H), 3.93 (br s, 1H), 4.77 (br s, 1H), 5.89 (br s, 1H), 7.33 (d, 2H), 7.60 (d, 2H)

Protected Intermediate 18B$^{Boc}$

Tert-butyl [(2R)-1-(4-cyanophenyl)-3-hydroxy-3-methylbutan-2-yl]carbamate

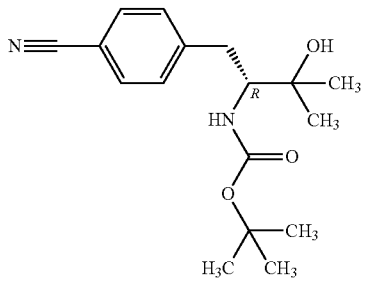

To a stirred solution of intermediate 54B$^{Boc}$, methyl N-(tert-butoxycarbonyl)-4-cyano-D-phenylalaninate, 200 mg (0.657 mmol) in tetrahydrofuran (6.5 mL) was added dropwise methylmagnesium bromide, 0.87 mL (3M in diethylether, 2.63 mmol, 4 eq.) at 0° C. and the resulting mixture was stirred at r.t. for 40 h. The mixture was cooled to 0° C., quenched with aq. 1N hydrochloric acid and extracted with ethyl acetate (3×). The combined organic layers were washed with brine, dried over sodium sulfate, filtered and concentrated to give the product, 198 mg (99%) as a white solid.

LC-MS (Method 1): R$_t$=2.98 min; MS (ES+): m/z=249 ([M−tBu)]+H)$^+$, 231 ([M−tBu−H$_2$O]+H)$^+$.

$^1$H-NMR (500 MHz, CDCl$_3$) δ [ppm]=1.28 (s, 9H), 1.30 (s, 3H), 1.32 (s, 3H), 2.68 (dd, 1H), 3.14 (dd, 1H), 3.73 (m, 1H), 4.57 (d, 1H), 7.32 (d, 2H), 7.57 (d, 2H).

Protected Intermediate 20B$^{Boc}$

Tert-butyl [(2R)-1-(4-cyanophenyl)-3-methoxypropan-2-yl]carbamate

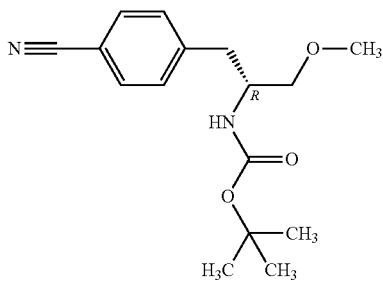

To a suspension of sodium hydride, 43 mg (60% dispersion in mineral oil, 1.09 mmol, 1.5 eq.) in dry THF (6 mL) under argon cooled at 0° C., was added a solution of tert-butyl [(2R)-1-(4-cyanophenyl)-3-hydroxypropan-2-yl]carbamate, 200 mg (0.724 mmol) in dry THF (4 mL). After 30 min stirring at 0° C., iodomethane, 90 μL (1.448 mmol, 2.0 eq.) was added to the reaction mixture which was stirred at 0° C. for 3 h then at r.t. overnight. Water and ethyl acetate were added to the reaction mixture. The phases were separated and the aqueous phase was extracted with ethyl acetate (3×). The combined organics were washed with brine, dried over sodium sulfate, filtered and concentrated. The residue (203 mg) was purified by chromatography on silica gel (puriflash, column 12 g, cyclohexane/ethyl acetate: 90/10>0/100) to give the product, 164 mg (76%) as a white solid.

LC-MS (Method 1): R$_t$=3.30 min; MS (ES+): m/z=235 (M+H−tBu)+, 191 (M+H-Boc)$^+$ $^1$H-NMR (500 MHz, CDCl$_3$) δ [ppm]=1.40 (s, 9H), 2.86-2.96 (m, 2H), 3.26 (dd, 1H), 3.31 (dd, 1H), 3.34 (s, 3H), 3.93 (br s, 1H), 4.85 (br s, 1H), 7.33 (d, 2H), 7.58 (d, 2H).

Intermediate 22B$^{Boc}$

Tert-butyl-[(2R,3R)-1-(4-cyanophenyl)-3-hydroxybutan-2-yl]carbamate and tert-butyl-[(2R,3S)-1-(4-cyanophenyl)-3-hydroxybutan-2-yl]carbamate

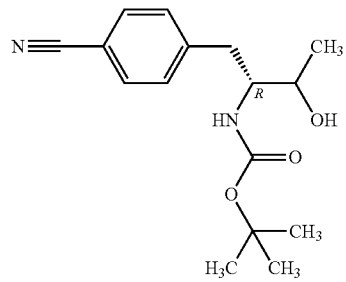

Tert-butyl N-[(1R)-1-[(4-cyanophenyl)methyl]-2-[methoxy(methyl)amino]-2-oxo-ethyl]carbamate

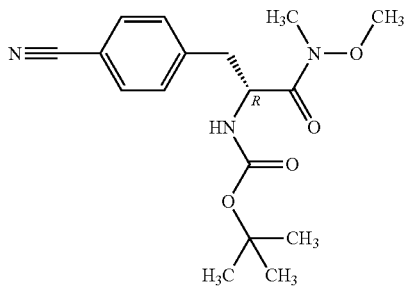

To a stirred solution of N-(tert-butoxycarbonyl)-4-cyano-D-phenylalanine, 1.50 g (5.17 mmol) in dichloromethane (25 mL) were added N,O-dimethylhydroxylamine hydrochloride, 655 mg (6.72 mmol, 1.3 eq.), 1-(3-dimethylaminopropyl)-3-ethylcarbodiimide hydrochloride, 1.19 g (6.20 mmol, 1.2 eq.) and 4-methylmorpholine, 0.80 mL (7.23 mmol, 1.4 eq.) and the resulting mixture was stirred at r.t. for 16 h. Most of the solvent was removed under reduced pressure and the residue was dissolved in ethyl acetate (50 mL). The organic layer was washed successively with aq. 1N hydrochloric acid, aq. sat. sodium hydrogen carbonate, water, brine, dried over sodium sulfate and concentrated. The residue was purified by flash column chromatography (Companion, 40 g column, cyclohexane/ethyl acetate, 1/0 to 3/7) to give the product, 877 mg (51%) as a white solid.

LC-MS (Method 1): R$_t$=3.13 min; MS (ES+): m/z=334 (M+H)<, 278 ([M−tBu]+H), 234 ([M−Boc]+H)$^+$.

$^1$H-NMR (500 MHz, DMSO-d$_6$) δ [ppm]=1.30 (s, 9H), 2.82 (dd, 1H), 2.94 (dd, 1H), 3.11 (s, 3H), 3.73 (s, 3H), 4.58 (m, 1H), 7.22 (d, 1H), 7.44 (d, 2H), 7.76 (d, 2H).

Tert-butyl [(2R)-1-(4-cyanophenyl)-3-oxopropan-2-yl]carbamate

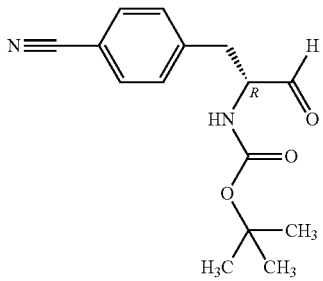

To a solution of tert-butyl N-[(1R)-1-[(4-cyanophenyl)methyl]-2-[methoxy(methyl)-amino]-2-oxo-ethyl]carbamate, 544 mg (1.63 mmol) in THF (16 mL) at −78° C. was added dropwise lithium aluminum hydride, 1.6 mL (2N in tetrahydrofuran, 3.26 mmol, 2.0 eq.) and the resulting solution was stirred at −78° C. for 1 h. Aq. 1N hydrochloric acid (5 mL) was added and the mixture was allowed to warm to r.t. After dilution in water, the mixture was extracted with ethyl acetate (3×). The combined organic phases were then washed with aq. 1N hydrochloric acid, brine, dried over sodium sulfate and concentrated to give the crude aldehyde, 442 mg (92%) as a white solid that was used without further purification.

LC-MS (Method 1): $R_t$=2.74 & 3.24 min; MS (ES−): m/z=273 (M−H)⁻, 319 ([M+HCO$_2$H]−H)⁻, 337 ([M+H$_2$O+HCO$_2$H]−H)⁻.

$^1$H-NMR (500 MHz, CDCl$_3$) δ [ppm]=1.42 (s, 9H), 3.09 (dd, 1H), 3.27 (dd, 1H), 4.43 (m, 1H), 5.05 (br s, 1H), 7.29 (d, 2H), 7.60 (d, 2H), 9.64 (s, 1H).

Tert-butyl-[(2R,3R)-1-(4-cyanophenyl)-3-hydroxybutan-2-yl]carbamate and tert-butyl-[(2R,3S)-1-(4-cyanophenyl)-3-hydroxybutan-2-yl]carbamate To a stirred solution of tert-butyl [(2R)-1-(4-cyanophenyl)-3-oxopropan-2-yl]-carbamate, 262 mg (0.96 mmol) in tetrahydrofuran (8.0 mL) was added dropwise methylmagnesium bromide, 0.96 mL (methylmagnesium bromide, 3M in diethylether, 2.88 mmol, 3.0 eq.) at −10° C. and the resulting mixture was stirred at −10° C. for 4 h. The mixture was allowed to warm to 0° C., quenched with sat. aq. ammonium chloride solution and extracted with ethyl acetate (3×). The combined organic layers were washed with brine, dried over sodium sulfate, filtered and concentrated. The residue was purified by preparative TLC (dichloromethane/methanol: 98/2, 2 migrations) to give an impure fraction, that was purified again by preparative TLC (dichloromethane/methanol: 96/4) to provide the product, 61 mg (23%) as an off-white solid (mixture of stereoisomers).

LC-MS (Method 1): $R_t$=2.99 min; MS (ES+): m/z=291 (M+H)⁺, 235 ([M−tBu]+H)⁺

$^1$H-NMR (500 MHz, CD$_3$OD) δ [ppm]=1.15 & 1.22 (2d, 3H), 1.30 & 1.33 (2s, 9H), 2.62 (dd, 0.4H), 2.77 (dd, 0.6H), 2.96 (dd, 0.6H), 3.16 (dd, 0.4H), 3.58-3.72 (m, 1.4H), 3.74-3.81 (m, 0.6H), 7.38-7.46 (m, 2H), 7.59-7.67 (m, 2H).

Intermediate 24B$^{Boc}$

Tert-butyl 1[(1R)-2-(4-cyanophenyl)-1-(1H-imidazol-2-yl)ethyl]carbamate

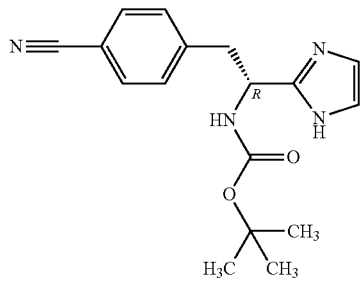

To a stirred solution of tert-butyl [(2R)-1-(4-cyanophenyl)-3-oxopropan-2-yl]-carbamate, 55 mg (0.20 mmol, prepared for 22B$^{Boc}$) in methanol (1.0 mL) at 0° C. were added glyoxal, 18 μL (40% aq., 0.40 mmol, 2.0 eq.) and ammonia, 286 μL (7N in methanol, 2.0 mmol, 10 eq.). The mixture was stirred at r.t. for 16 h. Glyoxal, 36 μL (40% aq., 0.80 mmol, 4.0 eq.) and ammonia, 286 μL (7N in methanol, 2.0 mmol, 10 eq.) were added and the mixture was stirred at r.t. for a further 4 h. Glyoxal, 36 μL (40% aq., 0.80 mmol, 4.0 eq.) and ammonia, 286 μL (7N in methanol, 2.0 mmol, 10 eq.) were added and the mixture was stirred at r.t. for a further 3 h. Most of the solvent was removed under reduced pressure and the residue was dissolved in dichloromethane (20 mL). The organic layer was washed successively with aq. sat. sodium hydrogen carbonate (2×), water (2×), brine, dried over sodium sulfate and concentrated. The product was obtained as a brown oil, 70 mg, that was used without further purification.

LC-MS (Method 1): $R_t$=2.07 min; MS (ES+): m/z=313 (M+H)⁺; MS (ES−): m/z=311 (M−H)⁻.

Protected Intermediate 49B$^{Boc}$

Tert-butyl [(2R)-1-(4-carbamoylphenyl)-3-hydroxypropan-2-yl]carbamate

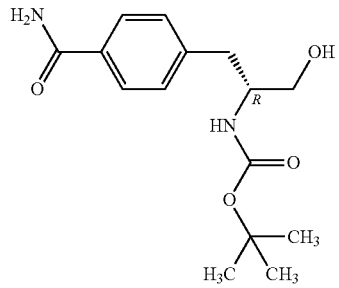

To a stirred solution of tert-butyl [(2R)-1-(4-cyanophenyl)-3-hydroxypropan-2-yl]-carbamate, 300 mg (1.08 mmol) in methanol (6.0 mL) was added aq. sodium hydroxide, 0.18 mL (6N in water, 1.08 mmol) followed by hydrogen peroxide, 0.39 mL (30% in water, 3.80 mmol, 3.5 eq.) at r.t. and the resulting mixture was stirred at 50° C. for 3 h. After cooling to r.t., the mixture was acidified to pH~7 by dropwise addition of aq. 1N hydrochloric acid and the volatiles were removed under reduced pressure. The residue was triturated in water, filtered, washed with water and dried to give the product, 216 mg (67%) as a white solid.

LC-MS (Method 1): $R_t$=2.35 min; MS (ES+): m/z=239 ([M−tBu]+H), 195 ([M−Boc]+H)$^+$.

$^1$H-NMR (500 MHz, DMSO-d$_6$) δ [ppm]=1.31 (s, 9H), 2.60 (dd, 1H), 2.87 (dd, 1H), 3.26 (m, 1H), 3.34 (m, 1H), 3.60 (m, 1H), 4.70 (t, 1H), 6.59 (d, 1H), 7.23 (s, 1H), 7.25 (d, 2H), 7.77 (d, 2H), 7.86 (s, 1H).

Intermediate 52B$^{Boc}$

Tert-butyl [(2R)-1-(4-cyanophenyl)-3-(1,3-dioxo-1,3-dihydro-2H-isoindol-2-yl)propan-2-yl]carbamate

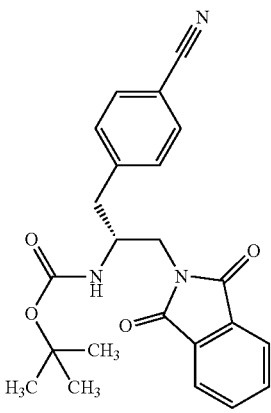 [SMILES: CC(C)(C)OC(=O)N[C@H](Cc1ccc(C#N)cc1)CN1C(=O)c2ccccc2C1=O]

A yellow solution of di-tert-butyl azodicarboxylate, 2.7 g (11.7 mmol, 1.2 eq.) in THF (20 mL) was added dropwise at 0° C. into a solution of triphenylphosphine, 3.08 g (11.7 mmol, 1.2 eq.) in THF (90 mL). The resulting solution was stirred for 2 min at 0° C., then phtalimide, 1.72 g (11.7 mmol, 1.2 eq.) was added in 3 portions, followed by a solution of alcohol intermediate 15B$^{Boc}$, tert-butyl [(2R)-1-(4-cyanophenyl)-3-hydroxypropan-2-yl]carbamate, 2.7 g (9.8 mmol, 1.0 eq.) in THF (20 mL). The resulting yellow solution was stirred at r.t. for 17 h. The reaction medium was concentrated in vacuum and the residue was dry loaded into a silica gel column (12 cm diameter×20 cm height) using DCM and eluted (cyclohexane/ethyl acetate 9/1>6/4). The pure fractions were combined to provide the desired product, 3.4 g (86%).

LC-MS (Method 1): $R_t$=3.46 min; MS (ES+): m/z=406 (M+H)$^-$, 350 ([M−tBu)]+H)$^+$, 306 ([M−Boc]+H)$^+$.

$^1$H-NMR (500 MHz, DMSO-d$_6$) δ [ppm]=1.10 (s, 9H), 2.77 (dd, 1H), 2.93 (dd, 1H), 3.65 (d, 2H), 4.01 (m, 1H), 6.88 (d, 1H), 7.42 (d, 2H), 7.72 (d, 2H), 7.79-7.88 (m, 4H).

Protected Intermediate 54B$^{Boc}$

Methyl N-(tert-butoxycarbonyl)-4-cyano-D-phenylalaninate

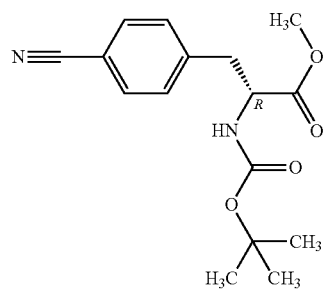

To a stirred solution of N-(tert-butoxycarbonyl)-4-cyano-D-phenylalanine, 200 mg (0.69 mmol) and sodium hydrogen carbonate, 116 mg (1.38 mmol, 2 eq.) in N,N-dimethylformamide (1.4 mL) was added iodomethane, 0.21 mL (3.44 mmol, 5 eq.) and the resulting mixture was stirred at r.t. for 18 h. The mixture was poured into water and extracted with ethyl acetate (2×). The combined organic layers were washed with brine, dried over sodium sulfate, filtered and concentrated to give the product, 203 mg (93%) as a white solid.

LC-MS (Method 1): $R_t$=3.22 min; MS (ES+): m/z=305 (M+H)$^-$, 249 ([M−tBu)]+H)$^-$, 205 ([M−Boc]+H)$^+$.

$^1$H-NMR (500 MHz, CDCl$_3$) δ [ppm]=1.41 (s, 9H), 3.06 (dd, 1H), 3.21 (dd, 1H), 3.72 (s, 3H), 4.61 (m, 1H), 5.01 (m, 1H), 7.25 (d, 2H), 7.59 (d, 2H).

Intermediate 45B$^{Boc}$

Tert-butyl [(2R,3R)-1-(4-cyanophenyl)-3-hydroxy-5-methylhexan-2-yl]carbamate

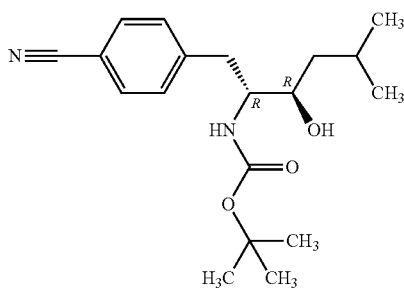

To a cold (0° C.) solution of aldehyde tert-butyl [(2R)-1-(4-cyanophenyl)-3-oxopropan-2-yl]carbamate, 260 mg (0.95 mmol, prepared for 22B$^{Boc}$) in THF (10 mL) was added slowly isobutyl magnesium chloride, 1.42 mL (2.0 N in THF, 2.84 mmol, 3.0 eq.). The resulting solution was stirred at r.t. for 2 h, and then poured into a cold (0° C.) ammonium chloride aqueous solution. The mixture was extracted using ethyl acetate, then dried over sodium sulfate and concentrated to a white residue. Crude mixture LC-MS analysis (Method 9, 18 min) showed a 86/14 ratio of isomers. The crude was purified by flash chromatography (silica, Companion, 40 g column, cyhexane/ethyl acetate 9/1>65/35) to provide the product, 125 mg (40%) as a white solid. LC-MS analysis (Method 9, 18 min) showed a diastereomeric ratio of 91/9.

LC-MS (Method 9): $R_t$=8.55 min; MS (ES+): m/z=333 (M+H)$^+$. Minor dia was observed at Rt=8.34 min.

$^1$H-NMR (500 MHz, CDCl$_3$) δ [ppm]=0.87 (d, 6H), 1.30 (m, 1H), 1.38 (s, 9H), 1.69 (m, 2H), 2.95 (br d, 2H), 3.65 (ddd, 1H), 3.75 (m, 1H), 4.80 (br d, 1H), 7.36 (d, 2H), 7.59 (d, 2H)

Intermediate 46B$^{Boc}$

Tert-butyl [(2R,3S)-1-(4-cyanophenyl)-3-hydroxy-5-methylhexan-2-yl]carbamate

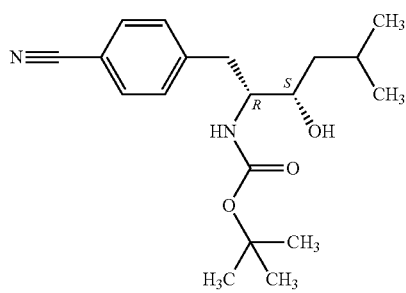

Tert-butyl[(2R)-1-(4-cyanophenyl)-5-methyl-3-oxo-hexan-2-yl]carbamate

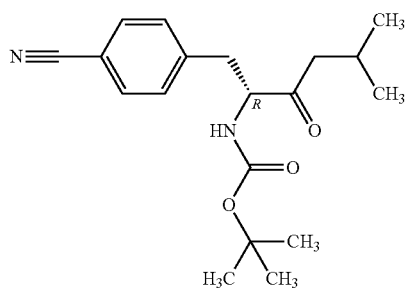

To a stirred solution of tert-butyl N-[(1R)-1-[(4-cyanophenyl)methyl]-2-[methoxy-(methyl)amino]-2-oxo-ethyl]carbamate, 343 mg (1.03 mmol, prepared for 22B$^{Boc}$) in THF (4 mL) at 0° C. was added dropwise isobutyl magnesium chloride (2N solution in THF, 1.54 mL, 3.09 mmol, 3.0 eq.). The resulting mixture was stirred for 16 h at r.t., and then more isobutyl magnesium chloride (2N solution in THF, 1.0 mL, 2.0 mmol, 2.0 eq.) was added. The resulting mixture was stirred another 4 h at r.t., and then poured into a 0.5 N hydrochloric acid solution. The resulting mixture was extracted using ethyl acetate. The combined organic phase was washed with brine, dried over sodium sulfate and concentrated to provide the crude product, 330 mg (97%) that was used directly without further purification.

LC-MS (Method 1): $R_t$=3.71 min; MS (ES+): m/z=331 (M+H)$^+$.

Tert-butyl [(2R,3S)-1-(4-cyanophenyl)-3-hydroxy-5-methylhexan-2-yl]carbamate

A solution of ketone tert-butyl [(2R)-1-(4-cyanophenyl)-5-methyl-3-oxohexan-2-yl]carbamate, 330 mg (1.0 mmol) in methanol (7 mL) was cooled at −10° C. and sodium borohydride, 113 mg (3.0 mmol, 3.0 eq) was added. The resulting yellow solution was immediately cooled at −22° C. and stirred at that temperature for 30 min, and then left to warm to r.t. over 2 h. The resulting solution was then poured into a cold (0° C.) ammonium chloride aqueous solution. The mixture was extracted using ethyl acetate, then dried over sodium sulfate and concentrated. LC-MS analysis of the crude mixture (Method 9, 18 min) showed a 84/16 ratio of diastereoisomers. The crude was purified by flash chromatography (silica, Companion, 40 g column, cyhexane/ethyl acetate 9/1>65/35) to provide the product, 151 mg (45%). LC-MS analysis (Method 9, 18 min) showed a 93/7 ratio of diastereoisomers.

LC-MS (Method 9): $R_t$=8.33 min; MS (ES+): m/z=333 (M+H)$^+$. Minor dia was observed at Rt=8.55 min.

$^1$H-NMR (500 MHz, CDCl$_3$) δ [ppm]=0.95 (d, 3H), 1.00 (d, 3H), 1.35 (s, 9H), 1.49 (m, 1H), 1.60 (br s, 1H), 1.82 (m, 1H), 2.81 (m, 1H), 2.98 (dd, 1H), 3.82 (br d, 2H), 4.68 (m, 1H), 7.35 (d, 2H), 7.60 (d, 2H)

Intermediate 26B$^{Boc}$

Tert-butyl [(2R)-1-(4-cyanophenyl)-3-(4-methylpiperazin-1-yl)propan-2-yl]-carbamate

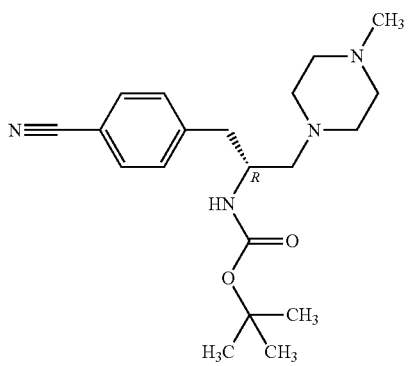

To a stirred solution of tert-butyl [(2R)-1-(4-cyanophenyl)-3-oxopropan-2-yl]-carbamate, 100 mg (0.365 mmol, prepared for 22B$^{Boc}$) in dichloromethane (3.6 mL) was added 1-methylpiperazine, 49 µL (0.437 mmol, 1.2 eq.) followed by sodium triacetoxyborohydride, 101 mg (0.474 mmol, 1.3 eq.) at r.t. and the resulting mixture was stirred at r.t. for 16 h. Aq. sat. sodium hydrogen carbonate was added and the mixture was extracted with dichloromethane (4×). The combined organic extracts were dried over sodium sulfate, filtered and concentrated to give the product, 130 mg (99% yield) as a light yellow solid.

LC-MS (Method 1): $R_t$=2.12 min; MS (ES+): m/z=359 (M+H)$^+$, 303 ([M−tBu]+H)$^+$.

$^1$H-NMR (500 MHz, DMSO-d$_6$) δ [ppm]=1.28 (s, 9H), 2.12 (s, 3H), 2.21-2.36 (m, 10H), 2.60 (dd, 1H), 2.91 (dd, 1H), 3.78 (m, 1H), 6.65 (d, 1H), 7.37 (d, 2H), 7.72 (d, 2H).

Using the same procedure, the following examples have been prepared from commercially available amines. Product purification may be done by flash chromatography on silica gel using dichloromethane/methanol mixtures as eluent.

| Intermediate No | Starting material | Structure/Name | Analytics |
|---|---|---|---|
| 27B$^{Boc}$ | Morpholine | tert-butyl [(2R)-1-(4-cyanophenyl)-3-(morpholin-4-yl)propan-2-yl]carbamate | LC-MS (Method 1): R$_t$ = 2.12 min; MS (ES+): m/z = 346 (M + H)$^+$ $^1$H-NMR (500 MHz, CDCl$_3$) δ [ppm] = 1.39 (s, 9H), 2.78-3.00 (m, 4H), 3.12 (m, 1H), 3.37-3.60 (m, 3H), 3.87-4.20 (m, 4H), 4.31 (m, 2H), 7.36 (d, 2H), 7.61 (d, 2H). |
| 50B$^{Boc}$ | Pyrrolidine | tert-butyl [(2R)-1-(4-cyanophenyl)-3-(pyrrolidin-1-yl)propan-2-yl]carbamate | LC-MS (Method 1): R$_t$ = 2.14 min; MS (ES+): m/z = 330 (M + H)$^+$. $^1$H-NMR (500 MHz, CD$_3$OD) δ [ppm] = 1.33 (s, 9H), 1.78-1.85 (m, 4H), 2.52-2.73 (m, 7H), 2.98 (dd, 1H), 3.93 (m, 1H), 7.41 (d, 2H), 7.63 (d, 2H). |
| 28B$^{Boc}$ | Ethanolamine | tert-butyl {(2R)-1-(4-cyanophenyl)-3-[(2-hydroxyethyl)amino]propan-2-yl}carbamate | LC-MS (Method 1): R$_t$ = 2.05 min; MS (ES+): m/z = 320 (M + H)$^+$, 264 ([M − tBu)] + H)$^+$. $^1$H-NMR (500 MHz, DMSO-d$_6$) δ [ppm] = 1.28 (s, 9H), 2.47-2.52 (m, 2H), 2.53-2.56 (m, 2H), 2.63 (dd, 1H), 2.91 (dd, 1H), 3.41 (d, 1H), 3.43 (d, 1H), 3.67 (m, 1H), 4.42 (t, 1H), 6.69 (d, 1H), 7.38 (d, 2H), 7.72 (d, 2H). |

| Intermediate No | Starting material | Structure/Name | Analytics |
|---|---|---|---|
| 51B[Boc] | Dimethylamine (2N solution in THF) | 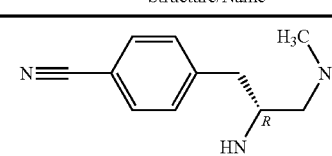<br>tert-butyl [(2R)-1-(4-cyanophenyl)-3-(dimethylamino)propan-2-yl]carbamate | LC-MS (Method 1): $R_t$ = 2.08 min; MS (ES+): m/z = 304 (M + H)+, 248 ([M − tBu)] + H)+.<br>1H-NMR (500 MHz, DMSO-$d_6$) δ [ppm] = 1.27 (s, 9H), 2.15 (s, 6H), 2.18-2.21 (m, 2H), 2.58 (dd, 1H), 2.94 (dd, 1H), 3.71 (m, 1H), 6.66 (d, 1H), 7.37 (d, 2H), 7.72 (d, 2H). |

Intermediate 25B[Boc]

Tert-butyl [(1R)-2-(4-cyanophenyl)-1-(1H-1,2,4-triazol-5-yl)ethyl]carbamate

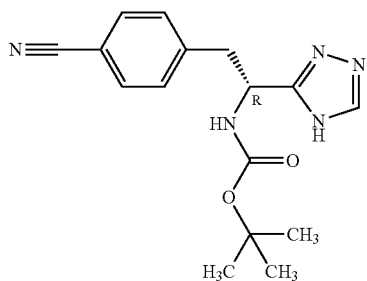

Tert-butyl N-[(1R)-2-amino-1-[(4-cyanophenyl)methyl]-2-oxo-ethyl]carbamate

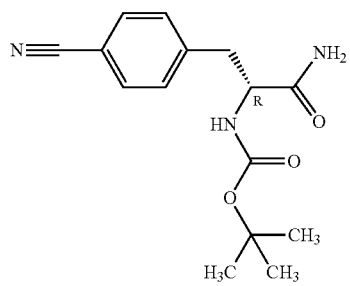

To a stirred solution of N-(tert-butoxycarbonyl)-4-cyano-D-phenylalanine 2.0 g (6.89 mmol) and triethylamine, 1.06 mL (7.58 mmol, 1.1 eq.) in tetrahydrofuran (30 mL, Acros Organics, Extra dry, over 4A MS) was added dropwise ethyl chloroformate, 0.72 mL (7.58 mmol, 1.1 eq.) at −10° C. (ice/sodium chloride bath) and the resulting mixture was stirred at −10° C. for 20 min. To the resulting suspension was added slowly aq. ammonium hydroxide (30% aq. solution, 2.7 mL, 20.7 mmol, 3 eq.) at −10° C. and the resulting mixture was stirred at −10° C. for 4 h. The solvent was removed under reduced pressure and the residue was partitioned between ethyl acetate and aq. 1N hydrochloric acid. The layers were separated, the organic layer was washed with aq. sat. sodium hydrogen carbonate, brine, dried over sodium sulfate, filtered and concentrated to give the product, 1.72 g (85%) as a white solid.

LC-MS (Method 1): $R_t$=2.72 min; MS (ES+): m/z=234 ([M−tBu)]+H)+, 190 ([M−Boc]+H)+.

1H-NMR (500 MHz, CDCl$_3$) δ [ppm]=1.40 (s, 9H), 3.06 (dd, 1H), 3.21 (dd, 1H), 4.40 (m, 1H), 4.99 (br s, 1H), 5.41 (br s, 1H), 5.92 (br s, 1H), 7.35 (d, 2H), 7.60 (d, 2H).

Tert-butyl [(2R)-1-amino-3-(4-cyanophenyl)-1-thioxopropan-2-yl]carbamate

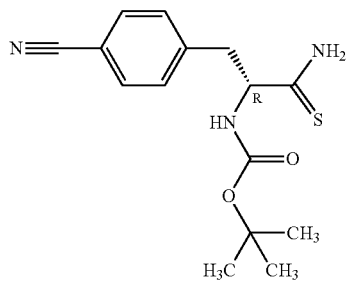

A solution of tert-butyl N-[(1R)-2-amino-1-[(4-cyanophenyl)methyl]-2-oxo-ethyl]-carbamate, 190 mg (0.66 mmol) in dry THF (2 mL) was treated with Lawesson's reagent, 133 mg (0.33 mmol). The resulting yellow solution was stirred at 50° C. for 1.5 h. Lawesson's reagent, 13 mg (0.03 mmol) was added and the mixture was stirred at 50° C. for 30 minutes. The reaction medium was then concentrated and the residue was purified by flash chromatography with combiflash (12 g column, silica gel, eluent: cyclohexane/ethyl acetate, 1/0 to 1/1) to afford the product, 118 mg (59%) as a white foam.

LC-MS (Method 1): $R_t$=3.15 min; MS (ES+): m/z=306 (M+H)+, 250 ([M−tBu)]+H)+, 206 ([M−Boc]+H)+.

¹H-NMR (500 MHz, CD₃OD) δ [ppm]=1.36 (s, 9H), 2.97 (dd, 1H), 3.30 (m, 1H), 4.60 (m, 1H), 7.47 (d, 2H), 7.64 (d, 2H).

Methyl (2R)-2-[(tert-butoxycarbonyl)amino]-3-(4-cyanophenyl) propanimidothioate hydroiodide (1:1)

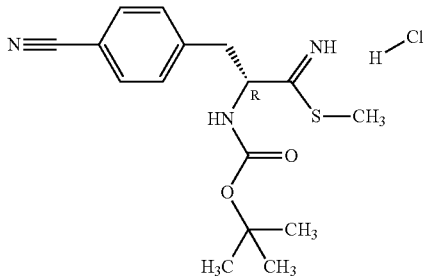

A solution of tert-butyl [(2R)-1-amino-3-(4-cyanophenyl)-1-thioxopropan-2-yl]-carbamate, 95 mg (0.31 mmol) in dry THF (0.62 mL) was treated at r.t. with iodomethane, 97 µL (1.56 mmol) and the mixture was stirred at r.t. for 16 h. The yellow slurry was then diluted with diethyl ether and filtered. The residual solid was rinsed with diethyl ether and then dried under vacuum to give the product, 123 mg (72%), as an off-white solid. The latter was used without further purification.

LC-MS (Method 1): R$_t$=2.48 min; MS (ES+): m/z=320 (M+H)⁺

Tert-butyl [(1R)-2-(4-cyanophenyl)-1-(1H-1,2,4-triazol-5-yl)ethyl]carbamate

A colourless solution of methyl (2R)-2-[(tert-butoxycarbonyl)amino]-3-(4-cyano-phenyl)propanimidothioate hydroiodide (1:1), 185 mg (0.41 mmol) in absolute ethanol (2 mL) was treated successively with DIPEA, 216 µL (1.23 mmol) and formic hydrazide, 32 mg (0.61 mmol). The resulting mixture was stirred at 60° C. After 3.5 h. Formic hydrazide, 100 mg (1.66 mmol) was added and the mixture was stirred at 60° C. for 3 days. Formic hydrazide, 100 mg (1.66 mmol) was added and the reaction medium was stirred at 60° C. during 24 h. The mixture was concentrated and the brown residue was purified by flash chromatography on silica gel with combiflash (12 g column, eluent: dichloromethane/ethyl acetate, 1/0 to 0/1) to give the product, 22 mg (17%) as an off-white solid.

LC-MS (Method 1): R$_t$=2.82 min; MS (ES+): m/z=314 (M+H)⁺.

¹H-NMR (500 MHz, CD₃OD) δ [ppm]=1.36 (s, 9H), 3.15 (dd, 1H), 3.34 (m, 1H), 5.07-5.09 (m, 1H), 7.38 (d, 2H), 7.61 (d, 2H), 8.29 (br s, 1H).

Protected Intermediate 29B$^{Boc}$

Tert-butyl [(2R)-1-(4-cyanophenyl)-4-(4-methylpiperazin-1-yl)butan-2-yl]-carbamate

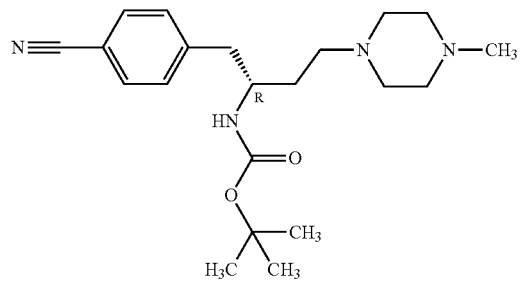

Tert-butyl {(2R)-1-(4-cyanophenyl)-4-[methoxy(methyl)amino]-4-oxobutan-2-yl}-carbamate

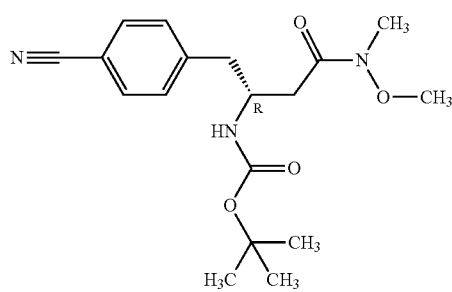

To a stirred solution of (3R)-3-(tert-butoxycarbonylamino)-4-(4-cyanophenyl)butanoic acid, 2.65 g (8.71 mmol) in dichloromethane (80 mL) were added 1-(3-dimethylaminopropyl)-3-ethylcarbodiimide hydrochloride, 2.0 g (10.4 mmol, 1.2 eq.), 4-methylmorpholine, 1.24 mL (11.3 mmol, 1.3 eq.) and N,O-dimethylhydroxylamine hydrochloride, 1.02 g (10.4 mmol, 1.2 eq.) and the resulting mixture was stirred at r.t. for 18 h. Most of the solvent was removed under reduced pressure and the residue was dissolved in ethyl acetate (100 mL). The organic layer was washed successively with aq. 1N hydrochloric acid, aq. sat. sodium hydrogen carbonate, brine, dried over sodium sulfate and concentrated. The residue (3.10 g, orange oil) was purified by flash column chromatography (eluent: cyclohexane/ethyl acetate, 3/2) to give the product, 2.86 g (95%) as a light yellow solid.

LC-MS (Method 1): R$_t$=3.05 min; MS (ES+): m/z=348 (M+H)⁺, 292 ([M−tBu]+H)⁺, 248 ([M−Boc]+H)⁺.

¹H-NMR (500 MHz, CDCl₃) δ [ppm]=1.37 (s, 9H), 2.59 (dd, 1H), 2.66 (dd, 1H), 2.94 (dd, 1H), 3.06 (m, 1H), 3.18 (s, 3H), 3.60 (s, 3H), 4.16 (m, 1H), 5.49 (br s, 1H), 7.33 (d, 2H), 7.57 (d, 2H).

Tert-butyl [(2R)-1-(4-cyanophenyl)-4-oxobutan-2-yl]carbamate

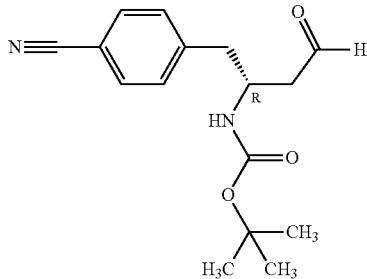

To a solution of tert-butyl {(2R)-1-(4-cyanophenyl)-4-[methoxy(methyl)amino]-4-oxobutan-2-yl}carbamate, 490 mg (1.41 mmol) in tetrahydrofuran (14 mL) at −78° C. was added dropwise lithium aluminum hydride, 1.41 mL (2N in tetrahydrofuran, 2.82 mmol, 2.0 eq.) and the resulting solution was stirred at −78° C. for 1 h. Aq. 1N hydrochloric acid was added and the mixture was allowed to warm to r.t. The solvent was removed under reduced pressure and after dilution in water, the mixture was extracted with ethyl acetate (3×). The combined organic phases were washed with brine, dried over sodium sulfate and concentrated to give the crude aldehyde, 398 mg (92% yield) as a white solid that was used without further purification.

LC-MS (Method 1): $R_t$=2.68 & 3.11 min; MS (ES−): m/z=287 (M−H)⁻, 333 ([M+HCO₂H]−H)⁻, 351 ([M+HCO₂H+H₂O]−H)⁻.

$^1$H-NMR (500 MHz, CDCl₃) δ [ppm]=1.37 (s, 9H), 2.61-2.71 (m, 2H), 2.90 (dd, 1H), 2.99 (m, 1H), 4.24 (m, 1H), 4.78 (br s, 1H), 7.30 (d, 2H), 7.60 (d, 2H), 9.74 (s, 1H).

Tert-butyl [(2R)-1-(4-cyanophenyl)-4-(4-methylpiperazin-1-yl)butan-2-yl]carbamate To a stirred solution of tert-butyl [(2R)-1-(4-cyanophenyl)-4-oxobutan-2-yl]carbamate, 120 mg (0.416 mmol) in dichloromethane (4.2 mL) was added 1-methylpiperazine, 55 μL (0.50 mmol, 1.2 eq.) followed by sodium triacetoxyborohydride, 115 mg (0.541 mmol, 1.3 eq.) at r.t. and the resulting mixture was stirred at r.t. for 16 h. Aq. sat. sodium hydrogen carbonate was added and the mixture was extracted with dichloromethane. The combined organic extracts were dried over sodium sulfate, filtered and concentrated. The residue was purified by flash column chromatography on silica gel (eluent: dichloromethane/7N ammonia in methanol, 98/2) to give the product, 110 mg (71%) as a white solid.

LC-MS (Method 1): $R_t$=2.12 min; MS (ES+): m/z=373 (M+H)⁺, 317 ([M−tBu]+H)⁺.

$^1$H-NMR (500 MHz, CDCl₃) δ [ppm]=1.38 (s, 9H), 1.70-1.76 (m, 2H), 2.44 (s, 3H), 2.58-2.91 (m, 12H), 3.89 (m, 1H), 5.33 (br s, 1H), 7.30 (d, 2H), 7.58 (d, 2H).

Using the same procedure as for protected intermediate 29$^{Boc}$, the following examples have been prepared from commercially available amines as indicated.

| Intermediate No | Starting material | Structure | Analytics |
|---|---|---|---|
| 30B$^{Boc}$ | 2-propylamine | tert-butyl [(2R)-1-(4-cyanophenyl)-4-(isopropylamino)butan-2-yl]carbamate | LC-MS (Method 1): $R_t$ = 2.14 min; MS (ES+): m/z = 322 (M + H)⁺, 276 ([M − tBu)] + H)⁺. $^1$H-NMR (500 MHz, DMSO-d₆) δ [ppm] = 0.92 (d, 6H), 1.29 (s, 9H), 1.45 (m, 1H), 1.52 (m, 1H), 2.47-2.52 (m, 2H), 2.61 (m, 1H), 2.69 (dd, 1H), 2.78 (dd, 1H), 3.68 (m, 1H), 6.78 (d, 1H), 7.38 (d, 2H), 7.72 (d, 2H). |

-continued

| Intermediate No | Starting material | Structure | Analytics |
|---|---|---|---|
| 31B[Boc] | tert-butyl (2R)-2-methylpiperazine-1-carboxylate [170033-47-3] | 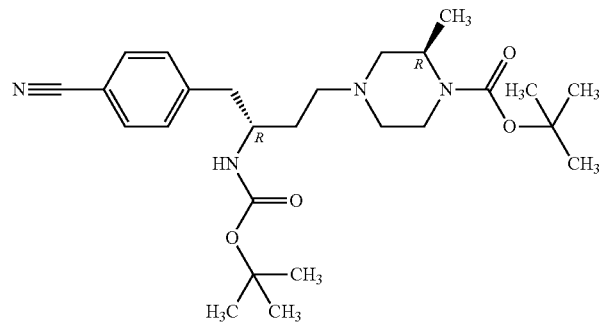<br>tert-butyl (2R)-4-[(3R)-3-[(tert-butoxycarbonyl)amino]-4-(4-cyanophenyl)butyl]-2-methylpiperazine-1-carboxylate | LC-MS (Method 1): $R_t$ = 2.47 min; MS (ES+): m/z = 473 (M + H)+. |
| 32B[Boc] | tert-butyl (2R)-2-methylpiperazine-1-carboxylate [1699447-70-5] | 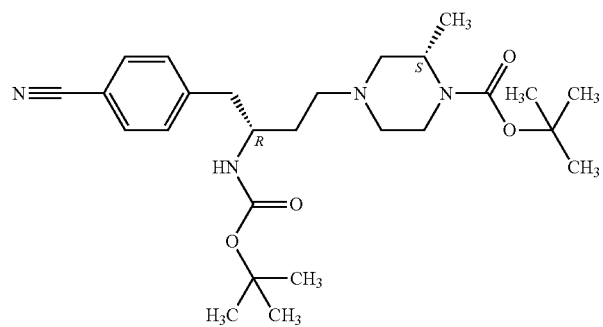<br>tert-butyl (2S)-4-[(3R)-3-[(tert-butoxycarbonyl)amino]-4-(4-cyanophenyl)butyl]-2-methylpiperazine-1-carboxylate | LC-MS (Method 1): $R_t$ = 2.45 min; MS (ES+): m/z = 473 (M + H)+. |
| 33B[Boc] | Morpholine | 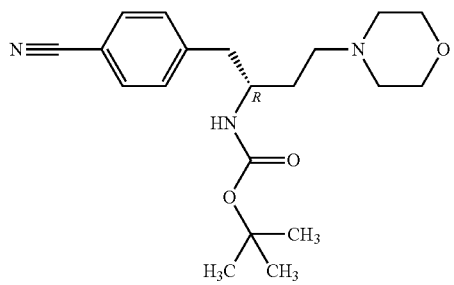<br>tert-butyl [(2R)-1-(4-cyanophenyl)-4-(morpholin-4-yl)butan-2-yl]carbamate | LC-MS (Method 1): $R_t$ = 2.11 min; MS (ES+): m/z = 360 (M + H)+.<br>$^1$H-NMR (500 MHz, DMSO-$d_6$) δ [ppm] = 1.28 (s, 9H), 1.48-1.59 (m, 2H), 2.25-2.32 (m, 6H), 2.69 (dd, 1H), 2.81 (dd, 1H), 3.53-3.55 (m, 4H), 3.66 (m, 1H), 6.76 (d, 1H), 7.38 (d, 2H), 7.73 (d, 2H). |

-continued

| Intermediate No | Starting material | Structure | Analytics |
|---|---|---|---|
| 34B$^{Boc}$ | (3S)-1,3-dimethylpiperazine dihydrochloride [1152367-80-0] | 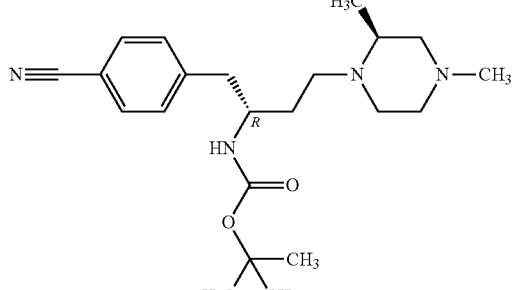<br>tert-butyl {(2R)-1-(4-cyanophenyl)-4-[(2S)-2,4-dimethylpiperazin-1-yl]butan-2-yl}carbamate | LC-MS (Method 1): R$_t$ = 2.07 min; MS (ES+): m/z = 387 (M + H)$^+$, 331 ([M − tBu)] + H)$^+$, 287 ([M − Boc] + H)$^+$.<br>$^1$H-NMR (500 MHz, CDCl$_3$) δ [ppm] = 1.02 (d, 3H), 1.41 (s, 9H), 1.45 (m, 1H), 1.91 (m, 1H), 2.18-2.27 (m, 3H), 2.24 (s, 3H), 2.41 (m, 1H), 2.60-2.64 (m, 2H), 2.77 (dd, 1H), 2.80-2.84 (m, 2H), 2.98 (m, 1H), 3.79 (br s, 1H), 5.77 (br s, 1H), 7.30 (d, 2H), 7.57 (d, 2H). |
| 35B$^{Boc}$ | (3R)-1,3-dimethylpiperazine dihydrochloride [1033717-21-3] | 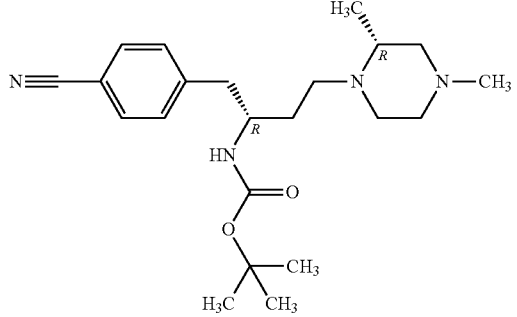<br>tert-butyl {(2R)-1-(4-cyanophenyl)-4-[(2R)-2,4-dimethylpiperazin-1-yl]butan-2-yl}carbamate | LC-MS (Method 1): R$_t$ = 2.05 min; MS (ES+): m/z = 387 (M + H)$^+$, 331 ([M − tBu)] + H)$^+$, 287 ([M − Boc] + H)$^+$.<br>$^1$H-NMR (500 MHz, CDCl$_3$) δ [ppm] = 1.06 (d, 3H), 1.36 (m, 1H), 1.39 (s, 9H), 1.72 (m, 1H), 1.90 (m, 1H), 2.15-2.22 (m, 3H), 2.24 (s, 3H), 2.62-2.69 (m, 2H), 2.77 (dd, 1H), 2.83 (m, 1H), 2.92-2.99 (m, 2H), 3.89 (br s, 1H), 5.87 (br s, 1H), 7.30 (d, 2H), 7.57 (d, 2H). |
| 36B$^{Boc}$ | 1-(1-methylpiperidin-4-yl)methanamine [7149-42-0] | 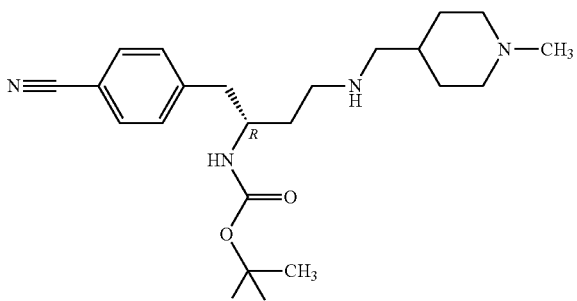<br>tert-butyl [(2R)-1-(4-cyanophenyl)-4-{[(1-methylpiperidin-4-yl)methyl]amino}butan-2-yl]carbamate | LC-MS (Method 1): R$_t$ = 1.85 min; MS (ES+): m/z = 401 (M + H)$^+$, 301 ([M − Boc] + H)$^+$.<br>$^1$H-NMR (500 MHz, CDCl$_3$) δ [ppm] = 1.21-1.29 (m, 2H), 1.39 (s, 9H), 1.65-1.72 (m, 3H), 1.88 (td, 2H), 2.25 (s, 3H), 2.62-2.69 (m, 2H), 2.40-2.47 (m, 2H), 2.63 (m, 1H), 2.73 (m, 1H), 2.79 (dd, 1H), 2.81-2.85 (m, 2H), 2.94 (m, 1H), 3.90 (br s, 1H), 5.59 (br d, 1H), 7.30 (d, 2H), 7.57 (d, 2H). |

-continued

| Intermediate No | Starting material | Structure | Analytics |
|---|---|---|---|
| 37B[Boc] | (3R)-1-methylpyrrolidin-3-amine [457097-75-5] | 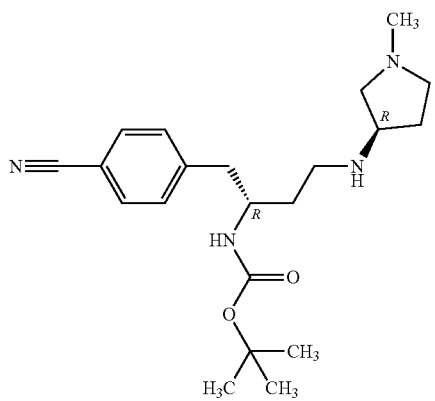<br>tert-butyl [(2R)-1-(4-cyanophenyl)-4-{[(3R)-1-methylpyrrolidin-3-yl]amino}butan-2-yl]carbamate | LC-MS (Method 1): $R_t$ = 0.39 & 1.84 min; MS (ES+): m/z = 373 (M + H)+, 317 ([M − tBu)] + H)+, 273 ([M − Boc] + H)+.<br>$^1$H-NMR (500 MHz, CDCl$_3$) δ [ppm] = 1.35-1.44 (m, 2H), 1.39 (s, 9H), 1.50-1.56 (m, 2H), 1.68 (m, 1H), 2.10 (m, 1H), 2.30 (m, 1H), 2.46 (m, 1H), 2.56-2.61 (m, 2H), 2.64-2.69 (m, 2H), 2.80 (dd, 1H), 2.88 (m, 1H), 3.25 (m, 1H), 3.91 (br s, 1H), 5.06 (br d, 1H), 7.29 (d, 2H), 7.57 (d, 2H). |
| 38B[Boc] | (3S)-1-methylpyrrolidin-3-amine [214357-95-6] | 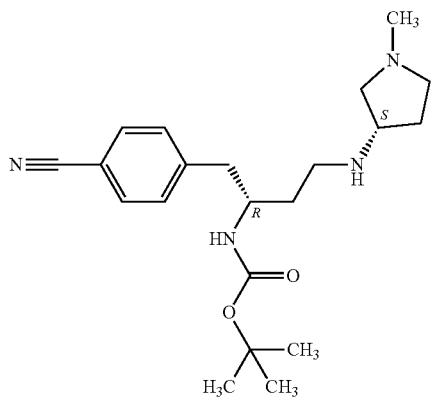<br>tert-butyl [(2R)-1-(4-cyanophenyl)-4-{[(3S)-1-methylpyrrolidin-3-yl]amino}butan-2-yl]carbamate | LC-MS (Method 1): $R_t$ = 1.78 min; MS (ES+): m/z = 373 (M + H)+, 317 ([M − tBu] + H)+, 273 ([M − Boc] + H)+.<br>$^1$H-NMR (500 MHz, CDCl$_3$) δ [ppm] = 1.36-1.46 (m, 2H), 1.39 (s, 9H), 1.50-1.56 (m, 2H), 1.67 (m, 1H), 2.10 (m, 1H), 2.30 (m, 1H), 2.43 (m, 1H), 2.57-2.68 (m, 4H), 2.80 (dd, 1H), 2.89 (m, 1H), 3.23 (m, 1H), 3.90 (br s, 1H), 5.09 (br d, 1H), 7.29 (d, 2H), 7.57 (d, 2H). |
| 39B[Boc] | 2-methyl-2,6-diazaspiro[3.3]heptane dihydrochloride [1203567-11-6] | 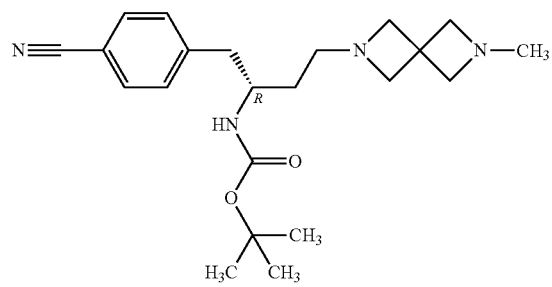<br>tert-butyl [(2R)-1-(4-cyanophenyl)-4-(6-methyl-2,6-diazaspiro[3.3]hept-2-yl)butan-2-yl]carbamate | LC-MS (Method 1): $R_t$ = 1.78 min; MS (ES+): m/z = 385 (M + H)+, 329 ([M − tBu] + H)+.<br>$^1$H-NMR (500 MHz, CDCl$_3$) δ [ppm] = 1.31 (m, 1H), 1.38 (s, 9H), 1.49 (m, 1H), 2.27 (s, 3H), 2.39 (m, 1H), 2.52 (m, 1H), 2.76 (dd, 1H), 2.88 (m, 1H), 3.20 (s, 4H), 3.25 (s, 4H), 3.83 (m, 1H), 5.40 (br d, 1H), 7.28 (d, 2H), 7.56 (d, 2H). |

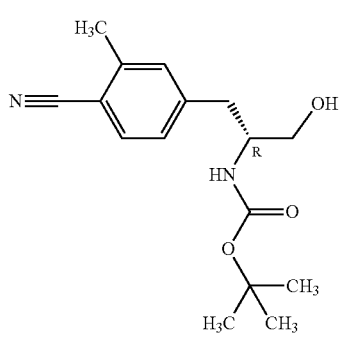

Methyl N-tert-butoxycarbonyl)-4-cyano-3-methyl-D-phenylalaninate

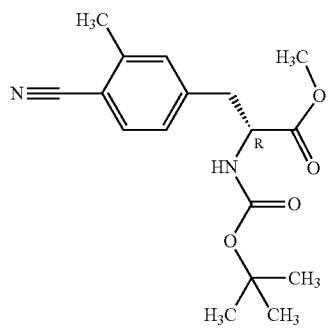

To a stirred suspension of zinc dust, 179 mg (2.73 mmol, 3 eq.) in dry N,N-dimethylformamide (1 mL) were added successively iodine, 35 mg (0.137 mmol, 15 mol %), (S)-methyl 2-((tert-butoxycarbonyl)amino)-3-iodopropanoate, 300 mg (0.911 mmol) and iodine, 35 mg (0.137 mmol, 15 mol %) and the resulting mixture was stirred at r.t. for 1 h (light exotherm observed). Tris-(dibenzylideneacetone)dipalladium, 42 mg (46 μmol, 5 mol %), dicyclohexyl(2',6'-dimethoxybiphenyl-2-yl)phosphine, 37 mg (91 μmol, 10 mol %) followed by 4-bromo-2-methylbenzonitrile, 232 mg (1.18 mmol, 1.3 eq.) were added and the mixture was stirred at 50° C. for 18 h. The solvent was removed under reduced pressure and the residue was purified by flash column chromatography on silica gel (eluent: cyclohexane/ethyl acetate, 9:1) to give the product, 184 mg (63%) as an orange oil.

LC-MS (Method 1): $R_t$=3.39 min; MS (ES+): m/z=319 (M+H), 263 ([M−tBu]+H)$^+$, 219 ([M−Boc]+H)$^+$.

$^1$H-NMR (500 MHz, CDCl$_3$) δ [ppm]=1.41 (s, 9H), 2.52 (s, 3H), 3.02 (dd, 1H), 3.16 (dd, 1H), 3.73 (s, 3H), 4.58 (q, 1H), 5.00 (d, 1H), 7.04 (d, 1H), 7.10 (s, 1H), 7.52 (d, 1H).

Tert-butyl [(2R)-1-(4-cyano-3-methylphenyl)-3-hydroxypropan-2-yl]carbamate

To a stirred solution of methyl N-(tert-butoxycarbonyl)-4-cyano-3-methyl-D-phenylalaninate, 182 mg (0.572 mmol) in a mixture tetrahydrofuran/methanol (6 mL, 1/1) was added sodium borohydride, 108 mg (2.86 mmol, 5 eq.) at 0° C. and the resulting mixture was stirred at r.t. for 2 h. The solvents were removed under reduced pressure and the residue was partitioned between water and ethyl acetate. The layers were separated and the aqueous phase was extracted with ethyl acetate (2×). The combined organic extracts were washed with brine, dried over sodium sulfate, filtered and concentrated to give the product, 147 mg (87%) as a white solid.

LC-MS (Method 1): $R_t$=2.95 min; MS (ES+): m/z=291 (M+H)$^+$, 235 ([M−tBu]+H)$^+$, 191 ([M−Boc]+H)$^+$.

$^1$H-NMR (500 MHz, CDCl$_3$) δ [ppm]=1.41 (s, 9H), 2.52 (s, 3H), 2.87 (d, 2H), 3.55 (dd, 1H), 3.67 (dd, 1H), 3.86 (br s, 1H), 4.75 (br s, 1H), 7.13 (d, 1H), 7.19 (s, 1H), 7.52 (d, 1H)

The following examples were prepared using the same two step procedure, from commercially available starting materials as indicated via the methyl ester intermediate.

| Intermediate No | Aryl derivative | Structure/Name | Analytics |
|---|---|---|---|
| 41B$^{Boc}$ | Ester 41B | ![structure] tert-butyl [(2R)-1-(4-cyano-5-fluoro-2-methylphenyl)-3-hydroxypropan-2-yl]carbamate | LC-MS (Method 1): $R_t$ = 3.03 min; MS (ES+): m/z = 309 (M + H)$^+$, 253 ([M − tBu] + H)$^+$, 209 ([M − Boc] + H)$^+$. $^1$H-NMR (500 MHz, CDCl$_3$) δ [ppm] = 1.40 (s, 9H), 2.36 (s, 3H), 2.86 (dd, 1H), 2.93 (dd, 1H), 3.59 (m, 1H), 3.71 (m, 1H), 3.86 (m, 1H), 4.82 (m, 1H), 7.05 (d, 1H), 7.38 (d, 1H). |

| Intermediate No | Aryl derivative | Structure/Name | Analytics |
|---|---|---|---|
| Ester[41B] | 4-bromo-2-fluoro-5-methylbenzonitrile | 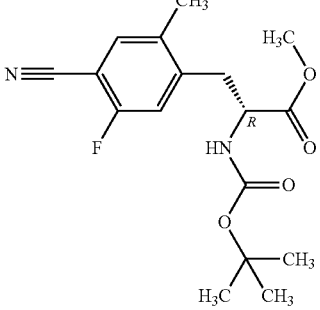methyl N-(tert-butoxycarbonyl)-4-cyano-3-fluoro-6-methyl-D-phenylalaninate | LC-MS (Method 1): $R_t$ = 3.41 min; MS (ES+): m/z = 337 (M + H)+, 281 ([M – tBu] + H)+, 237 ([M – Boc] + H)+. $^1$H-NMR (500 MHz, CDCl$_3$) δ [ppm] = 1.38 (s, 9H), 2.34 (s, 3H), 2.93 (dd, 1H), 3.20 (dd, 1H), 3.74 (s, 3H), 4.57 (q, 1H), 5.07 (d, 1H), 6.96 (d, 1H), 7.39 (d, 1H). |
| 42B[Boc] | Ester 42B | 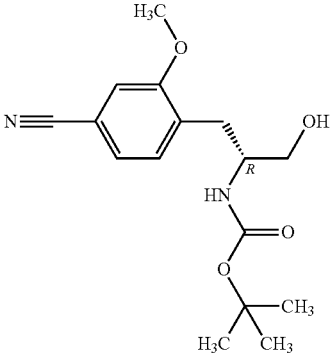tert-butyl [(2R)-1-(4-cyano-2-methoxyphenyl)-3-hydroxypropan-2-yl]carbamate | LC-MS (Method 1): $R_t$ = 2.91 min; MS (ES+): m/z = 307 (M + H)+, 251 ([M – tBu] + H)+, 207 ([M – Boc] + H)+. $^1$H-NMR (500 MHz, CDCl$_3$) δ [ppm] = 1.38 (s, 9H), 2.86 (dd, 1H), 2.92 (dd, 1H), 3.52 (dd, 1H), 3.62 (dd, 1H), 3.87 (m, 1H), 3.89 (s, 3H), 4.90 (br s, 1H), 7.09 (d, 1H), 7.23 (dd, 1H), 7.27 (d, 1H). |
| Ester[42B] | 4-bromo-3-methoxybenzonitrile | 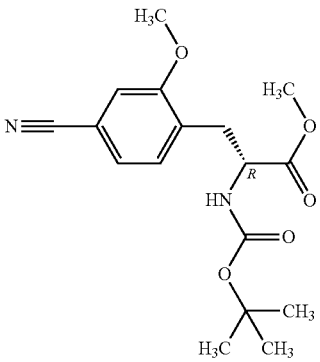methyl N-(tert-butoxycarbonyl)-4-cyano-2-methoxy-D-phenylalaninate | LC-MS (Method 1): $R_t$ = 3.32 min; MS (ES+): m/z = 335 (M + H)+, 279 ([M – tBu] + H)+, 235 ([M – Boc] + H)+. $^1$H-NMR (500 MHz, CDCl$_3$) δ [ppm] = 1.37 (s, 9H), 3.02 (dd, 1H), 3.18 (dd, 1H), 3.71 (s, 3H), 3.87 (s, 3H), 4.57 (q, 1H), 5.05 (d, 1H), 7.07 (s, 1H), 7.17-7.22 (m, 2H). |

| Intermediate No | Aryl derivative | Structure/Name | Analytics |
|---|---|---|---|
| 43B[Boc] | Ester 43B | tert-butyl [(2R)-1-(3-amino-4-cyanophenyl)-3-hydroxypropan-2-yl]carbamate | LC-MS (Method 1): $R_t$ = 2.69 min; MS (ES+): m/z = 292 (M + H)+, 236 ([M − tBu] + H)+, 192 ([M − Boc] + H)+. <br>1H-NMR (500 MHz, CDCl3) δ [ppm] = 1.42 (s, 9H), 2.78 (d, 2H), 3.55 (m, 1H), 3.66 (m, 1H), 3.83 (m, 1H), 4.38 (s, 2H), 4.75 (m, 1H), 6.60-6.62 (m, 2H), 7.31 (d, 1H). |
| Ester[43B] | 2-amino-4-bromobenzonitrile | methyl 3-amino-N-(tert-butoxycarbonyl)-4-cyano-D-phenylalaninate | LC-MS (Method 1): $R_t$ = 3.06 min; MS (ES+): m/z = 320 (M + H)+, 264 ([M − tBu] + H)+, 220 ([M − Boc] + H)+. <br>1H-NMR (500 MHz, CDCl3) δ [ppm] = 1.42 (s, 9H), 2.94 (dd, 1H), 3.05 (dd, 1H), 3.72 (s, 3H), 4.36 (s, 2H), 4.57 (m, 1H), 4.99 (d, 1H), 6.52 (d, 1H), 6.53 (s, 1H), 7.30 (d, 1H). |
| 44B[Boc] | Ester 44B | tert-butyl [(2R)-1-(2-amino-4-cyanophenyl)-3-hydroxypropan-2-yl]carbamate | LC-MS (Method 1): $R_t$ = 2.79 min; MS (ES+): m/z = 292 (M + H)+, 236 ([M − tBu] + H)+, 192 ([M − Boc] + H)+. <br>1H-NMR (500 MHz, CDCl3) δ [ppm] = 1.46 (s, 9H), 2.76 (dd, 1H), 2.87 (m, 1H), 3.55 (dd, 1H), 3.65-3.72 (m, 2H), 4.63 (s, 2H), 5.15 (m, 1H), 6.89 (d, 1H), 6.93 (d, 1H), 7.05 (d, 1H). |

In case of the protected Intermediate 44B$^{Boc}$ the ester was prepared via the following route:

Ester 44B

Methyl 2-amino-N-(tert-butoxycarbonyl)-4-cyano-D-phenylalaninate

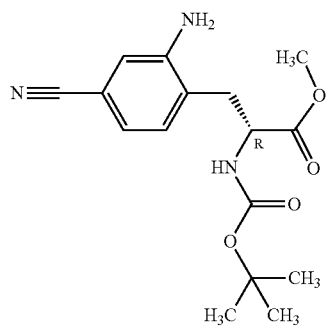

To a stirred suspension of zinc dust, 179 mg (2.73 mmol, 3 eq.) in dry N,N-dimethylformamide (1 mL) were added successively iodine, 35 mg (0.137 mmol, 15 mol %), (S)-methyl 2-((tert-butoxycarbonyl)amino)-3-iodopropanoate, 300 mg (0.911 mmol) and iodine, 35 mg (0.137 mmol, 15 mol %) and the resulting mixture was stirred at r.t. for 1 h (light exotherm observed). Tris-(dibenzylideneacetone)dipalladium, 42 mg (46 µmol, 5 mol %), dicyclohexyl(2',6'-dimethoxybiphenyl-2-yl)phosphine, 37 mg (91 µmol, 10 mol %) followed by 4-iodo-3-aminobenzonitrile, 289 mg (1.18 mmol, 1.3 eq.) were added and the mixture was stirred at r.t. for 2 h. The solvent was removed under reduced pressure and the residue was purified by flash column chromatography on silica gel (eluent: cyclohexane/ethyl acetate, 4/1) to give the product, 101 mg (30%) as an orange oil (contaminated with 15% of, tert-butyl [(3R)-7-cyano-2-oxo-1,2,3,4-tetrahydroquinolin-3-yl]carbamate).

LC-MS (Method 1): $R_t$=3.11 min; MS (ES+): m/z=320 (M+H)$^+$, 264 ([M–tBu]+H)$^+$, 220 ([M–Boc]+H)$^+$.

Protected Intermediate 56B$^{Boc}$

Tert-butyl [(2R)-1-(4-cyano-3-methylphenyl)-3-(1,3-dioxo-1,3-dihydro-2H-isoindol-2-yl)propan-2-yl]carbamate

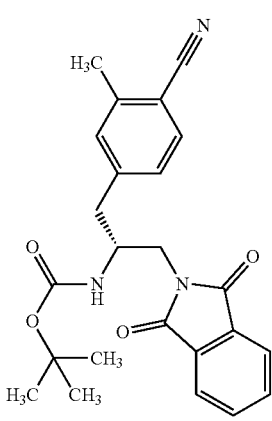

To a stirred solution of triphenylphosphine, 393 mg (1.50 mmol, 1.2 eq.) in tetrahydrofuran (10 mL) was added dropwise a solution of di-tert-butyl azodicarboxylate, 345 mg (1.50 mmol, 1.2 eq.) in tetrahydrofuran (2.5 mL) at 0° C. After 5 min at 0° C., phtalimide, 221 mg (1.50 mmol, 1.2 eq.) followed by a solution of 40B$^{Boc}$, tert-butyl [(2R)-1-(4-cyano-3-methylphenyl)-3-hydroxypropan-2-yl]carbamate, 363 mg (1.25 mmol) in tetrahydrofuran (2.5 mL) were added at 0° C. and the resulting yellow solution was stirred at r.t. for 18 h. The colorless solution was concentrated under reduced pressure and the residue was purified by flash column chromatography on silica gel (eluent: cyclohexane/ethyl acetate, 4/1) to give the product, 372 mg (71%) as a white solid.

LC-MS (Method 1): $R_t$=3.52 min; MS (ES+): m/z=420 (M+H)$^+$, 364 ([M–tBu]+H)$^+$, 320 ([M–Boc]+H)$^+$.

$^1$H-NMR (500 MHz, CDCl$_3$) δ [ppm]=1.24 (s, 9H), 2.51 (s, 3H), 2.84-2.92 (m, 2H), 3.73 (d, 2H), 4.28 (m, 1H), 4.70 (d, 1H), 7.14 (d, 1H), 7.20 (s, 1H), 7.51 (d, 1H), 7.71-7.73 (m, 2H), 7.83-7.84 (m, 2H)

Protected Intermediate 57$^{Boc}$

N-{trans-4-[(tert-butoxycarbonyl)amino]cyclohexyl}-4-cyano-D-phenylalaninamide

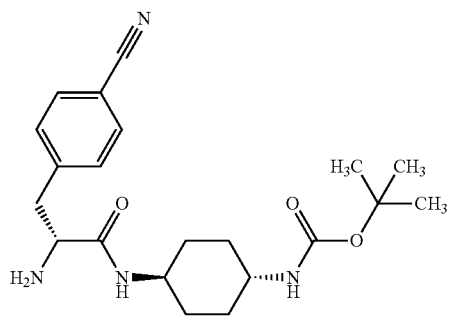 [SMILES: CC(C)(C)OC(=O)N[C@H]1CC[C@H](NC(=O)[C@H](N)Cc2ccc(C#N)cc2)CC1]

N-[(benzyloxy)carbonyl]-4-cyano-D-phenylalanine

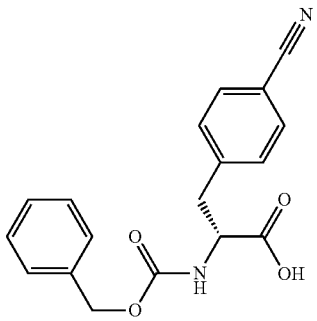 [SMILES: N#Cc1ccc(C[C@@H](NC(=O)OCc2ccccc2)C(=O)O)cc1]

To a stirred solution of 4-cyano-D-phenylalanine, 286 mg (1.5 mmol) and sodium hydrogen carbonate, 379 mg (4.51 mmol, 3.0 eq.) in a mixture tetrahydrofuran/water (12 mL, 1/1) was added dropwise benzyl chloroformate, 0.24 mL (1.65 mmol, 1.1 eq.) at 0° C. and the resulting mixture was stirred at r.t. for 1 h. The mixture was quenched with water (3 mL) and extracted with MTBE. The aqueous phase was acidified to pH 2 with 2M aqueous solution of hydrochloric acid (1.2 mL) and extracted with ethyl acetate (3×). The combined organic extracts were washed with brine, dried over sodium sulfate, filtered and concentrated to give the title product, 430 mg (95%) as a white solid.

LC-MS (Method 1): $R_t$=3.22 min; MS (ES−): m/z=323 (M−H)⁻

¹H-NMR (500 MHz, DMSO-$d_6$) δ [ppm]=2.91 (dd, 1H), 3.17 (dd, 1H), 4.24 (m, 1H), 4.96 (s, 2H), 7.24 (d, 2H), 7.27-7.37 (m, 3H), 7.46 (d, 2H), 7.68 (d, 1H), 7.74 (d, 2H), 12.83 (br s, 1H)

Tert-butyl N-[4-[[(2R)-2-(benzyloxycarbonylamino)-3-(4-cyanophenyl) propanoyl]-amino]cyclohexyl]carbamate

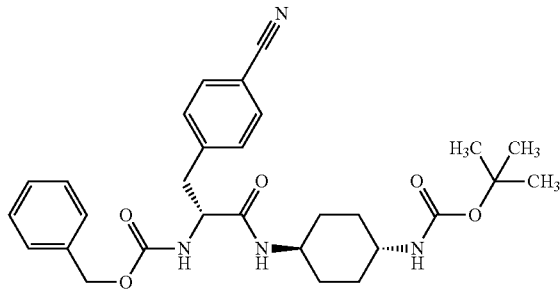 [SMILES: CC(C)(C)OC(=O)N[C@H]1CC[C@H](NC(=O)[C@@H](Cc2ccc(C#N)cc2)NC(=O)OCc2ccccc2)CC1]

To a stirred solution of N-[(benzyloxy)carbonyl]-4-cyano-D-phenylalanine, 146 mg (0.45 mmol) in tetrahydrofuran (5 mL) were added TBTU, 152 mg (0.47 mmol, 1.05 eq.) and triethylamine, 188 µL (1.35 mmol, 3.0 eq.) at r.t. After 20 min stirring, tert-butyl (trans-4-aminocyclohexyl)carbamate (CAS [177906-48-8]), 100 mg (0.47 mmol, 1.04 eq.) was added and the resulting mixture was stirred at r.t. for 16 h. Most of the solvent was removed under reduced pressure and the residue was dissolved in ethyl acetate (30 mL). The organic layer was washed successively with aq. sat. sodium hydrogen carbonate, water, brine, dried over sodium sulfate and concentrated. In order to remove residual tetramethylurea, the solid was dissolved in ethyl acetate (100 mL) and the organic phase was washed successively with a 1/1 mixture of water and sat. sodium bicarbonate (2×), water, brine, dried over sodium sulfate and concentrated to give the product, 190 mg (77%) as an off-white solid.

LC-MS (Method 1): $R_t$=3.47 min; MS (ES+): m/z=521 (M+H)⁺, 465 (M+H−tBu)⁺

¹H-NMR (500 MHz, DMSO-$d_6$) δ [ppm]=1.08-1.28 (m, 4H), 1.36 (s, 9H), 1.63-1.69 (m, 1H), 1.70-1.80 (m, 3H), 2.82 (dd, 1H), 2.98 (dd, 1H), 3.16 (m, 1H), 3.41 (m, 1H), 4.21 (m, 1H), 4.91-4.95 (2d, AB, 2H), 6.70 (d, 1H), 7.22 (d, 2H), 7.28-7.36 (m, 3H), 7.42-7.51 (m, 3H), 7.73 (d, 2H), 7.87 (d, 1H)

N-{trans-4[(tert-butoxycarbonyl)amino]cyclohexyl}-4-cyano-D-phenylalaninamide

To a stirred suspension of tert-butyl N-[4-[[(2R)-2-(benzyloxycarbonylamino)-3-(4-cyanophenyl)propanoyl]amino]cyclohexyl]carbamate, 190 mg (0.365 mmol) was added 10% Pd/C, 40 mg. The heterogeneous mixture was purged with argon and then backfilled with hydrogen. The reaction mixture was hydrogenated at r.t. (1 atm) for 16 h. To the suspension was added another portion of 10% Pd/C, 40 mg and the heterogeneous mixture was further hydrogenated at r.t. (1 atm) for 24 h. The reaction mixture was filtered on a pad of celite, rinsed with ethanol and the solvent was removed under reduced pressure to give the crude product, 133 mg (83%) as an off-white solid that was used without further purification.

LC-MS (Method 1): $R_t$=2.21 min; MS (ES+): m/z=331 (M+H−tBu)⁺, 387 (M+H)⁺

EXAMPLES

Example 1

2-Chloro-N-[(2R)-1-(4-cyanophenyl)-4-(dimethylamino)-4-oxobutan-2-yl]-5-[5-({[(1R)-1-(4-methylphenyl)ethyl]amino}methyl)furan-2-yl]benzamide

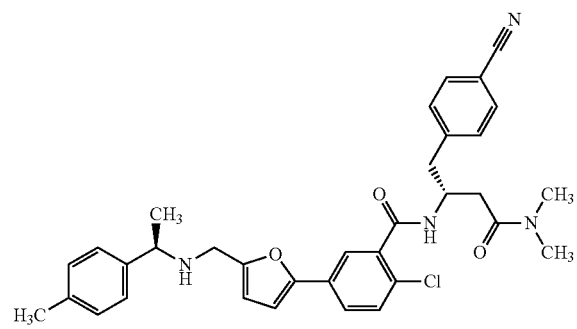

To a stirred suspension of 2-Chloro-5-[5-({[(1R)-1-(4-methylphenyl)ethyl]amino}methyl)furan-2-yl]benzoic acid, 100 mg (0.27 mmol, intermediate 1A) in acetonitrile (1.7 mL) were added triethylamine, 76 µL (0.54 mmol) followed by TBTU, 87 mg (0.27 mmol, 1.0 eq.) in acetonitrile (1 mL) at r.t. (solution gets clear). After 15 min, (3R)-3-amino-4-(4-cyanophenyl)-N,N-dimethylbutanamide, 75 mg (0.324 mmol, intermediate 2B) in solution in 0.5 mL of THF was added and the resulting mixture was stirred at r.t. overnight. The reaction mixture was concentrated and then dissolved in MeOH/MeCN (1/9, 1.5 mL) for prep HPLC purification (Basic conditions, method 6). The desired product was isolated as a beige solid, 59 mg (35%).

LC-MS (Method 5): $R_t$=2.57 min; (ES+): m/z=583/585 (M+H)⁺

¹H-NMR (500 MHz, $CD_3OD$) δ [ppm]=1.36 (d, 3H), 2.30 (s, 3H), 2.73 (dd, 1H), 2.81 (dd, 1H), 2.95 (s, 3H), 2.97 (dd, 1H), 3.10 (s, 3H), 3.16 (dd, 1H), 3.60 and 3.65 (2d, AB, 2H), 3.77 (q, 1H), 4.75 (m, 1H), 6.30 (d, 1H), 6.72 (d, 1H), 7.15 (d, 2H), 7.22 (d, 2H), 7.40 (d, 1H), 7.46 (d, 1H), 7.50 (d, 2H), 7.66 (m, 3H).

The following Examples were prepared in analogy of Example 1 by amide coupling of the corresponding intermediates xA and xB:

| Example No | Intermediates | Structure/Name | Analytics |
|---|---|---|---|
| 2 | 1A; 6B | 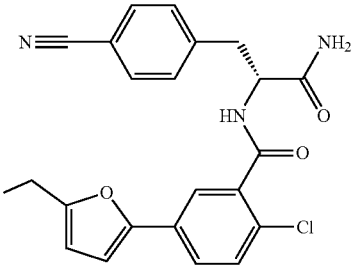<br>Nα-{2-chloro-5-[5-({[(1R)-1-(4-methylphenyl)ethyl]amino}methyl)-2-furyl]benzoyl}-4-cyano-D-phenylalaninamide | LC-MS (Method 1): Rt = 2.38 min; MS (ES+): m/z = 541-543 (M + H)+.<br>1H-NMR (500 MHz, DMSO-d6) δ [ppm] = 1.24 (d, 3H), 2.27 (s, 3H), 2.96 (dd, 1H), 3.21 (dd, 1H), 3.50 (d, 1H), 3.58 (d, 1H), 3.71 (q, 1H), 4.72 (m, 1H), 6.31 (d, 1H), 6.89 (d, 1H), 7.12 (d, 2H), 7.20 (br s, 1H), 7.23 (d, 2H), 7.45 (d, 1H), 7.47 (d, 1H), 7.52-7.53 (m, 3H), 7.66 (dd, 1H), 7.77 (d, 2H), 8.70 (d, 1H). |
| 3 | 1A; 3B | 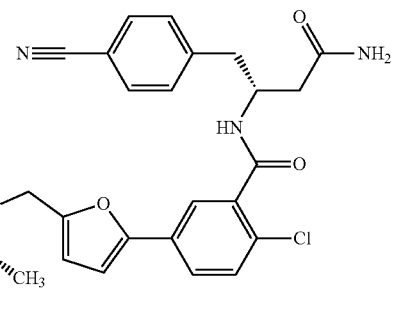<br>N-[(2R)-4-amino-1-(4-cyanophenyl)-4-oxobutan-2-yl]-2-chloro-5-[5-({[(1R)-1-(4-methylphenyl)ethyl]amino}methyl)furan-2-yl]benzamide | LC-MS (Method 1): $R_t$ = 2.36 min; MS (ES+): m/z = 555/557 (M + H)$^+$<br>$^1$H-NMR (500 MHz, CD$_3$OD) δ [ppm] = 1.38 (d, 3H), 2.31 (s, 3H), 2.59 (d, 2H), 2.97 (dd, 1H), 3.14 (dd, 1H), 3.62 (d, 1H), 3.67 (d, 1H), 3.80 (q, 1H), 4.73 (m, 1H), 6.30 (d, 1H), 6.73 (d, 1H), 7.15 (d, 2H), 7.23 (d, 2H), 7.40 (d, 1H), 7.46 (d, 1H), 7.50 (d, 2H), 7.65-7.68 (m, 3H). |
| 4 | 1A; 15B | 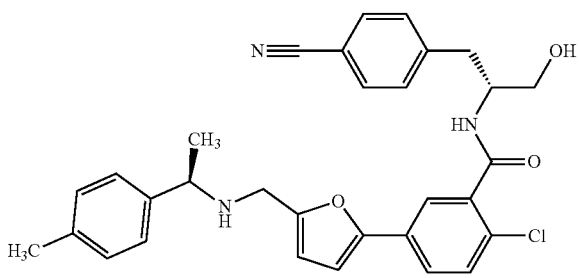 [SMILES: Cc1ccc([C@@H](C)NCc2ccc(-c3ccc(Cl)c(C(=O)N[C@@H](CO)Cc4ccc(C#N)cc4)c3)o2)cc1]<br>2-chloro-N-[(2R)-1-(4-cyanophenyl)-3-hydroxypropan-2-yl]-5-[5-({[(1R)-1-(4-methylphenyl)ethyl]amino}methyl)-2-furyl]benzamide | LC-MS (Method 5): $R_t$ = 2.55 min; MS (ES+): m/z = 528/530 (M + H)$^+$<br>$^1$H-NMR (500 MHz, CD$_3$OD) δ [ppm] = 1.37 (d, 3H), 2.31 (s, 3H), 2.89 (dd, 1H), 3.17 (dd, 1H), 3.60 & 3.66 (2d, AB, 2H), 3.65-3.72 (m, 2H) 3.78 (q, 1H), 4.39-4.44 (m, 1H), 6.29 (d, 1H), 6.73 (d, 1H), 7.15 (d, 2H), 7.23 (d, 2H), 7.41 (d, 1H), 7.51 (d, 2H), 7.53 (d, 1H), 7.65 (d, 2H), 7.67 (dd, 1H). |

-continued

| Example No | Intermediates | Structure/Name | Analytics |
|---|---|---|---|
| 5 | 1A; 4B | 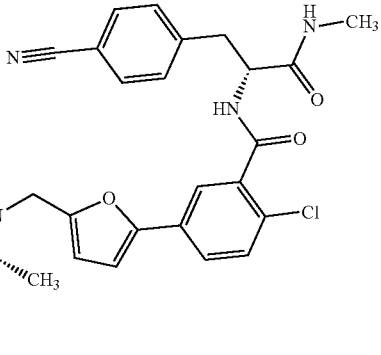<br>Nα-{2-chloro-5-[5-({[(1R)-1-(4-methylphenyl)ethyl]amino}methyl)furan-2-yl]benzoyl}-4-cyano-N-methyl-D-phenylalaninamide | LC-MS (Method 5): R$_t$ = 2.48 min; MS (ES+): m/z = 555/557 (M + H)$^+$<br>$^1$H-NMR (500 MHz, CD$_3$OD) δ [ppm] = 1.37 (d, 3H), 2.31 (s, 3H), 2.75 (s, 3H), 3.09 (dd, 1H), 3.30 (dd, 1H), 3.60 and 3.65 (2d, AB, 2H), 3.78 (q, 1H), 4.87 (dd, 1H), 6.30 (d, 1H), 6.74 (d, 1H), 7.15 (d, 2H), 7.22 (d, 2H), 7.41 (d, 1H), 7.50 (d, 2H), 7.62 (d, 1H), 7.67 (d, 2H), 7.69 (dd, 1H) |
| 6 | 1A; 14B | 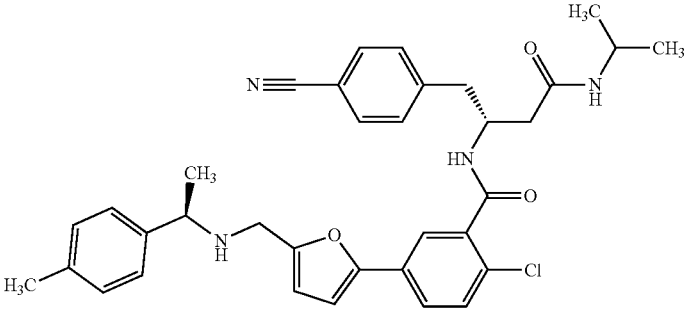 [SMILES: Cc1ccc([C@@H](C)NCc2ccc(-c3ccc(Cl)c(C(=O)N[C@@H](CC(=O)NC(C)C)Cc4ccc(C#N)cc4)c3)o2)cc1]<br>2-chloro-N-[(2R)-1-(4-cyanophenyl)-4-(isopropylamino)-4-oxobutan-2-yl]-5-[5-({[(1R)-1-(4-methylphenyl)ethyl]amino}methyl)-2-furyl]benzamide | LC-MS (Method 5): R$_t$ = 2.66 min; MS (ES+): m/z = 597/599 (M + H)$^+$.<br>$^1$H-NMR (500 MHz, DMSO-d$_6$) δ [ppm] = 1.03 (d, 6H), 1.25 (d, 3H), 2.27 (s, 3H), 2.34-2.39 (m, 2H), 2.86 (dd, 1H), 2.97 (dd, 1H), 3.50 (d, 1H), 3.57 (d, 1H), 3.71 (q, 1H), 3.84 (m, 1H), 4.50 (m, 1H), 6.32 (d, 1H), 6.88 (d, 1H), 7.12 (d, 2H), 7.23 (d, 2H), 7.41 (d, 1H), 7.45-7.46 (m, 3H), 7.66 (dd, 1H), 7.73-7.77 (m, 3H), 8.39 (d, 1H). |
| 7 | 1A; 7B | 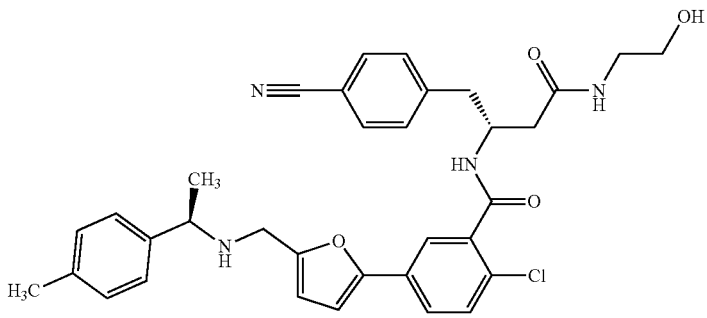 [SMILES: Cc1ccc([C@@H](C)NCc2ccc(-c3ccc(Cl)c(C(=O)N[C@@H](CC(=O)NCCO)Cc4ccc(C#N)cc4)c3)o2)cc1]<br>2-chloro-N-{(2R)-1-(4-cyanophenyl)-4-[(2-hydroxyethyl)amino]-4-oxobutan-2-yl}-5-[5-({[(1R)-1-(4-methylphenyl)ethyl]amino}methyl)-2-furyl]benzamide | LC-MS (Method 5): R$_t$ = 2.41 min; MS (ES+): m/z = 599/601 (M + H)$^+$.<br>$^1$H-NMR (500 MHz, DMSO-d$_6$) δ [ppm] = 1.25 (d, 3H), 2.27 (s, 3H), 2.41-2.43 (m, 2H), 2.85 (dd, 1H), 2.99 (dd, 1H), 3.12-3.16 (m, 2H), 3.39-3.42 (m, 2H), 3.51 (dd, 1H), 3.58 (dd, 1H), 3.71 (m, 1H), 4.51 (m, 1H), 4.64 (t, 1H), 6.31 (d, 1H), 6.88 (d, 1H), 7.12 (d, 2H), 7.23 (d, 2H), 7.41 (d, 1H), 7.45-7.47 (m, 3H), 7.66 (dd, 1H), 7.76 (m, 2H), 7.91 (t, 1H), 8.42 (d, 1H). |

| Example No | Intermediates | Structure/Name | Analytics |
|---|---|---|---|
| 8 | 1A; 8B | 2-chloro-N-{(2R)-1-(4-cyanophenyl)-4-[(3-hydroxypropyl)amino]-4-oxobutan-2-yl}-5-[5-({[(1R)-1-(4-methylphenyl)ethyl]amino}methyl)-2-furyl]benzamide | LC-MS (Method 5): $R_t$ = 2.42 min; MS (ES+): m/z = 613/614 (M + H)$^+$. $^1$H-NMR (500 MHz, DMSO-$d_6$) δ [ppm] = 1.25 (d, 3H), 1.52-1.58 (m, 2H), 2.27 (s, 3H), 2.39-2.42 (m, 2H), 2.85 (dd, 1H), 2.98 (dd, 1H), 3.10-3.14 (m, 2H), 3.38-3.42 (m, 2H), 3.50 (d, 1H), 3.57 (d, 1H), 3.71 (m, 1H), 4.40 (t, 1H), 4.52 (m, 1H), 6.31 (d, 1H), 6.88 (d, 1H), 7.12 (d, 2H), 7.23 (d, 2H), 7.40 (d, 1H), 7.44-7.47 (m, 3H), 7.66 (dd, 1H), 7.76 (d, 2H), 7.88 (t, 1H), 8.42 (d, 1H). |
| 9 | 1A; 9B | 2-chloro-N-[(2R)-1-(4-cyanophenyl)-4-oxo-4-(pyrrolidin-1-yl)butan-2-yl]-5-[5-({[(1R)-1-(4-methylphenyl)ethyl]amino}methyl)-2-furyl]benzamide | LC-MS (Method 5): $R_t$ = 2.68 min; MS (ES+): m/z = 609/611 (M + H)$^+$. $^1$H-NMR (500 MHz, DMSO-$d_6$) δ [ppm] = 1.25 (d, 3H), 1.72-1.78 (m, 2H), 1.83-1.89 (m, 2H), 2.27 (s, 3H), 2.51 (dd, 1H), 2.63 (dd, 1H), 2.89 (dd, 1H), 3.05 (dd, 1H), 3.28-3.31 (m, 2H), 3.38-3.47 (m, 2H), 3.50 (d, 1H), 3.57 (d, 1H), 3.71 (q, 1H), 4.54 (m, 1H), 6.32 (d, 1H), 6.88 (d, 1H), 7.12 (d, 2H), 7.23 (d, 2H), 7.39 (d, 1H), 7.45-7.48 (m, 3H), 7.66 (dd, 1H), 7.77 (d, 2H), 8.46 (d, 1H). |
| 10 | 1A; 10B | 2-chloro-N-[(2R)-1-(4-cyanophenyl)-4-(morpholin-4-yl)-4-oxobutan-2-yl]-5-[5-({[(1R)-1-(4-methylphenyl)ethyl]amino}methyl)-2-furyl]benzamide | LC-MS (Method 5): $R_t$ = 2.59 min; MS (ES+): m/z = 625/627 (M + H)$^+$. $^1$H-NMR (500 MHz, DMSO-$d_6$) δ [ppm] = 1.25 (d, 3H), 2.27 (s, 3H), 2.62 (dd, 1H), 2.68 (dd, 1H), 2.86 (dd, 1H), 3.05 (dd, 1H), 3.42-3.62 (m, 8H), 3.38-3.47 (m, 2H), 3.71 (q, 1H), 4.54 (m, 1H), 6.32 (d, 1H), 6.87 (d, 1H), 7.12 (d, 2H), 7.24 (d, 2H), 7.42 (d, 1H), 7.45 (d, 1H), 7.48 (d, 2H), 7.66 (dd, 1H), 7.77 (d, 2H), 8.46 (d, 1H). |

-continued

| Example No | Intermediates | Structure/Name | Analytics |
|---|---|---|---|
| 11 | 1A; 11B | 2-chloro-N-[(2R)-1-(4-cyanophenyl)-4-(4-methylpiperazin-1-yl)-4-oxobutan-2-yl]-5-[5-({[(1R)-1-(4-methylphenyl)ethyl]amino}methyl)-2-furyl]benzamide | LC-MS (Method 1): $R_t$ = 2.12 min; MS (ES+): m/z = 638/640 (M + H)+. $^1$H-NMR (500 MHz, DMSO-$d_6$) δ [ppm] = 1.25 (d, 3H), 2.16 (s, 3H), 2.20-2.25 (m, 2H), 2.27 (s, 3H), 2.32-2.36 (m, 2H), 2.60 (dd, 1H), 2.69 (dd, 1H), 2.86 (dd, 1H), 3.04 (dd, 1H), 3.42-3.52 (m, 5H), 3.57 (d, 1H), 3.71 (q, 1H), 4.53 (m, 1H), 6.32 (d, 1H), 6.88 (d, 1H), 7.12 (d, 2H), 7.23 (d, 2H), 7.42 (d, 1H), 7.45 (d, 1H), 7.47 (d, 2H), 7.66 (dd, 1H), 7.77 (d, 2H), 8.44 (d, 1H). |
| 12 | 1A; 18B | 2-chloro-N-[(2R)-1-(4-cyanophenyl)-3-hydroxy-3-methylbutan-2-yl]-5-[5-({[(1R)-1-(4-methylphenyl)ethyl]amino}methyl)-2-furyl]benzamide | LC-MS (Method 1): $R_t$ = 2.44 min; MS (ES+) m/z = 556-558 (M + H)+ $^1$H-NMR (500 MHz, CD$_3$OD) δ [ppm] = 1.32 (s, 3H), 1.37 (d, 3H), 1.42 (s, 3H), 2.30 (s, 3H), 2.76 (dd, 1H), 3.35 (dd, 1H), 3.64 & 3.68 (2d, AB, 2H), 3.80 (q, 1H), 4.36 (dd, 1H), 6.31 (d, 1H), 6.68 (d, 1H), 7.13 (d, 1H), 7.15 (d, 2H), 7.23 (d, 2H), 7.38 (d, 1H), 7.48 (d, 2H), 7.63-7.66 (m, 3H). |
| 13 | 1A; 19B | 2-chloro-N-[(2R)-1-(4-cyanophenyl)-4-hydroxybutan-2-yl]-5-[5-({[(1R)-1-(4-methylphenyl)ethyl]amino}methyl)-2-furyl]benzamide | LC-MS (Method 5): $R_t$ = 2.44 min; MS (ES+) m/z = 542-544 (M + H)+ $^1$H-NMR (500 M-z, CD$_3$OD) δ [ppm] = 1.37 (d, 3H), 1.76-180 (m, 1H), 1.88-1.92 (m, 1H), 2.30 (s, 3H), 2.92 (dd, 1H), 3.08 (dd, 1H), 3.62 & 3.67 (2d, AB, 2H), 3.73-3.76 (m, 2H), 3.79 (q, 1H), 4.48-4.53 (m, 1H), 6.30 (d, 1H), 6.71 (d, 1H), 7.15 (d, 2H), 7.23 (d, 2H), 7.36 (d, 1H), 7.41 (d, 1H), 7.49 (d, 2H), 7.65-7.68 (m, 3H). |

-continued

| Example No | Intermediates | Structure/Name | Analytics |
|---|---|---|---|
| 14 | 1A; 20B | 2-chloro-N-[(2R)-1-(4-cyanophenyl)-3-methoxypropan-2-yl]-5-[5-({[(1R)-1-(4-methylphenyl)ethyl]amino}methyl)-2-furyl]benzamide | LC-MS (Method 5): $R_t$ = 2.81 min; MS (ES+) m/z = 542-544 (M + H)+ <br> 1H-NMR (500 MHz, CD3OD) δ [ppm] = 1.36 (d, 3H), 2.31 (s, 3H), 2.92 (dd, 1H), 3.13 (dd, 1H), 3.41 (s, 3H), 3.50 (dd, 1H), 3.53 (dd, 1H), 3.60 & 3.66 (2d, AB, 2H), 3.78 (q, 1H), 4.49-4.55 (m, 1H), 6.29 (d, 1H), 6.72 (d, 1H), 7.15 (d, 2H), 7.23 (d, 2H), 7.41 (d, 1H), 7.47 (d, 1H), 7.49 (d, 2H), 7.65-7.69 (m, 3H). |
| 15 | 1A; 53B | methyl N-{2-chloro-5-[5-({[(1R)-1-(4-methylphenyl)ethyl]amino}methyl)-2-furyl]benzoyl}-4-cyano-D-phenylalaninate | LC-MS (Method 1): $R_t$ = 2.54 min; MS (ES+): m/z = 556/558 (M + H)+. <br> 1H-NMR (500 MHz, DMSO-d6) δ [ppm] = 1.25 (d, 3H), 2.27 (s, 3H), 3.08 (dd, 1H), 3.29 (dd, 1H), 3.51 (d, 1H), 3.58 (d, 1H), 3.69 (s, 3H), 3.71 (q, 1H), 4.78 (m, 1H), 6.32 (d, 1H), 6.90 (d, 1H), 7.12 (d, 2H), 7.24 (d, 2H), 7.41 (d, 1H), 7.48 (d, 1H), 7.52 (d, 2H), 7.69 (dd, 1H), 7.78 (d, 2H), 9.01 (d, 1H). |
| 16 (dia#1) and 17 (dia#2) | 1A; 22B | | Dia#1: <br> LC-MS (Method 5): $R_t$ = 2.50 min; MS (ES+) m/z = 542/544 (M + H)+ <br> 1H-NMR (500 MHz, DMSO-d6) δ [ppm] = 1.15 (d, 3H), 1.25 (d, 3H), 2.27 (s, 3H), 2.84 (dd, 1H), 3.01 (dd, 1H), 3.52 & 3.60 (2d, AB, 2H), 3.68-3.76 (m, 1H), 3.80-3.88 (m, 1H), 4.13-4.20 (m, 1H), 4.84 (d, 1H), 6.33 (s, 1H), 6.89 (d, 1H), 7.13 (d, 2H), 7.24 (d, 2H), 7.33 (d, 1H), 7.45 (d, 1H), 7.50 (d, 2H), 7.65 (dd, 1H), 7.76 (d, 2H), 8.27 (d, 1H). 1H missing |

| Example No | Intermediates | Structure/Name | Analytics |
|---|---|---|---|
| | | 2-chloro-N-[(2R,3R)-1-(4-cyanophenyl)-3-hydroxybutan-2-yl]-5-[5-({[(1R)-1-(4-methylphenyl)ethyl]amino}methyl)-2-furyl]benzamide and 2-chloro-N-[(2R,3S)-1-(4-cyanophenyl)-3-hydroxybutan-2-yl]-5-[5-({[(1R)-1-(4-methylphenyl)ethyl]amino}methyl)-2-furyl]benzamide | Dia#2:<br>LC-MS (Method 5): $R_t$ = 2.47 min; MS (ES+) m/z = 542/544 (M + H)⁺<br>¹H-NMR (500 MHz, DMSO-$d_6$) δ [ppm] = 1.22 (d, 3H), 1.26 (d, 3H), 2.27 (s, 3H), 2.71 (dd, 1H), 3.25 (dd, 1H), 3.53 & 3.60 (2d, AB, 2H), 3.59-3.66 (m, 1H), 3.68-3.76 (m, 1H), 3.97-4.06 (m, 1H), 4.91 (d, 1H), 6.33 (d, 1H), 6.88 (d, 1H), 7.13 (d, 2H), 7.22 (d, 1H), 7.24 (d, 2H), 7.44 (d, 1H), 7.47 (d, 2H), 7.65 (dd, 1H), 7.75 (d, 2H), 8.32 (d, 1H). |
| 18 | 1A; 23B | 2-chloro-N-[(2R)-1-hydroxy-3-(4-iodophenyl)propan-2-yl]-5-[5-({[(1R)-1-(4-methylphenyl)ethyl]amino}methyl)-2-furyl]benzamide | LC-MS (Method 1): $R_t$ = 2.57 min; MS (ES+): m/z = 629/631 (M + H)⁺.<br>¹H-NMR (500 MHz, DMSO-$d_6$) δ [ppm] = 1.25 (d, 3H), 2.27 (s, 3H), 2.65 (dd, 1H), 2.94 (dd, 1H), 3.40 (m, 1H), 3.50 (m, 1H), 3.52 (d, 1H), 3.59 (d, 1H), 3.72 (q, 1H), 4.10 (m, 1H), 4.86 (t, 1H), 6.32 (d, 1H), 6.89 (d, 1H), 7.10 (d, 2H), 7.12 (d, 2H), 7.24 (d, 2H), 7.43 (d, 1H), 7.46 (d, 1H), 7.63 (d, 2H), 7.66 (dd, 1H), 8.31 (d, 1H). |
| 19 | 1A; 24B | 2-chloro-N-[2-(4-cyanophenyl)-1-(1H-imidazol-2-yl)ethyl]-5-[5-({[(1S)-1-(4-methylphenyl)ethyl]amino}methyl)-2-furyl]benzamide | LC-MS (Method 1): $R_t$ = 2.19 min; MS (ES+): m/z = 564/566 (M + H)⁺.<br>¹H-NMR (500 MHz, DMSO-$d_6$) δ [ppm] = 1.24 (d, 3H), 2.27 (s, 3H), 3.22 (dd, 1H), 3.45 (dd, 1H), 3.50 & 3.57 (2d, AB, 2H), 3.71 (m, 1H), 5.43 (m, 1H), 6.31 (d, 1H), 6.87 (br s, 1H), 6.88 (d, 1H), 7.06 (br s, 1H), 7.12 (d, 2H), 7.24 (d, 2H), 7.43-7.50 (m, 3H), 7.54 (m, 1H), 7.63-7.78 (m, 3H), 8.97 (d, 1H). |

| Example No | Intermediates | Structure/Name | Analytics |
|---|---|---|---|
| 20 | 1A; 25B | 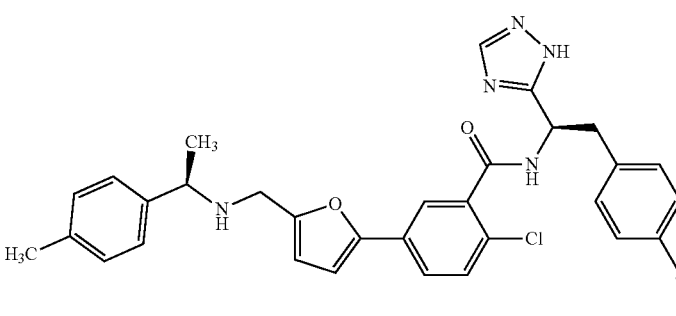<br>2-chloro-N-[(1R)-2-(4-cyanophenyl)-1-(1H-1,2,4-triazol-5-yl)ethyl]-5-[5-({[(1R)-1-(4-methylphenyl)ethyl]amino}methyl)-2-furyl]benzamide | LC-MS (Method 1): $R_t$ = 2.48 min; MS (ES+): m/z = 565/567 (M + H)$^+$.<br>$^1$H-NMR (500 MHz, DMSO-$d_6$) δ [ppm] = 1.24 (s, 1H), 1.26 (d, 3H), 2.27 (s, 3H), 3.24 (dd, 1H), 3.41 (br s, 1H), 3.49-3.63 (m, 2H), 3.73 (m, 1H), 5.48 (m, 1H), 6.33 (s, 1H), 6.90 (d, 1H), 7.13 (d, 2H), 7.24 (d, 2H), 7.45 (s, 1H), 7.50 (d, 2H), 7.66 (dd, 1H), 7.76 (d, 2H), 8.51 (br s 1H), 9.03 (br s, 2H), 13.90 (br s, 1H). |
| 21 | 1A; 26B | 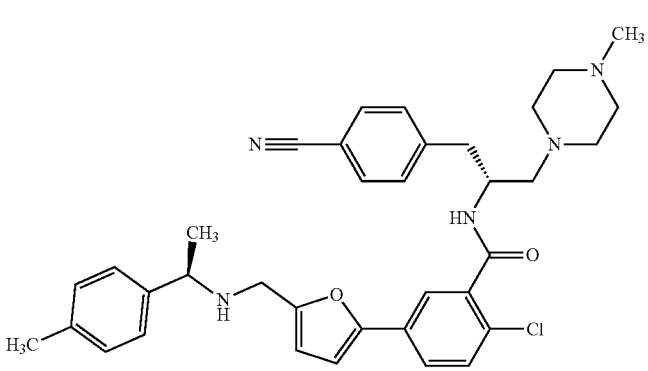<br>2-chloro-N-[(2R)-1-(4-cyanophenyl)-3-(4-methylpiperazin-1-yl)propan-2-yl]-5-[5-({[(1R)-1-(4-methylphenyl)ethyl]amino}methyl)-2-furyl]benzamide | LC-MS (Method 1): $R_t$ = 2.16 min; MS (ES+): m/z = 610/612 (M + H)$^+$.<br>$^1$H-NMR (500 MHz, DMSO-$d_6$) δ [ppm] = 1.25 (d, 3H), 2.12 (s, 3H), 2.27 (s, 3H), 2.27-2.50 (m, 10H), 2.74 (dd, 1H), 3.07 (dd, 1H), 3.51 (d, 1H), 3.58 (d, 1H), 3.72 (m, 1H), 4.35 (m, 1H), 6.33 (d, 1H), 6.88 (d, 1H), 7.12 (d, 2H), 7.23 (d, 2H), 7.40 (m, 1H), 7.45 (d, 1H), 7.47 (d, 2H), 7.66 (dd, 1H), 7.74-7.77 (m, 2H), 8.31 (d, 1H).<br>$^{13}$C-NMR (125 MHz, DMSO-$d_6$) δ [ppm] = 20.6, 24.3, 38.3, 43.6, 45.7, 47.6, 52.7, 54.8, 56.4, 61.4, 107.6, 108.8, 108.9, 119.0, 122.8, 124.9, 126.5, 127.9, 128.8, 129.1, 130.0, 130.4, 131.8, 135.6, 137.6, 142.5, 145.2, 150.0, 155.4, 165.5. |

-continued

| Example No | Intermediates | Structure/Name | Analytics |
|---|---|---|---|
| 22 | 1A; 27B | 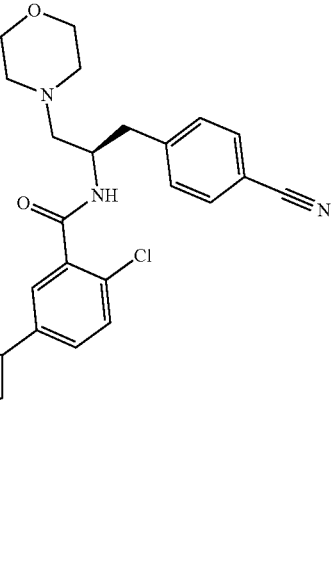<br>2-chloro-N-[(2R)-1-(4-cyanophenyl)-3-(morpholin-4-yl)propan-2-yl]-5-[5-({[(1R)-1-(4-methylphenyl)ethyl]amino}methyl)-2-furyl]benzamide | LC-MS (Method 1): $R_t$ = 2.26 min; MS (ES+): m/z = 597/599 (M + H)$^+$.<br>$^1$H-NMR (500 MHz, DMSO-$d_6$) δ [ppm] = 1.26 (d, 3H), 2.28 (s, 3H), 2.40-2.50 (m, 6H), 2.77 (dd, 1H), 3.08 (dd, 1H), 3.50-3.65 (m, 6H), 3.73 (q, 1H), 4.38 (m, 1H), 6.33 (d, 1H), 6.90 (d, 1H), 7.13 (d, 2H), 7.24 (d, 2H), 7.41 (d, 1H), 7.46 (d, 1H), 7.50 (d, 2H), 7.67 (dd, 1H), 7.77 (d, 2H), 8.36 (d, 1H).<br>$^{13}$C-NMR (125 MHz, DMSO-$d_6$) δ [ppm] = 20.6, 24.3, 38.2, 43.5, 47.4, 53.4, 56.4, 61.8, 66.3, 107.7, 108.8, 109.1, 119.0, 122.8, 124.9, 126.5, 127.9, 128.8, 129.1, 130.0, 130.4, 131.9, 135.6, 137.6, 142.5, 145.2, 150.0, 155.4, 165.6 |
| 23 | 1A; 28B | 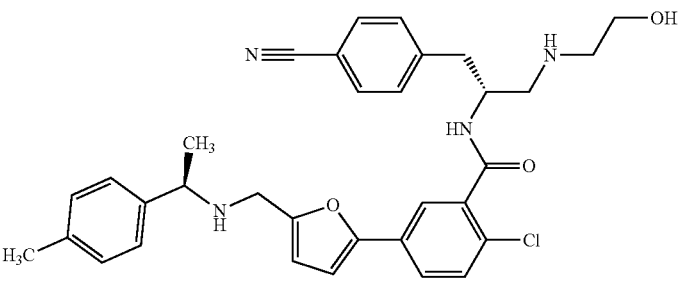 [SMILES: Cc1ccc([C@@H](C)NCc2ccc(-c3ccc(Cl)c(C(=O)N[C@@H](CNCCO)Cc4ccc(C#N)cc4)c3)o2)cc1]<br>2-chloro-N-{(2R)-1-(4-cyanophenyl)-3-[(2-hydroxyethyl)amino]propan-2-yl}-5-[5-({[(1R)-1-(4-methylphenyl)ethyl]amino}methyl)-2-furyl]benzamide | LC-MS (Method 1): $R_t$ = 2.18 min; MS (ES+): m/z = 571/573 (M + H)$^+$.<br>$^1$H-NMR (500 MHz, DMSO-$d_6$) δ [ppm] = 1.25 (d, 3H), 2.27 (s, 3H), 2.58-2.65 (m, 2H), 2.66-2.72 (m, 2H), 2.79 (dd, 1H), 3.07 (dd, 1H), 3.46 (q, 2H), 3.51 (d, 1H), 3.58 (d, 1H), 3.71 (q, 1H), 4.26 (m, 1H), 4.48 (t, 1H), 6.31 (d, 1H), 6.89 (d, 1H), 7.12 (d, 2H), 7.24 (d, 2H), 7.42 (d, 1H), 7.46 (d, 1H), 7.48 (d, 2H), 7.66 (dd, 1H), 7.76 (d, 2H), 8.38 (d, 1H). |
| 24 | 1A; 51B | 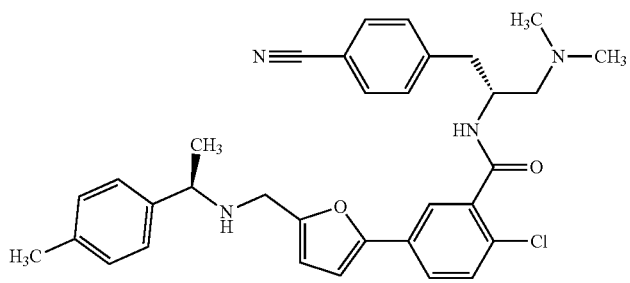<br>2-chloro-N-[(2R)-1-(4-cyanophenyl)-3-(dimethylamino)propan-2-yl]-5-[5-({[(1R)-1-(4-methylphenyl)ethyl]amino}methyl)-2-furyl]benzamide | LC-MS (Method 1): $R_t$ = 2.22 min; MS (ES+): m/z = 555 (M + H)$^+$.<br>$^1$H-NMR (500 MHz, DMSO-$d_6$) δ [ppm] = 1.25 (d, 3H), 2.23 (s, 6H), 2.27 (s, 3H), 2.35-2.38 (m, 2H), 2.75 (dd, 1H), 3.11 (dd, 1H), 3.51 & 3.58 (2 d, AB, 2H), 3.72 (m, 1H), 4.30 (m, 1H), 6.31 (d, 1H), 6.89 (d, 1H), 7.12 (d, 2H), 7.24 (d, 2H), 7.36 (d, 1H), 7.45 (d, 1H), 7.48 (d, 2H), 7.66 (dd, 1H), 7.77 (m, 2H), 8.35 (d, 1H). |

-continued

| Example No | Intermediates | Structure/Name | Analytics |
|---|---|---|---|
| 25 | 1A; 29B | 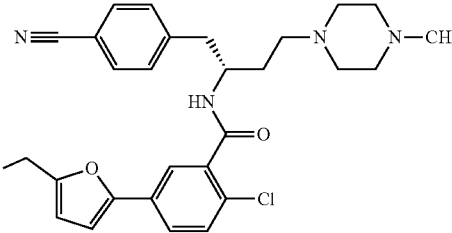<br>2-chloro-N-[(2R)-1-(4-cyanophenyl)-4-(4-methylpiperazin-1-yl)butan-2-yl]-5-[5-({[(1R)-1-(4-methylphenyl)ethyl]amino}methyl)-2-furyl]benzamide | LC-MS (Method 1): $R_t$ = 2.05 min; MS (ES+): m/z = 624/626 (M + H)+.<br>$^1$H-NMR (500 MHz, DMSO-$d_6$) δ [ppm] = 1.24 (d, 3H), 1.62 (m, 1H), 1.71 (m, 1H), 2.11 (s, 3H), 2.26 (s, 3H), 2.20-2.42 (m, 10H), 2.84 (dd, 1H), 2.97 (dd, 1H), 3.51 (d, 1H), 3.58 (d, 1H), 3.71 (q, 1H), 4.20 (m, 1H), 6.31 (d, 1H), 6.89 (d, 1H), 7.12 (d, 2H), 7.23 (d, 2H), 7.33 (d, 1H), 7.46 (d, 1H), 7.47 (d, 2H), 7.66 (dd, 1H), 7.77 (d, 2H), 8.44 (d, 1H). |
| 26 | 1A; 30B | 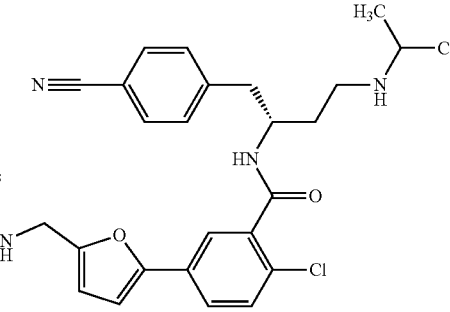<br>2-chloro-N-[(2R)-1-(4-cyanophenyl)-4-(isopropylamino)butan-2-yl]-5-[5-({[(1R)-1-(4-methylphenyl)ethyl]amino}methyl)-2-furyl]benzamide | LC-MS (Method 1): $R_t$ = 2.12 min; MS (ES+): m/z = 583/585 (M + H)+.<br>$^1$H-NMR (500 MHz, DMSO-$d_6$) δ [ppm] = 0.93 (d, 3H), 0.94 (d, 3H), 1.25 (d, 3H), 1.58 (m, 1H), 1.70 (m, 1H), 2.26 (s, 3H), 2.60-2.69 (m, 3H), 2.83 (dd, 1H), 2.96 (dd, 1H), 3.51 (d, 1H), 3.58 (d, 1H), 3.71 (q, 1H), 4.25 (m, 1H), 6.32 (d, 1H), 6.88 (d, 1H), 7.12 (d, 2H), 7.23 (d, 2H), 7.30 (d, 1H), 7.47 (d, 1H), 7.48 (d, 2H), 7.66 (dd, 1H), 7.77 (d, 2H), 8.44 (d, 1H). |
| 27 | 1A; 31B | 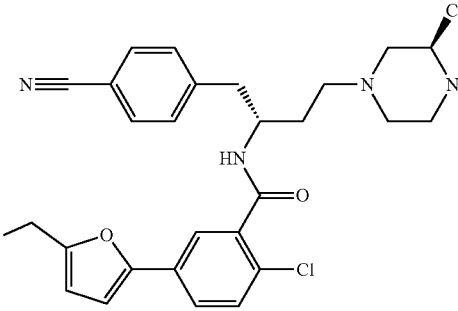<br>2-chloro-N-{(2R)-1-(4-cyanophenyl)-4-[(3R)-3-methylpiperazin-1-yl]butan-2-yl}-5-[5-({[(1R)-1-(4-methylphenyl)ethyl]amino}methyl)-2-furyl]benzamide | LC-MS (Method 12): $R_t$ = 2.94 min; MS (ES+): m/z = 624/626 (M + H)+.<br>UPLC-MS (Method 11): $R_t$ = 1.04 min; MS (ES+): m/z = 624/626 (M + H)+.<br>$^1$H-NMR (500 MHz, DMSO-$d_6$) δ [ppm] = 0.89 (d, 3H), 1.25 (d, 3H), 1.50 (t, 1H), 1.57-1.84 (m, 3H), 2.27 (s, 3H), 2.30-2.44 (m, 2H), 2.55-2.65 (m, 3H), 2.68 (br s, 1H), 2.74 (m, 1H), 2.83 (dd, 1H), 2.97 (dd, 1H), 3.52 & 3.59 (2d, AB, 2H), 3.71 (q, 1H), 4.21 (m, 1H), 6.32 (d, 1H), 6.89 (d, 1H), 7.12 (d, 2H), 7.23 (d, 2H), 7.33 (d, 1H), 7.47 (d, 1H), 7.48 (d, 2H), 7.66 (dd, 1H), 7.77 (d, 2H), 8.43 (d, 1H). |

-continued

| Example No | Intermediates | Structure/Name | Analytics |
|---|---|---|---|
| 28 | 1A; 32B | 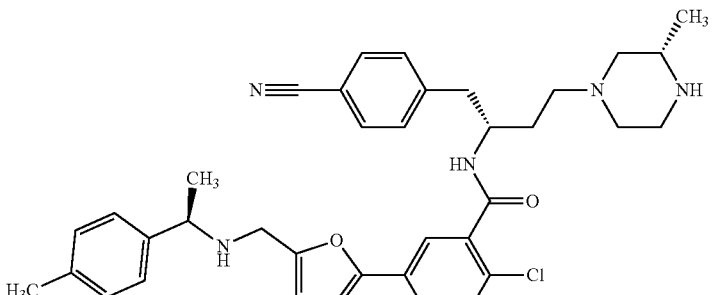<br>2-chloro-N-{(2R)-1-(4-cyanophenyl)-4-[(3S)-3-methylpiperazin-1-yl]butan-2-yl}-5-[5-({[(1R)-1-(4-methylphenyl)ethyl]amino}methyl)-2-furyl]benzamide | LC-MS (Method 1): $R_t$ = 2.14 min; MS (ES+): m/z = 624/626 (M + H)$^+$. $^1$H-NMR (500 MHz, DMSO-d$_6$) δ [ppm] = 0.87 (d, 3H), 1.25 (d, 3H), 1.46 (t, 1H), 1.64 (m, 1H), 1.71 (m, 1H), 1.82 (m, 1H), 2.27 (s, 3H), 2.33-2.38 (m, 2H), 2.55-2.67 (m, 4H), 2.75 (m, 1H), 2.85 (dd, 1H), 2.96 (dd, 1H), 3.51 (d, 1H), 3.58 (d, 1H), 3.71 (q, 1H), 4.20 (m, 1H), 6.32 (d, 1H), 6.89 (d, 1H), 7.12 (d, 2H), 7.23 (d, 2H), 7.34 (d, 1H), 7.47 (d, 1H), 7.48 (d, 2H), 7.66 (dd, 1H), 7.77 (d, 2H), 8.43 (d, 1H). |
| 29 | 1A; 33B | 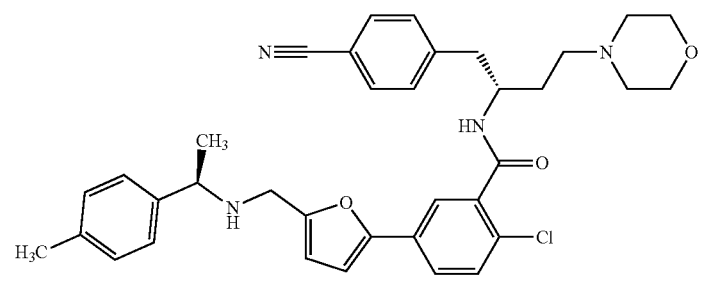 [SMILES: Cc1ccc([C@@H](C)NCc2ccc(-c3ccc(Cl)c(C(=O)N[C@@H](CCN4CCOCC4)Cc4ccc(C#N)cc4)c3)o2)cc1]<br>2-chloro-N-[(2R)-1-(4-cyanophenyl)-4-(morpholin-4-yl)butan-2-yl]-5-[5-({[(1R)-1-(4-methylphenyl)ethyl]amino}methyl)-2-furyl]benzamide | LC-MS (Method 1): $R_t$ = 2.16 min; MS (ES+): m/z = 610/612 (M + H)$^+$. $^1$H-NMR (500 MHz, DMSO-d$_6$) δ [ppm] = 1.25 (d, 3H), 1.65 (m, 1H), 1.74 (m, 1H), 2.27 (s, 3H), 2.33-2.44 (m, 6H), 2.84 (dd, 1H), 2.98 (dd, 1H), 3.50-3.60 (m, 6H), 3.71 (q, 1H), 4.23 (m, 1H), 6.32 (d, 1H), 6.89 (d, 1H), 7.12 (d, 2H), 7.23 (d, 2H), 7.32 (d, 1H), 7.47 (d, 1H), 7.48 (d, 2H), 7.66 (dd, 1H), 7.77 (d, 2H), 8.41 (d, 1H). |
| 30 | 1A; 47B | 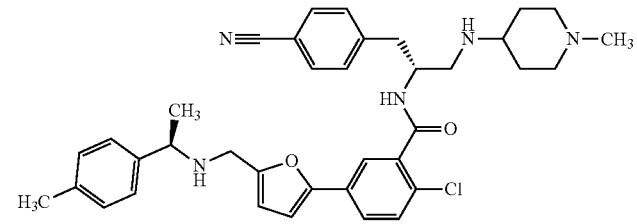<br>Nα-{2-chloro-5-[5-({[(1R)-1-(4-methylphenyl)ethyl]amino}methyl)-2-furyl]benzoyl}-4-cyano-N-(1-methylpiperidin-4-yl)-D-phenylalaninamide | LC-MS (Method 1): $R_t$ = 2.21 min; MS (ES+): m/z = 638/640 (M + H)$^+$, 520/522 (M + H − 118)$^+$ $^1$H-NMR (500 MHz, DMSO-d$_6$) δ [ppm] = 1.25 (d, 3H), 1.29-1.38 (m, 1H), 1.39-1.48 (m, 1H), 1.61-1.68 (m, 1H), 1.69-1.77 (m, 1H), 1.89-2.00 (m, 2H), 2.15 (s, 3H), 2.27 (s, 3H), 2.62-2.73 (m, 2H), 2.97 (dd, 1H), 3.11 (dd, 1H), 3.52 (m, 1H), 3.50 & 3.58 (2 d, AB, 2H), 3.71 (q, 1H), 4.74 (m, 1H), 6.32 (d, 1H), 6.89 (d, 1H), 7.13 (d, 2H), 7.24 (d, 2H), 7.43 (d, 1H), 7.45 (d, 1H), 7.51 (d, 2H), 7.67 (dd, 1H), 7.77 (d, 2H), 7.94 (d, 1H), 8.74 (d, 1H) |

| Example No | Intermediates | Structure/Name | Analytics |
|---|---|---|---|
| 31 | 1A; 34B | 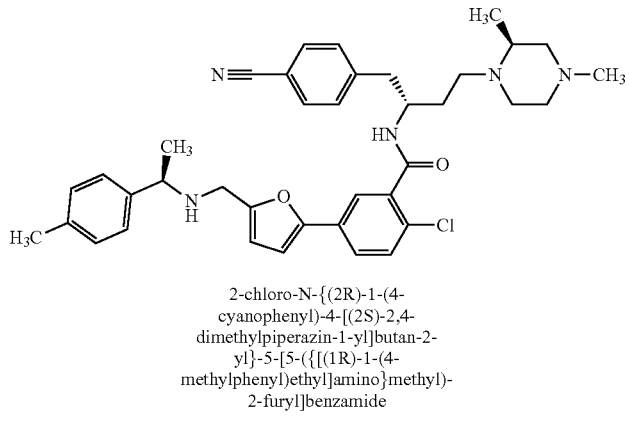2-chloro-N-{(2R)-1-(4-cyanophenyl)-4-[(2S)-2,4-dimethylpiperazin-1-yl]butan-2-yl}-5-[5-({[(1R)-1-(4-methylphenyl)ethyl]amino}methyl)-2-furyl]benzamide | LC-MS (Method 1): $R_t$ = 2.13 min; MS (ES+): m/z = 638/640 (M + H)+. $^1$H-NMR (500 MHz, DMSO-$d_6$) δ [ppm] = 0.93 (d, 3H), 1.25 (d, 3H), 1.57 (m, 1H), 1.71-1.77 (m, 2H), 2.03 (m, 1H), 2.09 (s, 3H), 2.15-2.24 (m, 2H), 2.27 (s, 3H), 2.33 (m, 1H), 2.46-2.54 (m, 2H), 2.73 (m, 1H), 2.79-2.83 (m, 2H), 2.98 (dd, 1H), 3.51 (d, 1H), 3.58 (d, 1H), 3.71 (q, 1H), 4.19 (m, 1H), 6.32 (d, 1H), 6.88 (d, 1H), 7.12 (d, 2H), 7.23 (d, 2H), 7.29 (d, 1H), 7.46 (d, 1H), 7.47 (d, 2H), 7.66 (dd, 1H), 7.77 (d, 2H), 8.44 (d, 1H). |
| 32 | 1A; 35B | 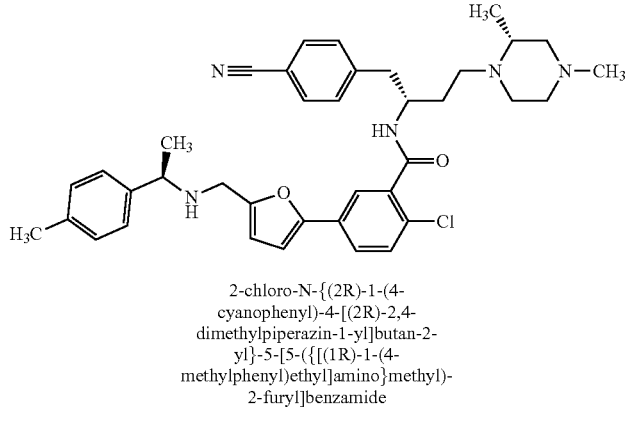2-chloro-N-{(2R)-1-(4-cyanophenyl)-4-[(2R)-2,4-dimethylpiperazin-1-yl]butan-2-yl}-5-[5-({[(1R)-1-(4-methylphenyl)ethyl]amino}methyl)-2-furyl]benzamide | LC-MS (Method 1): $R_t$ = 2.12 min; MS (ES+): m/z = 638/640 (M + H)+. $^1$H-NMR (500 MHz, DMSO-$d_6$) δ [ppm] = 0.94 (d, 3H), 1.25 (d, 3H), 1.60 (m, 1H), 1.65-1.72 (m, 2H), 1.97 (m, 1H), 2.08 (s, 3H), 2.15 (m, 1H), 2.27 (s, 3H), 2.29-2.32 (m, 2H), 2.46-2.50 (m, 2H), 2.67 (m, 1H), 2.79 (m, 1H), 2.86 (dd, 1H), 2.96 (dd, 1H), 3.51 (d, 1H), 3.58 (d, 1H), 3.71 (q, 1H), 4.21 (m, 1H), 6.32 (d, 1H), 6.88 (d, 1H), 7.12 (d, 2H), 7.23 (d, 2H), 7.34 (d, 1H), 7.46 (d, 1H), 7.48 (d, 2H), 7.67 (dd, 1H), 7.77 (d, 2H), 8.46 (d, 1H). |
| 33 | 1A; 36B | 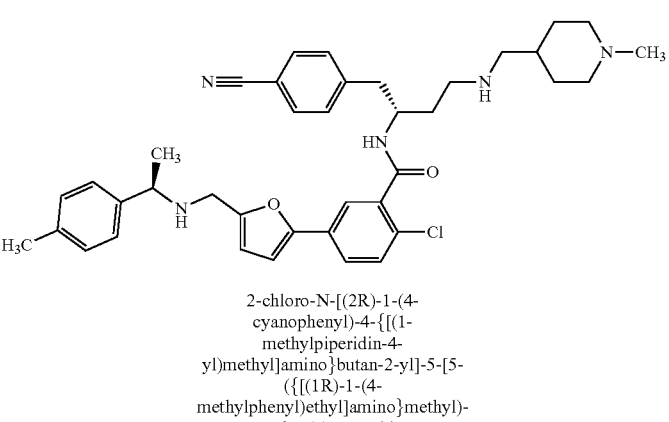2-chloro-N-[(2R)-1-(4-cyanophenyl)-4-{[(1-methylpiperidin-4-yl)methyl]amino}butan-2-yl]-5-[5-({[(1R)-1-(4-methylphenyl)ethyl]amino}methyl)-2-furyl]benzamide | LC-MS (Method 1): $R_t$ = 2.13 min; MS (ES+): m/z = 652/654 (M + H)+. $^1$H-NMR (500 MHz, DMSO-$d_6$) δ [ppm] = 1.01-1.10 (m, 2H), 1.23 (m, 1H), 1.25 (d, 3H), 1.57-1.61 (m, 3H), 1.70-1.75 (m, 3H), 2.09 (s, 3H), 2.26 (s, 3H), 2.33 (d, 2H), 2.58-2.68 (m, 4H), 2.83 (dd, 1H), 2.96 (dd, 1H), 3.52 (d, 1H), 3.59 (d, 1H), 3.71 (q, 1H), 4.24 (m, 1H), 6.32 (d, 1H), 6.89 (d, 1H), 7.12 (d, 2H), 7.23 (d, 2H), 7.30 (d, 1H), 7.47 (d, 1H), 7.48 (d, 2H), 7.66 (dd, 1H), 7.77 (d, 2H), 8.46 (d, 1H). |

-continued

| Example No | Intermediates | Structure/Name | Analytics |
|---|---|---|---|
| 34 | 1A; 37B | 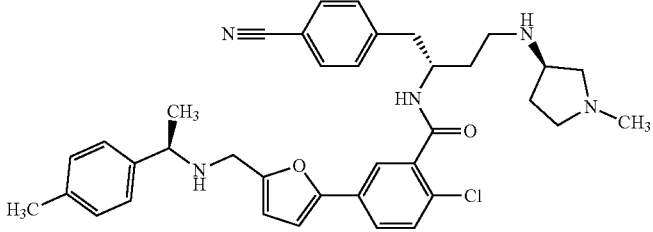<br>2-chloro-N-[(2R)-1-(4-cyanophenyl)-4-{[(3R)-1-methylpyrrolidin-3-yl]amino}butan-2-yl]-5-[5-({[(1R)-1-(4-methylphenyl)ethyl]amino}methyl)-2-furyl]benzamide | LC-MS (Method 1): $R_t$ = 2.15 min; MS (ES+): m/z = 624/626 (M + H)+. 1H-NMR (500 MHz, DMSO-$d_6$) δ [ppm] = 1.25 (d, 3H), 1.46 (m, 1H), 1.60 (m, 1H), 1.69 (m, 1H), 1.92 (m, 1H), 2.14 (m, 1H), 2.18 (s, 3H), 2.27 (s, 3H), 2.36-2.41 (m, 2H), 2.58-2.64 (m, 3H), 2.83 (dd, 1H), 2.96 (dd, 1H), 3.17 (m, 1H), 3.52 (d, 1H), 3.59 (d, 1H), 3.71 (q, 1H), 4.23 (m, 1H), 6.32 (d, 1H), 6.88 (d, 1H), 7.12 (d,2H), 7.24 (d, 2H), 7.30 (d, 1H), 7.46 (d, 1H), 7.48 (d, 2H), 7.67 (dd, 1H), 7.77 (d, 2H), 8.43 (d, 1H). |
| 35 | 1A; 38B | 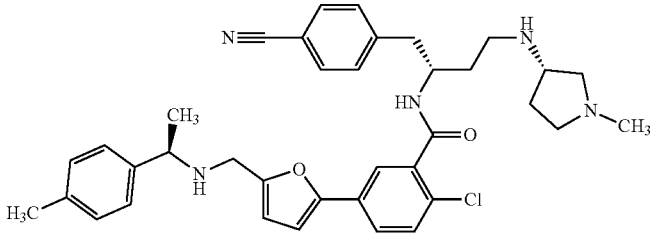<br>2-chloro-N-[(2R)-1-(4-cyanophenyl)-4-{[(3S)-1-methylpyrrolidin-3-yl]amino}butan-2-yl]-5-[5-({[(1R)-1-(4-methylphenyl)ethyl]amino}methyl)-2-furyl]benzamide | LC-MS (Method 1): $R_t$ = 2.11 min; MS (ES+): m/z = 624/626 (M + H)+. 1H-NMR (500 MHz, DMSO-$d_6$) δ [ppm] = 1.25 (d, 3H), 1.42 (m, 1H), 1.59 (m, 1H), 1.69 (m, 1H), 1.92 (m, 1H), 2.13 (m, 1H), 2.17 (s, 3H), 2.27 (s, 3H), 2.35-2.38 (m, 2H), 2.56-2.61 (m, 3H), 2.82 (dd, 1H), 2.96 (dd, 1H), 3.13 (m, 1H), 3.52 (d, 1H), 3.59 (d, 1H), 3.71 (q, 1H), 4.24 (m, 1H), 6.32 (d, 1H), 6.89 (d, 1H), 7.12 (d, 2H), 7.24 (d, 2H), 7.30 (d, 1H), 7.47 (d, 1H), 7.48 (d, 2H), 7.67 (dd, 1H), 7.77 (d, 2H), 8.43 (d, 1H). |
| 36 | 1A; 39B | 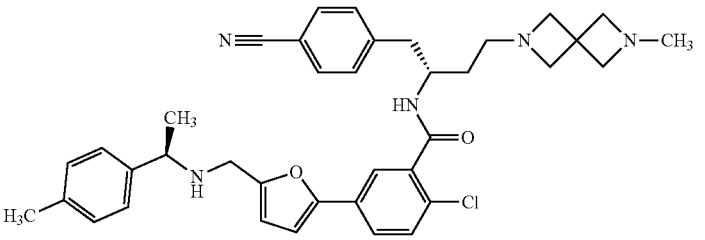<br>2-chloro-N-[(2R)-1-(4-cyanophenyl)-4-(6-methyl-2,6-diazaspiro[3.3]hept-2-yl)butan-2-yl]-5-[5-({[(1R)-1-(4-methylphenyl)ethyl]amino}methyl)-2-furyl]benzamide | LC-MS (Method 1): $R_t$ = 2.12 min; MS (ES+): m/z = 636/638 (M + H)+. 1H-NMR (500 MHz, DMSO-$d_6$) δ [ppm] = 1.25 (d, 3H), 1.44-1.52 (m, 2H), 2.13 (s, 3H), 2.27 (s, 3H), 2.40-2.43 (m, 2H), 2.81 (dd, 1H), 2.93 (dd, 1H), 3.08 (s, 4H), 3.10 (s, 4H), 3.51 (d, 1H), 3.58 (d, 1H), 3.71 (q, 1H), 4.16 (m, 1H), 6.32 (d, 1H), 6.90 (d, 1H), 7.12 (d, 2H), 7.24 (d, 2H), 7.32 (d, 1H), 7.46 (d, 2H), 7.47 (d, 1H), 7.66 (dd, 1H), 7.76 (d, 2H), 8.40 (d, 1H). |

-continued

| Example No | Intermediates | Structure/Name | Analytics |
|---|---|---|---|
| 37 | 1A; 40B | 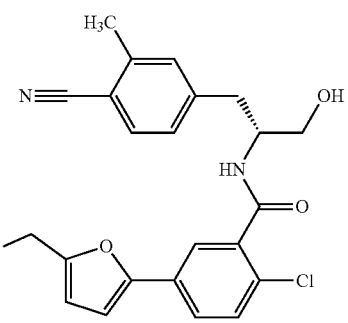<br>2-chloro-N-[(2R)-1-(4-cyano-3-methylphenyl)-3-hydroxypropan-2-yl]-5-[5-({[(1R)-1-(4-methylphenyl)ethyl]amino}methyl)-2-furyl]benzamide | LC-MS (Method 1): $R_t$ = 2.42 min; MS (ES+): m/z = 542/544 (M + H)+.<br>$^1$H-NMR (500 MHz, DMSO-$d_6$) δ [ppm] = 1.24 (d, 3H), 2.27 (s, 3H), 2.43 (s, 3H), 2.74 (dd, 1H), 3.04 (dd, 1H), 3.41 (m, 1H), 3.49 (d, 1H), 3.54 (m, 1H), 3.56 (d, 1H), 3.71 (q, 1H), 4.15 (m, 1H), 4.92 (t, 1H), 6.32 (d, 1H), 6.90 (d, 1H), 7.12 (d, 2H), 7.23 (d, 2H), 7.29 (d, 1H), 7.36 (s, 1H), 7.46-7.47 (m, 2H), 7.66 (dd, 1H), 7.68 (d, 1H), 8.36 (d, 1H). |
| 38 | 1A; 41B | 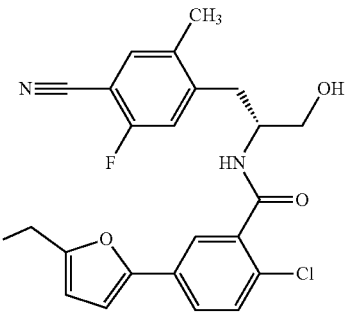<br>2-chloro-N-[(2R)-1-(4-cyano-5-fluoro-2-methylphenyl)-3-hydroxypropan-2-yl]-5-[5-({[(1R)-1-(4-methylphenyl)ethyl]amino}methyl)-2-furyl]benzamide | LC-MS (Method 1): $R_t$ = 2.48 min; MS (ES+): m/z = 560/562 (M + H)+.<br>$^1$H-NMR (500 MHz, DMSO-$d_6$) δ [ppm] = 1.24 (d, 3H), 2.27 (s, 3H), 2.35 (s, 3H), 2.70 (dd, 1H), 3.11 (dd, 1H), 3.44 (m, 1H), 3.50 (d, 1H), 3.56 (d, 1H), 3.59 (m, 1H), 3.71 (q, 1H), 4.20 (m, 1H), 5.01 (t, 1H), 6.32 (d, 1H), 6.91 (d, 1H), 7.12 (d, 2H), 7.23 (d, 2H), 7.33 (d, 1H), 7.46-7.48 (m, 2H), 7.67 (dd, 1H), 7.71 (d, 1H), 8.40 (d, 1H). |
| 39 | 1A; 42B | 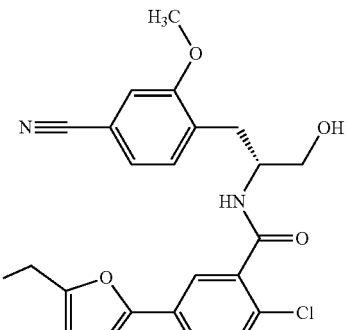<br>2-chloro-N-[(2R)-1-(4-cyano-2-methoxyphenyl)-3-hydroxypropan-2-yl]-5-[5-({[(1R)-1-(4-methylphenyl)ethyl]amino}methyl)-2-furyl]benzamide | LC-MS (Method 1): Rt = 2.42 min; MS (ES+): m/z = 558/560 (M + H)+.<br>1H-NMR (500 MHz, DMSO-d6) δ [ppm] = 1.25 (d, 3H), 2.27 (s, 3H), 2.66 (dd, 1H), 3.08 (dd, 1H), 3.43 (m, 1H), 3.50 (d, 1H), 3.53 (m, 1H), 3.57 (d, 1H), 3.71 (q, 1H), 3.86 (s, 3H), 4.26 (m, 1H), 4.88 (t, 1H), 6.31 (d, 1H), 6.89 (d, 1H), 7.12 (d, 2H), 7.24 (d, 2H), 7.36 (dd, 1H), 7.39-7.42 (m, 3H), 7.45 (d, 1H), 7.65 (dd, 1H), 8.25 (d, 1H). |

-continued

| Example No | Intermediates | Structure/Name | Analytics |
|---|---|---|---|
| 40 | 1A; 43B | 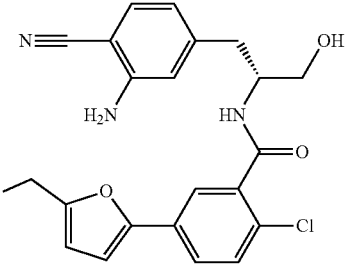<br>N-[(2R)-1-(3-amino-4-cyanophenyl)-3-hydroxypropan-2-yl]-2-chloro-5-[5-({[(1R)-1-(4-methylphenyl)ethyl]amino}methyl)-2-furyl]benzamide | LC-MS (Method 1): $R_t$ = 2.33 min; MS (ES+): m/z = 543/545 (M + H)+.<br>$^1$H-NMR (500 MHz, DMSO-$d_6$) δ [ppm] = 1.24 (d, 3H), 2.27 (s, 3H), 2.61 (dd, 1H), 2.86 (dd, 1H), 3.39 (m, 1H), 3.48-3.52 (m, 2H), 3.57 (d, 1H), 3.71 (q, 1H), 4.09 (m, 1H), 4.85 (t, 1H), 5.93 (s, 2H), 6.31 (d, 1H), 6.54 (dd, 1H), 6.70 (s, 1H), 6.90 (d, 1H), 7.12 (d, 2H), 7.23 (d, 2H), 7.29 (d, 1H), 7.47 (d, 1H), 7.49 (d, 1H), 7.66 (dd, 1H), 8.32 (d, 1H). |
| 41 | 1A; 44B | 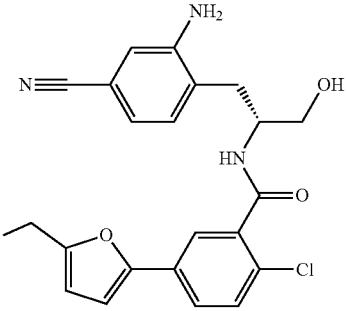<br>N-[(2R)-1-(2-amino-4-cyanophenyl)-3-hydroxypropan-2-yl]-2-chloro-5-[5-({[(1R)-1-(4-methylphenyl)ethyl]amino}methyl)-2-furyl]benzamide | LC-MS (Method 1): $R_t$ = 2.39 min; MS (ES+): m/z = 543/545 (M + H)+.<br>$^1$H-NMR (500 MHz, DMSO-$d_6$) δ [ppm] = 1.24 (d, 3H), 2.27 (s, 3H), 2.70 (dd, 1H), 2.80 (dd, 1H), 3.45 (m, 1H), 3.49 (d, 1H), 3.54 (m, 1H), 3.57 (d, 1H), 3.70 (q, 1H), 4.07 (m, 1H), 4.88 (t, 1H), 5.63 (s, 2H), 6.31 (d, 1H), 6.89 (dd, 1H), 6.92 (d, 1H), 6.95 (d, 1H), 7.12 (d, 2H), 7.16 (d, 1H), 7.23 (d, 2H), 7.49 (d, 1H), 7.58 (d, 1H), 7.68 (dd, 1H), 8.49 (d, 1H). |
| 42 | 1A; 16B | 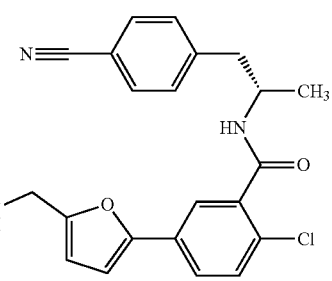<br>2-chloro-N-[(2S)-1-(4-cyanophenyl)propan-2-yl]-5-[5-({[(1R)-1-(4-methylphenyl)ethyl]amino}methyl)-2-furyl]benzamide | LC-MS (Method 1): Rt = 2.54 min; MS (ES+): m/z = 512/514 (M + H)+.<br>1H-NMR (500 MHz, MeOD) δ [ppm] = 1.30 (d, 3H), 1.37 (d, 3H), 2.31 (s, 3H), 2.93-3.00 (m, 2H), 3.60 & 3.67 (2 d, AB, 2H), 3.79 (q, 1H), 4.43 (m, 1H), 6.30 (d, 1H), 6.73 (d, 1H), 7.15 (d, 2H), 7.22 (d, 2H), 7.44 (d, 1H), 7.49 (m, 3H), 7.65-7.70 (m, 3H). |

| Example No | Intermediates | Structure/Name | Analytics |
|---|---|---|---|
| 43 | 1A; 17B | 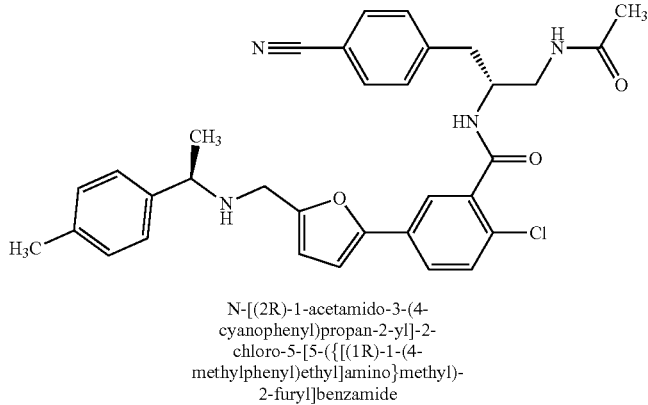<br>N-[(2R)-1-acetamido-3-(4-cyanophenyl)propan-2-yl]-2-chloro-5-[5-({[(1R)-1-(4-methylphenyl)ethyl]amino}methyl)-2-furyl]benzamide | LC-MS (Method 1): $R_t$ = 2.42 min; MS (ES+): m/z = 569/571 (M + H)$^+$<br>$^1$H-NMR (500 MHz, DMSO-d$_6$) δ [ppm] = 1.25 (d, 3H), 1.85 (s, 3H), 2.27 (s, 3H), 2.77 (dd, 1H), 2.97 (dd, 1H), 3.28 (m, 2H), 3.52 & 3.56 (2 d, AB, 2H), 3.70 (q, 1H), 4.26 (m, 1H), 6.32 (d, 1H), 6.90 (d, 1H), 7.12 (d, 2H), 7.23 (d, 2H), 7.44-7.49 (m, 4H), 7.64 (dd, 1H), 7.76 (d, 2H), 7.97 (t, 1H), 8.34 (d, 1H). |
| 44 | 1A; 21B | 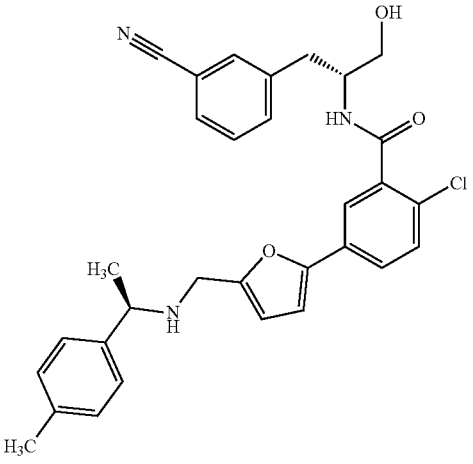 [SMILES: Cc1ccc([C@@H](C)NCc2ccc(-c3ccc(Cl)c(C(=O)N[C@@H](CO)Cc4cccc(C#N)c4)c3)o2)cc1]<br>2-chloro-N-[(2R)-1-(3-cyanophenyl)-3-hydroxypropan-2-yl]-5-[5-({[(1R)-1-(4-methylphenyl)ethyl]amino}methyl)-2-furyl]benzamide | LC-MS (Method 5): $R_t$ = 2.58 min; MS (ES+) m/z = 528-530 (M + H)$^+$<br>$^1$H-NMR (500 MHz, CD$_3$OD) δ [ppm] = 1.36 (d, 3H), 2.31 (s, 3H), 2.85 (dd, 1H), 3.15 (dd, 1H), 3.59 & 3.65 (2d, AB, 2H), 3.67 (dd, 1H), 3.71 (dd, 1H), 3.77 (q, 1H), 4.36-4.41 (m, 1H), 6.29 (d, 1H), 6.75 (d, 1H), 7.15 (d, 2H), 7.22 (d, 2H), 7.41 (d, 1H), 7.48 (t, 1H), 7.55-7.57 (m, 2H), 7.65 (d, 1H), 7.67-7.69 (m, 2H). |

| Example No | Intermediates | Structure/Name | Analytics |
|---|---|---|---|
| 45 | 1A; 45B | 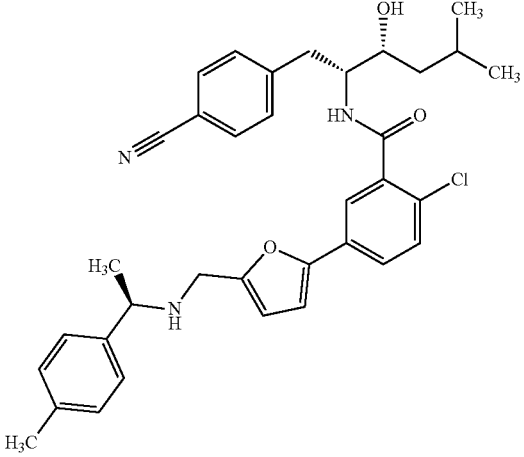 [SMILES: Cc1ccc([C@@H](C)NCc2ccc(-c3ccc(Cl)c(C(=O)N[C@H](Cc4ccc(C#N)cc4)[C@H](O)CC(C)C)c3)o2)cc1]<br>2-chloro-N-[(2R,3R)-1-(4-cyanophenyl)-3-hydroxy-5-methylhexan-2-yl]-5-[5-({[(1R)-1-(4-methylphenyl)ethyl]amino}methyl)-2-furyl]benzamide | LC-MS (Method 1): $R_t$ = 2.66 min; MS (ES+) m/z = 584/586 (M + H)$^+$<br>LC-MS (Method 10): $R_t$ = 9.91 min; MS (ES+): m/z = 584/586 (M + H)$^+$<br>$^1$H-NMR (500 MHz, DMSO-d6) δ [ppm] = 0.85 (d, 3H), 0.87 (d, 3H), 1.26 (d, 3H), 1.28-1.42 (m, 2H), 1.79 (m, 1H), 2.26 (s, 3H), 2.84 (dd, 1H), 3.01 (dd, 1H), 3.52 & 3.59 (2d, AB, 2H), 3.70 (m, 2H), 4.17 (m, 1H), 4.77 (d, 1H), 6.32 (d, 1H), 6.82 (d, 1H), 7.11 (d, 2H), 7.23 (d, 2H), 7.30 (d, 1H), 7.45 (d, 1H), 7.50 (d, 2H), 7.66 (dd, 1H), 7.75 (d,2H), 8.24 (d, 1H) |
| 46 | 1A; 46B | 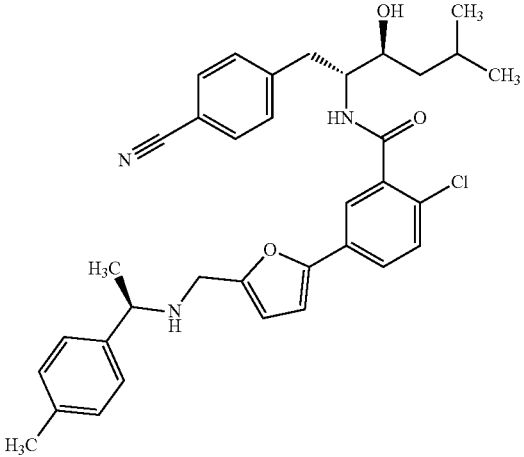 [SMILES: Cc1ccc([C@@H](C)NCc2ccc(-c3ccc(Cl)c(C(=O)N[C@H](Cc4ccc(C#N)cc4)[C@@H](O)CC(C)C)c3)o2)cc1]<br>2-chloro-N-[(2R,3S)-1-(4-cyanophenyl)-3-hydroxy-5-methylhexan-2-yl]-5-[5-({[(1R)-1-(4-methylphenyl)ethyl]amino}methyl)-2-furyl]benzamide | LC-MS (Method 1): $R_t$ = 2.63 min; MS (ES+) m/z = 584/586 (M + H)$^+$<br>LC-MS (Method 10): $R_t$ = 9.71 min; MS (ES+): m/z = 584/586 (M + H)$^+$<br>$^1$H-NMR (500 MHz, DMSO-d6) δ [ppm] = 0.86 (d, 3H), 0.91 (d, 3H), 1.25 (d, 3H), 1.34 (m, 1H), 1.45 (m, 1H), 1.83 (m, 1H), 2.27 (s, 3H), 2.71 (dd, 1H), 3.23 (dd, 1H), 3.51 (m, 1H), 3.52 & 3.60 (2d, AB, 2H), 3.71 (q, 1H), 4.01 (m, 1H), 4.80 (d, 1H), 6.32 (d, 1H), 6.85 (d, 1H), 7.11 (d, 2H), 7.21 (d, 1H), 7.23 (d, 2H), 7.44 (d, 1H), 7.46 (d, 2H), 7.65 (dd, 1H), 7.75 (d, 2H), 8.32 (d, 1H) |

| Example No | Intermediates | Structure/Name | Analytics |
|---|---|---|---|
| 47 | 1A; 48B | 2-chloro-N-[(2R)-1-hydroxy-3-(pyridin-4-yl)propan-2-yl]-5-[5-({[(1R)-1-(4-methylphenyl)ethyl]amino}methyl)-2-furyl]benzamide | LC-MS (Method 5): Rt = 2.33 min; MS (ES+) m/z = 504-506 (M + H)+ 1H-NMR (500 MHz, CD3OD) δ [ppm] = 1.36 (d, 3H), 2.31 (s, 3H), 2.86 (dd, 1H), 3.15 (dd, 1H), 3.59 & 3.64 (2d, AB, 2H), 3.67 (dd, 1H), 3.71 (dd, 1H), 3.77 (q, 1H), 4.44-4.49 (m, 1H), 6.28 (d, 1H), 6.73 (d, 1H), 7.15 (d, 2H), 7.22 (d, 2H), 7.39-7.41 (m, 3H), 7.53 (d, 1H), 7.67 (dd, 1H), 8.44 (d, 2H). |
| 48 | 1A; 49B | N-[(2R)-1-(4-carbamoylphenyl)-3-hydroxypropan-2-yl]-2-chloro-5-[5-({[(1R)-1-(4-methylphenyl)ethyl]amino}methyl)-2-furyl]benzamide | LC-MS (Method 1): $R_t$ = 2.22 min; MS (ES+): m/z = 546/548 (M + H)+. 1H-NMR (500 MHz, DMSO-$d_6$) δ [ppm] = 1.24 (d, 3H), 2.27 (s, 3H), 2.76 (dd, 1H), 3.03 (dd, 1H), 3.42 (m, 1H), 3.49-3.55 (m, 2H), 3.57 (d, 1H), 3.71 (q, 1H), 4.16 (m, 1H), 4.87 (t, 1H), 6.31 (d, 1H), 6.88 (d, 1H), 7.12 (d, 2H), 7.23-7.25 (m, 3H), 7.35 (d, 2H), 7.45-7.47 (m, 2H), 7.65 (dd, 1H), 7.82 (d, 2H), 7.89 (br s, 1H), 8.35 (d, 1H). |

| Example No | Intermediates | Structure/Name | Analytics |
|---|---|---|---|
| 49 | 1A; 50B | 2-chloro-N-[(2R)-1-(4-cyanophenyl)-3-(pyrrolidin-1-yl)propan-2-yl]-5-[5-({[(1R)-1-(4-methylphenyl)ethyl]amino}methyl)-2-furyl]benzamide | LC-MS (Method 1): $R_t$ = 2.18 min; MS (ES+): m/z = 581/583 (M + H)$^+$. $^1$H-NMR (500 MHz, DMSO-$d_6$) δ [ppm] = 1.25 (d, 3H), 1.67-1.72 (m, 4H), 2.27 (s, 3H), 2.51-2.55 (m, 5H), 2.59 (dd, 1H), 2.76 (m, 1H), 3.12 (dd, 1H), 3.51 (d, 1H), 3.57 (d, 1H), 3.72 (m, 1H), 4.29 (m, 1H), 6.32 (m, 1H), 6.88 (d, 1H), 7.12 (d, 2H), 7.23 (d, 2H), 7.37 (t, 1H), 7.45 (d, 1H), 7.48 (d, 2H), 7.66 (dd, 1H), 7.75-7.77 (m, 2H), 8.35 (d, 1H) |
| 50 | 1A; 52B | methyl (3R)-3-({2-chloro-5-[5-({[(1R)-1-(4-methylphenyl)ethyl]amino}methyl)-2-furyl]benzoyl}amino)-4-(4-cyanophenyl)butanoate | LC-MS (Method 1): $R_t$ = 2.50 min; MS (ES+): m/z = 570/572 (M + H)$^+$. $^1$H-NMR (500 MHz, CD$_3$OD) δ [ppm] = 1.36 (d, 3H), 2.31 (s, 3H), 2.68 (dd, 1H), 2.70 (dd, 1H), 2.97 (dd, 1H), 3.11 (dd, 1H), 3.60 & 3.67 (2 d, AB, 2H), 3.70 (s, 3H), 3.79 (q, 1H), 4.74 (m, 1H), 6.30 (d, 1H), 6.72 (d, 1H), 7.15 (d, 2H), 7.23 (d, 2H), 7.40 (d, 1H), 7.44 (d, 1H), 7.50 (d, 2H), 7.64-7.69 (m, 3H). |

-continued

| Example No | Intermediates | Structure/Name | Analytics |
|---|---|---|---|
| 51 | 1A; 54B | 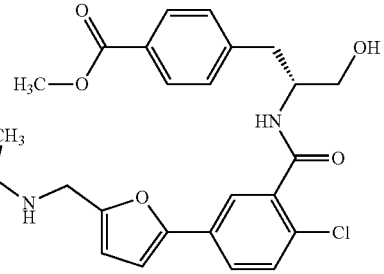<br>methyl 4-[(2R)-2-({2-chloro-5-[5-({[(1R)-1-(4-methylphenyl)ethyl]amino}methyl)-2-furyl]benzoyl}amino)-3-hydroxypropyl]benzoate | LC-MS (Method 1): $R_t$ = 2.43 min; MS (ES+): m/z = 561/563 (M + H)⁺.<br>¹H-NMR (500 MHz, DMSO-$d_6$) δ [ppm] = 1.25 (d, 3H), 2.27 (s, 3H), 2.78 (dd, 1H), 3.07 (dd, 1H), 3.42 (m, 1H), 3.50-3.56 (m, 2H), 3.58 (d, 1H), 3.71 (m, 1H), 3.83 (s, 3H), 4.17 (m, 1H), 4.90 (t, 1H), 6.32 (d, 1H), 6.88 (d, 1H), 7.12 (d, 2H), 7.24 (d, 2H), 7.43-7.46 (m, 4H), 7.65 (dd, 1H), 7.89 (d, 2H), 8.35 (d, 1H). |

Example 53

N-[(2R)-1-amino-3-(4-cyanophenyl)propan-2-yl]-2-chloro-5-[5-({[(1R)-1-(4-methylphenyl)ethyl]amino}methyl)-2-furyl]benzamide

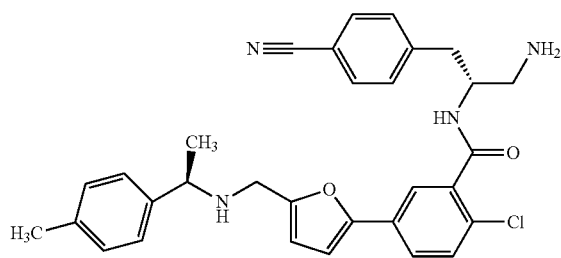 [SMILES: Cc1ccc([C@@H](C)NCc2ccc(-c3ccc(Cl)c(C(=O)N[C@@H](CN)Cc4ccc(C#N)cc4)c3)o2)cc1]

2-chloro-N-[(2R)-1-(4-cyanophenyl)-3-(1,3-dioxo-1,3-dihydro-2H-isoindol-2-yl)propan-2-yl]-5-[5-({[(1R)-1-(4-methylphenyl)ethyl]amino}methyl)-2-furyl]benzamide

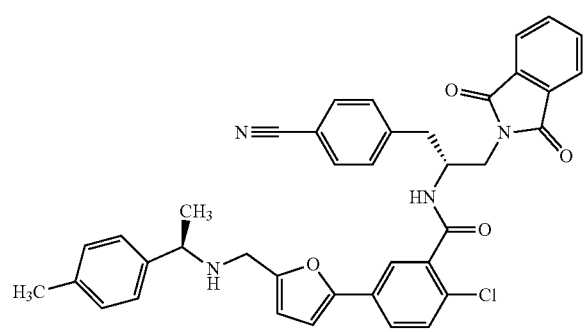 [SMILES: Cc1ccc([C@@H](C)NCc2ccc(-c3ccc(Cl)c(C(=O)N[C@H](Cc4ccc(C#N)cc4)CN4C(=O)c5ccccc5C4=O)c3)o2)cc1]

To a stirred solution of intermediate 1A, 1.80 g (4.87 mmol) in tetrahydrofuran (80 mL) and DMF (4 mL) was added triethylamine, 0.67 mL (4.87 mmol) followed by TBTU, 1.64 g (5.11 mmol, 1.05 eq.). The mixture was stirred for 30 min at r.t., and then amine intermediate 52B, 1.66 g (4.87 mmol, 1 eq.) and triethylamine, 2.0 mL (14.6 mmol, 3.0 eq.) were added. The resulting mixture was stirred at r.t. for 16 h. Most of the solvent was removed under reduced pressure, the residue was diluted with ethyl acetate and washed with sat. aq. sodium hydrogen carbonate, brine and then dried over sodium sulfate. The solution was concentrated and the residue purified by flash chromatography on silica (dichloromethane/methanol, 1/0>100/4) to give the product, 2.8 g (82%) as beige solid.

LC-MS (Method 1): $R_t$=2.66 min; MS (ES+): nm/z=657/659 (M+H)⁺

¹H-NMR (500 MHz, DMSO-d6) δ [ppm]=1.31 (d, 3H), 2.27 (s, 3H), 2.86 (dd, 1H), 3.14 (dd, 1H), 3.66 (br s, 2H), 3.78-3.90 (m, 3H), 4.61 (m, 1H), 6.40 (br s, 1H), 6.86 (d, 1H), 7.14 (d, 2H), 7.27-7.30 (m, 3H), 7.38 (d, 1H), 7.50 (d, 2H), 7.61 (dd, 1H), 7.75 (d, 2H), 7.80 (m, 2H), 7.88 (m, 2H), 8.52 (d, 1H).

N-[(2R)-1-amino-3-(4-cyanophenyl)propan-2-yl]-2-chloro-5-[5-({[(1R)-1-(4-methylphenyl)ethyl]amino}methyl)-2-furyl]benzamide To a stirred solution of 2-chloro-N-[(2R)-1-(4-cyanophenyl)-3-(1,3-dioxo-1,3-dihydro-2H-isoindol-2-yl)propan-2-yl]-5-[5-({[(1R)-1-(4-methylphenyl)ethyl]-amino}methyl)-2-furyl]benzamide, 205 mg (0.31 mmol) in absolute ethanol (5 mL) was added hydrazine, 1.56 mL (1M in THF, 1.56 mmol, 5 eq.). The resulting solution was stirred at 35° C. for 16 h, and then at 70° C. for 3 h. The solvent was then removed in vacuum, the residue triturated in ethyl acetate and filtered. The filtrate was concentrated and the residue obtained was purified by preparative TLC on silica (dichloromethane/ammonia 7N in methanol, 100/2 to 100/4) to give the product, 110 mg (66%) as an off white solid.

LC-MS (Method 1): $R_t$=2.13 min; MS (ES+): m/z=527/529 (M+H)⁺

¹H-NMR (500 MHz, DMSO-d6) δ [ppm]=1.25 (d, 3H), 1.65 (br s, 2H), 2.27 (s, 3H), 2.67 (d, 2H), 2.77 (dd, 1H), 3.05 (dd, 1H), 3.51 & 3.57 (2 d, AB, 2H), 3.71 (q, 1H), 4.10 (m, 1H), 6.31 (d, 1H), 6.91 (d, 1H), 7.12 (d, 2H), 7.23 (d, 2H), 7.42 (d, 1H), 7.46 (d, 1H), 7.48 (d, 2H), 7.66 (dd, 1H), 7.76 (d, 2H), 8.34 (d, 1H).

Example 54

2-chloro-N-{(2R)-1-(4-cyanophenyl)-3-[(methylsulfonyl)amino]propan-2-yl}-5-[5-({[(1R)-1-(4-methylphenyl)ethyl]amino}methyl)-2-furyl]benzamide

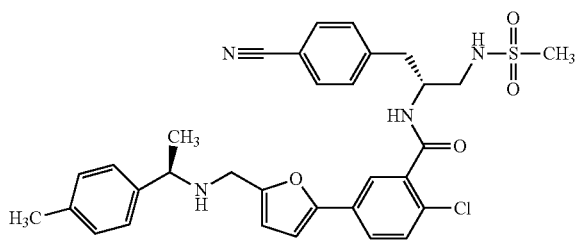

To a solution of Example 53, N-[(2R)-1-amino-3-(4-cyanophenyl)propan-2-yl]-2-chloro-5-[5-({[(1R)-1-(4-methylphenyl)ethyl]amino}methyl)-2-furyl]benzamide, 70 mg (0.133 mmol) in THF (1.5 mL) cooled to 0° C., was added successively triethylamine, 0.019 µL (0.139 mmol, 1.05 eq.) and methanesulfonyl chloride, 0.010 mL (0.133 mmol, 1.0 eq.). The reaction mixture was stirred at 0° C. for 1 h. Ethyl acetate and an aqueous saturated sodium hydrogenocarbonate solution were added. The phases were separated and the aqueous phase was extracted with ethyl acetate (2×). The combined organics were washed with brine, dried over sodium sulfate and concentrated. The residue was purified by preparative TLC (dichloromethane/methanol: 96/4) to provide the product, 68 mg (81%) as an off-white solid.

LC-MS (Method 1): $R_t$=2.49 min; MS (ES+): m/z=605/607 (M+H)$^+$ $^1$H-NMR (500 MHz, DMSO-d6) δ [ppm]=1.26 (d, 3H), 2.27 (s, 3H), 2.78 (dd, 1H), 2.96 (s, 3H), 3.09 (dd, 1H), 3.11-3.21 (m, 2H), 3.28 (s, 1H), 3.51 & 3.56 (2 d, AB, 2H), 3.67-3.75 (m, 1H), 4.28 (m, 1H), 6.32 (d, 1H), 6.89 (d, 1H), 7.12 (d, 2H), 7.24 (d, 2H), 7.27 (t, 1H), 7.45 (d, 1H), 7.49 (d, 2H), 7.53 (d, 1H), 7.66 (dd, 1H), 7.77 (d, 2H), 8.43 (d, 1H)

Example 55

2-chloro-N-[(2R)-1-(4-cyanophenyl)-3-{[2-oxo-2-(piperazin-1-yl)ethyl]amino}propan-2-yl]-5-[5-({[(1R)-1-(4-methylphenyl)ethyl]amino}methyl)-2-furyl]benzamide

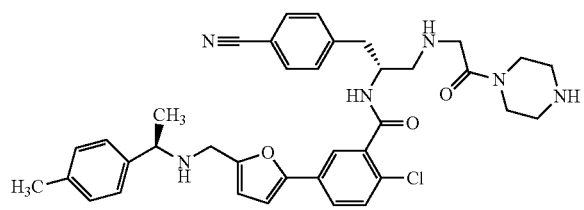 [SMILES: Cc1ccc([C@@H](C)NCc2ccc(-c3ccc(Cl)c(C(=O)N[C@@H](CNCC(=O)N4CCNCC4)Cc4ccc(C#N)cc4)c3)o2)cc1]

Tert-butyl 4-{N-[(2R)-2-({2-chloro-5-[5-({[(1R)-1-(4-methylphenyl)ethyl]amino}methyl)-2-furyl]benzo}amino)-3-(4-cyanophenyl)propyl]glycyl}piperazine-1-carboxylate

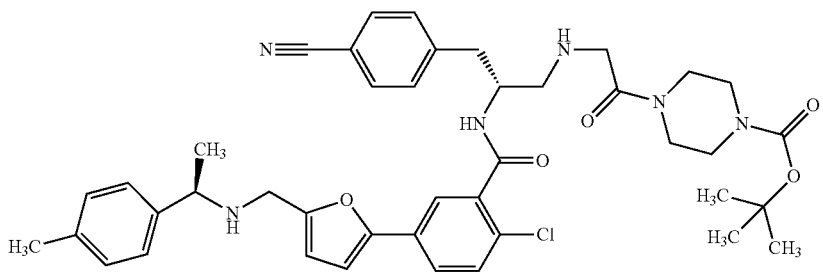 [SMILES: Cc1ccc([C@@H](C)NCc2ccc(-c3ccc(Cl)c(C(=O)N[C@@H](CNCC(=O)N4CCN(C(=O)OC(C)(C)C)CC4)Cc4ccc(C#N)cc4)c3)o2)cc1]

To a stirred solution of Example 53, N-[(2R)-1-amino-3-(4-cyanophenyl)propan-2-yl]-2-chloro-5-[5-({[(1R)-1-(4-methylphenyl)ethyl]amino}methyl)-2-furyl]benzamide, 125 mg (0.237 mmol) in acetonitrile (5.0 mL) was added triethylamine, 50 µL (0.356 mmol, 1.5 eq) and tert-butyl 4-(bromoacetyl)piperazine-1-carboxylate, 95 mg (0.31 mmol, 1.3 eq.). The mixture was stirred at r.t. for 24 h. The mixture was diluted with ethyl acetate (20 mL) and the organic layer was washed successively with aq. sat. sodium hydrogen carbonate, water, brine, dried over sodium sulfate and concentrated. The residue was purified by preparative TLC (eluent: dichloromethane/ammonia 7N in methanol, 97/3) to give an impure fraction that was purified by preparative TLC (elu ent: dichloromethane/ammonia 7N in methanol, 97.5/2.5) to give the pure product, 52 mg (29%) as an off-white solid.

LC-MS (Method 1): $R_t$=2.50 min; MS (ES+): m/z=753/755 (M+H)$^+$, 535/537 (M+H−218)$^+$ $^1$H-NMR (500 MHz, DMSO-d$_6$) δ [ppm]=1.25 (d, 3H), 1.40 (s, 9H), 2.27 (s, 3H), 2.65-2.72 (m, 2H), 2.80 (dd, 1H), 3.05 (dd, 1H), 3.24-3.35 (m, 5H), 3.35-3.48 (m, 5H), 3.50 & 3.58 (2 d, AB, 2H), 3.70 (m, 1H), 4.27 (m, 1H), 6.32 (d, 1H), 6.92 (d, 1H), 7.12 (d, 2H), 7.24 (d, 2H), 7.44-7.51 (m, 4H), 7.66 (dd, 1H), 7.76 (d, 2H), 8.40 (d, 1H).

2-chloro-N-[(2R)-1-(4-cyanophenyl)-3-{[2-oxo-2-(piperazin-1-yl)ethyl]amino}propan-2-yl]-5-[5-({[(1R)-1-(4-methylphenyl)ethyl]amino}methyl)-2-furyl]benzamide To a stirred solution of tert-butyl 4-{N-[(2R)-2-({2-chloro-5-[5-({[(1R)-1-(4-methylphenyl)ethyl]amino}methyl)-2-furyl]benzoyl}amino)-3-(4-cyanophenyl)propyl]-glycyl}piperazine-1-carboxylate, 52 mg (0.069 mmol) in dichloromethane (1.5 mL) and dioxane (1.5 mL) was added slowly hydrochloric acid, 0.173 mL (4M in 1,4-dioxane, 0.69 mmol, 10 eq.) at 0° C. and the resulting mixture was stirred at r.t. for 16 h. The reaction mixture was concentrated to dryness. The resulting solid was partitioned between aq. sat. sodium hydrogen carbonate and ethyl acetate. The aqueous phase was extracted with ethyl acetate. The combined organic phase was dried over sodium sulfate and concentrated. The residue was purified by preparative TLC (silica, DCM/ammonia 7N in methanol, 96/4) to give an impure product that was purified a second time by preparative TLC (silica, DCM/ammonia 7N in methanol, 97/3) to give the pure product, 31 mg (69%) as an off white solid.

LC-MS (Method 1): $R_t$=2.08 min; MS (ES+): m/z=653/655 (M+H)$^+$; 535/537 (M−118+H)$^+$ $^1$H-NMR (500 MHz, DMSO-d$_6$) δ [ppm]=1.25 (d, 3H), 2.27 (s, 3H), 2.60-2.71 (m, 6H), 2.80 (dd, 1H), 3.06 (dd, 1H), 3.31-3.46 (m, 6H), 3.51 & 3.58 (2 d, AB, 2H), 3.71 (q, 1H), 4.28 (m, 1H), 6.31 (d, 1H), 6.93 (d, 1H), 7.12 (d, 2H), 7.24 (d, 2H), 7.44-7.51 (m, 4H), 7.66 (dd, 1H), 7.76 (d, 2H), 8.41 (d, 1H).

Example 56

N-[(2R)-2-({2-chloro-5-[5-({[(1R)-1-(4-methylphenyl)ethyl]amino}methyl)-2-furyl]benzoyl}amino)-3-(4-cyanophenyl)propyl]piperidine-4-carboxamide

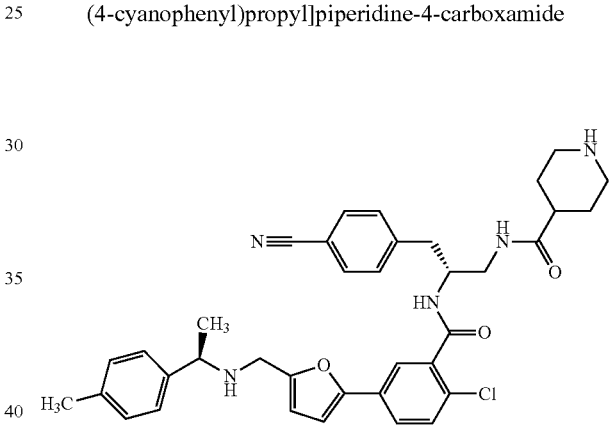

Tert-butyl 4-{[(2R)-2-({2-chloro-5-[5-({[(1R)-1-(4-methylphenyl)ethyl]amino}methyl)-2-furyl]benzoyl}amino)-3-(4-cyanophenyl)propyl]carbamoyl}piperidine-1-carboxylate

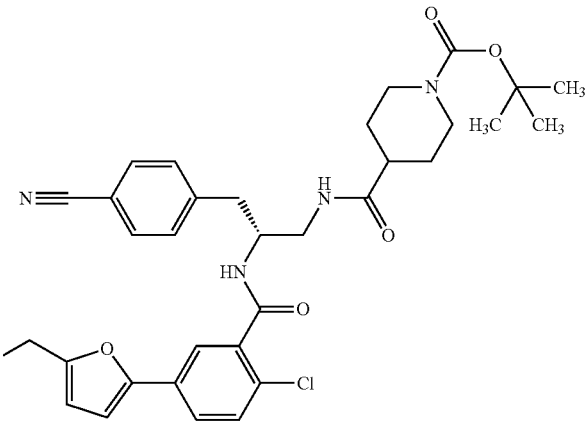

To a stirred solution of N-Boc-isonipecotic acid, 53 mg (0.228 mmol) in tetrahydrofuran (3 mL) were added TBTU, 73 mg (0.228 mmol, 1.0 eq.) and triethylamine, 0.095 mL (0.683 mmol, 3.0 eq.) at r.t. After 20 min, Example 53, N-[(2R)-1-amino-3-(4-cyanophenyl)propan-2-yl]-2-chloro-5-[5-({[(1R)-1-(4-methylphenyl)ethyl]amino}methyl)-2-furyl]benzamide, 120 mg (0.228 mmol, 1.0 eq.) was added and the resulting mixture was stirred at r.t. for 5 h. Most of the solvent was removed under reduced pressure and the residue was dissolved in ethyl acetate. The organic layer was washed successively with water, aq. sat. sodium hydrogen carbonate, brine, dried over sodium sulfate and concentrated. The residue (156 mg) was purified by preparative TLC (eluent: dichloromethane/methanol, 97/3) to give the product, 110 mg (62%) as a light yellow solid.

LC-MS (Method 1): $R_t$=2.66 min; MS (ES+): m/z=738/740 (M+H)$^+$ $^1$H-NMR (500 MHz, DMSO-d$_6$) δ [ppm]=1.25 (d, 3H), 1.36 (s, 9H), 1.32-1.47 (m, 3H), 1.61-1.72 (m, 2H), 2.27 (s, 3H), 2.28-2.33 (m, 1H), 2.70 (m, 2H), 2.76 (dd, 1H), 2.95 (dd, 1H), 3.21-3.35 (m, 2H), 3.51 & 3.57 (2 d, AB, 2H), 3.71 (q, 1H), 3.84-3.96 (m, 2H), 4.30 (m, 1H), 6.32 (d, 1H), 6.90 (d, 1H), 7.12 (d, 2H), 7.24 (d, 2H), 7.41-7.48 (m, 3H), 7.51 (d, 1H), 7.65 (dd, 1H), 7.76 (d, 2H), 7.96 (t, 1H), 8.34 (d, 1H)

N-[(2R)-2-({2-chloro-5-[5-({[(1R)-1-(4-methylphenyl)ethyl]amino}methyl)-2-furyl]-benzoyl}amino)-3-(4-cyanophenyl)propyl]piperidine-4-carboxamide To a stirred solution of tert-butyl 4-{[(2R)-2-({2-chloro-5-[5-({[(1R)-1-(4-methyl-phenyl)ethyl]amino}methyl)-2-furyl]benzoyl}amino)-3-(4-cyanophenyl)propyl]-carbamoyl}piperidine-1-carboxylate, 110 mg (0.149 mmol) in dichloromethane (4 mL) was added slowly hydrochloric acid, 0.37 mL (4M in 1,4-dioxane, 1.49 mmol, 10 eq.) at 0° C. and the resulting mixture was stirred at r.t. for 16 h. The reaction mixture was concentrated to dryness. The resulting solid was partitioned between aq. sat. sodium hydrogen carbonate and ethyl acetate. The aqueous phase was extracted with ethyl acetate. The combined organic phase was dried over sodium sulfate and concentrated. The residue was purified by preparative TLC (silica, DCM/ammonia 7N in methanol, 94/6) to give the product, 58 mg (60%) as an off-white solid.

LC-MS (Method 1): $R_t$=2.18 min; MS (ES+): m/z=638/640 (M+H)$^+$; 520/522 (M−118+H)$^+$ $^1$H-NMR (500 MHz, DMSO-d$_6$) δ [ppm]=1.25 (d, 3H), 1.39-1.49 (m, 2H), 1.54-1.63 (m, 2H), 2.13-2.21 (m, 1H), 2.27 (s, 3H), 2.37-2.45 (m, 2H), 2.76 (dd, 1H), 2.86-2.93 (m, 2H), 2.95 (dd, 1H), 3.19-3.28 (m, 2H), 3.50 & 3.58 (2 d, AB, 2H), 3.71 (q, 1H), 4.29 (m, 1H), 6.32 (d, 1H), 6.90 (d, 1H), 7.12 (d, 2H), 7.24 (d, 2H), 7.45-7.51 (m, 4H), 7.66 (dd, 1H), 7.76 (d, 2H), 7.83 (t, 1H), 8.34 (d, 1H).

Example 57

2-chloro-N-{(2R)-1-(4-cyanophenyl)-3-[(piperidin-4-ylacetyl)amino]propan-2-yl}-5-[5-({[(1R)-1-(4-methylphenyl)ethyl]amino}methyl)-2-furyl]benzamide

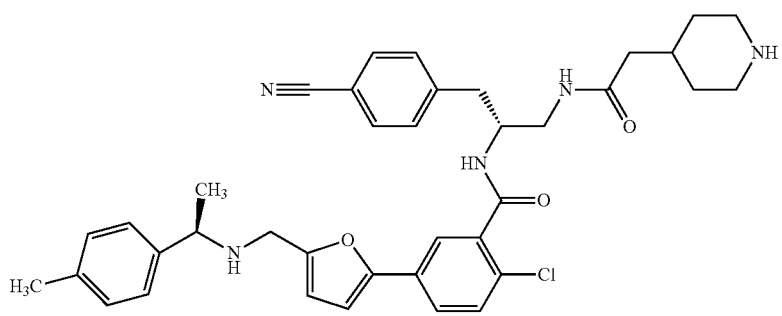 [SMILES: Cc1ccc([C@@H](C)NCc2ccc(-c3ccc(Cl)c(C(=O)N[C@@H](CNC(=O)CC4CCNCC4)Cc4ccc(C#N)cc4)c3)o2)cc1]

Using the same procedures as described for Example 56
LC-MS (Method 1): $R_t$=2.19 min; MS (ES+): m/z=652/654 (M+H); 534/536 (M−118+H)$^+$ $^1$H-NMR (500 MHz, DMSO-d$_6$) δ [ppm]=0.93-1.05 (m, 2H), 1.25 (d, 3H), 1.48-1.56 (m, 2H), 1.70-1.80 (m, 1H), 1.95-2.05 (m, 2H), 2.27 (s, 3H), 2.30-2.40 (m, 2H), 2.76 (dd, 1H), 2.77-2.86 (m, 2H), 2.96 (dd, 1H), 3.27 (m, 2H), 3.51 & 3.58 (2 d, AB, 2H), 3.71 (q, 1H), 4.27 (m, 1H), 6.33 (d, 1H), 6.90 (d, 1H), 7.12 (d, 2H), 7.24 (d, 2H), 7.43-7.48 (m, 3H), 7.50 (d, 1H), 7.65 (dd, 1H), 7.76 (d, 2H), 7.94 (t, 1H), 8.34 (d, 1H)

Example 58

2-chloro-N-{(2R)-1-(4-cyanophenyl)-3-[(1-methyl-piperidin-4-yl)amino]propan-2-yl}-5-[5-({[(1R)-1-(4-methylphenyl)ethyl]amino}methyl)-2-furyl]benzamide

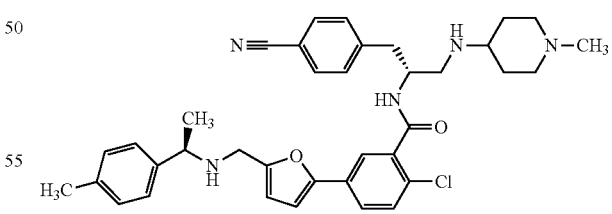

To a stirred solution of Example 53, N-[(2R)-1-amino-3-(4-cyanophenyl)propan-2-yl]-2-chloro-5-[5-({[(1R)-1-(4-methylphenyl)ethyl]amino}methyl)-2-furyl]benzamide, 75 mg (0.14 mmol) and acetic acid, 16 μL (0.28 mmol, 2.0 eq) in THF (2 mL) was added 1-methyl-4-piperidone, 18 mg (0.16 mmol, 1.1 eq). The mixture was stirred at r.t. for 30 min and then sodium triacetoxyborohydride, 45 mg (0.21 mmol, 1.5 eq.) was added. The mixture was stirred at r.t. for 16 h, and then diluted with ethyl acetate (20 mL) and the organic layer was washed successively with aq. sat. sodium hydrogen carbonate, water, brine, dried over sodium sulfate and concentrated. The residue was purified by preparative TLC (eluent: dichloromethane/ammonia 7N in methanol, 97/3) to give the product, 50 mg (56%) as a white solid.

LC-MS (Method 1): $R_t$=2.07 min; MS (ES+): m/z=624 (M+H)$^+$.

$^1$H-NMR (500 MHz, DMSO-d$_6$) δ [ppm]=1.25 (d, 3H and m, overlap, 2H), 1.75 (m, 2H), 1.88 (m, 2H), 2.13 (s, 3H), 2.28 (s, 3H), 2.36 (m, 1H), 2.65-2.70 (m, 4H), 2.79 (dd, 1H), 3.09 (dd, 1H), 3.51 & 3.58 (2 d, AB, 2H), 3.72 (q, 1H), 4.24 (m, 1H), 6.33 (d, 1H), 6.91 (d, 1H), 7.13 (d, 2H), 7.24 (d, 2H), 7.40 (d, 1H), 7.48 (d, 1H), 7.49 (d, 2H), 7.68 (dd, 1H), 7.77 (d, 2H), 8.37 (d, 1H).

The following examples were prepared using the same procedure, from corresponding commercially available starting material as indicated.

| Example No | Starting material | Structure/Name | Analytics |
|---|---|---|---|
| 59 | 1-benzylpiperidin-4-one | N-[(2R)-1-[(1-benzylpiperidin-4-yl)amino]-3-(4-cyanophenyl)propan-2-yl]-2-chloro-5-[5-({[(1R)-1-(4-methylpheny)ethyl]amino}methyl)-2-furyl]benzamide | LC-MS (Method 1): $R_t$ = 2.14 min; MS (ES+): m/z = 700.7 (M + H)$^+$. $^1$H-NMR (500 MHz, DMSO-d$_6$) δ [ppm] = 1.24 (d, 3H), 1.27 (m, 2H), 1.75 (m, 2H), 1.96 (t, 2H), 2.26 (s, 3H), 2.42 (m, 1H), 2.65-2.75 (m, 4H), 2.78 (dd, 1H), 3.08 (dd, 1H), 3.42 (s, 2H), 3.51 & 3.57 (2 d, AB, 2H), 3.70 (q, 1H), 4.22 (m, 1H), 6.31 (d, 1H), 6.90 (d, 1H), 7.11 (d, 2H), 7.21-7.32 (m, 7H), 7.38 (d, 1H), 7.46 (d, 1H), 7.48 (d, 2H), 7.66 (dd, 1H), 7.76 (d, 2H), 8.35 (d, 1H). |
| 60 | Benzaldehyde | N-[(2R)-1-(benzylamino)-3-(4-cyanophenyl)propan-2-yl]-2-chloro-5-[5-({[(1R)-1-(4-methylphenyl)ethyl]amino}methyl)-2-furyl]benzamide | LC-MS (Method 1): $R_t$ = 2.34 min; MS (ES+): m/z = 617 (M + H)$^+$. $^1$H-NMR (500 MHz, DMSO-d$_6$) δ [ppm] = 1.26 (d, 3H), 2.28 (s, 3H), 2.64 (m, 2H), 2.81 (dd, 1H), 3.11 (dd, 1H), 3.58 (m, 2H), 3.74 (m, 3H), 4.35 (m, 1H), 6.33 (br s, 1H), 6.90 (d, 1H), 7.13 (d, 2H), 7.25 (m, 3H), 7.30-7.41 (m, 5H), 7.47 (m, 3H), 7.67 (dd, 1H), 7.76 (d, 2H), 8.39 (d, 1H). |
| 61 | 2-methylpropanal | 2-chloro-N-[(2R)-1-(4-cyanophenyl)-3-(isobutylamino)propan-2-yl]-5-[5-({[(1R)-1-(4-methylphenyl)ethyl]amino}methyl)-2-furyl]benzamide | LC-MS (Method 1): $R_t$ = 2.34 min; MS (ES+): m/z = 583/585 (M + H)$^+$. $^1$H-NMR (500 MHz, DMSO-d$_6$) δ [ppm] = 0.86 (d, 6H), 1.25 (d, 3H), 1.64 (m, 1H), 2.27 (s, 3H), 2.30-2.42 (m, 2H), 2.65 (m, 2H), 2.78 (dd, 1H), 3.07 (dd, 1H), 3.50 & 3.57 (2d, AB, 2H), 3.71 (q, 1H), 4.27 (m, 1H), 6.32 (d, 1H), 6.90 (d, 1H), 7.11 (d, 2H), 7.23 (d, 2H), 7.39 (d, 1H), 7.45 (d, 1H), 7.48 (d, 2H), 7.66 (dd, 1H), 7.76 (d, 2H), 8.36 (d, 1H). |

-continued

| Example No | Starting material | Structure/Name | Analytics |
|---|---|---|---|
| 62 | 1-ethylpiperidin-4-one | 2-chloro-N-{(2R)-1-(4-cyanophenyl)-3-[(1-ethylpiperidin-4-yl)amino]propan-2-yl}-5-[5-({[(1R)-1-(4-methylphenyl)ethyl]amino}methyl)-2-furyl]benzamide | LC-MS (Method 1): $R_t$ = 1.99 min; MS (ES+): m/z = 638/640 (M + H)$^+$. $^1$H-NMR (500 MHz, DMSO-d$_6$) δ [ppm] = 0.97 (t, 3H), 1.22 (m, 2H), 1.25 (d, 3H), 1.61 (br s, 1H), 1.74 (m, 2H), 1.86 (m, 2H), 2.24-2.29 (m, 2H and s, overlap, 3H), 2.39 (m, 1H), 2.68 (d, 2H), 2.75-2.81 (m, 3H), 3.09 (dd, 1H), 3.50 & 3.58 (2d, AB, 2H), 3.71 (q, 1H), 4.22 (m, 1H), 6.31 (d, 1H), 6.90 (d, 1H), 7.12 (d, 2H), 7.23 (d, 2H), 7.39 (d, 1H), 7.47 (d, 1H), 7.48 (d, 2H), 7.66 (dd, 1H), 7.76 (d, 2H), 8.36 (d, 1H). |
| 63 | 1-isobutylpiperidin-4-one | 2-chloro-N-{(2R)-1-(4-cyanophenyl)-3-[(1-isobutylpiperidin-4-yl)amino]propan-2-yl}-5-[5-({[(1R)-1-(4-methylphenyl)ethyl]amino}methyl)-2-furyl]benzamide | LC-MS (Method 1): $R_t$ = 2.02 min; MS (ES+): m/z = 666/668 (M + H)$^+$. $^1$H-NMR (500 MHz, DMSO-d$_6$) δ [ppm] = 0.84 (d, 6H), 1.25 (m, 5H), 1.60-1.75 (m, 4H), 1.85 (t, 2H), 1.98 (d, 2H), 2.28 (s, 3H), 2.38 (m, 1H), 2.68-2.74 (m, 4H), 2.77 (dd, 1H), 3.10 (dd, 1H), 3.50 & 3.58 (2d, AB, 2H), 3.72 (m, 1H), 4.23 (m, 1H), 6.32 (d, 1H), 6.91 (d, 1H), 7.12 (d, 2H), 7.23 (d, 2H), 7.40 (d, 1H), 7.47 (d, 1H), 7.48 (d, 2H), 7.67 (dd, 1H), 7.77 (d, 2H), 8.36 (d, 1H) |
| 64 | tert-butyl 4-oxopiperidine-1-carboxylate | tert-butyl 4-{[(2R)-2-({2-chloro-5-({[(1R)-1-(4-methylphenyl)ethyl]amino}methyl)-2-furyl]benzoyl}amino)-3-(4-cyanophenyl)propyl]amino}piperidine-1-carboxylate | LC-MS (Method 1): $R_t$ = 2.33 min; MS (ES+): m/z = 710 (M + H)$^+$. $^1$H-NMR (500 MHz, DMSO-d$_6$) δ [ppm] = 1.12 (m, 2H), 1.25 (d, 3H), 1.40 (s, 9H), 1.75 (m, 3H), 2.28 (s, 3H), 2.61 (m, 1H), 2.70 (d, 2H), 2.76-2.82 (m, 3H), 3.10 (dd, 1H), 3.50 & 3.58 (2d, AB, 2H), 3.72 (m, 1H), 3.80 (br d, 2H), 4.24 (m, 1H), 6.33 (d, 1H), 6.91 (d, 1H), 7.13 (d, 2H), 7.24 (d, 2H), 7.39 (d, 1H), 7.48 (d, 1H), 7.49 (d, 2H), 7.68 (dd, 1H), 7.77 (d, 2H), 8.37 (d, 1H). |

| Example No | Starting material | Structure/Name | Analytics |
|---|---|---|---|
| 65 | 1-methylpiperidin-3-one | 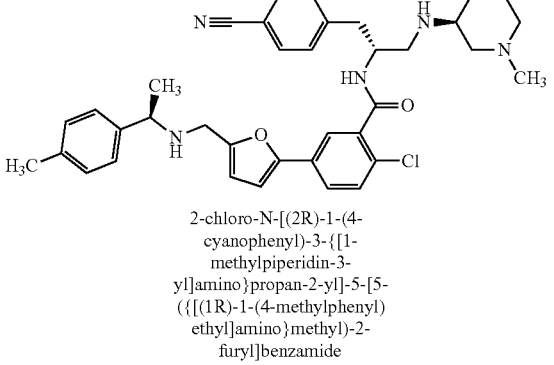<br>2-chloro-N-[(2R)-1-(4-cyanophenyl)-3-{[1-methylpiperidin-3-yl]amino}propan-2-yl]-5-[5-({[(1R)-1-(4-methylphenyl)ethyl]amino}methyl)-2-furyl]benzamide | LC-MS (Method 1): R$_t$ = 2.24 min; MS (ES+): m/z = 624/626 (M + H)$^+$, 506/508 (M + H-118)$^+$<br>$^1$H-NMR (500 MHz, DMSO-d$_6$) δ [ppm] = 1.00 (m, 1H), 1.25 (d, 3H), 1.42 (m, 1H), 1.55-1.78 (m, 4H), 1.85 (m, 1H), 2.11-2.13 (2s, 3H), 2.27 (s, 3H), 2.54-2.75 (m, 4H), 2.78 (dd, 1H), 3.07 (dd, 1H), 3.51 & 3.58 (2d, AB, 2H), 3.71 (q, 1H), 4.20 (m, 1H), 6.32 (d, 1H), 6.90 & 6.91 (2d, 1H), 7.12 (d, 2H), 7.23 (d, 2H), 7.38 & 7.40 (2d, 1H), 7.45-7.50 (m, 3H), 7.66 (dd, 1H), 7.76 (d, 2H), 8.36 & 8.38 (2d, 1H). |
| 66$^{Boc}$ | tert-butyl (1R,5S,6r)-6-formyl-3-azabicyclo[3.1.0]hexane-3-carboxylate [419572-19-3] | 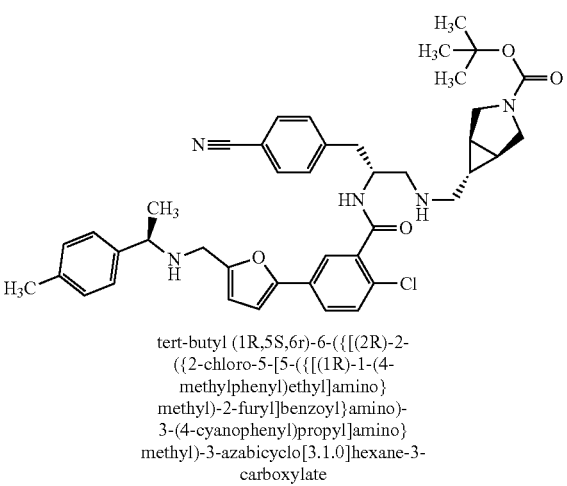 [SMILES: Cc1ccc([C@@H](C)NCc2ccc(-c3ccc(Cl)c(C(=O)N[C@@H](CNC[C@@H]4[C@H]5CN(C(=O)OC(C)(C)C)C[C@@H]45)Cc4ccc(C#N)cc4)c3)o2)cc1]<br>tert-butyl (1R,5S,6r)-6-({[(2R)-2-({2-chloro-5-[5-({[(1R)-1-(4-methylphenyl)ethyl]amino}methyl)-2-furyl]benzoyl}amino)-3-(4-cyanophenyl)propyl]amino}methyl)-3-azabicyclo[3.1.0]hexane-3-carboxylate | LC-MS (Method 1): R$_t$ = 2.50 min; MS (ES+): m/z = 722/724 (M + H)$^+$, 604/606 (M + H)$^+$<br>$^1$H-NMR (500 MHz, DMSO-d$_6$) δ [ppm] = 0.6 (m, 1H), 1.25 (d, 3H), 1.35 (m, 1H), 1.36 (s, 9H), 1.77 (m, 1H), 2.27 (s, 3H), 2.47 (m, 2H), 2.62-2.71 (m, 2H), 2.80 (dd, 1H), 3.06 (dd, 1H), 3.18-3.28 (m, 2H), 3.39 (t, 2H), 3.51 & 3.58 (2d, AB, 2H), 3.71 (q, 1H), 4.27 (m, 1H), 6.32 (d, 1H), 6.91 (d, 1H), 7.12 (d, 2H), 7.24 (d, 2H), 7.40 (d, 1H), 7.45-7.51 (m, 3H), 7.66 (dd, 1H), 7.76 (d, 2H), 8.37 (d, 1H). |

Example 66

N-[(2R)-1-{[(1R,5S,6r)-3-azabicyclo[3.1.0]hex-6-ylmethyl]amino}-3-(4-cyanophenyl)propan-2-yl]-2-chloro-5-[5-({[(1R)-1-(4-methylphenyl)ethyl]amino}methyl)-2-furyl]benzamide

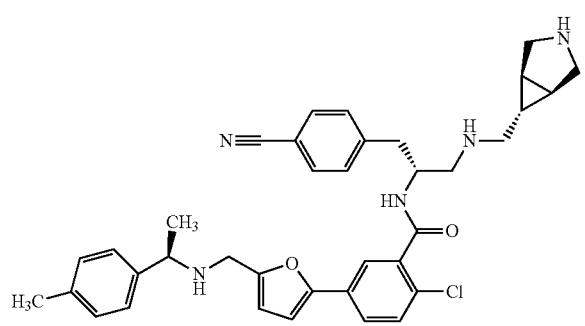 [SMILES: Cc1ccc([C@@H](C)NCc2ccc(-c3ccc(Cl)c(C(=O)N[C@@H](CNC[C@@H]4[C@H]5CNC[C@@H]45)Cc4ccc(C#N)cc4)c3)o2)cc1]

To a stirred solution of, tert-butyl (1R,5S,6r)-6-({[(2R)-2-({2-chloro-5-[5-({[(1R)-1-(4-methylphenyl)ethyl]amino}methyl)-2-furyl]benzoyl}amino)-3-(4-cyanophenyl)propyl]amino}methyl)-3-azabicyclo[3.1.0]hexane-3-carboxylate, 82 mg (0.114 mmol) in dichloromethane (2 mL) was added slowly hydrochloric acid, 0.28 mL (4M in 1,4-dioxane, 1.265 mmol, 10 eq.) at 0° C. and the resulting mixture was stirred at r.t. for 16 h. The reaction mixture was concentrated to dryness. The resulting solid was partitioned between aq. sat. sodium hydrogen carbonate and ethyl acetate. The aqueous phase was extracted with ethyl acetate. The combined organic phase was dried over sodium sulfate and concentrated. The residue was purified by preparative TLC (silica, DCM/ammonia 7N in methanol, 94/6) to give the product, 66 mg (89%) as a beige solid.

LC-MS (Method 1): R$_t$=2.27 min; MS (ES+): m/z=622/624 (M+H)$^+$; 504/506 (M−118+H)$^+$ $^1$H-NMR (500 MHz, DMSO-d$_6$) δ [ppm]=0.8 (m, 1H), 1.12-1.20 (m, 2H), 1.24 (m, 1H), 1.25 (d, 3H), 1.36 (m, 1H), 2.27 (s, 3H), 2.60 (dd, 2H), 2.65-2.68 (m, 2H), 2.75-2.82 (m, 3H), 3.06 (dd, 1H), 3.26-3.31 (m, 2H), 3.51 & 3.58 (2 d, AB, 2H), 3.71 (q, 1H), 4.26 (m, 1H), 6.32 (d, 1H), 6.91 (d, 1H), 7.12 (d, 2H), 7.24 (d, 2H), 7.38 (d, 1H), 7.45-7.51 (m, 3H), 7.66 (dd, 1H), 7.77 (d, 2H), 8.37 (d, 1H).

The following examples were prepared using the same procedure, from corresponding N-Boc intermediates as indicated. The N-Boc intermediates were prepared in analogy to Example 55 and 56, from the corresponding commercially available starting material and Example 53 as indicated.

| Example No | Intermediate | Structure/Name | Analytics |
|---|---|---|---|
| 67 | 64 | 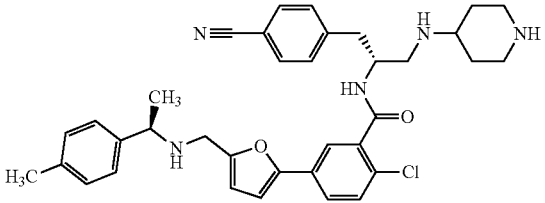<br>2-chloro-N-[(2R)-1-(4-cyanophenyl)-3-(piperidin-4-ylamino)propan-2-yl]-5-[5-({[(1R)-1-(4-methylphenyl)ethyl]amino}methyl)-2-furyl]benzamide | LC-MS (Method 1): $R_t$ = 1.97 min; MS (ES+): m/z = 610/612 (M + H)$^+$.<br>$^1$H-NMR (500 MHz, DMSO-d$_6$) δ [ppm] = 1.10-1.25 (m, 3H), 1.25 (d, 3H), 1.76 (m, 2H), 2.26 (s, 3H), 2.53 (m, overlap with DMSO signal, 1H), 2.68 (d, 2H), 2.77 (dd, 1H), 2.96 (br d, 2H), 3.09 (dd, 1H), 3.35-3.50 (m, 1H), 3.50 & 3.57 (2d, AB, 2H), 3.71 (q, 1H), 4.22 (m, 1H), 6.31 (d, 1H), 6.90 (d, 1H), 7.12 (d, 2H), 7.23 (d, 2H), 7.38 (d, 1H), 7.46 (d, 1H), 7.48 (d, 2H), 7.66 (dd, 1H), 7.76 (d, 2H), 8.37 (d, 1H). |
| 68 | 68$^{Boc}$ | 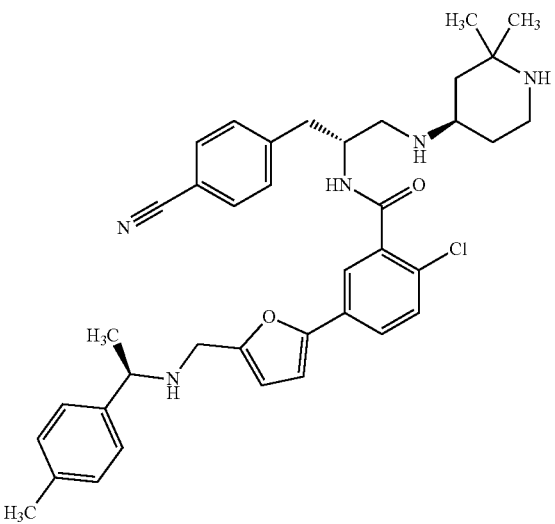<br>2-chloro-N-[(2R)-1-(4-cyanophenyl)-3-{[(4R)-2,2-dimethylpiperidin-4-yl]amino}propan-2-yl]-5-[5-({[(1R)-1-(4-methylphenyl)ethyl]amino}methyl)-2-furyl]benzamide | LC-MS (Method 1): $R_t$ = 2.11 min; MS (ES+): m/z = 638/640 (M + H)$^+$<br>$^1$H-NMR (500 MHz, DMSO-d$_6$) δ [ppm] = 0.85-1.00 (m, 2H), 1.02 (m, 6H), 1.25 (d, 3H), 1.62 (br d, 1H), 1.77 (t, 1H), 2.27 (s, 3H), 2.57-2.83 (m, 6H), 3.07 (m, 1H), 3.51 & 3.58 (2d, AB, 2H), 3.71 (q, 1H), 4.22 (m, 1H), 6.32 (d, 1H), 6.89 (d, 1H), 7.12 (d, 2H), 7.23 (d, 2H), 7.38 (d, 1H), 7.45-7.50 (m, 3H), 7.66 (dd, 1H), 7.76 (d, 2H), 8.34 & 8.35 (2d, 1H, epimer 1 & 2).<br>The product was obtained as a 1/1 mixture of epimers. |

-continued

| Example No | Inter- mediate | Structure/Name | Analytics |
|---|---|---|---|
| 68[Boc] | tert-butyl 2,2-dimethyl-4-oxopiperidine-1-carboxylate | 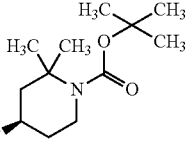<br>tert-butyl rel-(4R)-4-{[(2R)-2-({2-chloro-5-[5-({[(1R)-1-(4-methyl-phenyl)ethyl]amino}methyl)-2-furyl]benzoyl}amino)-3-(4-cyanophenyl)propyl]amino}-2,2-dimethylpiperidine-1-carboxylate | LC-MS (Method 1): $R_t$ = 2.49 min; MS (ES+): m/z = 738/740 (M + H)+.<br>$^1$H-NMR (500 MHz, DMSO-$d_6$) δ [ppm] = 1.15 (m, 1H), 1.24 (s, 3H), 1.26 (d, 3H), 1.33 (m, 2H), 1.40 (s, 9H), 1.44 (s, 3H), 1.65 (m, 1H), 1.87 (m, 1H), 2.28 (s, 3H), 2.65-2.84 (m, 3H), 3.06-3.13 (m, 2H), 3.52 & 3.59 (2d, AB, 2H), 3.65 (m, 1H), 3.72 (q, 1H), 4.24 (m, 1H), 6.32 (d, 1H), 6.91 (d, 1H), 7.13 (d, 2H), 7.24 (d, 2H), 7.40 (br s, 1H), 7.48 (d, 1H), 7.49 (d, 2H), 7.67 (br d, 1H), 7.77 (d, 2H), 8.37 & 8.38 (2d, 1H, epimer 1 & 2). The product was obtained as a 1/1 mixture of epimers. |
| 69 | 69[Boc] | 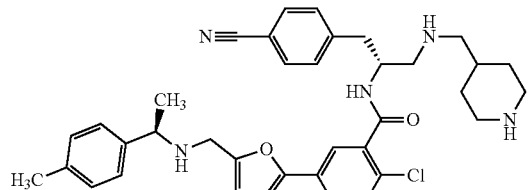<br>2-chloro-N-{(2R)-1-(4-cyanophenyl)-3-[(piperidin-4-ylmethyl)amino]propan-2-yl}-5-[5-({[(1R)-1-(4-methylphenyl)ethyl]amino}methyl)-2-furyl]benzamide | LC-MS (Method 1): $R_t$ = 2.11 min; MS (ES+): m/z = 624/626 (M + H)+.<br>$^1$H-NMR (500 MHz, DMSO-$d_6$) δ [ppm] = 1.00 (m, 2H), 1.23 (m, 1H), 1.24 (d, 3H), 1.38 (m, 1H), 1.61 (m, 2H), 2.27 (s, 3H), 2.34-2.45 (m, 4H), 2.63 (m, 1H), 2.77 (dd, 1H), 2.88 (br d, 2H), 3.06 (dd, 1H), 3.51 & 3.58 (2d, AB, 2H), 3.71 (q, 1H), 4.26 (m, 1H), 6.32 (d, 1H), 6.89 (d, 1H), 7.12 (d, 2H), 7.23 (d, 2H), 7.38 (d, 1H), 7.46 (d, 1H), 7.47 (d, 2H), 7.66 (dd, 1H), 7.76 (d, 2H), 8.35 (d, 1H). |
| 69[Boc] | tert-butyl 4-formylpiperidine-1-carboxylate | 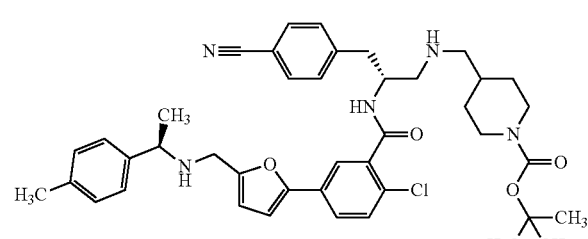<br>tert-butyl 4-({[(2R)-2-({2-chloro-5-[5-({[(1R)-1-(4-methylphenyl)ethyl]amino}methyl)-2-furyl]benzoyl}amino)-3-(4-cyanophenyl)propyl]amino}methyl)piperidine-1-carboxylate | LC-MS (Method 1): $R_t$ = 2.59 min; MS (ES+): m/z = 724/726 (M + H)+. |

| Example No | Intermediate | Structure/Name | Analytics |
|---|---|---|---|
| 70 | 70[Boc] | 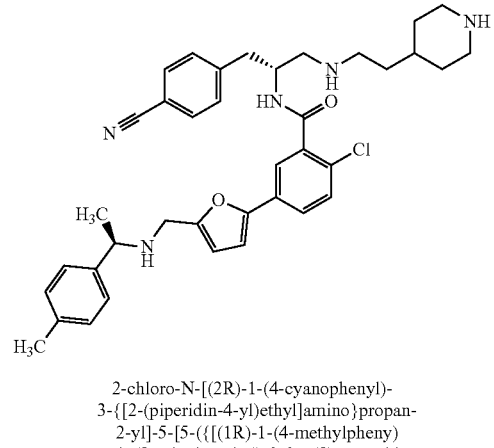<br>2-chloro-N-[(2R)-1-(4-cyanophenyl)-3-{[2-(piperidin-4-yl)ethyl]amino}propan-2-yl]-5-[5-({[(1R)-1-(4-methylpheny)ethyl]amino}methyl)-2-furyl]benzamide | LC-MS (Method 1): $R_t$ = 2.06 min; MS (ES+): m/z = 638/640 (M + H)+<br>¹H-NMR (500 MHz, DMSO-d₆) δ [ppm] = 1.18 (m, 2H), 1.25 (d, 3H), 1.34 (q, 2H), 1.55 (m, 1H), 1.73 (br d, 2H), 2.27 (s, 3H), 2.50-2.72 (m, 6H), 2.77 (dd, 1H), 3.07 (dd, 1H), 3.12 (br d, 2H), 3.51 & 3.58 (2d, AB, 2H), 3.71 (q, 1H), 4.27 (m, 1H), 6.32 (d, 1H), 6.90 (d, 1H), 7.12 (d, 2H), 7.24 (d, 2H), 7.38 (d, 1H), 7.46 (d, 1H), 7.48 (d, 2H), 7.66 (dd, 1H), 7.77 (d, 2H), 8.36 (d, 1H). |
| 70[Boc] | tert-butyl 4-(2-oxoethyl)piperidine-1-carboxylate | 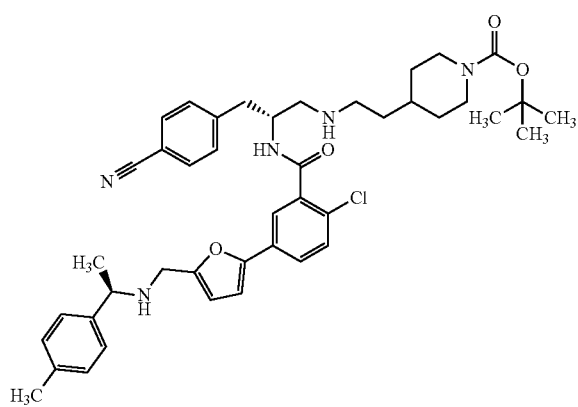<br>tert-butyl 4-(2-{[(2R)-2-({2-chloro-5-[5-({[(1R)-1-(4-methyl-phenyl)ethyl]amino}methyl)-2-furyl]benzoyl}amino)-3-(4-cyanophenyl)propyl]amino}ethyl)piperidine-1-carboxylate | LC-MS (Method 1): $R_t$ = 2.71 min; MS (ES+): m/z = 738/740 (M + H)+. |
| 71 | 71[Boc]<br>Diastereomer 1 | 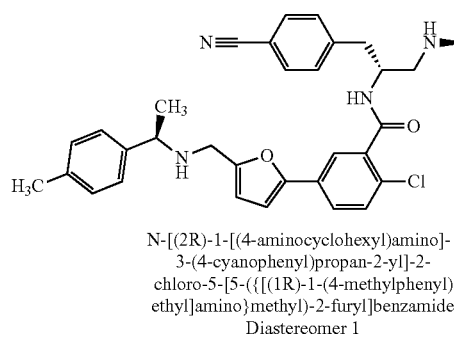<br>N-[(2R)-1-[(4-aminocyclohexyl)amino]-3-(4-cyanophenyl)propan-2-yl]-2-chloro-5-[5-({[(1R)-1-(4-methylphenyl)ethyl]amino}methyl)-2-furyl]benzamide<br>Diastereomer 1 | LC-MS (Method 1): $R_t$ = 2.10 min; MS (ES+): m/z = 624/626 (M + H)+; 506/508 (M − 118 + H)+<br>¹H-NMR (500 MHz, DMSO-d₆) δ [ppm] = 1.24 (m, 1H), 1.25 (d, 3H), 1.38-1.49 (m, 6H), 1.50-1.60 (m, 2H), 2.27 (s, 3H), 2.55-2.75 (m, 5H), 2.79 (dd, 1H), 3.11 (dd, 1H), 3.51 & 3.58 (2d, AB, 2H), 3.70 (q, 1H), 4.24 (m, 1 H), 6.32 (d, 1H), 6.90 (d, 1H), 7.12 (d, 2H), 7.24 (d, 2H), 7.37 (d, 1H), 7.45-7.51 (m, 3H), 7.66 (dd, 1H), 7.77 (d, 2H), 8.38 (d, 1H) |

| Example No | Intermediate | Structure/Name | Analytics |
|---|---|---|---|
| 72 | 72^Boc Diastereomer 2 | <br>N-[(2R)-1-[(4-aminocyclohexyl)amino]-3-(4-cyanophenyl)propan-2-yl]-2-chloro-5-[5-({[(1R)-1-(4-methylphenyl)ethyl]amino}methyl)-2-furyl]benzamide Diastereomer 2 | LC-MS (Method 1): $R_t$ = 2.14 min; MS (ES+): m/z = 624/626 (M + H)$^+$; 506/508 (M − 118 + H)$^+$<br>$^1$H-NMR (500 MHz, DMSO-d$_6$) δ [ppm] = 1.00 (m, 4H), 1.25 (d, 3H), 1.71 (m, 2H), 1.80 (m, 2H), 2.27 (s, 3H), 2.36 (m, 1H), 2.47 (m, 1H), 2.66 (m, 2H), 2.77 (dd, 1H), 3.07 (dd, 1H), 3.50 & 3.58 (2d, AB, 2H), 3.71 (q, 1H), 4.22 (m, 1H), 6.32 (d, 1H), 6.90 (d, 1H), 7.12 (d, 2H), 7.23 (d, 2H), 7.38 (d, 1H), 7.46 (d, 1H), 7.48 (d, 2H), 7.66 (dd, 1H), 7.76 (d, 2H), 8.35 (d, 1H). |
| 71/72^Boc | tert-butyl (4-oxocyclohexyl)carbamate | 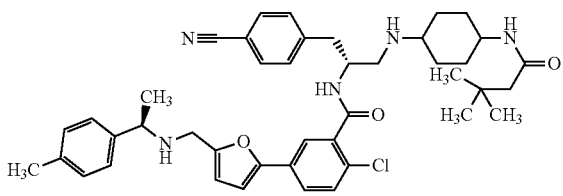<br>tert-butyl (4-{[(2R)-2-({2-chloro-5-[5-({[(1R)-1-(4-methylpheny)ethyl]amino}methyl)-2-furyl]benzoyl}amino)-3-(4-cyanophenyl)propyl]amino}cyclohexyl)carbamate | Two isomers were isolated (cis and trans). The relative stereochemistry was not assigned.<br>Diastereomer 1:<br>LC-MS (Method 1): $R_t$ = 2.45 min; MS (ES+): m/z = 724/726 (M + H)$^+$, 606/608 (M − 118 + H)$^+$<br>$^1$H-NMR (500 MHz, DMSO-d$_6$) δ [ppm] = 1.25 (d, 3H), 1.37 (s, 9H), 1.39-1.64 (m, 9H), 2.27 (s, 3H), 2.56-2.70 (m, 3H), 2.78 (dd, 1H), 3.12 (dd, 1H), 3.51 & 3.58 (2d, AB, 2H), 3.71 (m, 1H), 4.24 (m, 1H), 6.32 (d, 1H), 6.64 (br d, 1H), 6.90 (d, 1H), 7.12 (d, 2H), 7.24 (d, 2H), 7.38 (d, 1H), 7.45-7.51 (m, 3H), 7.66 (dd, 1H), 7.77 (d, 2H), 8.37 (d, 1H)<br>Diastereomer 2:<br>LC-MS (Method 1): $R_t$ = 2.40 min; MS (ES+): m/z = 724/726 (M + H)$^+$, 606/608 (M − 118 + H)$^+$<br>$^1$H-NMR (500 MHz, DMSO-d$_6$) δ [ppm] = 0.96-1.09 (m, 2H), 1.10-1.20 (m, 2H), 1.25 (d, 3H), 1.37 (s, 9H), 1.67-1.90 (m, 4H), 2.27 (s, 3H), 2.33 (m, 1H), 2.64-2.71 (m, 2H), 2.77 (dd, 1H), 3.08 (dd, 1H), 3.16 (m, 1H), 3.51 & 3.58 (2d, AB, 2H), 3.71 (m, 1H), 4.22 (m, 1H), 6.32 (d, 1H), 6.66 (br d, 1H), 6.90 (d, 1H), 7.12 (d, 2H), 7.24 (d, 2H), 7.38 (d, 1H), 7.45-7.51 (m, 3H), 7.66 (dd, 1H), 7.77 (d, 2H), 8.36 (d, 1H) |

| Example No | Intermediate | Structure/Name | Analytics |
|---|---|---|---|
| 73 | 73$^{Boc}$ | 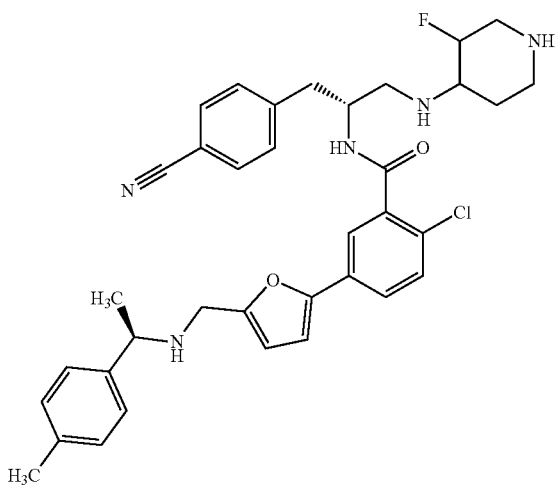<br>2-chloro-N-[(2R)-1-(4-cyanophenyl)-3-{[3-fluoropiperidin-4-yl]amino}propan-2-yl]-5-[5-({[(1R)-1-(4-methylphenyl)ethyl]amino}methyl)-2-furyl]benzamide | LC-MS (Method 1): R$_t$ = 2.17 min; MS (ES+): m/z = 628/630 (M + H)$^+$; 510/512 (M − 118 + H)$^+$<br>$^1$H-NMR (500 MHz, DMSO-d$_6$) δ [ppm] = 1.25 (d, 3H), 1.32-1.43 (m, 1H), 1.55-1.66 (m, 1H), 2.27 (s, 3H), 2.38-2.92 (m, 7H), 3.03-3.13 (m, 2H), 3.51 & 3.58 (2d, AB, 2H), 3.71 (q, 1H), 4.24 (m, 1H), 4.56 & 4.67 (2d, 1H), 6.32 (d, 1H), 6.90 (d, 1H), 7.12 (d, 2H), 7.24 (d, 2H), 7.38 (t, 1H), 7.45-7.51 (m, 3H), 7.66 (d, 1H), 7.76 (d, 2H), 8.40 (d, 1H). The product was obtained as a 1/1 mixture of epimers. |
| 73$^{Boc}$ | tert-butyl 3-fluoro-4-oxopiperidine-1-carboxylate [211108-50-8] | 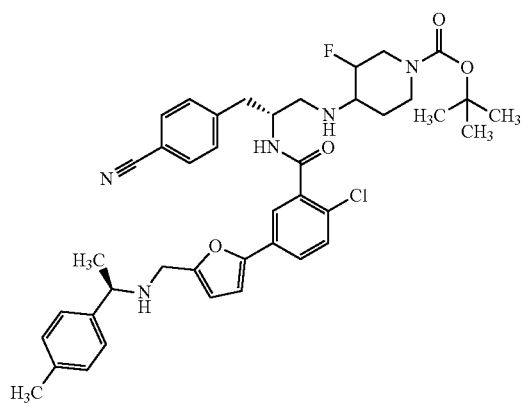<br>tert-butyl 4-[[(2R)-2-[[2-chloro-5-[5-[[[(1R)-1-(p-tolyl)ethyl]amino]methyl]-2-furyl]benzoyl]amino]-3-(4-cyanophenyl)propyl]amino]-3-fluoro-piperidine-1-carboxylate | LC-MS (Method 1): R$_t$ = 2.41 min; MS (ES+): m/z = 728/730 (M + H)$^+$.<br>$^1$H-NMR (500 MHz, DMSO-d$_6$) δ [ppm] = 1.25 (d, 3H), 1.39 (s, 9H), 1.68 (m, 1H), 1.79 (m, 1H), 2.27 (s, 3H), 2.62-2.86 (m, 5H), 3.05-3.19 (m, 2H), 3.51 & 3.58 (2d, AB, 2H), 3.71 (m, 1H), 3.91 (m, 1H), 4.13 (m, 1H), 4.24 (m, 1H), 4.69 & 4.80 (2d, 1H), 6.32 (d, 1H), 6.91 (d, 1H), 7.12 (d, 2H), 7.24 (d, 2H), 7.38 (s, 1H), 7.45-7.51 (m, 3H), 7.67 (d, 1H), 7.77 (d, 2H), 8.40 (d, 1H). The product was obtained as a 1/1 mixture of epimers. |

Example 74

N-[(2R)-1-amino-3-(4-cyanophenyl)propan-2-yl]-2-chloro-5-{5-[({2-[4-(trifluoro-methyl)phenyl]propan-2-yl}amino)methyl]-2-furyl}benzamide

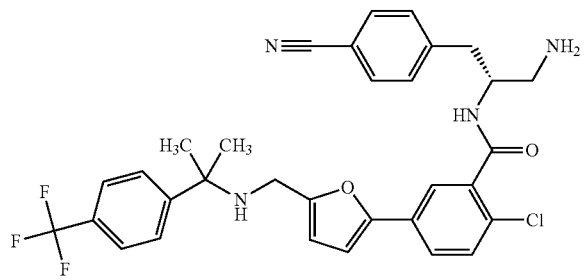 [SMILES: CC(C)(NCc1ccc(-c2ccc(Cl)c(C(=O)N[C@@H](CN)Cc3ccc(C#N)cc3)c2)o1)c1ccc(C(F)(F)F)cc1]

2-chloro-N-[(2R)-1-(4-cyanophenyl)-3-(1,3-dioxo-1,3-dihydro-2H-isoindol-2-yl)-propan-2-yl]-5-{5-[({2-[4-trifluoromethyl)phenyl]propan-2-}amino)methyl]-2-furyl}benzamide

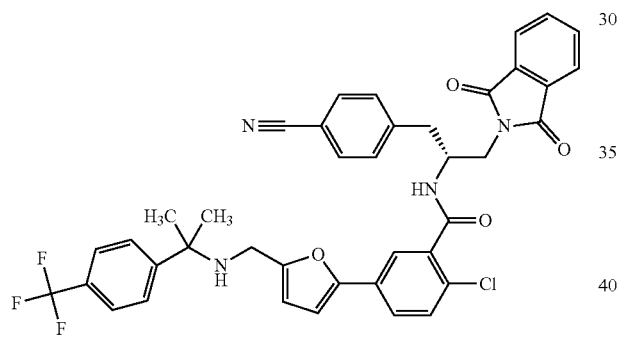

A suspension of intermediate 4A, 2-chloro-5-{5-[({2-[4-(trifluoromethyl)-phenyl]propan-2-yl}amino)methyl]-2-furyl}benzoic acid, 75 mg (0.17 mmol) in acetonitrile (2 mL) was treated with triethylamine, 48 µL (0.34 mmol) and TBTU, 83 mg (0.26 mmol). The orange solution was then stirred at r.t. for 45 minutes before addition of intermediate 52B, 4-[(2R)-2-amino-3-(1,3-dioxo-1,3-dihydro-2H-isoindol-2-yl)propyl]benzonitrile hydrochloride (1:1), 88 mg (0.26 mmol). The reaction medium was stirred at r.t. for 17 h. The reaction medium was concentrated to dryness. The residue was taken up in dichloromethane and washed with aq. sat. bicarbonate solution, aq. 1 N hydrochloric acid solution and water before being dried over sodium sulfate, filtered and concentrated. The residue was purified by preparative TLC (eluent: dichloromethane/ethyl acetate, 1/0 to 6/4) to afford the product, 77 mg (53%) as an orange solid.

LC-MS (Method 1): $R_t$=2.87 min; MS (ES+) m/z=725/727 (M+H)$^+$ $^1$H-NMR (500 MHz, DMSO-d6) δ [ppm]=1.48 (s, 6H), 2.87 (dd, 1H), 3.14 (dd, 1H), 3.51 (s, 2H), 3.79-3.87 (m, 2H), 4.59 (m, 1H), 6.39 (d, 1H), 6.84 (d, 1H), 7.29 (d, 1H), 7.36 (d, 1H), 7.50 (d, 2H), 7.61 (dd, 1H), 7.68 (d, 2H), 7.75 (d, 2H), 7.78-7.80 (m, 4H), 7.86-7.88 (m, 2H), 8.52 (d, 1H).

N-[(2R)-1-amino-3-4-cyanophenyl)propan-2-yl]-2-chloro-5-{5-[({2-[4-(trifluoro-methyl)phenyl]propan-2-yl}amino)methyl]-2-furyl}benzamide To a stirred solution of 2-chloro-N-[(2R)-1-(4-cyanophenyl)-3-(1,3-dioxo-1,3-dihydro-2H-isoindol-2-yl)propan-2-yl]-5-{5-[({2-[4-(trifluoromethyl)phenyl]propan-2-yl}-amino)methyl]-2-furyl}benzamide, 75 mg (0.10 mmol) in absolute ethanol (1.7 mL) was added hydrazine, 0.52 mL (1M in THF, 0.52 mmol, 5 eq.). The resulting solution was stirred at 70° C. for 3 h. The reaction medium (yellow suspension) was filtered and rinsed with ethyl acetate. The filtrate was concentrated and the residue obtained (60 mg) was purified by preparative TLC on silica (dichloromethane/ammonia 7N in methanol, 95/5) to give the product, 36 mg (57%) as an off white solid.

LC-MS (Method 1): $R_t$=0.46 & 2.25 min; MS (ES+): m/z=595/597 (M+H)$^+$ $^1$H-NMR (500 MHz, DMSO-d6) δ [ppm]=1.46 (s, 6H), 1.84 (br s, 2H), 2.67 (d, 2H), 2.77 (dd, 2H), 3.05 (dd, 1H), 3.47 (s, 2H), 4.09-4.13 (m, 1H), 6.35 (d, 1H), 6.90 (d, 1H), 7.43 (d, 1H), 7.46-7.49 (m, 3H), 7.65-7.68 (m, 3H), 7.75-7.78 (m, 4H), 8.35 (d, 1H).

Example 75

N-[(2R)-1-amino-3-(4-cyanophenyl)propan-2-yl]-2-chloro-5-{5-[({(1R)-1-1-[4-(trifluoromethyl)phenyl]ethyl}amino)methyl]-2-furyl}benzamide

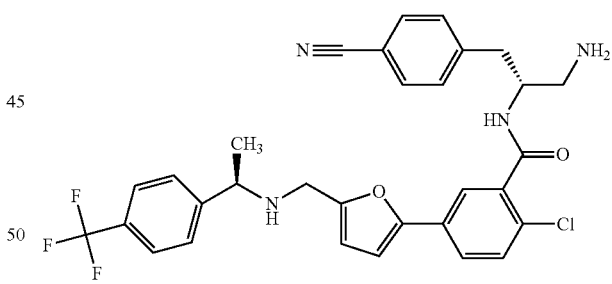

Obtained through the same sequence as described for example 74, starting from (1R)-1-[4-(trifluoromethyl)phenyl]ethylamine in the synthesis of intermediate 4A.

LC-MS (Method 1): $R_t$=2.24 min; MS (ES+): m/z=581/583 (M+H)$^+$ $^1$H-NMR (500 MHz, CD$_3$OD) δ [ppm]=1.40 (d, 3H), 2.79-2.93 (m, 3H), 3.11 (dd, 1H), 3.65 & 3.69 (2d, AB, 2H), 3.92 (q, 1H), 4.37-4.43 (m, 1H), 6.29 (d, 1H), 6.71 (d, 1H), 7.42 (d, 1H), 7.46 (d, 1H), 7.50 (d, 2H), 7.55 (d, 2H), 7.62 (d, 2H), 7.67 (m, 3H).

Example 76

Cis-chloro-N-[4-(4-cyanophenyl)piperidin-3-yl]-5-[5-({[(1R)-1-(4-methylphenyl)-ethyl]amino}methyl)-2-furyl]benzamide

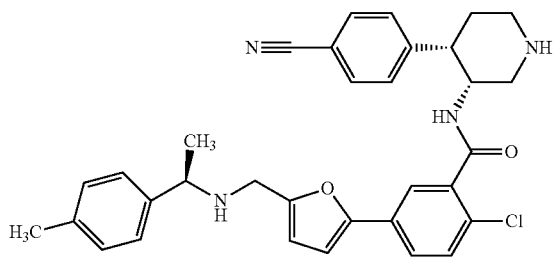 [SMILES: Cc1ccc([C@@H](C)NCc2ccc(-c3ccc(Cl)c(C(=O)N[C@H]4CNCC[C@H]4c4ccc(C#N)cc4)c3)o2)cc1]

Tert-butyl 6-(4-cyanophenyl)-7-oxa-3-azabicyclo[4.1.0]heptane-3-carboxylate

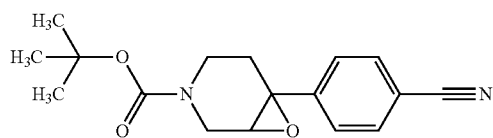 [SMILES: CC(C)(C)OC(=O)N1CCC2(c3ccc(C#N)cc3)OC2C1]

To a cooled (0° C.) solution of tert-butyl 4-(4-cyanophenyl)-3,6-dihydropyridine-1(2H)-carboxylate, 498 mg (1.75 mmol) in dichloromethane (8 mL) was added m-chloroperoxybenzoic acid, 647 mg (2.63 mmol, 1.5 eq.). The reaction mixture was stirred at r.t. overnight. A mixture of aqueous saturated sodium thiosulfate solution and aqueous saturated sodium hydrogen carbonate solution was added to the mixture. After 20 min stirring, the phases were separated and the aqueous phase was extracted with dichloromethane. The combined organics were washed with water, brine, dried over sodium sulfate, filtered and concentrated to dryness. The oily residue (560 mg) was purified by chromatography on silica gel (40 g column, cyclohexane/ethyl acetate: 95/5 to 60/40) to provide the pure epoxide, 400 mg (72%) as a light yellow oil.

LC-MS (Method 1): $R_t$=3.53 min; MS (ES+) m/z=245 (M+H−56)$^+$, 201 (M+H−Boc)$^+$ $^1$H-NMR (500 MHz, CDCl$_3$) δ [ppm]=1.48 (s, 9H), 2.15 (br d, 1H), 2.41-2.50 (m, 1H), 3.13-3.21 (m, 2H), 3.68 (br d, 1H), 3.79 (br s, 1H), 3.97-4.16 (m, 1H), 7.47 (d, 2H), 7.67 (d, 2H)

$R_f$=0.46 (cyclohexane/ettyl acetate: 70/30)

Tert-butyl 4-(4-cyanophenyl)-3-hydroxypiperidine-1-carboxylate

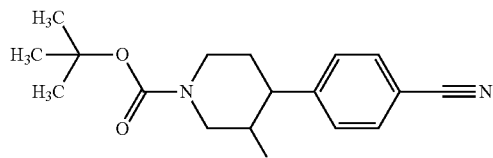

A solution of tert-butyl (1R,6R)-6-(4-cyanophenyl)-7-oxa-3-azabicyclo[4.1.0]heptane-3-carboxylate, 400 mg (1.33 mmol) in methanol (25 mL) and triethylamine, 1.48 mL (10.65 mmol, 8.0 eq.) was passed through a 10% w/w Pd/C cartridge on a H-Cube apparatus (pH2=10 bars, flow=0.5 mL/min, 25° C.). The reaction mixture was concentrated under reduced pressure to give the product, 390 mg (97%) as an off-white solid.

LC-MS (Method 1): $R_t$=3.23 min; MS (ES+): m/z=247 (M+H-56)$^+$ $^1$H-NMR (500 MHz, CDCl$_3$) δ [ppm]=1.48 (s, 9H), 1.63 (brd, 2H), 2.19-2.30 (m, 1H), 2.79-2.89 (m, 2H), 3.02 (d, 1H), 3.98 (s, 1H), 4.31 (br d, 2H), 7.41 (d, 2H), 7.63 (dd, 2H)

$R_f$=0.26 (cyclohexane/ethyl acetate: 70/30)

Tert-butyl 4-(4-cyanophenyl)-3-oxopiperidine-1-carboxylate

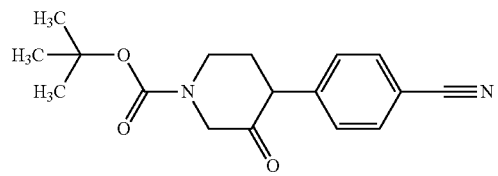 [SMILES: CC(C)(C)OC(=O)N1CCC(c2ccc(C#N)cc2)C(=O)C1]

To a solution of tert-butyl 4-(4-cyanophenyl)-3-hydroxypiperidine-1-carboxylate, 500 mg (1.65 mmol) in dichloromethane (32 mL) was added Dess-Martin periodinane, 842 mg (1.98 mmol, 1.2 eq). The reaction mixture was stirred at r.t. for 2.5 h. The heterogeneous reaction was treated with a mixture of aqueous saturated sodium thiosulfate solution and aqueous saturated sodium hydrogen carbonate solution. After stirring for 20 min, the phases were separated and the aqueous phase was extracted with dichloromethane (4×), dried over sodium sulfate, filtered and concentrated to dryness. The oily residue was purified by chromatography on silica gel (column 12 g, cyclohexane/ethyl acetate: 95/5 to 40/60) to provide the product, 355 mg (68%) as a yellow oil.

LC-MS (Method 1): $R_t$=3.09 & 3.35 min; MS (ES+): m/z=301 (M+H)$^+$.

$^1$H-NMR (500 MHz, CDCl$_3$) δ [ppm]=1.49 (s, 9H), 2.17-2.27 (m, 1H), 2.29-2.37 (m, 1H), 3.48-3.58 (m, 1H), 3.71 (dd, 1H), 3.95-4.13 (m, 2H), 4.26 (d, 1H), 7.25 (d, 2H), 7.65 (d, 2H).

Tert-butyl 3-amino-4-(4-cyanophenyl)piperidine-1-carboxylate

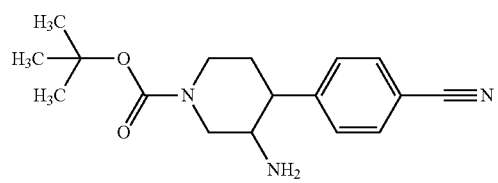 [SMILES: CC(C)(C)OC(=O)N1CCC(c2ccc(C#N)cc2)C(N)C1]

Under argon, tert-butyl 4-(4-cyanophenyl)-3-oxopiperidine-1-carboxylate, 150 mg (0.50 mmol) was dissolved in anhydrous methanol, 5 mL, and cooled at 0° C. Ammonium acetate, 385 mg (dried by azeotropic evaporation with toluene, 5.0 mmol, 10 eq.) was added. The resulting mixture was stirred at 0° C. 30 min, then sodium cyanoborohydride, 47 mg (0.75 mmol, 1.5 eq.) was added and the mixture stirred at r.t. for 5 h and then at 50° C. for 2 h. The reaction mixture was then stored at −20° C. for 3 days. The mixture was concentrated, the residue partitioned between ethyl acetate and aq. 1M sodium hydroxide solution. The aqueous phase was extracted using ethyl acetate. The combined organic phases were concentrated, the residue was partitioned between MTBE and a 0.5 N hydrochloric acid solution. The phase were separated and the aqueous phase was extracted with MTBE. The acidic solution was then made basic using 2N sodium hydroxide, and extracted using ethyl acetate. The organic phase obtained was dried over sodium sulfate and concentrated to give the crude expected amine, 65 mg (39%). The crude product was used without further purification.

LC-MS (Method 1): $R_t$=2.10 & 2.21 min; MS (ES+): m/z=302 (M+H)$^+$, 246 (M+H−tBu)+

Tert-butyl 3-({2-chloro-5-[5-({[(1R)-1-(4-methyl-phenyl)ethyl]amino}methyl-2-furyl]-benzoyl}amino)-4-(4-cyanophenyl)piperidine-1-carboxylate

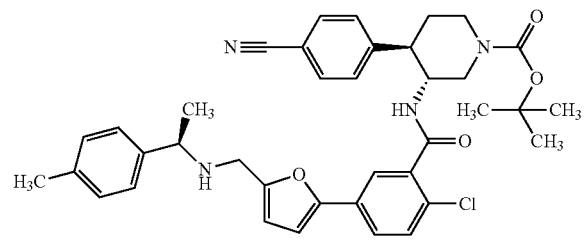 [SMILES: Cc1ccc([C@@H](C)NCc2ccc(-c3ccc(Cl)c(C(=O)N[C@H]4CN(C(=O)OC(C)(C)C)CC[C@@H]4c4ccc(C#N)cc4)c3)o2)cc1]

To a stirred solution of intermediate 1A, 2-chloro-5-[5-({[(1R)-1-(4-methylphenyl)ethyl]amino}methyl-2-furyl] benzoic acid, 75 mg (0.203 mmol) in tetrahydrofuran (2.0 mL) were added TBTU, 65 mg (0.203 mmol, 1 eq.) and triethylamine, 0.11 mL (0.811 mmol, 4 eq.) at r.t. After 20 min, tert-butyl 3-amino-4-(4-cyanophenyl)piperidine-1-carboxylate (mixture of cis and trans isomers), 64 mg (0.213 mmol, 1.05 eq.) was added and the resulting mixture was stirred at r.t. for 16 h. Most of the solvent was removed under reduced pressure and the residue was dissolved in ethyl acetate (30 mL). The organic layer was washed successively with aq. sat. sodium hydrogen carbonate, water, brine, dried over sodium sulfate and concentrated. The residue (142 mg) was purified by preparative TLC (eluent: dichloromethane/methanol, 97/3). The product obtained was contaminated with residual tetramethylurea, thus it was taken up in MTBE (20 mL) and washed with a 1/1 mixture of aq. sat. sodium hydrogen carbonate and water (4×10 mL), then with brine, dried over sodium sulfate, filtered an concentrated to give the desired product, 70 mg (51%) as an off-white solid. The product was obtained as a mixture of cis and trans stereoisomers. $^1$H-NMR analysis showed a 85/15 ratio of cis/trans stereoisomers.

LC-MS (Method 1): $R_t$=2.78 min; MS (ES+): m/z=653/655 (M+H)$^+$ $^1$H-NMR (500 MHz, DMSO-d6) δ [ppm]=1.25 (d, 3H), 1.35 (m, 1H), 1.45 (s, 9H), 1.64-1.76 (m, 1H), 1.78-1.85 (m, 1H), 2.27 (s, 3H), 2.74-2.94 (m, 2H), 3.50 & 3.57 (2d, AB, 2H), 3.71 (m, 1H), 4.00-4.15 (m, 2H), 4.25 (m, 1H), 6.30 (t, 1H), 6.86 (d, 1H), 7.13 (d, 2H), 7.21 (t, 1H), 7.24 (d, 2H), 7.40 (d, 1H), 7.51 (d, 2H), 7.62 (dd, 1H), 7.77 (dd, 2H), 8.44 (d, 1H).

Trans-chloro-N-[4-(4-cyanophenyl)piperidin-3-yl]-5-[5-({[(1R)-1-(4-methylphenyl)-ethyl] amino}methyl)-2-furyl]benzamide and cis-chloro-N-[4-(4-cyanophenyl)piperidin-3-yl]-5-[5-({[(1R)-1-(4-methylphenyl)-ethyl]amino}methyl)-2-furyl] benzamide To a stirred solution of tert-butyl 3-({2-chloro-5-[5-({[(1R)-1-(4-methylphenyl)ethyl]-amino}methyl)-2-furyl] benzoyl}amino)-4-(4-cyanophenyl)piperidine-1-carboxylate, 70 mg (0.107 mmol) in dichloromethane (3 mL) was added slowly hydrochloric acid, 0.27 mL (4M in 1,4-dioxane, 1.07 mmol, 10 eq.) at 0° C. and the resulting mixture was stirred at r.t. for 16 h. The reaction mixture was concentrated to dryness. The resulting solid was partitioned between aq. sat. sodium hydrogen carbonate and ethyl acetate. The aqueous phase was extracted with ethyl acetate (4×). The combined organic phases were dried over sodium sulfate and concentrated. The residue was purified by preparative TLC (silica, DCM/ammonia 7N in methanol, 96/4) to give the trans isomer, 36 mg (60%, 1/1 mixture of stereoisomers) as an off-white solid.

LC-MS (Method 1): $R_t$=2.15 min; MS (ES+): m/z=553/555 (M+H); 435/437 (M−118+H)$^+$ $^1$H-NMR (500 MHz, DMSO-d$_6$) δ [ppm]=1.25 (d, 3H), 1.59-1.70 (m, 1H), 1.72-1.79 (m, 1H), 2.27 (s, 3H), 2.43 (t, 1H), 2.50-2.56 (m, 1H), 2.79 (td, 1H), 2.98 (br d, 1H), 3.15 (dd, 1H), 3.50 & 3.57 (2 d, AB, 2H), 3.70 (quint, 1H), 4.10 (m, 1H), 6.30 (app t, 1H), 6.84 (d, 1H), 7.12 (d, 2H), 7.16 (d, 1H), 7.23 (d, 2H), 7.39 (d, 1H), 7.48 (app dd, 2H), 7.61 (app dd, 1H), 7.77 (app dd, 2H), 8.28 (d, 1H)

and the cis isomer, 3.3 mg (5%, 1/1 mixture of stereoisomers), as an off-white solid, LC-MS (Method 1): $R_t$=2.22 min; MS (ES+): m/z=553/555 (M+H)$^+$; 435/437 (M−118+H)$^+$, $^1$H-NMR (500 MHz, DMSO-d$_6$) δ [ppm]=1.25 (d, 3H), 1.50-1.56 (m, 1H), 2.07-2.19 (m, 1H), 2.26 (s, 3H), 2.57-2.62 (m, 1H), 2.89-3.99 (m, 2H), 3.03-3.08 (br d, 1H), 3.16 (dt, 1H), 3.53 & 3.60 (2 d, AB, 2H), 3.72 (quint, 1H), 4.36 (m, 1H), 6.32 (app t, 1H), 6.89 (app dd, 1H), 7.12 (d, 2H), 7.24 (d, 2H), 7.27 (app t, 1H), 7.43 (d, 1H), 7.51 (d, 2H), 7.64 (m, 1H), 7.77 (app dd, 2H), 8.39 (app dd, 1H).

2D NMR COSY analysis allowed to assign the cis stereochemistry thanks to the multiplicity and $^3$J coupling constant of proton signals on cyclohexane ring especially proton on the same C as phenyl group (HC-Ph):

trans isomer: δ=2.79 ppm=td, $^3$J=12.8 Hz, 4.6 Hz, two axial-axial J.

cis-isomer: δ=3.16 ppm, dt, $^3$J=13.3 Hz, 3.6 Hz, one axial-axial J.

Example 77

2-chloro-N-[(2R)-1-(4-cyanophenyl)-3-hydroxypropan-2-yl]-3-fluoro-5-[5-({[(1R)-1-(4-methylphenyl)ethyl]amino}methyl)-2-furyl]benzamide

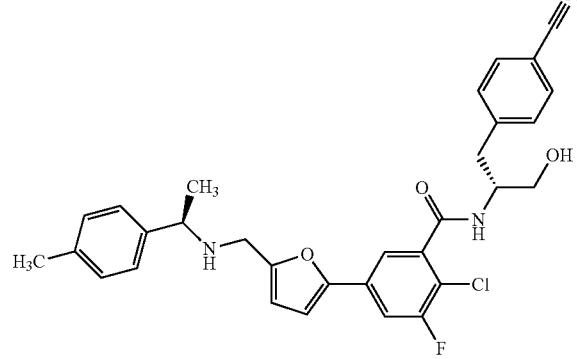

To a stirred solution of intermediate 3A, 2-chloro-3-fluoro-5-[5-({[(1R)-1-(4-methylphenyl)ethyl]amino}methyl)-2-furyl]benzoic acid, 42 mg (0.11 mmol) in tetrahydrofuran (3 mL) were added TBTU, 38 mg (0.12 mmol, 1.1 eq.) and triethylamine, 0.045 mL (0.33 mmol, 3 eq.) at r.t. After 20 min, 15B, 4-[(2R)-2-amino-3-hydroxypropyl]benzonitrile hydrochloride (1:1), 21 mg (0.12 mmol, 1.1 eq.) was added and the resulting mixture was stirred at r.t. for 16 h. Most of the solvent was removed under reduced pressure and the residue was dissolved in ethyl acetate (30 mL). The organic layer was washed successively with aq. sat. sodium hydrogen carbonate, water, brine, dried over sodium sulfate and concentrated. The residue was purified by preparative TLC (eluent: dichloromethane/7N ammonia in methanol, 97/3) to give the product, 40 mg (66%) as a beige solid.

LC-MS (Method 1): $R_t$=2.46 min; MS (ES+): m/z=546/548 (M+H)$^+$.

$^1$H-NMR (500 MHz, DMSO-d$_6$) δ [ppm]=1.25 (d, 3H), 2.27 (s, 3H), 2.77 (dd, 1H), 3.08 (dd, 1H), 3.44 (m, 1H), 3.50-3.60 (m, 3H), 3.70 (q, 1H), 4.19 (m, 1H), 4.95 (t, 1H), 6.34 (d, 1H), 7.02 (d, 1H), 7.12 (d, 2H), 7.22 (d, 2H), 7.31 (d, 1H), 7.48 (d, 2H), 7.71 (dd, 1H), 7.76 (d, 2H), 8.47 (d, 1H).

Example 78

2,4-dichloro-N-[(2R)-1-(4-cyanophenyl)-3-hydroxypropan-2-yl]-5-[5-({[(1R)-1-(4-methylphenyl)ethyl]amino}methyl)-2-furyl]benzamide

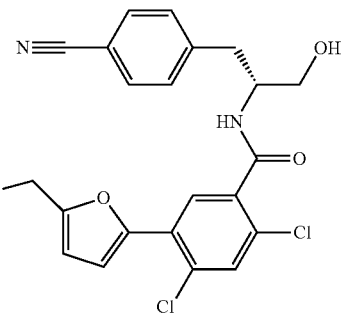

To a stirred solution of intermediate 5A, 2,4-dichloro-5-[5-({[(1R)-1-(4-methylphenyl)ethyl]amino}methyl)-2-furyl]benzoic acid, 75 mg (0.186 mmol) in tetrahydrofuran (1.9 mL) were added TBTU, 63 mg (0.195 mmol, 1.05 eq.) and triethylamine, 78 µL (0.557 mmol, 3 eq.) at r.t. After 20 min, 15B, 4-[(2R)-2-amino-3-hydroxypropyl]benzonitrile hydrochloride (1:1), 43 mg (0.204 mmol, 1.1 eq.) was added and the resulting mixture was stirred at r.t. for 2 h. Most of the solvent was removed under reduced pressure and the residue was dissolved in ethyl acetate (40 mL). The organic layer was washed successively with aq. sat. sodium hydrogen carbonate, water, brine, dried over sodium sulfate and concentrated. The residue (94 mg, orange oil) was purified by preparative TLC (eluent: dichloromethane/methanol, 95/5) to give the product, 50 mg (48%) as an orange foam.

LC-MS (Method 1): $R_t$=2.49 min; MS (ES+): m/z=562/564 (M+H)$^+$.

$^1$H-NMR (500 MHz, DMSO-d$_6$) δ [ppm]=1.25 (d, 3H), 2.26 (s, 3H), 2.77 (dd, 1H), 3.08 (dd, 1H), 3.43 (m, 1H), 3.51-3.57 (m, 2H), 3.61 (d, 1H), 3.73 (q, 1H), 4.18 (m, 1H), 4.95 (t, 1H), 6.40 (d, 1H), 7.11-7.12 (m, 3H), 7.24 (d, 2H), 7.47 (d, 2H), 7.63 (s, 1H), 7.71 (s, 1H), 7.73 (d, 2H), 8.44 (d, 1H).

Example 79

4-cyano-N-[(2R)-1-(4-cyanophenyl)-3-hydroxypropan-2-yl]-3-[5-({[(1R)-1-(4-methylphenyl)ethyl]amino}methyl)-2-furyl]benzamide

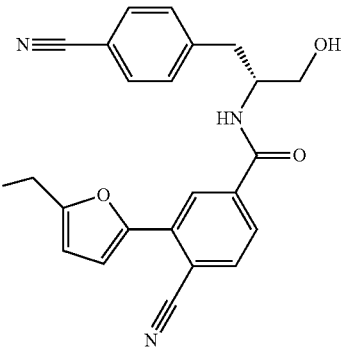

To a stirred solution of intermediate 6A, 4-cyano-3-[5-({[(1R)-1-(4-methylphenyl)ethyl]amino}methyl)-2-furyl]benzoic acid, 50 mg (0.139 mmol) in tetrahydrofuran (1.4 mL) were added TBTU, 47 mg (0.146 mmol, 1.05 eq.) and triethylamine, 58 µL (0.416 mmol, 3 eq.) at r.t. After 30 min, 15B, 4-[(2R)-2-amino-3-hydroxypropyl]benzonitrile hydrochloride (1:1), 30 mg (0.139 mmol) was added and the resulting mixture was stirred at r.t. for 2 h. Most of the solvent was removed under reduced pressure and the residue was dissolved in ethyl acetate (30 mL). The organic layer was washed successively with aq. 1N hydrochloric acid, aq. sat. sodium hydrogen carbonate, water (2×) and brine, dried over sodium sulfate, filtered and concentrated. The residue was purified by preparative TLC (dichloromethane/methanol, 95/5) to give the product, 54 mg (75%) as a light yellow foam.

LC-MS (Method 1): $R_t$=2.39 min; MS (ES+): m/z=519 (M+H)$^+$.

1H-NMR (500 MHz, DMSO-d6) δ [ppm]=1.26 (d, 3H), 2.26 (s, 3H), 2.88 (dd, 1H), 3.06 (dd, 1H), 3.46-3.65 (m, 4H), 3.76 (m, 1H), 4.22 (m, 1H), 4.94 (t, 1H), 6.47 (d, 1H), 7.12 (d, 2H), 7.20 (d, 1H), 7.25 (d, 2H), 7.46 (d, 2H), 7.71 (d, 2H), 7.75 (dd, 1H), 7.97 (d, 1H), 8.14 (d, 1H), 8.55 (d, 1H).

Example 80

N-[(2R)-1-(4-cyanophenyl)-3-hydroxypropan-2-yl]-4-methoxy-2-methyl-5-[5-({[(1R)-1-(4-methylphenyl)ethyl]amino}methyl)-2-furyl]benzamide

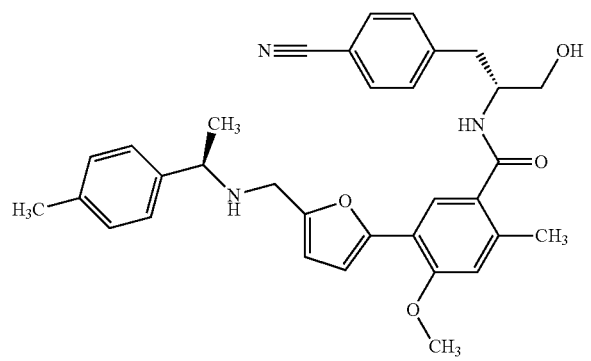 [SMILES: COc1cc(C)c(C(=O)N[C@@H](CO)Cc2ccc(C#N)cc2)cc1-c1ccc(CN[C@H](C)c2ccc(C)cc2)o1]

To a stirred solution of intermediate 7A, 4-methoxy-2-methyl-5-[5-({[(1R)-1-(4-methylphenyl)ethyl]amino}methyl)-2-furyl]benzoic acid, 55 mg (0.145 mmol) in tetrahydrofuran (1.5 mL) were added TBTU, 49 mg (0.152 mmol, 1.05 eq.) and triethylamine, 61 µL (0.435 mmol, 3 eq.) at r.t. After 20 min, 15B, 4-[(2R)-2-amino-3-hydroxypropyl]benzonitrile hydrochloride (1:1), 34 mg (0.159 mmol, 1.1 eq.) was added and the resulting mixture was stirred at r.t. for 4 h. Most of the solvent was removed under reduced pressure and the residue was dissolved in ethyl acetate (30 mL). The organic layer was washed successively with aq. sat. sodium hydrogen carbonate, water, brine, dried over sodium sulfate and concentrated. The residue was purified by preparative TLC (eluent: dichloromethane/methanol, 95/5) to give the product, 35 mg (43%) as an orange foam.

LC-MS (Method 1): $R_t$=2.40 min; MS (ES+): m/z=538 (M+H)$^+$.

$^1$H-NMR (500 MHz, DMSO-d$_6$) δ [ppm]=1.27 (d, 3H), 2.14 (s, 3H), 2.27 (s, 3H), 2.77 (dd, 1H), 3.09 (dd, 1H), 3.44 (m, 1H), 3.53 (m, 1H), 3.54 (d, 1H), 3.60 (d, 1H), 3.76 (q, 1H), 3.90 (s, 3H), 4.21 (m, 1H), 4.90 (t, 1H), 6.28 (d, 1H), 6.78 (d, 1H), 6.91 (s, 1H), 7.13 (d, 2H), 7.26 (d, 2H), 7.48 (d, 2H), 7.54 (s, 1H), 7.74 (d, 2H), 8.02 (d, 1H).

Example 81

2-chloro-N-[(2R)-1-(4-cyanophenyl)-3-hydroxypropan-2-yl]-4-methoxy-5-[5-({[(1R)-1-(4-methylphenyl)ethyl]amino}methyl)-2-furyl]benzamide

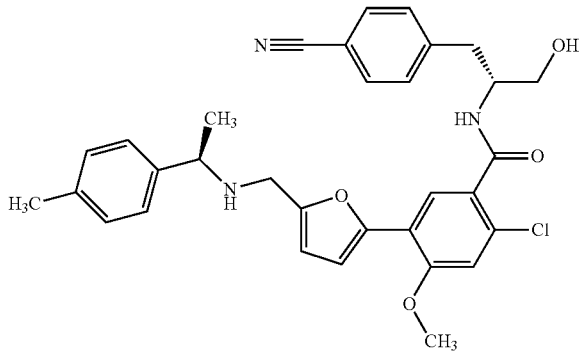 [SMILES: COc1cc(Cl)c(C(=O)N[C@@H](CO)Cc2ccc(C#N)cc2)cc1-c1ccc(CN[C@H](C)c2ccc(C)cc2)o1]

To a stirred solution of intermediate 8A, 2-chloro-4-methoxy-5-[5-({[(1R)-1-(4-methylphenyl)ethyl]amino}methyl)-2-furyl]benzoic acid, 36 mg (90 µmol) in tetrahydrofuran (1.8 mL) were added TBTU, 30 mg (95 µmol, 1.05 eq.) and triethylamine, 38 µL (0.27 mmol, 3 eq.) at r.t. After 20 min, 15B, 4-[(2R)-2-amino-3-hydroxypropyl]benzonitrile hydrochloride (1:1), 21 mg (99 µmol, 1.1 eq.) was added and the resulting mixture was stirred at r.t. for 2 h. Most of the solvent was removed under reduced pressure and the residue was dissolved in ethyl acetate (30 mL). The organic layer was washed successively with aq. sat. sodium hydrogen carbonate, water, brine, dried over sodium sulfate and concentrated. The residue (55 mg, orange oil) was purified by preparative TLC (eluent: dichloromethane/methanol, 95/5) to give the product, 36 mg (72%) as an orange foam.

LC-MS (Method 1): $R_t$=2.45 min; MS (ES+): m/z=558/560 (M+H)$^+$.

$^1$H-NMR (500 MHz, DMSO-d$_6$) δ [ppm]=1.25 (d, 3H), 2.26 (s, 3H), 2.78 (dd, 1H), 3.09 (dd, 1H), 3.41 (m, 1H), 3.51-3.56 (m, 2H), 3.59 (d, 1H), 3.73 (q, 1H), 3.94 (s, 3H), 4.16 (m, 1H), 4.92 (t, 1H), 6.31 (d, 1H), 6.85 (d, 1H), 7.12 (d, 2H), 7.15 (s, 1H), 7.24 (d, 2H), 7.48 (d, 2H), 7.56 (s, 1H), 7.73 (d, 2H), 8.22 (d, 1H).

The following examples were prepared using the same procedure, from corresponding amines as indicated.
ammonia 7N in methanol as eluent.

| Example No | Amine | Structure/ Name | Analytics |
|---|---|---|---|
| 83[Phthal.] | 52B | 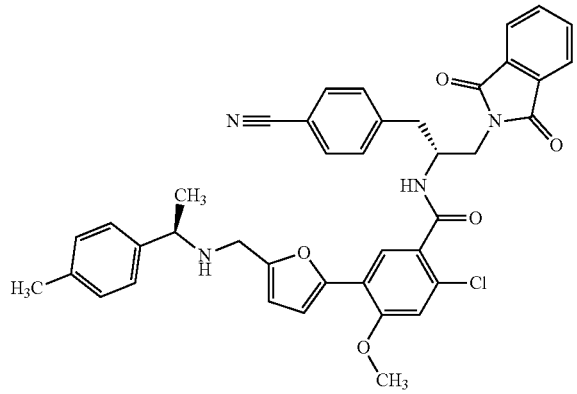

2-chloro-N-[(2R)-1-(4-cyanophenyl)-3-(1,3-dioxo-1,3-dihydro-2H-isoindol-2-yl)propan-2-yl]-4-methoxy-5-[5-({[(1R)-1-(4-methylphenyl)ethyl]amino}methyl)-2-furyl]benzamide | LC-MS (Method 1): $R_t$ = 2.65 min; MS (ES+): m/z = 687/689 (M + H)⁺.<br>¹H-NMR (500 MHz, DMSO-d₆) δ [ppm] = 1.28 (d, 3H), 2.24 (s, 3H), 2.87 (dd, 1H), 3.12 (dd, 1H), 3.62 (d, 1H), 3.66 (d, 1H), 3.76-3.85 (m, 3H), 3.90 (s, 3H), 4.57 (m, 1H), 6.33 (d, 1H), 6.84 (d, 1H), 7.06 (s, 1H), 7.11 (d, 2H), 7.27 (d, 2H), 7.46 (s, 1H), 7.50 (d, 2H), 7.73 (d, 2H), 7.76-7.78 (m, 2H), 7.85-7.86 (m, 2H), 8.39 (d, 1H). |
| 85[Boc] | 57B[Boc] | 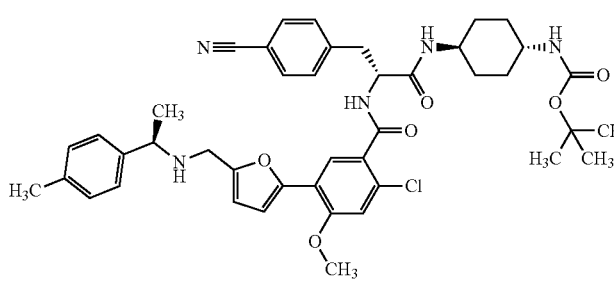

N-{trans-4-[(tert-butoxycarbonyl)amino]cyclohexyl}-Nα-{2-chloro-4-methoxy-5-[5-({[(1R)-1-(4-methylphenyl)ethyl]amino}methyl)-2-furyl]benzoyl}-4-cyano-D-phenylalaninamide | LC-MS (Method 1): $R_t$ = 2.82 min; MS (ES+): m/z = 768/770 (M + H)⁺<br>¹H-NMR (500 MHz, DMSO-d₆) δ [ppm] = 1.12-1.28 (m, 4H), 1.25 (d, 3H), 1.8 (s, 9H), 1.69-1.84 (m, 4H), 2.26 (s, 3H), 2.97 (dd, 1H), 3.11 (dd, 1H), 3.19 (m, 1H), 3.46 (m, 1H), 3.52 & 3.60 (2d, AB, 2H), 3.72 (q, 1H), 3.94 (s, 3H), 4.65-4.72 (m, 1H), 6.31 (d, 1H), 6.71 (d, 1H), 6.86 (d, 1H), 7.12 (d, 2H), 7.15 (s, 1H), 7.24 (d, 2H), 7.50 (d, 2H), 7.59 (s, 1H), 7.74 (d, 2H), 7.91 (d, 1H), 8.56 (d, 1H) |
| 82 | 40B | 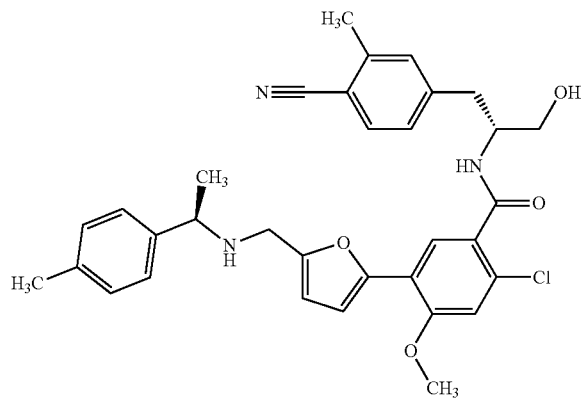

2-chloro-N-[(2R)-1-(4-cyano-3-methyl-phenyl)-3-hydroxypropan-2-yl]-4-methoxy-5-[5-({[(1R)-1-(4-methylphenyl)ethyl]amino}methyl)-2-furyl]benzamide | LC-MS (Method 1): $R_t$ = 2.54 min; MS (ES+): m/z = 572/574 (M + H)⁺<br>¹H-NMR (500 MHz, DMSO-d₆) δ [ppm] = 1.25 (d, 3H), 2.26 (s, 3H), 2.41 (s, 3H), 2.75 (dd, 1H), 3.04 (dd, 1H), 3.38-344 (m, 1H), 3.49-3.61 (m, 3H), 3.72 (q, 1H), 3.94 (s, 3H), 4.14 (m, 1H), 4.91 (t, 1H), 6.31 (d, 1H), 6.86 (d, 1H), 7.12 (d, 2H), 7.17 (s, 1H), 7.23 (d, 2H), 7.28 (d, 1H), 7.35 (s, 1H), 7.58 (s, 1H), 7.66 (d, 2H), 8.23 (d, 1H). |

| Example No | Amine | Structure/ Name | Analytics |
|---|---|---|---|
| 84[Phthal.] | 56B | 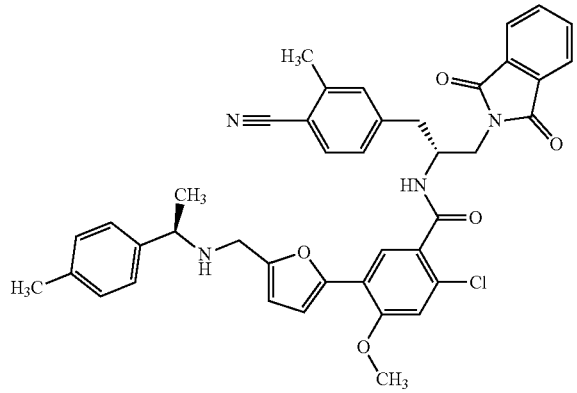<br>2-chloro-N-[(2R)-1-(4-cyano-3-methyl-phenyl)-3-(1,3-dioxo-1,3-dihydro-2H-isoindol-2-yl)propan-2-yl]-4-methoxy-5-[5-({[(1R)-1-(4-methylphenyl)ethyl]amino}methyl)-2-furyl]benzamide | LC-MS (Method 1): $R_t$ = 2.75 min; MS (ES+): m/z = 701/703 (M + H)$^+$.<br>$^1$H-NMR (500 MHz, DMSO-$d_6$) δ [ppm] = 1.27 (d, 3H), 2.24 (s, 3H), 2.40 (s, 3H), 2.86 (dd, 1H), 3.05 (dd, 1H), 3.63 (m, 2H), 3.75-3.82 (m, 3H), 3.90 (s, 3H), 4.58 (m, 1H), 6.33 (d, 1H), 6.85 (d, 1H), 7.07 (s, 1H), 7.11 (d, 2H), 7.27 (d, 2H), 7.30 (d, 1H), 7.36 (s, 1H), 7.49 (s, 1H), 7.65 (d, 1H), 7.76 (m, 2H), 7.85 (m, 2H), 8.41 (d, 1H). |

Example 83

N-[(2R)-1-amino-3-(4-cyanophenyl)propan-2-yl]-2-chloro-4-methoxy-5-[5-({[(1R)-1-(4-methylphenyl)ethyl]amino}methyl)-2-furyl]benzamide

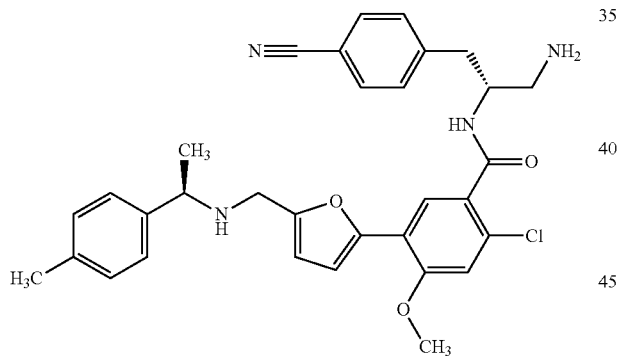

To a stirred solution of 83$^{Phthal}$, 2-chloro-N-[(2R)-1-(4-cyanophenyl)-3-(1,3-dioxo-1,3-dihydro-2H-isoindol-2-yl)propan-2-yl]-4-methoxy-5-[5-({[(1R)-1-(4-methyl-phenyl)ethyl]amino}methyl)-2-furyl]benzamide, 362 mg (0.527 mmol) in absolute ethanol (8 mL) was added hydrazine, 2.6 mL (1M in tetrahydrofuran, 2.63 mmol, 5 eq.) and the mixture was stirred at 70° C. for 4 h. The solvent was then removed in vacuum, the residue was triturated in dichloromethane and filtered. The filtrate was concentrated and the residue (306 mg, orange oil) was purified by flash column chromatography on silica gel (eluent: dichloromethane/7N ammonia in methanol, 98/2) to give the product, 254 mg (79%) as an orange solid.

LC-MS (Method 1): $R_t$=2.17 min; MS (ES+): m/z=557/559 (M+H)$^+$.

$^1$H-NMR (500 MHz, CD$_3$OD) δ [ppm]=1.37 (d, 3H), 2.29 (s, 3H), 2.80 (dd, 1H), 2.85-2.90 (m, 2H), 3.10 (dd, 1H), 3.66 (m, 2H), 3.80 (q, 1H), 3.97 (s, 3H), 4.36 (m, 1H), 6.30 (d, 1H), 6.88 (d, 1H), 7.11 (s, 1H), 7.14 (d, 2H), 7.24 (d, 2H), 7.49 (d, 2H), 7.62 (d, 2H), 7.68 (s, 1H).

Example 84

N-[(2R)-1-amino-3-(4-cyano-3-methylphenyl)propan-2-yl]-2-chloro-4-methoxy-5-[5-({[(1R)-1-(4-methylphenyl)ethyl]amino}methyl)-2-furyl]benzamide

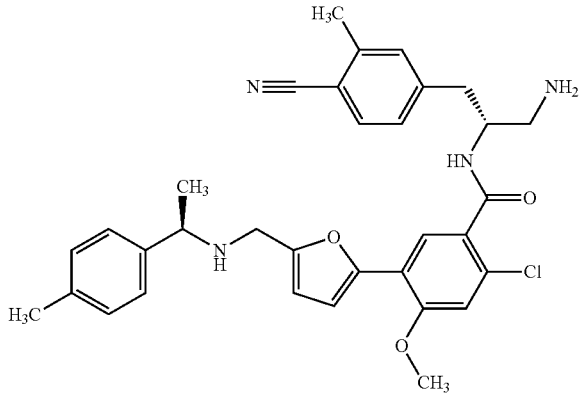 [SMILES: COc1cc(Cl)c(C(=O)N[C@@H](CN)Cc2ccc(C#N)c(C)c2)cc1-c1ccc(CN[C@H](C)c2ccc(C)cc2)o1]

To a stirred solution of example 84$^{Phthal}$, 2-chloro-N-[(2R)-1-(4-cyano-3-methylphenyl)-3-(1,3-dioxo-1,3-dihydro-2H-isoindol-2-yl)propan-2-yl]-4-methoxy-5-[5-({[(1-R)-1-(4-methylphenyl)ethyl]amino}methyl)-2-furyl]benzamide, 200 mg (0.527 mmol) in absolute ethanol (5 mL) was added hydrazine, 1.4 mL (1M in tetrahydrofuran, 1.4 mmol, 5 eq.) and the mixture was stirred at 70° C. for 4 h. The solvent was then removed in vacuum, the residue was triturated in ethyl acetate and filtered through celite to removed the solid. The filtrate was diluted with ethyl acetate and washed with aq. sat. sodium hydrogen carbonate, water (4×), brine, dried over sodium sulfate and concentrated to give the crude product, 159 mg (97%) as a brown sticky solid. A pure sample has been obtained by preparative TLC purification (eluent: dichloromethane/7N ammonia in methanol, 97/3 to 96/4, 2 migrations).

LC-MS (Method 1): $R_t$=2.20 min; MS (ES+): m/z=571/573 (M+H)$^+$.

$^1$H-NMR (500 MHz, DMSO-d$_6$) δ [ppm]=1.25 (d, 3H), 2.25 (s, 3H), 2.41 (s, 3H), 2.64 (d, 2H), 2.73 (dd, 1H), 2.99 (dd, 1H), 3.55 (m, 2H), 3.71 (q, 1H), 3.95 (s, 3H), 4.04 (m, 1H), 6.31 (d, 1H), 6.86 (d, 1H), 7.11 (d, 2H), 7.18 (s, 1H), 7.23 (d, 2H), 7.28 (d, 1H), 7.34 (s, 1H), 7.56 (s, 1H), 7.65 (d, 1H), 8.23 (d, 1H).

Example 85

N-(trans-4-aminocyclohexyl)-Nα-{2-chloro-4-methoxy-5-[(5-({[(1R)-1-(4-methylphenyl)ethyl]amino}methyl)-2-furyl]benzoyl}-4-cyano-D-phenyl-alaninamide

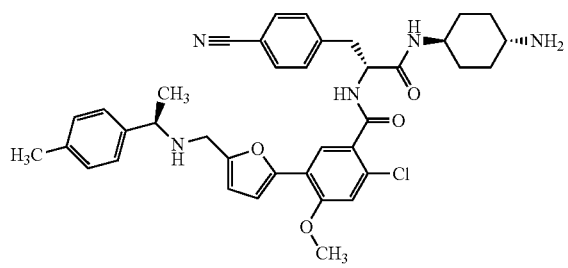 [SMILES: COc1cc(Cl)c(C(=O)N[C@H](Cc2ccc(C#N)cc2)C(=O)N[C@H]2CC[C@H](N)CC2)cc1-c1ccc(CN[C@H](C)c2ccc(C)cc2)o1]

To a stirred solution of example 85$^{Boc}$, N-{trans-4-[(tert-butoxycarbonyl)amino]cyclohexyl}-Nα-{2-chloro-4-methoxy-5-({[(1R)-1-(4-methylphenyl)ethyl]amino}methyl)-2-furyl]benzoyl}-4-cyano-D-phenylalaninamide, 42 mg (0.055 mmol) in dichloromethane (3 mL) was added slowly hydrochloric acid, 0.14 mL (4M in 1,4-dioxane, 0.547 mmol, 10 eq.) at 0° C. and the resulting mixture was stirred at r.t. for 16 h. More hydrochloric acid, 0.14 mL (4M in 1,4-dioxane, 0.547 mmol, 10 eq.) was added and the reaction mixture was stirred for 24 h. The volatiles were removed under reduced pressure and the residue was treated with aq. sat. sodium hydrogen carbonate and ethyl acetate. The aqueous phase was extracted using ethyl acetate. The combined organics were dried over sodium sulfate and concentrated. The residue was purified by preparative TLC (dichloromethane/7N ammonia in methanol: 96/4) to give the product, 18 mg (47%) as a beige solid.

LC-MS (Method 1): $R_t$=2.23 min; MS (ES+): m/z=668 (M+H)$^+$, 533 (M−135+H)$^+$ $^1$H-NMR (500 MHz, DMSO-d$_6$) δ [ppm]=1.02-1.27 (m, 5H), 1.25 (d, 3H), 1.68-1.82 (m, 4H), 2.27 (s, 3H), 2.48-2.47 (m, 2H), 2.97 (dd, 1H), 3.10 (dd, 1H), 3.47 (m, 1H), 3.52 & 3.60 (2d, AB, 2H), 3.70 (q, 1H), 3.95 (s, 3H), 4.70 (m, 1H), 6.31 (d, 1H), 6.86 (d, 1H), 7.12 (d, 2H), 7.15 (s, 1H), 7.24 (d, 2H), 7.50 (d, 2H), 7.59 (s, 1H), 7.75 (d, 2H), 7.86 (d, 1H), 8.56 (d, 1H)

Example 86

N-[(2R)-1-[(4-aminocyclohexyl)amino]-3-(4-cyanophenyl)propan-2-yl]-2-chloro-4-methoxy-5-[5-({[(1R)-1-(4-methylphenyl)ethyl]amino}methyl)-2-furyl]benzamide, dia #1

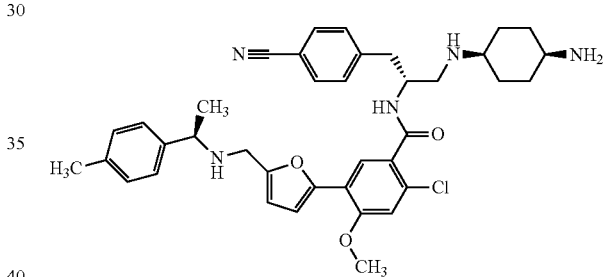

Tert-butyl-(trans-4-{[(2R)-2-({2-chloro-4-methoxy-5-[5-({[(1R)-1-(4-methylphenyl)-ethyl]amino}methyl)-2-furyl]benzoyl}amino)-3-(4-cyanophenyl)propyl]amino}cyclo-hexyl) carbamate and tert-butyl-(cis-4-{[(2R)-2-({2-chloro-4-methoxy-5-[5-({[(1R)-1-(4-methylphenyl)-ethyl]amino}methyl)-2-furyl]benzoyl}amino)-3-(4-cyanophenyl)propyl]amino}cyclo-hexyl)carbamate

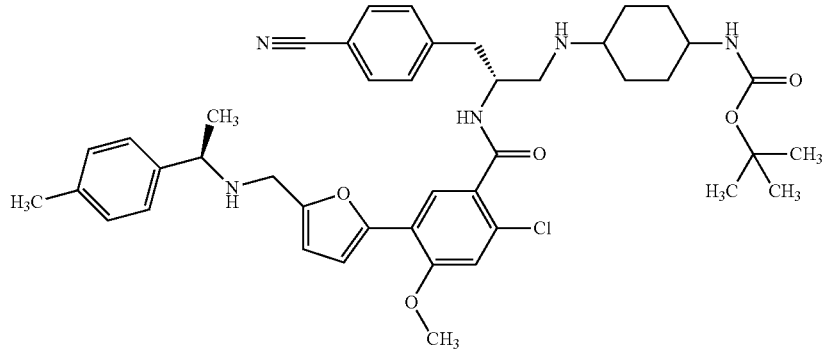 [SMILES: COc1cc(Cl)c(C(=O)N[C@@H](CNC2CCC(NC(=O)OC(C)(C)C)CC2)Cc2ccc(C#N)cc2)cc1-c1ccc(CN[C@H](C)c2ccc(C)cc2)o1]

To a stirred solution of example 83, N-[(2R)-1-amino-3-(4-cyanophenyl)propan-2-yl]-2-chloro-4-methoxy-5-[5-({[(1R)-1-(4-methylphenyl)ethyl]amino}methyl)-2-furyl]-benzamide, 100 mg (0.18 mmol) in dichloromethane (2 mL) was added 4-N-Boc-aminocyclohexanone, 50 mg (0.233 mmol, 1.3 eq.) followed by acetic acid, 51 µL (0.90 mmol, 5 eq.) and the mixture was stirred at r.t. for 30 min. Sodium triacetoxyborohydride, 57 mg (0.27 mmol, 1.5 eq.) was added in one portion and the resulting mixture was stirred at r.t. for 18 h. The mixture was poured into aq. sat. sodium hydrogen carbonate and extracted with dichloromethane (3×). The combined organic extracts were washed with brine, dried over sodium sulfate, filtered and concentrated. The residue (257 mg, orange oil) was purified by preparative TLC (eluent: dichloromethane/7N ammonia in methanol, 97:3) to give the two disatereomers:

Dia #1, 45 mg (32%) as an orange solid; LC-MS (Method 1): $R_t$=2.37 min; MS (ES+): m/z=754/756 (M+H)$^+$. $^1$H-NMR (500 MHz, DMSO-d$_6$) δ [ppm]=1.25 (d, 3H), 1.37 (s, 9H), 1.40-1.46 (m, 4H), 1.51-1.58 (m, 4H), 2.26 (s, 3H), 2.60-2.64 (m, 3H), 2.77 (dd, 1H), 3.11 (dd, 1H), 3.29 (m, 1H), 3.53 (d, 1H), 3.59 (d, 1H), 3.72 (q, 1H), 3.94 (s, 3H), 4.22 (m, 1H), 6.31 (d, 1H), 6.63 (br d, 1H), 6.86 (d, 1H), 7.11 (d, 2H), 7.16 (s, 1H), 7.24 (d, 2H), 7.48 (d, 2H), 7.51 (s, 1H), 7.74 (d, 2H), 8.25 (d, 1H).

Dia #2, 48 mg (35%) as an orange solid; LC-MS (Method 1): $R_t$=2.31 min; MS (ES+): m/z=754/756 (M+H)$^+$. $^1$H-NMR (500 MHz, DMSO-d$_6$) δ [ppm]=0.97-1.06 (m, 2H), 1.11-1.18 (m, 2H), 1.25 (d, 3H), 1.37 (s, 9H), 1.72-1.75 (m, 2H), 1.81-1.86 (m, 2H), 2.26 (s, 3H), 2.31 (m, 1H), 2.63-2.67 (m, 2H), 2.76 (dd, 1H), 3.06 (dd, 1H), 3.16 (m, 1H), 3.53 (d, 1H), 3.59 (d, 1H), 3.73 (q, 1H), 3.94 (s, 3H), 4.19 (m, 1H), 6.31 (d, 1H), 6.67 (br d, 1H), 6.86 (d, 1H), 7.11 (d, 2H), 7.16 (s, 1H), 7.24 (d, 2H), 7.47 (d, 2H), 7.52 (s, 1H), 7.73 (d, 2H), 8.23 (d, 1H).

N-[(2R)-1-[(4-aminocyclohexyl)amino]-3-(4-cyanophenyl)propan-2-yl]-2-chloro-4-methoxy-5-[5-({[(1R)-1-(4-methylphenyl)ethyl]amino}methyl)-2-furyl]benzamide, Dia #1

To a stirred suspension of, tert-butyl-(4-{[(2R)-2-({2-chloro-4-methoxy-5-[5-({[(1R)-1-(4-methylphenyl)ethyl]amino}methyl)-2-furyl]benzoyl}amino)-3-(4-cyanophenyl)propyl]amino}cyclohexyl)carbamate, dia #1, 44 mg (58 µmol) in dichloromethane (0.5 mL) was added slowly hydrochloric acid, 0.15 mL (4M in 1,4-dioxane, 0.58 mmol, 10 eq.) at 0° C. and the resulting mixture was stirred at r.t. for 48 h.

The volatiles were removed under reduced pressure and the residue was triturated in methyl tert-butyl ether, filtered, washed with methyl tert-butyl ether and dried under reduced pressure. The impure product obtained was treated with aq. sat. sodium hydrogen carbonate and ethyl acetate. The aqueous phase was extracted using ethyl acetate. The combined organics were dried over sodium sulfate and concentrated. The residue was purified by preparative TLC (eluent: dichloromethane/methanol, 96:4) to give the product, 16 mg (41%) as a beige solid.

LC-MS (Method 1): $R_t$=2.03 min; MS (ES+): m/z=654/656 (M+H)$^+$.

$^1$H-NMR (500 MHz, DMSO-d$_6$) δ [ppm]=1.25 (d, 3H), 1.38-1.47 (m, 5H), 1.50-1.60 (m, 3H), 2.26 (s, 3H), 2.57 (m, 1H), 2.63-2.66 (m, 2H), 2.71 (m, 1H), 2.78 (dd, 1H), 3.09 (dd, 1H), 3.53 (d, 1H), 3.60 (d, 1H), 3.73 (q, 1H), 3.94 (s, 3H), 4.23 (m, 1H), 6.31 (d, 1H), 6.86 (d, 1H), 7.11 (d, 2H), 7.17 (s, 1H), 7.24 (d, 2H), 7.48 (d, 2H), 7.51 (s, 1H), 7.74 (d, 2H), 8.25 (d, 1H).

Example 87

N-[(2R)-1-[(4-aminocyclohexyl)amino]-3-(4-cyanophenyl)propan-2-yl]-2-chloro-4-methoxy-5-[5-({[(1R)-1-(4-methylphenyl)ethyl]amino}methyl)-2-furyl]benzamide, Dia #2

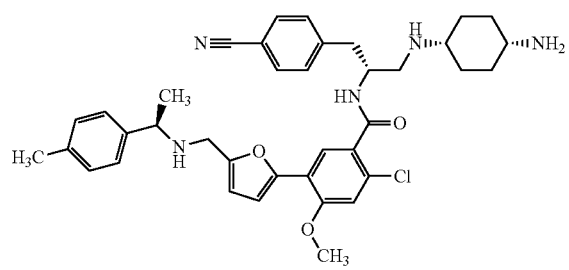 [SMILES: COc1cc(Cl)c(C(=O)N[C@@H](CN[C@H]2CC[C@@H](N)CC2)Cc2ccc(C#N)cc2)cc1-c1ccc(CN[C@H](C)c2ccc(C)cc2)o1]

Using the same procedure as for example 86 dia #1:

LC-MS (Method 1): $R_t$=2.00 min; MS (ES+): m/z=654/656 (M+H)$^+$.

$^1$H-NMR (500 MHz, DMSO-d$_6$) δ [ppm]=0.98-1.10 (m, 4H), 1.25 (d, 3H), 1.70-1.85 (m, 4H), 2.26 (s, 3H), 2.31 (m, 1H), 2.63-2.70 (m, 2H), 2.77 (dd, 1H), 3.06 (dd, 1H), 3.15 (m, 1H), 3.53 (d, 1H), 3.60 (d, 1H), 3.72 (q, 1H), 3.94 (s, 3H), 4.20 (m, 1H), 6.31 (d, 1H), 6.86 (d, 1H), 7.11 (d, 2H), 7.16 (s, 1H), 7.24 (d, 2H), 7.47 (d, 2H), 7.52 (s, 1H), 7.73 (d, 2H), 8.23 (d, 1H).

Example 88

N-[(2R)-1-[(4-aminocyclohexyl)amino]-3-(4-cyano-3-methylphenyl)propan-2-yl]-2-chloro-4-methoxy-5-[5-({[(1R)-1-(4-methylphenyl)ethyl]amino}methyl)-2-furyl]-benzamide, Dia #1

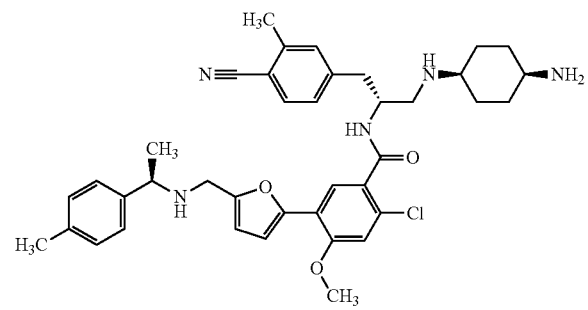 [SMILES: COc1cc(Cl)c(C(=O)N[C@@H](CN[C@H]2CC[C@@H](N)CC2)Cc2ccc(C#N)c(C)c2)cc1-c1ccc(CN[C@H](C)c2ccc(C)cc2)o1]

Tert-butyl trans-N-[4-[[(2R)-2-[[2-chloro-4-methoxy-5-[5-[[[(1R)-1-(p-tolyl)ethyl]-amino]methyl]-2-furyl]benzoyl]amino]-3-(4-cyano-3-methyl-phenyl)propyl]amino]-cyclohexyl]carbamate and tert-butyl cis-N-[4[[(2R)-2-[[2-chloro-4-methoxy-5-[5-[[[(1R)-1-(p-tolyl)ethyl]amino]-methyl]-2-furyl]benzoyl]amino]-3-(4-cyano-3-methyl-phenyl)propyl]amino]cyclohexyl]carbamate

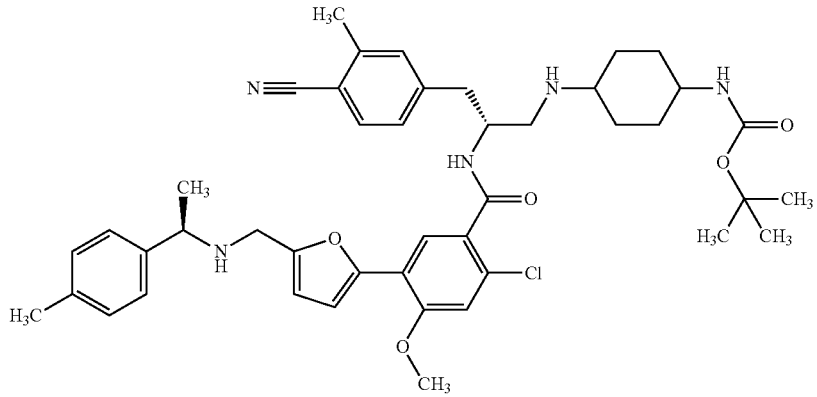 [SMILES: COc1cc(Cl)c(C(=O)N[C@@H](CNC2CCC(NC(=O)OC(C)(C)C)CC2)Cc2ccc(C#N)c(C)c2)cc1-c1ccc(CN[C@H](C)c2ccc(C)cc2)o1]

Example 84 was reacted with 4-N-Boc-aminocyclohexanone using the same procedure described in example 86 to deliver 2 diastereomers Dia #1, 33 mg (23%), orange solid; LC-MS (Method 1): $R_f$=2.70 min; MS (ES+): m/z=768/770 (M+H)$^+$. $^1$H-NMR (500 MHz, DMSO-d$_6$) δ [ppm]=1.26 (d, 3H), 1.38 (s, 9H), 1.40-1.65 (m, 8H), 2.27 (s, 3H), 2.42 (s, 3H), 2.57-2.67 (m, 4H), 2.75 (dd, 1H), 3.07 (dd, 1H), 3.52 & 3.58 (2 d, AB, 2H), 3.73 (q, 1H), 3.96 (s, 3H), 4.20 (m, 1H), 6.33 (d, 1H), 6.64 (br s 1H), 6.88 (d, 1H), 7.12 (d, 2H), 7.19 (s, 1H), 7.24 (d, 2H), 7.30 (d, 1H), 7.36 (s, 1H), 7.55 (s, 1H), 7.67 (d, 1H), 8.27 (d, 1H).

Dia #2, 44 mg (31%), orange solid; LC-MS (Method 1): $R_f$=2.71 min; MS (ES+): m/z=768/770 (M+H)$^+$. $^1$H-NMR (500 MHz, DMSO-d$_6$) δ [ppm]=0.95-1.20 (m, 4H), 1.25 (d, 3H), 1.37 (s, 9H), 1.70-1.90 (m, 4H), 2.26 (s, 3H), 2.30 (m, 1H), 2.41 (s, 3H), 2.64 (m, 2H), 2.73 (dd, 1H), 3.00 (dd, 1H), 3.17 (m, 1H), 3.52 & 3.58 (2 d, AB, 2H), 3.73 (q, 1H), 3.95 (s, 3H), 4.16 (m, 1H), 6.31 (d, 1H), 6.66 (d, 1H), 6.88 (d, 1H), 7.11 (d, 2H), 7.18 (s, 1H), 7.24 (d, 2H), 7.27 (d, 1H), 7.34 (s, 1H), 7.54 (s, 1H), 7.66 (d, 1H), 8.23 (d, 1H).

N-[(2R)-1-[(4-aminocyclohexyl)amino]-3-(4-cyano-3-methylphenyl)propan-2-yl]-2-chloro-4-methoxy-5-[5-({[(1R)-1-(4-methylphenyl)ethyl]amino}methyl)-2-furyl]-benzamide, Dia #1

Diastereomer #1 was deprotected by the same procedure as described in for example 86 to deliver 13 mg of the title compound:

LC-MS (Method 1): $R_f$=2.20 min; MS (ES+): m/z=668/670 (M+H)$^+$.

$^1$H-NMR (500 MHz, DMSO-d$_6$) δ [ppm]=1.15 (d, 3H), 1.37-1.46 (m, 5H), 1.48-1.58 (m, 3H), 2.26 (s, 3H), 2.41 (s, 3H), 2.50-2.73 (m, 4H), 2.75 (dd, 1H), 3.04 (dd, 1H), 3.52 & 3.58 (2d, AB, 2H), 3.73 (q, 1H), 3.95 (s, 3H), 4.20 (m, 1H), 6.32 (d, 1H), 6.87 (d, 1H), 7.11 (d, 2H), 7.18 (s, 1H), 7.24 (d, 2H), 7.29 (d, 1H), 7.35 (s, 1H), 7.54 (s, 1H), 7.66 (d, 1H), 8.26 (d, 1H).

Example 89

2-Chloro-5-[5-({[(1R)-1-(4-chlorophenyl)ethyl]amino}methyl)-2-furyl]-N-[(2R)-1-(4-cyanophenyl)-4-(methylamino)-4-oxobutan-2-yl]benzamide

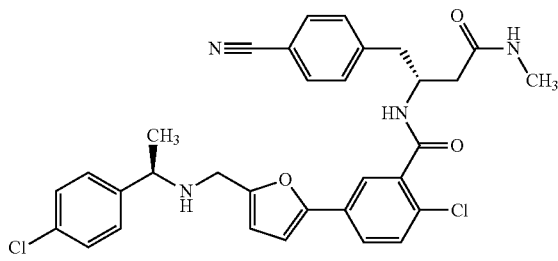 [SMILES: CNC(=O)C[C@@H](Cc1ccc(C#N)cc1)NC(=O)c1cc(-c2ccc(CN[C@H](C)c3ccc(Cl)cc3)o2)ccc1Cl]

2-chloro-5-(5-formyl-2-furyl)benzoic acid

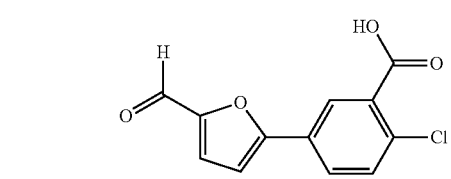 [SMILES: O=Cc1ccc(-c2ccc(Cl)c(C(=O)O)c2)o1]

To a solution of ester ethyl 2-chloro-5-(5-formylfuran-2-yl)benzoate, 2.0 g (7.17 mmol) in THF (290 mL) at 0° C. was added lithium hydroxide, 361 mg (8.61 mmol, 1.2 eq) in water (70 mL). The solution was stirred at 0° C. for 6 h, then stored at 4° C. overnight. LC-MS analysis showed full conversion. The mixture was diluted with water (70 mL), then acidified using 1N hydrochloric acid aqueous solution. The aqueous phase was extracted with ethyl acetate. The combined organics were dried over sodium sulfate and concentrated to an orange solid. The solid was triturated in ethyl acetate, filtered, rinse with ethyl acetate and dried under reduced pressure to give the product, 1.25 g (64%) as an orange solid.

LC-MS (Method 1): Rt=2.99 min; MS (ES-): m/z=249/251 (M-H)-

1H-NMR (500 MHz, DMSO-d6) δ [ppm]=7.44 (d, 1H), 7.66 (d, 1H), 7.69 (d, 1H), 8.01 (dd, 1H), 8.23 (d, 1H), 9.64 (s, 1H), 13.70 (br s, 1H)

2-chloro-N-[(2R)-1-(4-cyanophenyl)-4-(methylamino)-4-oxobutan-2-yl]-5-(5-formyl-2-furyl)benzamide

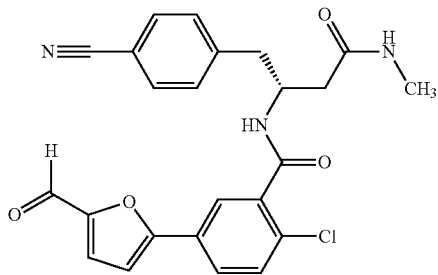 [SMILES: CNC(=O)C[C@@H](Cc1ccc(C#N)cc1)NC(=O)c1cc(-c2ccc(C=O)o2)ccc1Cl]

To a stirred solution of acid 2-chloro-5-(5-formyl-2-furyl)benzoic acid, 1.34 g (4.81 mmol) in tetrahydrofuran (75 mL) was added TBTU, 1.70 g (5.29 mmol) followed by triethylamine, 1.34 mL (9.62 mmol) at r.t. and the resulting mixture was stirred 15 min at r.t. (a solid formed). Then amine (3R)-3-amino-4-(4-cyanophenyl)-N-methylbutanamide, 1.15 g (5.29 mmol) was added. The mixture was stirred at r.t. overnight. The mixture was diluted in ethyl acetate (500 mL) and washed successively with aq. 1N hydrochloric acid (100 mL), aq. sat. sodium hydrogen carbonate (100 mL), water (100 mL) and brine (100 mL), dried over sodium sulfate, filtered and concentrated. The solid obtained was triturated in ethyl acetate, filtered, washed with ethyl acetate, then with pentane and dried under reduced pressure to give the product, 1.05 g (46%) as yellow solid.

LC-MS (Method 1): Rt=2.81 min; MS (ES+): m/z=450/452 (M+H)+.

1H NMR (DMSO-d6): 2.35-2.45 (m, 2H), 2.60 (d, 3H), 2.88 (dd, 1H), 2.99 (dd, 1H), 4.51 (m, 1H), 7.34 (d, 1H), 7.47 (d, 2H), 7.59 (d, 1H), 7.61 (d, 1H), 7.68 (d, 1H), 7.80-7.85 (m, 3H), 7.90 (dd, 1H), 8.49 (d, 1H), 9.66 (s, 1H).

Rf=0.12 (ethyl acetate), 0.5 (DCM/methanol 95/5).

2-chloro-5-[5-({[(1R)-1-(4-chlorophenyl)ethyl]amino}methyl)-2-furyl]-N-[(2R)-1-(4-cyanophenyl)-4-(methylamino)-4-oxobutan-2-yl]benzamide 2-Chloro-N-[(2R)-1-(4-cyanophenyl)-4-(methylamino)-4-oxobutan-2-yl]-5-(5-formyl-2-furyl)benzamide, 100 mg (0.222 mmol) was suspended in methanol (3 mL). (1R)-1-(4-chlorophenyl)ethanamine, 37 µL (0.267 mmol, 1.2 eq.) was added, followed by acetic acid, 13 µL (0.222 mmol, 1.0 eq.). The suspension was stirred at r.t. for 20 min, and then sodium cyanoborohydride, 21 mg (0.333 mmol, 1.5 eq.) was added. The reaction mixture was stirred at r.t. for 16 h. LC-MS analysis showed around 42% expected product and 48% of acetal along with small amount of aldehyde and aldehyde reduction. The reaction medium was filtered, rinsed with DMF (0.5 mL) and the filtrate was purified by preparative LC-MS followed by preparative TLC (dichloromethane/methanol 98/2>97/3) to provide the product, 12.3 mg (9%) as a beige solid.

LC-MS (Method 5): $R_t$=2.53 min; MS (ES+): m/z=589/591 (M+H)+

$^1$H-NMR (500 MHz, CD$_3$OD) δ [ppm]=1.37 (d, 3H), 2.52-2.60 (m, 2H), 2.74 (s, 3H), 2.98 (dd, 1H), 3.11 (dd, 1H), 3.63 & 3.68 (2 d, AB, 2H), 3.82 (q, 1H), 4.71 (m, 1H), 6.30 (d, 1H), 6.71 (d, 1H), 7.30-7.36 (m, 4H), 7.40 (d, 1H), 7.43 (d, 1H), 7.50 (d, 2H), 7.64-7.69 (in, 3H).

Example 90

2-chloro-N-[(2R)-1-(4-cyanophenyl)-3-hydroxypropan-2-yl]-4-hydroxy-5-[5-({[(1R)-1-(4-methylphenyl)ethyl]amino}methyl)-2-furyl]benzamide

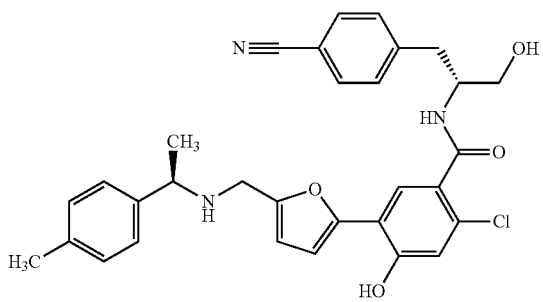 [SMILES: Cc1ccc([C@@H](C)NCc2ccc(-c3cc(C(=O)N[C@@H](CO)Cc4ccc(C#N)cc4)c(Cl)cc3O)o2)cc1]

5-bromo-2-chloro-N-[(2R)-1-(4-cyanophenyl)-3-hydroxypropan-2-yl]-4-hydroxybenzamide

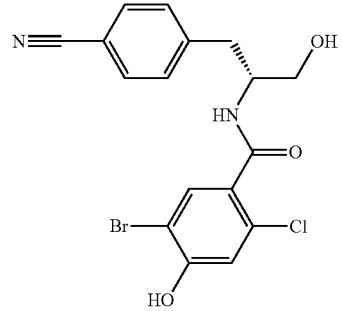 [SMILES: N#Cc1ccc(C[C@H](CO)NC(=O)c2cc(Br)c(O)cc2Cl)cc1]

To a stirred solution of 5-bromo-2-chloro-4-hydroxybenzoic acid, 100 mg (0.40 mmol) in tetrahydrofuran (4 mL) were added TBTU, 134 mg (0.42 mmol, 1.05 eq.) and triethylamine, 0.17 mL (1.2 mmol, 3 eq.) at r.t. After 20 min 4-[(2R)-2-amino-3-hydroxypropyl]benzonitrile hydrochloride (1:1), 93 mg (0.44 mmol, 1.1 eq.) was added and the resulting mixture was stirred at r.t. for 16 h. Most of the solvent was removed under reduced pressure and the residue was dissolved in ethyl acetate (30 mL). The organic layer was washed successively with aq. sat. sodium hydrogen carbonate, water, brine, dried over sodium sulfate and concentrated. The residue (155 mg, light yellow solid) was triturated in methyl tert-butyl ether, filtered, washed with methyl tert-butyl ether and dried to give the product, 77 mg (46%) as a white solid.

LC-MS (Method 1): R$_t$=2.70 min; MS (ES+): m/z=409/411 (M+H)$^+$.

$^1$H-NMR (500 MHz, CD$_3$OD) δ [ppm]=2.86 (dd, 1H), 3.13 (dd, 1H), 3.61-3.67 (m, 2H), 4.34 (m, 1H), 6.89 (s, 1H), 7.40 (s, 1H), 7.48 (d, 2H), 7.66 (d, 2H).

2-chloro-N-[(2R)-1-(4-cyanophenyl)-3-hydroxypropan-2-yl]-5-(5-formyl-2-furyl)-4-hydroxybenzamide

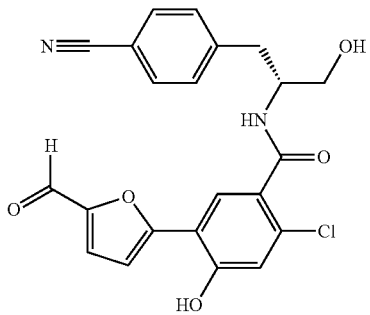 [SMILES: N#Cc1ccc(C[C@H](CO)NC(=O)c2cc(-c3ccc(C=O)o3)c(O)cc2Cl)cc1]

To a stirred solution of 5-bromo-2-chloro-N-[(2R)-1-(4-cyanophenyl)-3-hydroxypropan-2-yl]-4-hydroxybenzamide, 75 mg (0.183 mmol), 5-formylfuran-2-ylboronic acid, 38 mg (0.275 mmol, 1.5 eq.) and [1,1'-bis(diphenylphosphino)ferrocene]-dichloropalladium(II), complex with dichloromethane, 22 mg (27 μmol, 15 mol %) in degazed tetrahydrofuran (1.2 mL) was added a solution of sodium carbonate, 39 mg (0.366 mmol, 2.0 eq.) in degazed water (0.6 mL) and the resulting mixture was stirred at 50° C. for 18 h. After cooling to r.t., the solvent was removed under reduced pressure, water and ethyl acetate were added and the phases were separated. The aqueous layer was extracted with ethyl acetate (2×), the combined organic extracts were washed with brine, dried over sodium sulfate, filtered and concentrated to give the crude product, 92 mg (85%) as a dark brown solid that was used without further purification.

LC-MS (Method 1): R$_t$=2.71 min; MS (ES+): m/z=425/427 (M+H)$^+$.

2-chloro-N-[(2R)-1-(4-cyanophenyl)-3-hydroxypropan-2-yl]-4-hydroxy-5-[5-({[(1R)-1-4-methylphenyl)ethyl]amino}methyl)-2-furyl]benzamide To a stirred solution of 2-chloro-N-[(2R)-1-(4-cyanophenyl)-3-hydroxypropan-2-yl]-5-(5-formyl-2-furyl)-4-hydroxybenzamide, 91 mg (0.152 mmol) in a mixture of dichloromethane (1.5 mL) and N,N-dimethylformamide (0.30 mL) were added (R)-1-4-tolylethanamine, 25 μL (0.167 mmol, 1.1 eq.) followed by acetic acid, 44 μL (0.76 mmol, 5 eq.) and the mixture was stirred at r.t. for 30 min. Sodium triacetoxyborohydride, 48 mg (0.228 mmol, 1.5 eq.) was added in one portion and the resulting mixture was stirred at r.t. for 18 h. The mixture was poured into aq. sat. sodium hydrogen carbonate and extracted with dichloromethane (3×). The combined organic extracts were washed with brine, dried over sodium sulfate, filtered and concentrated. The residue (149 mg, brown oil) was purified by preparative TLC (eluent: dichloromethane/7N ammonia in methanol, 95:5) to give the product, 29 mg (35%) as an orange solid.

LC-MS (Method 1): R$_t$=2.34 min; MS (ES+): m/z=544/546 (M+H)$^+$.

$^1$H-NMR (500 MHz, DMSO-d$_6$) δ [ppm]=1.25 (d, 3H), 2.26 (s, 3H), 2.78 (dd, 1H), 3.08 (dd, 1H), 3.40 (m, 1H), 3.51-3.54 (m, 2H), 3.59 (d, 1H), 3.73 (q, 1H), 4.15 (m, 1H), 4.91 (t, 1H), 6.29 (d, 1H), 6.88 (d, 1H), 6.92 (s, 1H), 7.12 (d, 2H), 7.24 (d, 2H), 7.47 (d, 2H), 7.52 (s, 1H), 7.73 (d, 2H), 8.15 (d, 1H).

The following Examples were prepared in analogy of Example 1 by amide coupling of of intermediates xA or the corresponding dimethyl derivatives and of 1A and xB or commercially available amines:

| Example No | Intermediates | Structure/Name | Analytics |
|---|---|---|---|
| 91 | 6A; 1B | 4-Cyano-N-[(2R)-1-(4-cyanophenyl)-4-(methylamino)-4-oxobutan-2-yl]-3-[5-({[(1R)-1-(4-methylphenyl)ethyl]amino}methyl)-2-furyl]benzamide | LC-MS (Method 1): Rt = 2.40 min; MS (ES+): m/z = 560 (M + H)+. 1H-NMR (500 MHz, DMSO-d6) δ [ppm] = 1.27 (d, 3H), 2.27 (s, 3H), 2.42 (d, 2H), 2.56 (d, 3H), 2.93 (dd, 1H), 2.98 (dd, 1H), 3.59 (d, 1H), 3.64 (d, 1H), 3.77 (m, 1H), 4.53 (m, 1H), 6.48 (d, 1H), 7.12 (d, 2H), 7.20 (d, 1H), 7.25 (d, 2H), 7.42 (d, 2H), 7.69-7.73 (m, 3H), 7.83 (m, 1H), 7.98 (d, 1H), 8.09 (d, 1H), 8.63 (d, 1H). |

| Example No | Intermediates | Structure/Name | Analytics |
|---|---|---|---|
| 92 | 1A (3R)-3-amino-N-methyl-4-phenyl-butanamide | 2-Chloro-N-[(2R)-4-(methylamino)-4-oxo-1-phenylbutan-2-yl]-5-[5-({[(1R)-1-(4-methylphenyl)ethyl]amino}methyl)furan-2-yl]benzamide | MS: m/z = 544/546 [M + H]+ 1H-NMR (MeOD, 500 MHz): 1.37 (d, 3H), 2.31 (s, 3H), 2.52 (d, 2H), 2.73 (s, 3H), 2.90 (dd, 1H) 2.99 (dd, 1H), 3.60 and 3.65 (2d, AB, 2H), 3.77 (q, 1H), 4.67 (m, 1H), 6.30 (d, 1H), 6.70 (d, 1H), 7.10-7.35 (m, 9H), 7.39 (d, 1H), 7.41 (d, 1H), 7.65 (d, 1H). |
| 93 | 2-phenylpropan-2-amine 1B | 2-chloro-N-[(2R)-1-(4-cyanophenyl)-4-(methylamino)-4-oxobutan-2-yl]-5-(5-{[(2-phenylpropan-2-yl)amino]methyl}furan-2-yl)benzamide | LC-MS (Method 5): Rt = 2.45 min; MS (ES+) m/z = 569-571 (M + H)+ 1H-NMR (500 MHz, CD3OD) δ [ppm] = 1.54 (s, 6H), 2.55 (d, 2H), 2.74 (s, 3H), 2.94 (dd, 1H), 3.10 (dd, 1H), 3.51 (s, 2H), 4.69-4.74 (m, 1H), 6.29 (d, 1H), 6.70 (d, 1H), 7.21-7.4 (m, 1H), 7.35 (t, 2H), 7.40 (d, 1H), 7.44 (d, 1H), 7.50 (d, 2H), 7.53 (dd, 2H), 7.66-7.68 (m, 3H). |
| 94 | 2-(4-methylphenyl)propan-2-amine 1B | 2-Chloro-N-[(2R)-1-(4-cyanophenyl)-4-(methylamino)-4-oxobutan-2-yl]-5-[5-({[2-(4-methylphenyl)propan-2-yl]amino}methyl)-2-furyl]benzamide | LC-MS (Method 1): Rt = 2.44 min; MS (ES+): m/z = 583/585 (M + H)+ 1H-NMR (500 MHz, CD3OD) δ [ppm] = 1.52 (s, 6H), 2.30 (s, 3H), 2.56 (d, 2H), 2.74 (s, 3H), 2.98 (dd, 1H) 3.11 (dd, 1H), 3.50 (s, 2H), 4.71 (m, 1H), 6.28 (d, 1H), 6.70 (d, 1H), 7.16 (d, 2H), 7.38-7.42 (m, 3H), 7.43 (d, 1H), 7.50 (d, 2H), 7.64-7.68 (m, 3H). |

| Example No | Intermediates | Structure/Name | Analytics |
|---|---|---|---|
| 95 | 2-(4-chlorophenyl)propan-2-amine 6B | 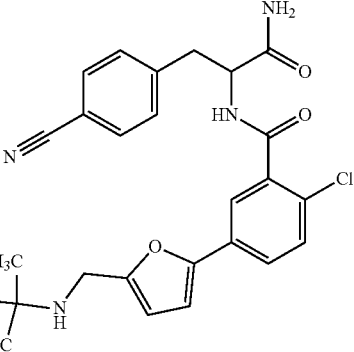<br>Nα-{2-chloro-5-[5-({[2-(4-chlorophenyl)propan-2-yl]amino}methyl)-2-furyl]benzoyl}-4-cyano-D-phenylalaninamide | LC-MS (Method 1): Rt = 2.46 min; MS (ES+) m/z = 575-577 (M + H)+ 1H-NMR (500 MHz, CD3OD) δ [ppm] = 1.52 (s, 6H), 3.08 (dd, 1H), 3.35 (dd, 1H), 3.52 (s, 2H), 4.94 (dd, 1H), 6.28 (d, 1H), 6.71 (d, 1H), 7.33 (d, 2H), 7.42 (d, 1H), 7.51-7.53 (m, 4H), 7.57 (d, 1H), 7.66-7.69 (m, 3H). |
| 96 | 1A (R)-3-amino-3-phenyl-propan-1-ol | 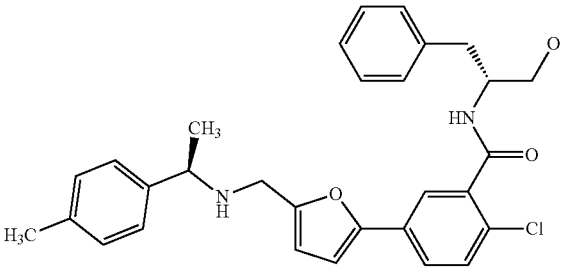<br>2-chloro-N-[(2R)-1-hydroxy-3-phenylpropan-2-yl]-5-[5-({(1R)-1-(4-methylphenyl)ethyl]amino}methyl)-2-furyl]benzamide | LC-MS (Method 1): Rt = 2.43 min; MS (ES+): m/z = 503-505 (M + H)+. 1H-NMR (500 MHz, DMSO-d6) δ [ppm] = 1.25 (d, 3H), 2.27 (s, 3H), 2.71 (dd, 1H), 2.98 (dd, 1H), 3.41 (m, 1H), 3.49-3.54 (m, 2H), 3.57 (d, 1H), 3.71 (q, 1H), 4.12 (m, 1H), 4.83 (t, 1H), 6.32 (d, 1H), 6.88 (d, 1H), 7.13 (d, 2H), 7.17 (m, 1H), 7.24 (d, 2H), 7.28-7.29 (m, 4H), 7.43 (d, 1H), 7.45 (d, 1H), 7.65 (dd, 1H), 8.31 (d, 1H). |

B. Assessment of the Physiological Activity

The ability of the compounds described in the present invention to disrupt the interaction between ATAD2 and acetylated Histone H4 (Ac-H4) was used as quantitative measure of their ATAD2-binding affinities.

To this end a TR-FRET assay which detects the binding of an Ac-H4-derived synthetic peptide (purchased from e.g. Biosyntan (Berlin, Germany)) of sequence HSGRGK-GGGGKGLGK(Ac)GGAKRHRK-Biotin to recombinant, N-terminally GST-tagged ATAD2 bromodomain amino acids 981-1108. The protein was produced in-house via *E. coli* expression followed by GSH-Sepharose affinity- and Superdex S200-size exclusion chromatography purification.

Typically, 11 different concentrations of each compound (0.1 nM, 0.33 nM, 1.1 nM, 3.8 nM, 13 nM, 44 nM, 0.15 μM, 0.51 μM, 1.7 μM, 5.9 μM and 20 μM) were tested in duplicate within the same microtiter plate. To this end, 100-fold concentrated compound solutions (in DMSO) were previously prepared with a Precision Pippeting System (BioTek) by serial dilution (1:3.4) of 2 mM stocks in clear, low-volume 384-well microtiter source plates (Greiner Bio-One). Subsequently, 50 nl of compounds were transferred into black, low-volume test plates from the same supplier using a Hummingbird capillary based liquid handling instrument (Digilab). Tests were started by the addition of 2 μl of 2.5-fold concentrated ATAD2 solution (25 nM=10 nM final concentration in the 5 μl assay volume) in aqueous assay buffer [50 mM HEPES pH 7.5, 50 mM potassium fluoride (KF), 100 mM sodium chloride (NaCl), 0.25 mM CHAPS, 0.05% bovine serum albumine (BSA) and 1 mM dithiothreitol (DTT)] to the compounds in the test plate with a Multidrop dispenser (Thermo-Fisher). Test plates were then incubated 10' at 22° C., in order to allow pre-equilibration of putative compound-ATAD2 complexes. Subsequently, 3 μl of a 1.67-fold concentrated solution containing Ac-H4 peptide (83.5 nM=50 nM final concentration) and TR-FRET detection reagents [16.7 nM Anti-GST-XL665 (Cisbio), =10 nM final concentration and 4.17 nM Lance EU W-1024 Streptavidin Europium Chelate (Perkin-Elmer)=2.5 nM final concentration were dispensed into the plates.

The mixture was further incubated in the dark for 1 hour at 22° C. Finally the inhibition of the formation of ATAD2/Ac-H4 complexes was assessed by measurement of the resonance energy transfer from the Streptavidin-Eu-Chelate to the anti-GST-XL665 antibody present in the reaction. To this end, the fluorescence emissions at 622 nm and 665 nm after excitation at 337 nm were measured in a TR-FRET reader, e.g. a Rubystar or Pherastar (both from BMG Lab Technologies) or a Viewlux (Perkin-Elmer) and the ratio of the emissions at 665 nm and at 622 nm was taken as indicator for the amount of ATAD2/Ac-H4 complexes in equilibrium.

The data were normalized using two sets of control wells (16 each). The first accounted for 100% ATAD2/Ac-H4 binding (0% inhibition), and contained all reaction components but DMSO instead of inhibitors. The second represented 0% ATAD2/Ac-H4 binding (100% inhibition), and included all assay components except ATAD2. IC50 values were calculated by fitting the normalized inhibition data to a 4-parameter logistic equation using either Screener software (Genedata) or a Bayer-proprietary analysis software.

| Example No | IC50 [M] |
| --- | --- |
| 1 | 7.40E−7 |
| 2 | 9.49E−7 |
| 3 | 9.27E−7 |
| 4 | 3.93E−7 |
| 5 | 1.89E−6 |
| 6 | 6.56E−7 |
| 7 | 8.32E−7 |
| 8 | 8.98E−7 |
| 9 | 7.49E−7 |
| 10 | 6.74E−7 |
| 11 | 8.22E−7 |
| 12 | 6.68E−7 |
| 13 | 3.86E−7 |
| 14 | 8.91E−7 |
| 15 | 8.12E−7 |
| 16 | 5.70E−7 |
| 17 | 3.41E−7 |
| 18 | 1.13E−6 |
| 19 | 6.40E−7 |
| 20 | 7.29E−7 |
| 21 | 5.80E−7 |
| 22 | 8.54E−7 |
| 23 | 5.61E−7 |
| 24 | 5.98E−7 |
| 25 | 3.52E−7 |
| 26 | 3.31E−7 |
| 27 | 1.16E−7 |
| 28 | 1.48E−7 |
| 29 | 6.75E−7 |
| 30 | 2.53E−7 |
| 31 | 2.97E−7 |
| 32 | 1.30E−7 |
| 33 | 1.84E−7 |
| 34 | 4.23E−7 |
| 35 | 4.66E−7 |
| 36 | 1.86E−7 |
| 37 | 4.43E−7 |
| 38 | 3.65E−7 |
| 39 | 5.85E−7 |
| 40 | 7.81E−7 |
| 41 | 7.59E−7 |
| 42 | 1.10E−6 |
| 43 | 1.71E−6 |
| 44 | 1.60E−6 |
| 45 | 1.80E−6 |
| 46 | 1.10E−6 |
| 47 | 2.10E−6 |
| 48 | 1.08E−6 |
| 49 | 1.76E−6 |
| 50 | 1.26E−6 |
| 51 | 8.10E−7 |
| 53 | 2.73E−7 |
| 54 | 7.05E−7 |
| 55 | 2.74E−7 |
| 56 | 5.10E−7 |
| 57 | 5.20E−7 |
| 58 | 1.72E−7 |
| 59 | 6.25E−7 |
| 60 | 1.90E−6 |
| 61 | 7.98E−7 |
| 62 | 3.32E−7 |
| 63 | 3.20E−7 |
| 64 | 1.18E−6 |
| 65 | 1.21E−7 |
| 66 | 2.45E−7 |
| 67 | 2.65E−7 |
| 68 | 1.09E−7 |
| 69 | 1.12E−7 |
| 70 | 8.58E−8 |
| 71 | 1.07E−7 |
| 72 | 1.38E−7 |
| 73 | 1.32E−7 |
| 74 | 6.71E−7 |
| 75 | 5.67E−7 |
| 76 | 4.41E−7 |
| 77 | 5.98E−7 |
| 78 | 1.23E−6 |
| 79 | 1.40E−6 |
| 80 | 4.07E−7 |
| 81 | 3.01E−7 |
| 82 | 3.50E−7 |
| 83 | 2.33E−7 |
| 84 | 2.70E−7 |
| 85 | 4.15E−7 |
| 86 | 1.66E−7 |
| 87 | 2.16E−7 |
| 88 | 1.28E−7 |
| 89 | 2.06E−6 |
| 90 | 3.67E−7 |
| 91 | 13.4E−6 |
| 92 | 8.37E−6 |
| 93 | 7.69E−6 |
| 94 | 2.98E−6 |
| 95 | 2.82E−6 |
| 96 | 2.65E−6 |

Cell Proliferation Assay

Previous reports demonstrated that ATAD2 is required for the cancer cell proliferation and growth and proposed ATAD2 as a therapeutic target for cancer. Consequently, down-regulation of ATAD2 by RNAi was shown to inhibit the proliferation and invasiveness of breast cancer cells (Kalashnikova et al., 2010, Cancer Res, 70: (22), 9402-9412; Revenko et al., 2010, Mol Cell Biol, 30: (22), 5260-5272), endometrial cancer cells (Raeder et al., 2013, PlosOne, 8: (2), e54873), ovarian cancer cells (Wan et al., 2014, Asian Pac J Cancer Prev, 15: (6) 2777-2783), liver cancer cells (Wu et al., 2014, BMC Cancer, 14: (107), 1-11), prostate cancer cells (Zou et al., 2009, Cancer Res, 69: (8) 3339-3346), cervical cancer cells (Zheng et al., 2015, Oncology Reports, 33: (5), 2337-2344), osteosarcoma (Ciro et al., 2009, Cancer Res, 69: (21), 8491-8498) and to promote apoptotic cancer cell death (Caron et al., 2010, Oncogene, 29: (37), 5171-5181).

The effect of ATAD2 inhibitory compounds on cancer cell proliferation might be measured as below. For example; MCF7 breast cancer cells might be seeded into 96-well microtiter plates at 2000 cells/well in 90 µl cell culture media (RPMI 1640, 10% FCS, 2 mM L-Glutamine, 10 µg/ml human Insulin, 100 µM Estradiol) and incubated for 24 h at 37° C. and 5% $CO_2$. Note, the culturing conditions might vary from cell line to cell line depending on their standard culturing conditions. Compounds might be then delivered to the microtiter assay plates and, following a 72 h long incubation period at 37° C. and 5% $CO_2$, the viability of the cells might be measured with addition of alamarBlue® (Invitrogen) to the medium in Victor X3 Multilabel Plate Reader (Perkin Elmer).

| Example No | MCF7 breast cancer GI50 [µM] | NCI-H526 lung cancer GI50 [µM] |
| --- | --- | --- |
| 71 | 3.18 µM | 1.25 µM |
| 86 | 3.2 µM | 2.40 µM |
| 36 | 1.28 µM | 1.29 µM |
| 53 | 2.51 µM | 3.6 µM |

-continued

| Example No | MCF7 breast cancer GI50 [μM] | NCl-H526 lung cancer GI50 [μM] |
|---|---|---|
| 33 | 1.42 μM | 1.25 μM |
| 66 | 3.76 μM | 5.10 μM |
| 90 | 10.8 μM | 19.1 μM |
| 81 | 10.4 μM | 10.2 μM |
| 4 | 11.5 μM | 15.4 μM |
| 42 | 11.9 μM | >30 μM |

GI50 means half-maximal growth inhibition.

Thus according to the data shown above the compound of the present invention are suitable for the treatment of breast cancer and lung cancer.

The invention claimed is:

1. A compound of general formula I

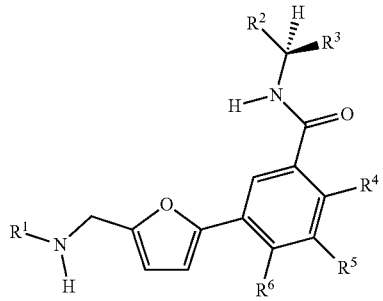

formula (I)

in which

R$^1$ represents a benzyl group wherein the α-position is substituted by one methyl group of R configuration or two methyl groups, and the 4-position may be substituted by a methyl group, a halogen atom, a 4-trifluoromethyl group, R$^2$ represents a $C_{1-6}$-alkyl group,
a $C_{1-6}$-hydroxyalkyl group,
a —$C_{1-3}$-alkylen-O—($C_{1-6}$-alkyl) group,
a —$C_{1-6}$-aminoalkyl group,
a —$C_{1-3}$-alkylen-N—($C_{1-6}$-alkyl)$_2$ group,
a —$C_{1-3}$-alkylen-NH—($C_{1-6}$-alkyl) group,
a —$C_{1-3}$-alkylen-NH—($C_{1-4}$-alkyl)-OH group,
a —$C_{1-3}$-alkylen-NH—($C_{3-7}$-cycloalkyl)-NH$_2$ group,
a —$C_{1-3}$-alkylen-NH—$C_{1-4}$-alkylen-heterocycloalkyl group which is optionally substituted with $C_{1-3}$-alkyl,
a —$C_{1-3}$-alkylen-NH-heterocycloalkyl group which is optionally substituted independently from each occurrence one or more times with $C_{1-4}$-alkyl, halogen, benzyl, C(O)R$^7$,
a —$C_{1-3}$-alkylen-NH—($C_{1-3}$-alkylen)-phenyl group,
a —$C_{1-3}$-alkylen-NH—C(O)($C_{1-4}$-alkyl) group,
a —$C_{1-3}$-alkylen-NH—C(O)—$C_{1-4}$-alkylen-heterocycloalkyl group,
a —$C_{1-3}$-alkylen-NH—C(O)—$C_{1-3}$-alkylen-C(O)-heterocycloalkyl group,
a —$C_{1-3}$-alkylen-NH—C(O)-heterocycloalkyl group,
a —$C_{1-3}$-alkylen-NH—S(O)$_2$-($C_{1-4}$-alkyl) group,
a —$C_{1-3}$-alkylen-(4-cyano-phenyl) group, a —$C_{1-3}$-alkylen-C(O)—NH—($C_{1-6}$-alkyl) group,
a —$C_{1-3}$-alkylen-C(O)—NH—($C_{1-4}$-alkyl)-OH group,
a —$C_{1-3}$-alkylen-C(O)—NR$^8$R$^9$ group,
a —$C_{1-3}$-alkylen-C(O)—R$^7$ group,
a —$C_{1-3}$-alkylen-C(O)-heterocycloalkyl group which is optionally substituted with $C_{1-3}$-alkyl,
a —$C_{1-3}$-alkylen-heterocycloalkyl group which is optionally one or more times substituted with $C_{1-3}$-alkyl,
a C(O)R$^7$ group,
a —C(O)—NR$^8$R$^9$ group,
a C(O)—NH—($C_{3-7}$-cycloalkyl)-NH$_2$ group,
a —C(O)—NH-heterocycloalkyl group which is optionally substituted with $C_{1-3}$-alkyl, a heteroaryl group, R$^3$ a —$C_{1-3}$-alkylen-phenyl group which is independently from each occurrence optionally substituted 1 to 3 times with a substituent selected from the group cyano, halogen, $C_{1-3}$-alkyl, $C_{1-3}$-alkoxy, amino, $C(O)R^7$, $C(O)NR^8R^9$, a —$C_{1-4}$-alkylen-heteroaryl group, or $R^2$ and $R^3$ together with the carbon atom to which they are attached form the following 6-membered ring whereby the star * indicates the carbon atoms which are attached to said carbon atom of absolute configuration R

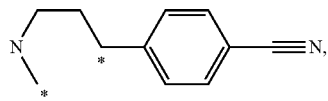

$R^4$ represents a hydrogen atom, a methyl group, a chlorine atom, $R^5$ represents a hydrogen atom or a halogen atom, $R^6$ represents a hydrogen atom, a halogen atom, a hydroxy group, a $C_{1-3}$ alkoxy group, or a cyano group, $R^7$ represents a —O—$C_{1-4}$-alkyl group, $R^8$, $R^9$, represents, independently for each occurrence, a hydrogen atom or a $C_{1-4}$-alkyl group, or the salts thereof, the solvates thereof or the solvates of the salts thereof, with the proviso that the following compounds 2-Chlor-N-[(2R)-1-(4-cyanphenyl)-4-(methylamino)-4-oxobutan-2-yl]-5-[5-({[(1R)-1-(4-methylphenyl)ethyl]amino}methyl)-2-furyl]benzamide N-[(2R)-1-(4-cyanophenyl)-4-(methylamino)-4-oxobutan-2-yl]-2-fluoro-5-[5-({[(1R)-1-(4-methylphenyl)ethyl]amino}methyl)-2-furyl]benzamide 2-chloro-N-[(2R)-1-(4-fluorophenyl)-4-(methylamino)-4-oxobutan-2-yl]-5-[5-({[(1R)-1-(4-methylphenyl)ethyl]amino}methyl)-2-furyl]benzamide N-[(2R)-1-(4-cyanophenyl)-4-(methylamino)-4-oxobutan-2-yl]-2-methyl-5-[5-({[(1R)-1-(4-methylphenyl)ethyl]amino}methyl)-2-furyl]benzamide 2-chloro-N-[(2R)-1-(4-cyanophenyl)-4-(methylamino)-4-oxobutan-2-yl]-5-[5-({[(1R)-1-(4-fluorophenyl)ethyl]amino}methyl)-2-furyl]benzamide are excluded.

2. The compound according to claim 1, in which in which $R^1$ represents a benzyl group wherein the α-position is substituted by one methyl group of R configuration or two methyl groups, and the 4-position may be substituted by a methyl group, a halogen atom, a 4-trifluoromethyl group, $R^2$ represents a $C_{1-3}$-alkyl group, a $C_{1-3}$-hydroxyalkyl group, a —$C_{1-3}$-alkylen-O—($C_{1-3}$-alkyl) group, a —$C_{1-3}$-aminoalkyl group, a —$C_{1-3}$-alkylen-N—($C_{1-3}$-alkyl)$_2$ group, a —$C_{1-3}$-alkylen-NH—($C_{1-3}$-alkyl) group, a —$C_{1-3}$-alkylen-NH—($C_{1-3}$-alkyl)-OH group, a —$C_{1-3}$-alkylen-NH—($C_{5-6}$-cycloalkyl)-NH$_2$ group, a —$C_{1-3}$-alkylen-NH—$C_{1-3}$-alkylen-heterocycloalkyl group which is optionally substituted with $C_{1-3}$-alkyl, a —$C_{1-3}$-alkylen-NH-heterocycloalkyl group which is optionally substituted independently from each occurrence one or more times with $C_{1-4}$-alkyl, halogen, benzyl, C(O)R$^7$, a —$C_{1-3}$-alkylen-NH—($C_{1-3}$-alkylen)-phenyl group, a —$C_{1-3}$-alkylen-NH—C(O)($C_{1-3}$-alkyl) group, a —$C_{1-3}$-alkylen-NH—C(O)—$C_{1-3}$-alkylen-heterocycloalkyl group, a —$C_{1-3}$-alkylen-NH—$C_{1-3}$-alkylen-C(O)-heterocycloalkyl group, a —$C_{1-3}$-alkylen-NH—C(O)-heterocycloalkyl group, a —$C_{1-3}$-alkylen-NH—S(O)$_2$-($C_{1-3}$-alkyl) group, a —$C_{1-3}$-alkylen-(4-cyano-phenyl) group, a —$C_{1-3}$-alkylen-C(O)—NH—($C_{1-3}$-alkyl) group, a —$C_{1-3}$-alkylen-C(O)—NH—($C_{1-3}$-alkyl)-OH group, a —$C_{1-3}$-alkylen-C(O)—NR$^8$R$^9$ group, a —$C_{1-3}$-alkylen-C(O)—R$^7$ group, a —$C_{1-3}$-alkylen-C(O)-heterocycloalkyl group which is optionally substituted with $C_{1-3}$-alkyl, a —$C_{1-3}$-alkylen-heterocycloalkyl group which is optionally one or more times substituted with $C_{1-3}$-alkyl, a C(O)R$^7$ group, a —C(O)—NR$^8$R$^9$ group, a C(O)—NH—($C_{5-6}$-cycloalkylen)-NH$_2$ group, a —C(O)—NH-heterocycloalkyl group which is optionally substituted with $C_{1-3}$-alkyl a heteroaryl group, $R^3$ a —$C_{1-3}$-alkylen-phenyl group which is independently from each occurrence optionally substituted 1 to 3 times with a substituent selected from the group cyano, halogen, $C_{1-3}$-alkyl, $C_{1-3}$-alkoxy, amino, C(O)R$^7$, C(O)NR$^8$R$^9$, a —$C_{1-4}$-alkylen-heteroaryl group, or $R^2$ and $R^3$ together with the carbon atom to which they are attached form the following 6-membered ring whereby the star * indicates the carbon atoms which are attached to said carbon atom

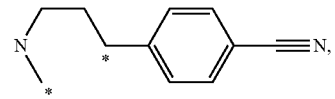

$R^4$ represents a hydrogen atom, a methyl group, a chlorine atom, $R^5$ represents a hydrogen atom or a halogen atom $R^6$ represents a hydrogen atom, a halogen atom, a hydroxy group, a $C_{1-3}$ alkoxy group, or a cyano group, $R^7$ represents a —O—$C_{1-4}$-alkyl group $R^8$, $R^9$, represents, independently for each occurrence, a hydrogen atom or a $C_{1-4}$-alkyl group, or the salts thereof, the solvates thereof or the solvates of the salts thereof, with the proviso that the following compounds 2-Chlor-N-[(2R)-1-(4-cyanphenyl)-4-(methylamino)-4-oxobutan-2-yl]-5-[5-({[(1R)-1-(4-methylphenyl)ethyl]amino}methyl)-2-furyl]benzamide N-[(2R)-1-(4-cyanophenyl)-4-(methylamino)-4-oxobutan-2-yl]-2-fluoro-5-[5-({[(1R)-1-(4-methylphenyl)ethyl]amino}methyl)-2-furyl]benzamide 2-chloro-N-[(2R)-1-(4-fluorophenyl)-4-(methylamino)-4-oxobutan-2-yl]-5-[5-({[(1R)-1-(4-methylphenyl)ethyl]amino}methyl)-2-furyl]benzamide N-[(2R)-1-(4-cyanophenyl)-4-(methylamino)-4-oxobutan-2-yl]-2-methyl-5-[5-({[(1R)-1-(4-methylphenyl)ethyl]amino}methyl)-2-furyl]benzamide 2-chloro-N-[(2R)-1-(4-cyanophenyl)-4-(methylamino)-4-oxobutan-2-yl]-5-[5-({[(1R)-1-(4-fluorophenyl)ethyl]amino}methyl)-2-furyl]benzamide are excluded.

3. The compound according to claim 1, in which

R¹ represents a benzyl group wherein the α-position is substituted by one methyl group of R configuration or two methyl groups, and the 4-position may be substituted by a methyl group, a halogen atom, a 4-trifluoromethyl group, R² represents a methyl group,
a hydroxymethyl group,
—(CH₂)₂OH,
—C(OH)(CH₃)₂,
—CH(OH)CH₃,
—C(OH)(CH₃)₂,
—CH(OH)—CH₂—CH(CH₃)₂,
—CH₂—O—CH₃,
—CH₂—NH₂,
—CH₂—N(CH₃)₂,
—(CH₂)₂—NH—CH(CH₃)₂,
—CH₂—NH—CH₂—CH(CH₃)₂,
—CH₂—NH—(CH₂)₂—OH,
—CH₂—NH-(1,4-cyclohexylen)-NH₂, —CH₂—NH—(CH₂)₂-piperidine-4-yl,
—(CH₂)₂—NH—CH₂-(1-methyl-piperidine-4-yl),
—CH₂—NH—CH₂-(3-azabicyclo[3.1.0]hex-6-yl),
—CH₂—NH-(1-ethyl-piperidine-4-yl),
—CH₂—NH-(1-isobutyl-piperidine-4-yl),
—CH₂—NH-(1-phenylmethyl-piperidine-4-yl),
—CH₂—NH-(1-tert.butoxycarbonyl-piperidine-4-yl),
—CH₂—NH-2,2-dimethyl-piperidine-4yl),
—(CH₂)₂—NH-(1-methyl-pyrrolidin-3-yl),
—CH₂—NH-(piperidin-4-yl),
—CH₂—NH-(1-methyl-piperidin-4-yl),
—CH₂—NH-(2-methyl-propyl-piperidin-3-yl),
—CH₂—NH-(3-fluoropiperidin-4-yl),
—CH₂—NH—CH₂-phenyl,
—CH₂—NH—C(O)—CH₃,
—CH₂—NH—C(O)—CH₂-piperidine-4-yl,
—CH₂—NH—CH₂—C(O)-piperazine-1-yl,
—CH₂—NH—C(O)-piperidine-4-yl,
—CH₂—NH—S(O)₂—CH₃,
—CH₂-(4-cyano-phenyl),
—CH₂—C(O)—NH—CH₃,
—CH₂—C(O)—NH—(CH₃)₂,
—CH₂—C(O)—NH—CH(CH₃)₂,
—CH₂—C(O)—NH—(CH₂)₂—OH,
—CH₂—C(O)—NH—(CH₂)₃—OH,
—CH₂—C(O)—NH₂,
—CH₂—C(O)—N(CH₃)₂,
—CH₂—C(O)—NH—CH₃,
—CH₂—C(O)—OCH₃,
—CH₂—C(O)-(morpholine-4-yl),
—CH₂—C(O)-(4-methyl-piperazine-1-yl),
—CH₂—C(O)-(N-pyrrolidine),
—(CH₂)₂-(3-methylpiperazine-1-yl),
—CH₂-(4-methyl-piperazine-1-yl),
—(CH₂)₂-(4-methyl-piperazine-1-yl),
—CH₂-(morpholine-4-yl),
—(CH₂)₂-(morpholine-4-yl),
—(CH₂)₂-(2,4-dimethylpiperazine-1-yl),
—(CH₂)₂-(6-methyl-2,6-diazaspiro[3.3]hept-2-yl),
—CH₂-(N-pyrrolidine),
C(O)OCH₃,
—C(O)—NH₂,
—C(O)NH-(4-amino-cyclohexylen),
—C(O)—NH-(1-methyl-piperidine-4-yl),
1H-1,2,4-triazol-5-yl, 1H-imidazol-2-yl, R³ a —CH₂-phenyl group which is independently from each occurrence optionally substituted 1 to 3 times with a substituent selected from the group cyano, halogen, C₁₋₃-alkyl, C₁₋₃-alkoxy, amino, C(O)R⁷, C(O)NR⁸R⁹, —CH₂-pyridine-4-yl, or R² and R³ together with the carbon atom to which they are attached form the following 6-membered ring whereby the star * indicates the carbon atoms which are attached to said carbon atom

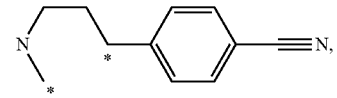

R⁴ represents a hydrogen atom, a methyl group, a chlorine atom,

R⁵ represents a hydrogen atom or a fluorine atom

R⁶ represents a hydrogen atom, a chlorine atom, a hydroxy group, a C₁₋₃ alkoxy group, or a cyano group, R⁷ represents a methoxy group R⁸, R⁹, represents, independently for each occurrence, a hydrogen atom or a methyl group, or the salts thereof, the solvates thereof or the solvates of the salts thereof, with the proviso that the following compounds 2-Chlor-N-[(2R)-1-(4-cyanphenyl)-4-(methylamino)-4-oxobutan-2-yl]-5-[5-({[(1R)-1-(4-methylphenyl)ethyl]amino}methyl)-2-furyl]benzamide N-[(2R)-1-(4-cyanophenyl)-4-(methylamino)-4-oxobutan-2-yl]-2-fluoro-5-[5-({[(1R)-1-(4-methylphenyl)ethyl]amino}methyl)-2-furyl]benzamide 2-chloro-N-[(2R)-1-(4-fluorophenyl)-4-(methylamino)-4-oxobutan-2-yl]-5-[5-({[(1R)-1-(4-methylphenyl)ethyl]amino}methyl)-2-furyl]benzamide N-[(2R)-1-(4-cyanophenyl)-4-(methylamino)-4-oxobutan-2-yl]-2-methyl-5-[5-({[(1R)-1-(4-methylphenyl)ethyl]amino}methyl)-2-furyl]benzamide 2-chloro-N-[(2R)-1-(4-cyanophenyl)-4-(methylamino)-4-oxobutan-2-yl]-5-[5-({[(1R)-1-(4-fluorophenyl)ethyl]amino}methyl)-2-furyl]benzamide are excluded.

4. The compound according to claim 1, which is selected from the group consisting of:

2-chloro-N-[(2R)-1-(4-cyanophenyl)-4-(dimethylamino)-4-oxobutan-2-yl]-5-[5-({[(1R)-1-(4-methylphenyl)ethyl]amino}methyl)furan-2-yl]benzamide, Nα-{2-chloro-5-[5-({[(1R)-1-(4-methylphenyl)ethyl]amino}methyl)-2-furyl]benzoyl}-4-cyano-D-phenylalaninamide, N-[(2R)-4-amino-1-(4-cyanophenyl)-4-oxobutan-2-yl]-2-chloro-5-[5-({[(1R)-1-(4-methylphenyl)ethyl]amino}methyl)furan-2-yl]benzamide, 2-chloro-N-[(2R)-1-(4-cyanophenyl)-3-hydroxypropan-2-yl]-5-[5-({[(1R)-1-(4-methyl-phenyl)ethyl]amino}methyl)-2-furyl]benzamide, Nα-{2-chloro-5-[5-({[(1R)-1-(4-methylphenyl)ethyl]amino}methyl)furan-2-yl]-benzoyl}-4-cyano-N-methyl-D-phenylalaninamide, 2-chloro-N-[(2R)-1-(4-cyanophenyl)-4-(isopropylamino)-4-oxobutan-2-yl]-5-[5-({[(1R)-1-(4-methyl-phenyl)ethyl]amino}methyl)-2-furyl]benzamide, 2-chloro-N-{(2R)-1-(4-cyanophenyl)-4-[(2-hydroxyethyl)amino]-4-oxobutan-2-yl}-5-[5-({[(1R)-1-(4-methylphenyl)ethyl]amino}methyl)-2-furyl]benzamide, 2-chloro-N-{(2R)-1-(4-cyanophenyl)-4-[(3-hydroxypropyl)amino]-4-oxobutan-2-yl}-5-[5-({[(1R)-1-(4-methylphenyl)ethyl]amino}methyl)-2-furyl]benzamide, 2-chloro-N-[(2R)-1-(4-cyanophenyl)-4-oxo-4-(pyrrolidin-1-yl)butan-2-yl]-5-[5-({[(1R)-1-(4-methylphenyl)ethyl]amino}methyl)-2-furyl]benzamide, 2-chloro-N-[(2R)-1-(4-cyanophenyl)-4-(morpholin-4-yl)-4-oxobutan-2-yl]-5-[5-({[(1R)-1-(4-methylphenyl)ethyl]amino}methyl)-2-furyl]benzamide, 2-chloro-N-[(2R)-1-(4-cyanophenyl)-4-(4-methylpiperazin-1-yl)-4-oxobutan-2-yl]-5-[5-({[(1R)-1-(4-methylphenyl)ethyl]amino}methyl)-2-furyl]benzamide, 2-chloro-N-[(2R)-1-(4-cyanophenyl)-3-hydroxy-3-methylbutan-2-yl]-5-[5-({[(1R)-1-(4-methylphenyl)ethyl]amino}methyl)furan-2-yl]benzamide, 2-chloro-N-[(2R)-1-(4-cyanophenyl)-4-hydroxybutan-2-yl]-5-[5-({[(1R)-1-(4-methyl-phenyl)ethyl]amino}methyl)furan-2-yl]benzamide, 2-chloro-N-[(2R)-1-(4-cyanophenyl)-3-methoxypropan-2-yl]-5-[5-({[(1R)-1-(4-methylphenyl)ethyl]amino}methyl)furan-2-yl]benzamide, methyl N-{2-chloro-5-[5-({[(1R)-1-(4-methylphenyl)ethyl]amino}methyl)furan-2-yl]-benzoyl}-4-cyano-D-phenylalaninate, 2-chloro-N-[(2R,3R)-1-(4-cyanophenyl)-3-hydroxybutan-2-yl]-5-[5-({[(1R)-1-(4-methylphenyl)ethyl]amino}methyl)furan-2-yl]benzamide, 2-chloro-N-[(2R,3R)-1-(4-cyanophenyl)-3-hydroxybutan-2-yl]-5-[5-({[(1R)-1-(4-methylphenyl)ethyl]amino}methyl)furan-2-yl]benzamide, 2-chloro-N-[(2R)-1-hydroxy-3-(4-iodophenyl)propan-2-yl]-5-[5-({[(1R)-1-(4-methyl-phenyl)ethyl]amino}methyl)furan-2-yl]benzamide, 2-chloro-N-[(1S)-2-(4-cyanophenyl)-1-(1H-imidazol-2-yl)ethyl]-5-[5-({[(1R)-1-(4-methylphenyl)ethyl]amino}methyl)furan-2-yl]benzamide, 2-chloro-N-[(1R)-2-(4-cyanophenyl)-1-(1H-1,2,4-triazol-5-yl)ethyl]-5-[5-({[(1R)-1-(4-methylphenyl)ethyl]amino}methyl)furan-2-yl]benzamide, 2-chloro-N-[(2R)-1-(4-cyanophenyl)-3-(4-methylpiperazin-1-yl)propan-2-yl]-5-[5-({[(1R)-1-(4-methylphenyl)ethyl]amino}methyl)furan-2-yl]benzamide, 2-chloro-N-[(2R)-1-(4-cyanophenyl)-3-(morpholin-4-yl)propan-2-yl]-5-[5-({[(1R)-1-(4-methylphenyl)ethyl]amino}methyl)furan-2-yl]benzamide, 2-chloro-N-{(2R)-1-(4-cyanophenyl)-3-[(2-hydroxyethyl)amino]propan-2-yl}-5-[5-({[(1R)-1-(4-methylphenyl)ethyl]amino}methyl)furan-2-yl]benzamide, 2-chloro-N-[(2R)-1-(4-cyanophenyl)-3-(dimethylamino)propan-2-yl]-5-[5-({[(1R)-1-(4-methylphenyl)ethyl]amino}methyl)furan-2-yl]benzamide, 2-chloro-N-[(2R)-1-(4-cyanophenyl)-4-(4-methylpiperazin-1-yl)butan-2-yl]-5-[5-({[(1R)-1-(4-methylphenyl)ethyl]amino}methyl)furan-2-yl]benzamide, 2-chloro-N-[(2R)-1-(4-cyanophenyl)-4-(propan-2-ylamino)butan-2-yl]-5-[5-({[(1R)-1-(4-methylphenyl)ethyl]amino}methyl)furan-2-yl]benzamide, 2-chloro-N-{(2R)-1-(4-cyanophenyl)-4-[(3R)-3-methylpiperazin-1-yl]butan-2-yl}-5-[5-({[(1R)-1-(4-methylphenyl)ethyl]amino}methyl)furan-2-yl]benzamide, 2-chloro-N-{(2R)-1-(4-cyanophenyl)-4-[(3S)-3-methylpiperazin-1-yl]butan-2-yl}-5-[5-({[(1R)-1-(4-methylphenyl)ethyl]amino}methyl)furan-2-yl]benzamide, 2-chloro-N-[(2R)-1-(4-cyanophenyl)-4-(morpholin-4-yl)butan-2-yl]-5-[5-({[(1R)-1-(4-methylphenyl)ethyl]amino}methyl)furan-2-yl]benzamide, Nα-{2-chloro-5-[5-({[(1R)-1-(4-methylphenyl)ethyl]amino}methyl)furan-2-yl]-benzoyl}-4-cyano-N-(1-methylpiperidin-4-yl)-D-phenylalaninamide, 2-chloro-N-{(2R)-1-(4-cyanophenyl)-4-[(2S)-2,4-dimethylpiperazin-1-yl]butan-2-yl}-5-[5-({[(1R)-1-(4-methylphenyl)ethyl]amino}methyl)furan-2-yl]benzamide, 2-chloro-N-{(2R)-1-(4-cyanophenyl)-4-[(2R)-2,4-dimethylpiperazin-1-yl]butan-2-yl}-5-[5-({[(1R)-1-(4-methylphenyl)ethyl]amino}methyl)furan-2-yl]benzamide, 2-chloro-N-[(2R)-1-(4-cyanophenyl)-4-{[(1-methylpiperidin-4-yl)methyl]amino}butan-2-yl]-5-[5-({[(1R)-1-(4-methylphenyl)ethyl]amino}methyl)furan-2-yl]benzamide, 2-chloro-N-[(2R)-1-(4-cyanophenyl)-4-{[(3R)-1-methylpyrrolidin-3-yl]amino}butan-2-yl]-5-[5-({[(1R)-1-(4-methylphenyl)ethyl]amino}methyl)furan-2-yl]benzamide, 2-chloro-N-[(2R)-1-(4-cyanophenyl)-4-{[(3S)-1-methylpyrrolidin-3-yl]amino}butan-2-yl]-5-[5-({[(1R)-1-(4-methylphenyl)ethyl]amino}methyl)furan-2-yl]benzamide, 2-chloro-N-[(2R)-1-(4-cyanophenyl)-4-(6-methyl-2,6-diazaspiro[3.3]hept-2-yl)butan-2-yl]-5-[5-({[(1R)-1-(4-methylphenyl)ethyl]amino}methyl)furan-2-yl]benzamide, 2-chloro-N-[(2R)-1-(4-cyano-3-methylphenyl)-3-hydroxypropan-2-yl]-5-[5-({[(1R)-1-(4-methylphenyl)ethyl]amino}methyl)furan-2-yl]benzamide, 2-chloro-N-[(2R)-1-(4-cyano-5-fluoro-2-methylphenyl)-3-hydroxypropan-2-yl]-5-[5-({[(1R)-1-(4-methylphenyl)ethyl]amino}methyl)furan-2-yl]benzamide, 2-chloro-N-[(2R)-1-(4-cyano-2-methoxyphenyl)-3-hydroxypropan-2-yl]-5-[5-({[(1R)-1-(4-methylphenyl)ethyl]amino}methyl)furan-2-yl]benzamide, N-[(2R)-1-(3-amino-4-cyanophenyl)-3-hydroxypropan-2-yl]-2-chloro-5-[5-({[(1R)-1-(4-methylphenyl)ethyl]amino}methyl)furan-2-yl]benzamide, N-[(2R)-1-(2-amino-4-cyanophenyl)-3-hydroxypropan-2-yl]-2-chloro-5-[5-({[(1R)-1-(4-methylphenyl)ethyl]amino}methyl)furan-2-yl]benzamide, 2-chloro-N-[(2S)-1-(4-cyanophenyl)propan-2-yl]-5-[5-({[(1R)-1-(4-methylphenyl)-ethyl]amino}methyl)-2-furyl]benzamide, N-[(2R)-1-(acetylamino)-3-(4-cyanophenyl)propan-2-yl]-2-chloro-5-[5-({[(1R)-1-(4-methylphenyl)ethyl]amino}methyl)furan-2-yl]benzamide, 2-chloro-N-[(2R)-1-(3-cyanophenyl)-3-hydroxypropan-2-yl]-5-[5-({[(1R)-1-(4-methyl-phenyl)ethyl]amino}methyl)furan-2-yl]benzamide, 2-chloro-N-[(2R,3R)-1-(4-cyanophenyl)-3-hydroxy-5-methylhexan-2-yl]-5-[5-({[(1R)-1-(4-methylphenyl)ethyl]amino}methyl)furan-2-yl]benzamide, 2-chloro-N-[(2R,3S)-1-(4-cyanophenyl)-3-hydroxy-5-methylhexan-2-yl]-5-[5-({[(1R)-1-(4-methylphenyl)ethyl]amino}methyl)furan-2-yl]benzamide, 2-chloro-N-[(2R)-1-hydroxy-3-(pyridin-4-yl)propan-2-yl]-5-[5-({[(1R)-1-(4-methyl-phenyl)ethyl]amino}methyl)furan-2-yl]benzamide, N-[(2R)-1-(4-carbamoylphenyl)-3-hydroxypropan-2-yl]-2-chloro-5-[5-({[(1R)-1-(4-methylphenyl)ethyl]amino}methyl)furan-2-yl]benzamide, 2-chloro-N-[(2R)-1-(4-cyanophenyl)-3-(pyrrolidin-1-yl)propan-2-yl]-5-[5-({[(1R)-1-(4-methylphenyl)ethyl]amino}methyl)furan-2-yl]benzamide, methyl (3R)-3-({2-chloro-5-[5-({[(1R)-1-(4-methylphenyl)ethyl]amino}methyl)-2-furyl]benzoyl}amino)-4-(4-cyanophenyl)butanoate, methyl 4-[(2R)-2-({2-chloro-5-[5-({[(1R)-1-(4-methylphenyl)ethyl]amino}methyl)-furan-2-yl]benzoyl}amino)-3-hydroxypropyl]benzoate, N-[(2R)-1-amino-3-(4-cyanophenyl)propan-2-yl]-2-chloro-5-[5-({[(1R)-1-(4-methyl-phenyl)ethyl]amino}methyl)furan-2-yl]benzamide, 2-chloro-N-{(2R)-1-(4-cyanophenyl)-3-[(methylsulfonyl)amino]propan-2-yl}-5-[5-({[(1R)-1-(4-methylphenyl)ethyl]amino}methyl)furan-2-yl]benzamide, 2-chloro-N-[(2R)-1-(4-cyanophenyl)-3-{[2-oxo-2-(piperazin-1-yl)ethyl]amino}propan-2-yl]-5-[5-({[(1R)-1-(4-methylphenyl)ethyl]amino}methyl)furan-2-yl]benzamide, N-[(2R)-2-({2-chloro-5-[5-({[(1R)-1-(4-methylphenyl)ethyl]amino}methyl)furan-2-yl]benzoyl}amino)-3-(4-cyanophenyl)propyl]piperidine-4-carboxamide, 2-chloro-N-{(2R)-1-(4-cyanophenyl)-3-[(piperidin-4-ylacetyl)amino]propan-2-yl}-5-[5-({[(1R)-1-(4-methylphenyl)ethyl]amino}methyl)furan-2-yl]benzamide, 2-chloro-N-{(2R)-1-(4-cyanophenyl)-3-[(1-methylpiperidin-4-yl)amino]propan-2-yl}-5-[5-({[(1R)-1-(4-methylphenyl)ethyl]amino}methyl)furan-2-yl]benzamide, N-[(2R)-1-[(1-benzylpiperidin-4-yl)amino]-3-(4-cyanophenyl)propan-2-yl]-2-chloro-5-[5-({[(1R)-1-(4-methylphenyl)ethyl]amino}methyl)furan-2-yl]benzamide, N-[(2R)-1-(benzylamino)-3-(4-cyanophenyl)propan-2-yl]-2-chloro-5-[5-({[(1R)-1-(4-methylphenyl)ethyl]amino}methyl)furan-2-yl]benzamide, 2-chloro-N-{(2R)-1-(4-cyanophenyl)-3-[(2-methylpropyl)amino]propan-2-yl}-5-[5-({[(1R)-1-(4-methylphenyl)ethyl]amino}methyl)furan-2-yl]benzamide, 2-chloro-N-{(2R)-1-(4-cyanophenyl)-3-[(1-ethylpiperidin-4-yl)amino]propan-2-yl}-5-[5-({[(1R)-1-(4-methylphenyl)ethyl]amino}methyl)furan-2-yl]benzamide, 2-chloro-N-[(2R)-1-(4-cyanophenyl)-3-{[-(2-methylpropyl)piperidin-4-yl]amino}-propan-2-yl]-5-[5-({[(1R)-1-(4-methylphenyl)ethyl]amino}methyl)furan-2-yl]benzamide, tert-butyl 4-{[(2R)-2-({2-chloro-5-[5-({[(1R)-1-(4-methylphenyl)ethyl]amino}methyl)-furan-2-yl]benzoyl}amino)-3-(4-cyanophenyl)propyl]amino}piperidine-1-carboxylate, 2-chloro-N-[(2R)-1-(4-cyanophenyl)-3-{[(3S)-1-methylpiperidin-3-yl]amino}propan-2-yl]-5-[5-({[(1R)-1-(4-methylphenyl)ethyl]amino}methyl)furan-2-yl]benzamide, N-[(2R)-1-{[(1R,5-azabicyclo[3.1.0]hex-6-ylmethyl]amino}-3-(4-cyanophenyl)-propan-2-yl]-2-chloro-5-[5-({[(1R)-1-(4-methylphenyl)ethyl]amino}methyl)furan-2-yl]benzamide, 2-chloro-N-[(2R)-1-(4-cyanophenyl)-3-(piperidin-4-ylamino)propan-2-yl]-5-[5-({[(1R)-1-(4-methylphenyl)ethyl]amino}methyl)furan-2-yl]benzamide, 2-chloro-N-[(2R)-1-(4-cyanophenyl)-3-{[(4R)-2,2-dimethylpiperidin-4-yl]amino}-propan-2-yl]-5-[5-({[(1R)-1-(4-methylphenyl)ethyl]amino}methyl)furan-2-yl]benzamide, 2-chloro-N-{(2R)-1-(4-cyanophenyl)-3-[(piperidin-4-ylmethyl)amino]propan-2-yl}-5-[5-({[(1R)-1-(4-methyl-phenyl)ethyl]amino}methyl)furan-2-yl]benzamide, 2-chloro-N-[(2R)-1-(4-cyanophenyl)-3-{[2-(piperidin-4-yl)ethyl]amino}propan-2-yl]-5-[5-({[(1R)-1-(4-methylphenyl)ethyl]amino}methyl)furan-2-yl]benzamide, N-[(2R)-1-[(cis-4-aminocyclohexyl)amino]-3-(4-cyanophenyl)propan-2-yl]-2-chloro-5-[5-({[(1R)-1-(4-methylphenyl)ethyl]amino}methyl)furan-2-yl]benzamide, N-[(2R)-1-[(cis-4-aminocyclohexyl)amino]-3-(4-cyanophenyl)propan-2-yl]-2-chloro-5-[5-({[(1R)-1-(4-methylphenyl)ethyl]amino}methyl)furan-2-yl]benzamide, 2-chloro-N-[(2R)-1-(4-cyanophenyl)-3-{[(3S,4R)-3-fluoropiperidin-4-yl]amino}propan-2-yl]-5-[5-({[(1R)-1-(4-methylphenyl)ethyl]amino}methyl)furan-2-yl]benzamide, N-[(2R)-1-amino-3-(4-cyanophenyl)propan-2-yl]-2-chloro-5-[5-[({2-[4-(trifluoro-methyl)phenyl]propan-2-yl}amino)methyl]furan-2-yl}benzamide, N-[(2R)-1-amino-3-(4-cyanophenyl)propan-2-yl]-2-chloro-5-{5-[({(1R)-1-[4-(trifluoromethyl)phenyl]ethyl}amino)methyl]furan-2-yl}benzamide, 2-chloro-N-[(3R,4R)-4-(4-cyanophenyl)piperidin-3-yl]-5-[5-({[(1R)-1-(4-methyl-phenyl)ethyl]amino}methyl)furan-2-yl]benzamide, 2-chloro-N-[(2R)-1-(4-cyanophenyl)-3-hydroxypropan-2-yl]-3-fluoro-5-[5-({[(1R)-1-(4-methylphenyl)ethyl]amino}methyl)furan-2-yl]benzamide, 2,4-dichloro-N-[(2R)-1-(4-cyanophenyl)-3-hydroxypropan-2-yl]-5-[5-({[(1R)-1-(4-methylphenyl)ethyl]amino}methyl)furan-2-yl]benzamide, 4-cyano-N-[(2R)-1-(4-cyanophenyl)-3-hydroxypropan-2-yl]-3-[5-({[(1R)-1-(4-methyl-phenyl)ethyl]amino}methyl)furan-2-yl]benzamide, N-[(2R)-1-(4-cyanophenyl)-3-hydroxypropan-2-yl]-4-methoxy-2-methyl-5-[5-({[(1R)-1-(4-methylphenyl)ethyl]amino}methyl)furan-2-yl]benzamide, 2-chloro-N-[(2R)-1-(4-cyanophenyl)-3-hydroxypropan-2-yl]-4-methoxy-5-[5-({[(1R)-1-(4-methylphenyl)ethyl]amino}methyl)furan-2-yl]benzamide, 2-chloro-N-[(2R)-1-(4-cyano-3-methylphenyl)-3-hydroxypropan-2-yl]-4-methoxy-5-[5-({[(1R)-1-(4-methylphenyl)ethyl]amino}methyl)furan-2-yl]benzamide, N-[(2R)-1-amino-3-(4-cyanophenyl)propan-2-yl]-2-chloro-4-methoxy-5-[5-({[(1R)-1-(4-methylphenyl)ethyl]amino}methyl)furan-2-yl]benzamide, N-[(2R)-1-amino-3-(4-cyano-3-methylphenyl)propan-2-yl]-2-chloro-4-methoxy-5-[5-({[(1R)-1-(4-methylphenyl)ethyl]amino}methyl)furan-2-yl]benzamide, N-(trans-4-aminocyclohexyl)-Nα-{2-chloro-4-methoxy-5-[5-({[(1R)-1-(4-methyl-phenyl)ethyl]amino}methyl)furan-2-yl]benzoyl}-4-cyano-D-phenylalaninamide, N-[(2R)-1-[(cis-4-aminocyclohexyl)amino]-3-(4-cyanophenyl)propan-2-yl]-2-chloro-4-methoxy-5-[5-({[(1R)-1-(4-methylphenyl)ethyl]amino}methyl)furan-2-yl]benzamide, N-[(2R)-1-[(cis-4-aminocyclohexyl)amino]-3-(4-cyanophenyl)propan-2-yl]-2-chloro-4-methoxy-5-[5-({[(1R)-1-(4-methylphenyl)ethyl]amino}methyl)furan-2-yl]benzamide, N-[(2R)-1-[(cis-4-aminocyclohexyl)amino]-3-(4-cyano-3-methylphenyl)propan-2-yl]-2-chloro-4-methoxy-5-[5-({[(1R)-1-(4-methylphenyl)ethyl]amino}methyl)furan-2-yl]-benzamide, 2-chloro-5-[5-({[(1R)-1-(4-chlorophenyl)ethyl]amino}methyl)furan-2-yl]-N-[(2R)-1-(4-cyanophenyl)-4-(methylamino)-4-oxobutan-2-yl]benzamide, 2-chloro-N-[(2R)-1-(4-cyanophenyl)-3-hydroxypropan-2-yl]-4-hydroxy-5-[5-({[(1R)-1-(4-methylphenyl)ethyl]amino}methyl)furan-2-yl]benzamide, 4-cyano-N-[(2R)-1-(4-cyanophenyl)-4-(methylamino)-4-oxobutan-2-yl]-3-[5-({[(1R)-1-(4-methylphenyl)ethyl]amino}methyl)-2-furyl]benzamide,
2-chloro-N-[(2R)-4-(methylamino)-4-oxo-1-phenylbutan-2-yl]-5-[5-({[(1R)-1-(4-methylphenyl)ethyl]amino}methyl)furan-2-yl]benzamide,
2-chloro-N-[(2R)-1-(4-cyanophenyl)-4-(methylamino)-4-oxobutan-2-yl]-5-(5-{[(2-phenylpropan-2-yl)amino]methyl}furan-2-yl)benzamide,
2-chloro-N-[(2R)-1-(4-cyanophenyl)-4-(methylamino)-4-oxobutan-2-yl]-5-[5-({[2-(4-methylphenyl)propan-2-yl]amino}methyl)-2-furyl]benzamide,
Nα-{2-chloro-5-[5-({[2-(4-chlorophenyl)propan-2-yl]amino}methyl)-2-furyl]benzoyl}-4-cyano-D-phenylalaninamide, and
2-chloro-N-[(2R)-1-hydroxy-3-phenylpropan-2-yl]-5-[5-({[(1R)-1-(4-methylphenyl)ethyl]amino}methyl)-2-furyl]benzamide,
or the salts thereof, the solvates thereof or the solvates of the salts thereof.

5. A process for the preparation of a compound of the formula (I) according to claim 1, comprising the step of allowing an intermediate compound of general formula (VI):

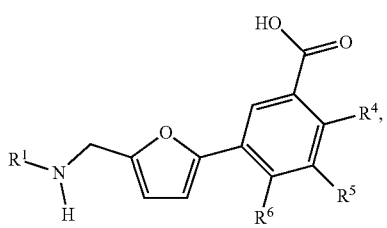

(VI)

in which $R^1$, $R^4$, $R^5$ and $R^6$ are as defined, to react with a compound of general formula (VII):

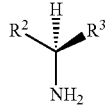

(VII)

in which $R^2$ and $R^3$ are as defined, thus providing a compound of general formula (I):

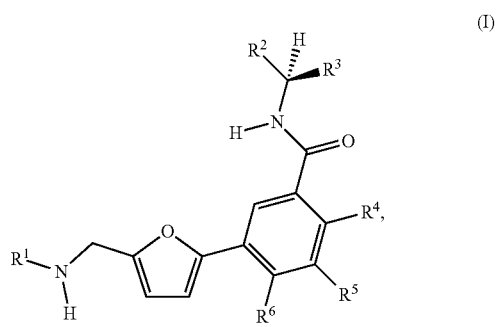

(I)

in which $R^1$, $R^2$, $R^3$, $R^4$, $R^5$ and $R^6$ are as defined.

6. A method for inhibiting proliferation of a breast cancer or lung cancer cell, comprising contacting the cell with a compound of formula (I) according to claim 1.

7. A method for treatment of breast cancer or lung cancer comprising administering a compound of formula (I) according to claim 1 to a patient in need thereof.

8. A compound of formula (I) according to claim 1 for the preparation of a pharmaceutical composition.

9. A pharmaceutical composition comprising a compound according to claim 1 in combination with a further anti-cancer agent.

10. A pharmaceutical composition comprising at least a compound according to claim 1 in combination with one or more pharmaceutically suitable excipient.

11. A method according to claim 7 comprising treatment of breast cancer.

12. A method according to claim 7 comprising treatment of lung cancer.

13. A method for treatment of breast cancer or lung cancer comprising administering a composition according to claim 9 to a patient in need thereof.

14. A method for treatment of breast cancer or lung cancer comprising administering a composition according to claim 10 to a patient in need thereof.

* * * * *

SEQUENCE LISTING

```
<160> NUMBER OF SEQ ID NOS: 1

<210> SEQ ID NO 1
<211> LENGTH: 21
<212> TYPE: PRT
<213> ORGANISM: Artificial Sequence
<220> FEATURE:
<223> OTHER INFORMATION: modified sequence
<220> FEATURE:
<221> NAME/KEY: MOD_RES
<222> LOCATION: 13
<223> OTHER INFORMATION: ACETYLATION
<220> FEATURE:
<221> NAME/KEY: MOD_RES
<222> LOCATION: 21
<223> OTHER INFORMATION: BIOTINYLATION

<400> SEQUENCE: 1

His Ser Gly Arg Gly Lys Gly Gly Lys Gly Leu Gly Lys Gly Gly Ala
1               5                   10                  15

Lys Arg His Arg Lys
            20
```